US012742732B2

(12) United States Patent
Benson et al.

(10) Patent No.: US 12,742,732 B2
(45) Date of Patent: Sep. 22, 2026

(54) COMPOSITIONS, SYSTEMS AND METHODS FOR BIOLOGICAL ANALYSIS INVOLVING ENERGY TRANSFER DYE CONJUGATES AND ANALYTES COMPRISING THE SAME

(71) Applicant: LIFE TECHNOLOGIES CORPORATION, Carlsbad, CA (US)

(72) Inventors: Scott Benson, Alameda, CA (US); Steven Menchen, Fremont, CA (US); Chu-An Chang, Castro Valley, CA (US); Linda Lee, Palo Alto, CA (US); Jacob Freudenthal, San Carlos, CA (US); Khairuzzaman Mullah, Union City, CA (US)

(73) Assignee: Life Technologies Corporation, Carlsbad, CA (US)

( * ) Notice: Subject to any disclaimer, the term of this patent is extended or adjusted under 35 U.S.C. 154(b) by 743 days.

(21) Appl. No.: 18/006,559

(22) PCT Filed: Jul. 23, 2021

(86) PCT No.: PCT/US2021/043000
§ 371 (c)(1),
(2) Date: Jan. 23, 2023

(87) PCT Pub. No.: WO2022/020731
PCT Pub. Date: Jan. 27, 2022

(65) Prior Publication Data

US 2023/0304932 A1 Sep. 28, 2023

Related U.S. Application Data

(60) Provisional application No. 62/705,935, filed on Jul. 23, 2020.

(51) Int. Cl.
*G01N 21/64* (2006.01)
*C12Q 1/6818* (2018.01)
(Continued)

(52) U.S. Cl.
CPC ....... *G01N 21/6428* (2013.01); *C12Q 1/6818* (2013.01); *C12Q 1/6848* (2013.01);
(Continued)

(58) Field of Classification Search
None
See application file for complete search history.

(56) References Cited

U.S. PATENT DOCUMENTS 10,048,208 B2 8/2018 Rothberg et al.
2002/0034746 A1 3/2002 McMillan et al.
(Continued)

FOREIGN PATENT DOCUMENTS

WO WO-2019191003 A1 10/2019

OTHER PUBLICATIONS

PCT/US2021/043000, International Search Report and Written Opinion, Jan. 24, 2022, 25 pages.

*Primary Examiner* — Neil N Turk

(57) ABSTRACT

A system (1000) comprising first and second excitation sources (101a, 101b) with respective excitation wavelengths for exciting first second and third dyes in a sample (110) and further comprising a detector (115), first and second emission spectral elements (121a, 121b) for transmitting respective first and second emission wavelengths as well as a processor (130) for automatically operating the elements of the system. The first dye comprises a first absorption spectrum comprising a first maximum absorption wavelength and the second dye comprises a second absorption spectrum comprising a second maximum absorption wavelength that is equal to or substantially equal to the first maximum absorption wavelength. The second dye comprises a second emission spectrum comprising a second maximum emission wavelength and the third dye comprises a third emission spectrum comprising a third maximum emission wavelength
(Continued)

that is equal to or substantially equal to the second maximum emission wavelength.

12 Claims, 24 Drawing Sheets

(51) Int. Cl.
*C12Q 1/6848* (2018.01)
*C12Q 1/686* (2018.01)
*C12Q 1/6869* (2018.01)

(52) U.S. Cl.
CPC ........... *C12Q 1/686* (2013.01); *C12Q 1/6869* (2013.01); *G01N 21/6452* (2013.01); *G01N 21/648* (2013.01); *G01N 21/6486* (2013.01); *G01N 2021/6419* (2013.01); *G01N 2021/6441* (2013.01)

(56) References Cited

U.S. PATENT DOCUMENTS

| | | | | |
|---|---|---|---|---|
| 2002/0056816 | A1 | 5/2002 | Stark | |
| 2004/0009586 | A1 | 1/2004 | Oldham et al. | |
| 2006/0006067 | A1 | 1/2006 | Unger | |
| 2006/0138344 | A1 | 6/2006 | Gunstream et al. | |
| 2006/0211028 | A1* | 9/2006 | Mao | C07D 417/06<br>546/102 |
| 2006/0211029 | A1* | 9/2006 | Mao | G01N 1/30<br>546/176 |
| 2006/0252079 | A1 | 11/2006 | Oldham et al. | |
| 2009/0305410 | A1 | 12/2009 | Mao et al. | |
| 2011/0097716 | A1 | 4/2011 | Natt et al. | |
| 2011/0105348 | A1 | 5/2011 | Hinnah et al. | |
| 2011/0294675 | A1* | 12/2011 | Brabetz | C12Q 1/686<br>435/6.12 |
| 2015/0141267 | A1 | 5/2015 | Rothberg et al. | |
| 2019/0271592 | A1 | 9/2019 | Gray et al. | |
| 2019/0383739 | A1 | 12/2019 | Rothberg et al. | |

* cited by examiner

Em Channels →

| Ex Channels | Ex (nm) \ Em (nm) | m1 (421a) 520±15 | m2 (421b) 558±12 | m3 (421c) 587±10 | m4 (421d) 623±14 | m5 (421e) 682±14 | m6 (421f) 711±12 |
|---|---|---|---|---|---|---|---|
| x1 (401a) | 480±10 | A1 | B12 | B13 | B14 | B15 | B16 |
| x2 (401b) | 520±10 | C21 | A2 | B23 | B24 | B25 | B26 |
| x3 (401c) | 550±10 | C31 | C32 | A3 | B34 | B35 | B36 |
| x4 (401d) | 580±10 | C41 | C42 | C43 | A4 | B45 | B46 |
| x5 (401e) | 640±10 | C51 | C52 | C53 | C54 | A5 | B56 |
| x6 (401f) | 662±10 | C61 | C62 | C63 | C64 | C65 | A6 |

Ex Channels

| Ex (nm) \ Em (nm) | m1 520±15 | m2 558±12 | m3 587±10 | m4 623±14 | m5 682±14 | m6 711±12 |
|---|---|---|---|---|---|---|
| x1 480±10 | A1 | B12 | B13 | B14 | B15 | B16 |
| x2 520±10 | C21 | A2 | B23 | B24 | B25 | B26 |
| x3 550±10 | C31 | C32 | A3 | B34 | B35 | B36 |
| x4 580±10 | C41 | C42 | C43 | A4 | B45 | B46 |
| x5 640±10 | C51 | C52 | C53 | C54 | A5 | B56 |
| x6 662±10 | C61 | C62 | C63 | C64 | C65 | A6 |

| | | m1 | m2 | m3 | m4 | m5 | m6 |
|---|---|---|---|---|---|---|---|
| | Ex (nm) \ Em (nm) | 520±15 | 558±12 | 587±10 | 623±14 | 682±14 | 711±12 |
| x1 | 480±10 | A1 | B12 | B13 | B14 | B15 | B16 |
| x2 | 520±10 | C21 | A2 | B23 | B24 | B25 | B26 |
| x3 | 550±10 | C31 | C32 | A3 | B34 | B35 | B36 |
| x4 | 580±10 | C41 | C42 | C43 | A4 | B45 | B46 |
| x5 | 640±10 | C51 | C52 | C53 | C54 | A5 | B56 |
| x6 | 662±10 | C61 | C62 | C63 | C64 | C65 | A6 |

Em Channels →

| | Ex (nm) \ Em (nm) | m1 (421a) | m2 (421b) | m3 (421c) | m4 (421d) | m5 (421e) | m6 (421f) |
|---|---|---|---|---|---|---|---|
| | | 520±15 | 558±12 | 587±10 | 623±14 | 682±14 | 711±12 |
| 401a x1 | 480±10 | A1 | B12 | B13 | B14 | B15 | B16 |
| 401b x2 | 520±10 | C21 | A2 | B23 | B24 | B25 | B26 |
| 401c x3 | 550±10 | C31 | C32 | A3 | B34 | B35 | B36 |
| 401d x4 | 580±10 | C41 | C42 | C43 | A4 | B45 | B46 |
| 401e x5 | 640±10 | C51 | C52 | C53 | C54 | A5 | B56 |
| 401f x6 | 662±10 | C61 | C62 | C63 | C64 | C65 | A6 |

Ex Channels ↑

FIG. 17

| | | 421a | 421b | 421c | 421d | 421e | 421f |
|---|---|---|---|---|---|---|---|
| | Em Channels → | m1 | m2 | m3 | m4 | m5 | m6 |
| | Ex (nm) \ Em (nm) | 520±15 | 558±12 | 587±10 | 623±14 | 682±14 | 711±12 |
| 401a | x1 480±10 | A1 | B12 | B13 | B14 | B15 | B16 |
| 401b | x2 520±10 | C21 | A2 | B23 | B24 | B25 | B26 |
| 401c | x3 550±10 | C31 | C32 | A3 | B34 | B35 | B36 |
| 401d | x4 580±10 | C41 | C42 | C43 | A4 | B45 | B46 |
| 401e | x5 640±10 | C51 | C52 | C53 | C54 | A5 | B56 |
| 401f | x6 662±10 | C61 | C62 | C63 | C64 | C65 | A6 |

Ex Channels

FIG. 19

Scheme 1

Z - Reactive Functionality
ZR - Z Reactive Functionality
PG - Protecting Group

Scheme 2

Z - Reactive Functionality
ZR - Z Reactive Functionality
PG - Protecting Group

Scheme 3

Z - Reactive Functionality
ZR - Z Reactive Functionality
PG - Protecting Group
PA - Phosphoramidite

| Linker | Product |
| --- | --- |
|  |  |
|  |  |
|  |  |

Z - Reactive Functionality
ZR - Z Reactive Functionality
PG - Protecting Group
PA - Phosphoramidite

COMPOSITIONS, SYSTEMS AND METHODS FOR BIOLOGICAL ANALYSIS INVOLVING ENERGY TRANSFER DYE CONJUGATES AND ANALYTES COMPRISING THE SAME

CROSS REFERENCE TO RELATED APPLICATIONS

This application claims the benefit under 35 U.S.C. § 119(e) of U.S. Provisional Application No. 62/705,935, filed Jul. 23, 2020, the disclosure of which is hereby incorporated by reference as if set forth in full

TECHNICAL FIELD

The present disclosure generally relates to energy transfer dye conjugate pairs comprising a donor dye covalently attached to an acceptor dye. The disclosure further relates to uses of energy transfer dye conjugate pairs, for example, as an energy transfer dye conjugate reporter moiety covalently attached to an analyte with or without a quencher moiety, for biological applications including, for example, quantitative polymerase chain reaction (qPCR) and digital PCR (dPCR). The present disclosure further relates to systems, devices, and methods for observing, testing, and/or analyzing one or more biological samples by qPCR, and more specifically to systems, devices, and methods comprising optical systems for observing, testing, and/or analyzing one or more biological samples by qPCR using the energy transfer dye conjugate pairs disclosed herein.

BACKGROUND

Current analyses of cell and tissue functionality often require extracting as much information as possible from materials that are often limited. For example, samples such as tumor biopsies are difficult to collect and usually yield only a small amount of usable nucleic acid. PCR detection and measurement of a single target analyte, referred to as a single-plex assay, has been the gold standard for analyzing clinical research samples on the nucleic acid level, and has been invaluable in extending the limits of biological knowledge for more than a quarter century.

However, the limited amount of nucleic acid obtained from clinical research specimens often forces choices to be made about how best to utilize these precious samples. Furthermore, if the sample is limited, the number of loci that can be analyzed is also limited, reducing the amount of information that can be extracted from a single sample. Finally, the additional time and materials required to set up multiple single-assay reactions could increase the expense of a complex project significantly.

Real-time systems for quantitative PCR (qPCR) are frequently used to conduct assays on cell and tissue samples. Nucleic acid detection/amplification methods, such as in real-time polymerase chain reactions, frequently use dual-labeled probes to detect and/or quantify target nucleic acids like specific gene sequences or expressed messenger RNA sequences. Fluorogenic probes for use in such methods are often labeled with both a reporter and a quencher moiety. In such cases, fluorescence from the reporter is unquenched when the two moieties are physically separated via hybridization of the oligonucleotide probe to a nucleic acid template and/or via nuclease activity which removes one of the quencher or reporter moieties components from the oligonucleotide probe.

Fluorescence resonance energy transfer (FRET) within dual-labeled oligonucleotide probes is widely used in assays for genetic analysis. FRET has been utilized to study DNA hybridization and amplification, the dynamics of protein folding, proteolytic degradation, and interactions between other biomolecules. FRET can occur between reporter and quencher groups and can involve different modes of energy transfer (ET). For example, energy transfer can involve fluorescence quenching mechanisms whereby an excitation electron can be transferred from a donor molecule to an acceptor molecule via a non-radiative path when there is interaction between the donor and acceptor. FRET also can occur between two dye molecules when excitation is transferred from a donor molecule to an acceptor molecule without emission of a photon.

Multiplex PCR analysis of nucleic acids, a strategy where more than one target is amplified and quantified from a single sample aliquot, is an attractive solution to problems associated with running multiple single-plex assays. In multiplex PCR, a sample aliquot is queried with multiple probes that contain fluorescent dyes in a single PCR reaction. This increases the amount of information that can be extracted from that sample. With multiplex PCR, significant savings in sample and materials can be realized. To increase the utility of this method, multiplexed PCR using several pairs of gene-specific primers and probes to amplify and measure multiple target sequences simultaneously have been developed. Multiplexing PCR provides the following advantages: 1) Efficiency: multiplexed PCR helps conserve sample material and avoid well-to-well variation by combining several PCR assays into a single reaction. Multiplexing makes more efficient use of limited samples, such as those harboring a rare target that cannot be split into multiple aliquots without compromising the sensitivity; 2) Economy: even though the targets are amplified in unison, each one is detected independently by using a gene-specific probe with a unique reporter dye to distinguish the amplifications based on their fluorescent signal. Once optimized, a multiplexed assay is more cost effective than the same assays amplified independently.

However, currently there are limitations to the number of targets that can be analyzed in a single multiplex PCR assay. The experimental design for multiplex PCR is more complicated than for single reactions. The probes used to detect individual targets must contain unique reporter moieties with distinct spectra. The settings for excitation and emission filters of real-time detection systems vary from manufacturer to manufacturer; therefore, instruments must be calibrated for each dye moiety as part of the experiment optimization process. Thus, one limitation in the development of multiplex PCR assays is the number of fluorophores, and hence probes, that can be effectively measured in a single reaction. Another limitation in multiplexed PCR results from signal interference ("cross-talk") between different fluorescence reporters that can compromise quantification or cause false positives or inaccurate quantification. Using traditional systems, it is therefore important to select fluorophores with minimal spectral overlap. Thus, when designing multiplexed reactions, different targets should be labeled with fluorophores that avoid overlapping excitation and/or emission profiles to avoid possible crosstalk issues. Additionally, the emission and excitation spectra of the fluorophores must be compatible with the PCR instrument to be used, and specifically, the band-pass specifications for each filter-set.

Signal cross-talk also can be minimized by using probes that quench well. When designing a fluorescent probe, it is necessary to ensure that the reporter and quencher moieties are compatible, given the type of detection chemistry. Previously, the most common dye/quencher combination for a TaqMan probe is a FAM fluorophore with a TAMRA quencher. More recently, however, “dark quenchers”, such as Dabcyl and Black Hole Quenchers (BHQ), have largely replaced fluorescent quenchers such as TAMRA. Dark quenchers emit the energy they absorb from the fluorophore as heat rather than light of a different wavelength. “Dark quenchers” tend to give results with lower background, and are especially useful in a multiplex reaction where it is important to avoid emitted light from the quencher creating cross-talk signal with one of the reporter dyes. Thus, highly efficient “dark quenchers” considerably reduce background fluorescence from fluorophore and quencher moieties leading to increased sensitivity and end-point signal. This is particularly useful for multiplex reactions because having several fluorophores in the same tube causes higher background fluorescence.

In general, multiplex PCR reactions have been limited due, for example, to complexities in the chemistry introduced when a large number of different probes are present within a single reaction mixture. For example, in duplex reactions, the most popular combination used is FAM and HEX (JOE/VIC®); in triplex reactions, dyes such as FAM, HEX (JOE/VIC®), NED or Cy5 are typically used; and in quadriplex reactions, dyes such as FAM, HEX (JOE/VIC®), Texas Red®, and Cy5 dyes are typically used. Until recently, the most common multiplex PCR instruments could take advantage of only four unique dye-quencher pairs. However, certain commercial instruments have the optical capability to perform higher levels of multiplexing, e.g., 6-plex PCR, 8-plex PCR, 10-plex PCR, 20-plex PCR, and the like.

Chemical complexities notwithstanding, higher-plex qPCR assays have also been limited by instrument capabilities or the way in which existing instruments are utilized. Currently available qPCR instruments divide a broad excitation and emission spectrum into distinct spectra (EX/EM “channels”) that are compatible with the excitation/emission spectra of corresponding sets of dyes or probes. For example, matched sets of EX/EM channels have typically been used up to accommodate quadriplex reactions, as discussed above. However, due at least in part to the unavailability of suitable probes, a fuller range of EX/EM channel combinations have yet to be utilized to provide assays able to quantify more than 4 targets in a common sample.

Thus, there is a need to provide additional probes that include unique fluorophore/quencher combinations that allow for increased multiplex reactions and detection through the additional spectral channels already available on some commercial instruments. Further, there is a need for new fluorophores and fluorophore/quencher combinations with unique optical properties that can facilitate even higher order multiplexing once instruments with additional channels and other related hardware and software improvements become available.

SUMMARY

In one aspect, the present disclosure provides an energy transfer fluorescent dye conjugate the includes i. a donor dye capable of absorbing light at a first wavelength and emitting excitation energy in response; ii. an acceptor dye capable of absorbing the excitation energy emitted by the donor dye and emitting light at a second wavelength in response; and iii. a linker covalently attaching the donor dye to the acceptor dye, wherein the linker includes one or more of an alkyl portion, an amino-alkyl portion, an oxy-alkylene portion, an amino-alkylene-dialkoxy portion, an alkenylene portion, an alkynylene portion, a polyether portion, an arylene portion, an amide portion, or a phosphodiester portion.

In certain embodiments, the energy transfer dye conjugates described herein can be linked to an analyte and have a basic structure selected from one of:

(LI)

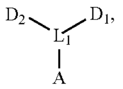

(LII)

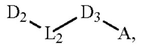 and (LIII)

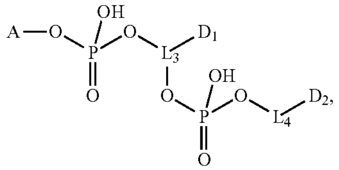

- wherein $L_1$ is a first linker, wherein $L_1$ is attached to $D_1$, $D_2$ and A through a covalent bond or through a spacer including one or more intervening atoms;
- wherein $L_2$ is a second linker, wherein $L_2$ is attached to each of $D_2$ and $D_3$ through a covalent bond or through a spacer including one or more intervening atoms;
- wherein $L_3$ is a third linker, wherein $L_3$ is attached to each $PO_4H$ and $D_1$ through a covalent bond or through a spacer including one or more intervening atoms;
- wherein $L_4$ is a fourth linker, wherein $L_4$ is attached to $PO_4H$ and $D_2$ through a covalent bond or through a spacer including one or more intervening atoms;
- wherein A is the analyte;
- wherein each of $D_1$, $D_2$, and $D_3$ is interchangeably a donor dye or an acceptor dye;
- wherein the combination of $D_1$ and $D_2$ in $L_1$ and $L_{III}$ and $D_2$ and $D_3$ in $L_{II}$ forms an energy transfer dye pair.

Representative examples of donor dyes include, without limitation, a xanthene dye, a cyanine dye, a BODIPY dye, a pyrene dye, a pyronine dye, and a coumarin dye. Representative examples of acceptor dyes include, without limitation, a fluorescein dye, a cyanine dye, a rhodamine dye, a BODIPY dye, a pyrene dye, a pyronine dye, and a coumarin dye.

In another aspect, an oligonucleotide probe is described that includes: i. an oligonucleotide; and ii. an energy transfer dye conjugate as described herein that is covalently attached to the oligonucleotide.

In yet another aspect, a composition is described that includes a fluorescently-labeled oligonucleotide probe that includes: an oligonucleotide probe covalently attached to the energy transfer dye conjugate as described herein. In some embodiments, the composition includes the oligonucleotide probe attached to the energy transfer dye conjugate and an aqueous medium, such as a buffer, master mix, or reaction mixture. In some embodiments, the composition includes the oligonucleotide probe attached to the energy transfer dye conjugate and a non-aqueous medium, such as a lyophilized or freeze-dried buffer, master mix, or reaction mixture In another aspect, a method of detecting or quantifying a target nucleic acid molecule in a sample is described that includes:

(i) contacting the sample including one or more target nucleic acid molecules with at least one oligonucleotide probe as disclosed herein having a sequence that is at least partially complementary to the target nucleic acid molecule, where the at least one probe undergoes a detectable change in fluorescence upon hybridization to the one or more target nucleic acid molecules; and;

(ii) detecting the presence or absence or quantifying the amount of the target nucleic acid molecules by measuring fluorescence of the probe.

In yet another aspect, a method of detecting or quantifying a target nucleic acid molecule in a sample by polymerase chain reaction (PCR) is described that includes:

(i) contacting the sample including one or more target nucleic acid molecules with a) at least one oligonucleotide probe as disclosed herein having a sequence that is at least partially complementary to the target nucleic acid molecule, where the at least one probe undergoes a detectable change in fluorescence upon amplification of the one or more target nucleic acid molecules; and with b) at least one oligonucleotide primer pair;

(ii) incubating the mixture of step (i) with a DNA polymerase under conditions sufficient to amplify one or more target nucleic acid molecules; and (iii) detecting the presence or absence or quantifying the amount of the amplified target nucleic acid molecules by measuring fluorescence of the probe.

In yet another aspect, a kit for polymerase chain reaction (PCR) is described that includes: i. one or more buffering agents, a nucleic acid synthesis enzyme; and ii. an oligonucleotide probe as described herein; and iii. instructions for performing a PCR assay, and optionally a purification medium or an organic solvent.

In yet another aspect, compositions are provided herein. For example, the composition can include: a) a first labeled oligonucleotide including an energy transfer dye conjugate as described herein; and b) a polymerase. In another embodiment, the composition can include: a) a fluorescent energy transfer dye conjugate as disclosed herein; and b) a nucleic acid molecule. In yet another embodiment, the composition can include: a) a fluorescent energy transfer dye conjugate as disclosed herein; and b) an enzyme. In yet another embodiment, the composition can include: a) a fluorescent energy transfer dye conjugate as disclosed herein; and b) a fluorophore having an excitation wavelength that is within 20 nm of the excitation wavelength of the donor dye in the energy transfer dye conjugate or within 20 nm of the emission wavelength of the acceptor dye in the energy transfer dye conjugate.

In still another aspect, a system comprises a first radiant source, an optional second radiant source, a detector, a first emission spectral element, and an optional second emission spectral element. The system may further include at least one processor comprising at least one memory including instructions. The first radiant is source characterized by a first average excitation wavelength, while the second radiant source, when present, is characterized by a second average excitation wavelength that is different than the first average excitation wavelength. A sample is disposed to receive radiation from the radiant source(s), wherein the sample comprises a first dye, a second dye and an optional third dye. The detector is configured to measure emissions from the sample. The first emission spectral element is characterized by a first average emission wavelength and the optional second emission spectral element is characterized by a second average emission wavelength that is different than the first average emission wavelength. The memory includes instructions to illuminate the sample with the first radiant source and, in response, (1) measure emissions from the sample using the detector and the first emission spectral element and (2) optionally measure emissions from the sample using the detector and the second emission spectral element. When present, the memory also includes instructions to illuminate the sample with the second radiant source and, in response, measure emissions from the sample using the detector and the second emission spectral element. The first dye comprises a first absorption spectrum comprising a first maximum absorption wavelength and the second dye comprises a second absorption spectrum comprising a second maximum absorption wavelength that is equal to or substantially equal to the first maximum absorption wavelength. Additionally or alternatively, the second dye comprises a second emission spectrum comprising a second maximum emission wavelength and the third dye comprises a third emission spectrum comprising a third maximum emission wavelength that is equal to or substantially equal to the second maximum emission wavelength.

Additional embodiments, features, and advantages of the disclosure will be apparent from the following detailed description and through practice of the disclosure. It will be understood that any of the embodiments described herein can be used in connection with any other embodiments described herein to the extent that the embodiments do not contradict one another.

BRIEF DESCRIPTION OF THE DRAWINGS

Embodiments of the present disclosure may be better understood from the following detailed description when read in conjunction with the accompanying drawings. Such embodiments, which are for illustrative purposes only, depict novel and non-obvious aspects of the present disclosure. The drawings include the following figures:

FIG. 17 is a tabular representation of a set of ex-em channels and dyes according to an embodiment of the present disclosure including the dyes shown in FIG. 16.

FIG. 19 is a tabular representation of a set of ex-em channels and dyes according to an embodiment of the present disclosure including a set of 10 dyes.

DETAILED DESCRIPTION

Figure 1:
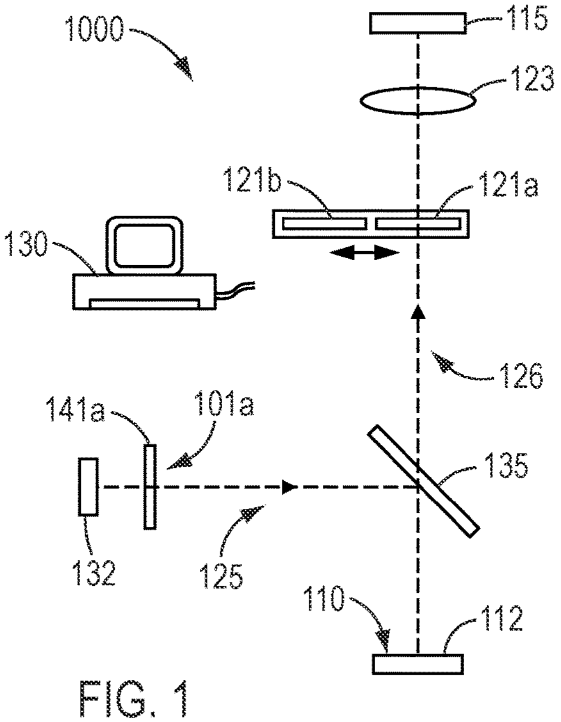
FIG. 1 is a schematic representation of a system according to an embodiment of the present disclosure.

Reference will now be made in detail to certain embodiments of the disclosure, examples of which are illustrated in the accompanying drawings. It is to be understood that both the general description and detailed description the embodiments discussed herein are generally directed to devices, systems, compositions and methods used in nucleic acid synthesis, such as polymerase chain reaction (PCR) devices, systems, compositions and methods, including for example, real-time PCR (qPCR) devices, systems, compositions and methods and end-point PCR devices, systems, compositions and methods, including, but not limited to digital PCR (dPCR) or melt curve analysis devices, system, compositions or methods. It is to be understood that both the general description and detailed description provided herein are exemplary and explanatory only and are not restrictive of the teachings. While the disclosure will be described in conjunction with the illustrated embodiments, it will be understood that they are not intended to limit the disclosure to those embodiments. On the contrary, the disclosure is intended to cover all alternatives, modifications, and equivalents, which may be included within the disclosure as defined by the appended claims.

For the purposes of interpreting of this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). It is noted that, as used in this specification and the appended and claims, the singular forms "a," "an," and "the," include plural referents unless expressly and unequivocally limited to one referent. The use of "or" means "and/or" unless stated otherwise. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. "About" indicates a degree of variation that does not substantially affect the properties of the described subject matter, e.g., within 10%, 5%, 2%, or 1%. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed considering the number of reported significant digits and by applying ordinary rounding techniques.

The section headings used herein are for organizational purposes only and are not to be construed as limiting the desired subject matter in any way. In the event that any literature incorporated by reference contradicts any term defined in this specification, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Definitions

To facilitate understanding of this disclosure, a number of terms are defined below. Unless stated otherwise, the following terms and phrases as used herein are intended to have the following meanings.

As used herein, "energy transfer (ET)" refers to FRET or Dexter energy transfer. As used herein, "FRET" (also referred to as fluorescence resonance energy transfer or Förster resonance energy transfer) refers to a form of molecular energy transfer (MET) by which energy is passed non-radiatively between a donor molecule and an acceptor molecule. Without being bound by theory, it is believed that when two fluorophores whose excitation and emission spectra overlap are in close proximity, excitation of one fluorophore can cause the first fluorophore to transfer its absorbed energy to the second fluorophore, causing the second fluorophore, in turn, to fluoresce. Stated differently, the excited-state energy of the first (donor) fluorophore is transferred by a process sometimes referred to as resonance induced dipole-dipole interaction to the neighboring second (acceptor) fluorophore. As a result, the lifetime of the donor molecule is decreased and its fluorescence is quenched, while the fluorescence intensity of the acceptor molecule is enhanced and depolarized. When the excited-state energy of the donor is transferred to a non-fluorophore acceptor, such as a quencher, the fluorescence of the donor is quenched without subsequent emission of fluorescence by the acceptor. Pairs of molecules that can engage in ET are termed ET pairs. In order for energy transfer to occur, the donor and acceptor molecules must typically be in close proximity (e.g., up to 70 to 100 Angstroms). As used herein, "Dexter energy transfer" refers to a fluorescence quenching mechanism whereby an excitation electron can be transferred from a donor molecule to an acceptor molecule via a non-radiative path. Dexter energy transfer can occur when there is interaction between the donor and acceptor. In some embodiments, the Dexter energy transfer can occur at a distance between the donor and acceptor of about 10 Angstroms or less. In some embodiments, in the Dexter energy transfer, the excited state may be exchanged in a single step. In some embodiments, in the Dexter energy transfer, the excited state may be exchanged in a two separate steps.

Commonly used methods for detecting nucleic acid amplification products require that the amplified product (i.e., amplicon) be separated from unreacted primers. This is often achieved either through the use of gel electrophoresis, which separates the amplification product from the primers on the basis of a size differential, or through the immobilization of the product, allowing washing away of free primer. Other methods for monitoring the amplification process without separation of the primers from the amplicon, such as for real-time detection, have been described. Some examples include TaqMan® probes (Roche Molecular Systems), molecular beacons, double-stranded intercalator dyes, such as SYBR® GREEN indicator dye (Life Technologies Corporation), LUX primers, and others. The principal drawback to intercalator-based detection of PCR product accumulation, such as using SYBR® GREEN indicator dye, is that both specific and nonspecific products generate a signal. Typically, intercalators are used for single-plex detection assays and are not suitable for use for multiplex detection.

Real-time systems for quantitative PCR (qPCR) are frequently used to conduct assays on cell and tissue samples (e.g., blood, saliva, semen, urine). Quantitative PCR assays that are probe-based provide a significant improvement over intercalator-based PCR product detection. One probe-based method for detection of amplification product without separation from the primers is the 5' nuclease PCR assay (also referred to as the TaqMan® assay or hydrolysis probe assay). This alternative method provides a real-time method for detecting only specific amplification products. During amplification, annealing of the detector probe, sometimes referred to as a "TaqMan probe" (e.g., 5'nuclease probe) or hydrolysis probe, to its target sequence generates a substrate that is cleaved by the 5' nuclease activity of a DNA polymerase, such as a *Thermus aquaticus* (Taq) DNA polymerase, when the enzyme extends from an upstream primer into the region of the probe. This dependence on polymerization ensures that cleavage of the probe occurs only if the target sequence is being amplified.

The term "reporter," "reporter group" or "reporter moiety" is used in a broad sense herein and refers to any identifiable tag, label, or moiety. In some embodiments, the reporter is a fluorescent reporter moiety or dye.

In general, a TaqMan detector probe can include an oligonucleotide covalently attached to a fluorescent reporter moiety or dye and a quencher moiety or dye. The reporter and quencher dyes are in close proximity, such that the quencher greatly reduces the fluorescence emitted by the reporter dye by FRET. Probe design and synthesis has been simplified by the finding that adequate quenching is typically observed for probes with the reporter at the 5' end and the quencher at the 3' end.

During the extension phase of PCR, if the target sequence is present, the detector probe anneals downstream from one of the primer sites and is cleaved by the 5' nuclease activity of a DNA polymerase possessing such activity, as this primer is extended. The cleavage of the probe separates the reporter dye from quencher dye by releasing them into solution, and thereby increasing the reporter dye signal. Cleavage further removes the probe from the target strand, allowing primer extension to continue to the end of the template strand. Thus, inclusion of the probe does not inhibit the overall PCR process. Additional reporter dye molecules are cleaved from their respective probes with each cycle, effecting an increase in fluorescence intensity proportional to the amount of amplicon produced.

The advantage of fluorogenic detector probes over DNA binding dyes, such as SYBR GREEN®, is that specific hybridization between probe and target is required to generate fluorescent signal. Thus, with fluorogenic detector probes, non-specific amplification due to mis-priming or primer-dimer artifact does not generate a signal. Another advantage of fluorogenic probes is that they can be labeled with different, distinguishable reporter dyes. By using detector probes labeled with different reporters, amplification of multiple distinct sequences can be detected in a single PCR reaction, often referred to as a multiplex assay.

As used herein, the term "probe" or "detector probe" generally refers to any of a variety of signaling molecules indicative of amplification, such as an "oligonucleotide probe." As used herein, "oligonucleotide probe" refers to an oligomer of synthetic or biologically produced nucleic acids (e.g., DNA or RNA or DNA/RNA hybrid) which, by design or selection, contain specific nucleotide sequences that allow it to hybridize under defined stringencies, specifically (i.e., preferentially) to a target nucleic acid sequence. Thus, some probes or detector probes can be sequence-based (also referred to as "sequence-specific detector probe"), for example 5' nuclease probes. Various detector probes are known in the art, for example (TaqMan® probes described herein (See also U.S. Pat. No. 5,538,848) various stem-loop molecular beacons (See, e.g., U.S. Pat. Nos. 6,103,476 and 5,925,517 and Tyagi and Kramer, 1996, Nature Biotechnology 14:303-308), stemless or linear beacons (See, e.g., WO 99/21881), PNA Molecular Beacons™ (See, e.g., U.S. Pat. Nos. 6,355,421 and 6,593,091), linear PNA beacons (See, e.g., Kubista et al., 2001, SPIE 4264:53-58), non-FRET probes (See, e.g., U.S. Pat. No. 6,150,097), Sunrise®/Amplifluor® probes (U.S. Pat. No. 6,548,250), stem-loop and duplex Scorpion™ probes (Solinas et al., 2001, Nucleic Acids Research 29:E96 and U.S. Pat. No. 6,589,743), bulge loop probes (U.S. Pat. No. 6,590,091), pseudo knot probes (U.S. Pat. No. 6,589,250), cyclicons (U.S. Pat. No. 6,383,752), MGB Eclipse™ probe (Epoch Biosciences), hairpin probes (U.S. Pat. No. 6,596,490), peptide nucleic acid (PNA) light-up probes, self-assembled nanoparticle probes, and ferrocene-modified probes described, for example, in U.S. Pat. No. 6,485,901; Mhlanga et al., 2001, Methods 25:463-471; Whitcombe et al., 1999, Nature Biotechnology. 17:804-807; Isacsson et al., 2000, Molecular Cell Probes. 14:321-328; Svanvik et al., 2000, Anal Biochem. 281:26-35; Wolffs et al., 2001, Biotechniques 766:769-771; Tsourkas et al., 2002, Nucleic Acids Research. 30:4208-4215; Riccelli et al., 2002, Nucleic Acids Research 30:4088-4093; Zhang et al., 2002 Shanghai. 34:329-332; Maxwell et al., 2002, J. Am. Chem. Soc. 124:9606-9612; Broude et al., 2002, Trends Biotechnol. 20:249-56; Huang et al., 2002, Chem Res. Toxicol. 15:118-126; and Yu et al., 2001, J. Am. Chem. Soc 14:11155-11161. Detector probes can include reporter dyes such as, for example, the novel dyes described herein as well as 6-carboxyfluorescein (6-FAM) or tetrachlorofluorescin (TET) and other dyes known to those of skill in the art. Detector probes can also include quencher moieties such as those described herein as well as tetramethylrhodamine (TAMRA), Black Hole Quenchers (Biosearch), Iowa Black (IDT), QSY quencher (Molecular Probes), and Dabsyl and Dabcyl sulfonate/carboxylate Quenchers (Epoch). In some embodiments, detector probes can also include a combination of two probes, wherein for example a fluor is on one probe, and a quencher on the other, wherein hybridization of the two probes together on a target quenches the signal, or wherein hybridization on a target alters the signal signature via a change in fluorescence.

"Primer" as used herein can refer to more than one primer and refers to an oligonucleotide, whether occurring naturally or produced synthetically, which is capable of acting as a point of initiation of synthesis when placed under conditions in which synthesis of a primer extension product which is complementary to a nucleic acid strand is induced i.e., in the presence of nucleotides and an agent for polymerization such as DNA polymerase, at a suitable temperature for a sufficient amount of time and in the presence of a buffering agent. Such conditions can include, for example, the presence of at least four different deoxyribonucleoside triphosphates (such as G, C, A, and T) and a polymerization-inducing agent such as DNA polymerase or reverse transcriptase, in a suitable buffer ("buffer" includes substituents which are cofactors, or which affect pH, ionic strength, etc.), and at a suitable temperature. In some embodiments, the primer may be single-stranded for maximum efficiency in amplification. The primers herein are selected to be substantially complementary to the different strands of each specific sequence to be amplified. This means that the primers must be sufficiently complementary to hybridize with their respective strands. A non-complementary nucleotide fragment may be attached to the 5'-end of the primer (such as having a "tail"), with the remainder of the primer sequence being complementary, or partially complementary, to the target region of the target nucleic acid. Commonly, the primers are complementary, except when non-complementary nucleotides may be present at a predetermined sequence or sequence range location, such as a primer terminus as described. In some embodiments, such non-complementary "tails" can comprise a universal sequence, for example, a sequence that is common to one or more oligonucleotides. In certain embodiments, the non-complementary fragment or tail may comprise a polynucleotide sequence such as a poly (T) sequence to hybridize, for example, to a polyadenylated oligonucleotide or sequence.

As used herein, a "sample" refers to any substance containing, or presumed to contain, one or more biomolecules (e.g., one or more nucleic acid and/or protein target molecules) and can include one or more of cells, a tissue or a fluid extracted and/or isolated from an individual or individuals. Samples may be derived from a mammalian or non-mammalian organism (e.g., including but not limited to a plant, virus, bacteriophage, bacteria, and/or fungus). As used herein, the sample may refer to the substance contained in an individual solution, container, vial, and/or reaction site or may refer to the substance that is partitioned between an array of solutions, containers, vials, and/or reaction sites (e.g., substance partitioned over an array of microtiter plate vials or over an array of array of through-holes or reaction regions of a sample plate; for example, for use in a dPCR assay). In some embodiments, a sample may be a crude sample. For example, the sample may be a crude biological sample that has not undergone any additional sample preparation or isolation. In some embodiments, the sample may be a processed sample that had undergone additional processing steps to further isolate the analyte(s) of interest and/or clean up other debris or contaminants from the sample.

As used herein, the terms "target", "target molecule", "target biomolecule", "target analyte", "target sequence", "target nucleic acid molecule", or the like, refers to a molecule having a particular chemical structure that is distinct from that of one or more other "targets", "target molecules", "target biomolecules", "target analytes", "target sequences", "target nucleic acid molecules", or the like. In general, each "target", "target molecule", "target biomolecule", "target analyte", "target sequence", "target nucleic acid molecule", or the like contains a structure or sequence that is distinct from any structure or sequence of the others and that may be utilized to attached to a particular probe or dye contained in sample or sample solution.

As used herein, the term "amplification" or "amplify" refers to an assay in which the amount or number of one or more target biomolecules is increased, for example, by an amount to allow detection and/or quantification of the one or more target biomolecules. For example, in some embodiments, a PCR assay may be used to amplify a target biomolecule. As used herein, a "polymerase chain reaction" or a "PCR", unless specifically defined otherwise, refers to either singleplex or multiplex PCR assays, and can be real time or quantitative PCR (wherein detection occurs during amplification) or end-point PCR (when detection occurs at the end of a PCR or after amplification; e.g., a dPCR assay). Other types of assays and methods of amplification or amplifying are also anticipated such as, for example, isothermal nucleic acid amplification and are readily understood by those of skill in the art.

As used herein, the terms "nucleic acid," "polynucleotide," and "oligonucleotide" can refer to primers, probes, oligomer fragments to be detected, oligomer controls—either labeled or unlabeled, and unlabeled blocking oligomers and shall be generic to polydeoxyribonucleotides (containing 2-deoxy-D-ribose), polyribonucleotides (containing D-ribose), and any other type of polynucleotide which is an N-glycoside of a purine or pyrimidine base, or modified purine or pyrimidine bases. There is no intended distinction in length between the term "nucleic acid," "polynucleotide," and "oligonucleotide," and these terms will be used interchangeably. "Nucleic acid", "DNA", "RNA", and similar terms can also include nucleic acid analogs. The oligonucleotides, as described herein, are not necessarily physically derived from any existing or natural sequence but may be generated in any manner, including chemical synthesis, DNA replication, reverse transcription or a combination thereof.

The term "analog" or "analogue" includes synthetic analogs having modified base moieties, modified sugar moieties, and/or modified phosphate ester moieties. As used herein, the term "modified base" refers generally to any modification of a base or the chemical linkage of a base in a nucleic acid that differs in structure from that found in a naturally occurring nucleic acid. Such modifications can include changes in the chemical structures of bases or in the chemical linkage of a base in a nucleic acid, or in the backbone structure of the nucleic acid. (See, e.g., Latorra, D. et al., *Hum Mut* 2003, 2:79-85. Nakiandwe, J. et al., *plant Method* 2007, 3:2.)

Oligonucleotides described herein, especially those functioning as a probe and/or primer, can include one or more modified bases in addition to the naturally occurring bases adenine, cytosine, guanine, thymine and uracil (represented as A, C, G, T, and U, respectively). In some embodiments, the modified base(s) may increase the difference in the $T_m$ between matched and mismatched target sequences and/or decrease mismatch priming efficiency, thereby improving not only assay specificity, but also selectivity. Modified bases can be those that differ from the naturally-occurring bases by addition or deletion of one or more functional groups, differences in the heterocyclic ring structure (i.e., substitution of carbon for a heteroatom, or vice versa), and/or attachment of one or more linker arm structures to the base. Such modified base(s) may include, for example, 8-Aza-7-deaza-dA (ppA), 8-Aza-7-deaza-dG (ppG), locked nucleic acid (LNA) or 2'-O,4'-C-ethylene nucleic acid (ENA) bases. Other examples of modified bases include, but are not limited to, the general class of base analogues 7-deazapurines and their derivatives and pyrazolopyrimidines and their derivatives (e.g., as described in PCT WO 90/14353, herein incorporated by reference). These base analogues, when present in an oligonucleotide, can strengthen hybridization and improve mismatch discrimination. All tautomeric forms of naturally occurring bases, modified bases and base analogues can be included. Modified internucleotide linkages can also be present in the oligonucleotides described herein. Such modified linkages include, but are not limited to, peptide, phosphate, phosphodiester, phosphotriester, alkylphosphate, alkanephosphonate, thiophosphate, phosphorothioate, phosphorodithioate, methylphosphonate, phosphoramidate, substituted phosphoramidate and the like. Several further modifications of bases, sugars and/or internucleotide linkages, that are compatible with their use in oligonucleotides serving as probes and/or primers, will be apparent to those of skill in the art.

In some embodiments, a modified base is located at (a) the 3'-end, (b) the 5'-end, (c) at an internal position, or at any combination of (a), (b) and/or (c) in the oligonucleotide probe and/or primer.

In some embodiments the primer and/or probes as disclosed herein are designed as oligomers that are single-stranded. In some embodiments, the primers and/or probes are linear. In other embodiments, the primers and/or probes are double-stranded or include a double-stranded segment. For example, in some embodiments, the primers and/or probes may form a stem-loop structure, including a loop portion and a stem portion. In some embodiments, the primers and/or probes are short oligonucleotides, having a length of 100 nucleotides or less, more preferably 50 nucleotides or less, still more preferably 30 nucleotides or less and most preferably 20 nucleotides or less with a lower limit being approximately 3-5 nucleotides. In some embodiments, the primer and/or probes as disclosed herein are between 5 to 35 nucleotides long. In some embodiments, the primers and/or probes as disclosed herein are 10, 15, 20, 25, 30, or any length in between 10 to 30 nucleotides long. In some embodiments, the primer and/or probes as disclosed herein are between 5 to 35 nucleotides long. In some embodiments, the primers and/or probes as disclosed herein are 10, 15, 20, 25, 30, or any length in between 10 to 30 nucleotides long.

In some embodiments, the $T_m$ of the primers and/or probes disclosed herein range from about 50 °C to about 75 °C In some embodiments, the primers and/or probes are between about 55 °C to about 65 °C In some embodiments, the primers and/or probes are between about 60 °C to 70 °C. For example, the $T_m$ of the primers and/or probes disclosed herein may be 56 °C, 57 °C, 58 °C, 60 °C, 61 °C, 62 °C, 63 °C, 64 °C, 65 °C, 66 °C, etc. In some other embodiments, the $T_m$ of the primers and/or probes disclosed herein may be 56 °C to 63 °C, 58 °C to 68 °C 61 °C to 69 °C, 62 °C to 68 °C, 63 °C to 67 °C, 64 °C to 66 °C, or any range in between. In some embodiments, the $T_m$ of the primers is lower than the $T_m$ of the probes as used herein. In some embodiments the $T_m$ of the primers as used herein is from about 55 °C to about 65 °C and the $T_m$ of the probes as used herein is from about 60 °C to about 70 °C In some embodiments, the $T_m$ range of the primers used in a PCR is about 5 °C to 15 °C lower than the $T_m$ range of the probes used in the same PCR. In yet other embodiments, the $T_m$ of the primers and/or probes is about 3 °C to 6 °C higher than the anneal/extend temperature in the PCR cycling conditions employed during amplification.

In some embodiments, the probes include a non-extendable blocker moiety at their 3'-ends. In some embodiments, the probes can further include other moieties (including, but not limited to additional non-extendable blocker moieties that are the same or different, quencher moieties, fluorescent moieties, etc) at their 3'-end, 5'-end, and/or any internal position in between. In some embodiments, the non-extendable blocker moiety can be, but is not limited to, an amine ($NH_2$), biotin, PEG, $DPI_3$, or $PO_4$. In some preferred embodiments, the blocker moiety is a minor groove binder (MGB) moiety.

As used herein, the terms "MGB," "MGB group," "MGB compound," or "MBG moiety" refers to a molecule that binds within the minor groove of double stranded DNA. When conjugated to the 3' end of an oligonucleotide, an MGB group can function as a non-extendable blocker moiety. MGB moieties can also increase the specificity of an oligonucleotide probe and/or primer. In some embodiments, the $T_m$ of an oligonucleotide, such the probes as disclosed herein, may be reduced by the inclusion of an MGB moiety. For example, the $T_m$ of a probe as disclosed herein which comprises an MGB moiety may range from about 45 °C to 55 °C. In some, embodiments, the $T_m$ of a probe is reduced by about 10 °C to 20 °C with the inclusion of an MGB moiety in the same probe.

Although a general chemical formula for all known MGB compounds cannot be provided because such compounds have widely varying chemical structures, compounds which are capable of binding in the minor groove of DNA, generally speaking, have a crescent shape three dimensional structure. Most MGB moieties have a strong preference for A-T (adenine and thymine) rich regions of the B form of double stranded DNA. Nevertheless, MGB compounds which would show preference to C-G (cytosine and guanine) rich regions are also theoretically possible. Therefore, oligonucleotides including a radical or moiety derived from minor groove binder molecules having preference for C-G regions are also within the scope of the present invention.

Some MGBs are capable of binding within the minor groove of double stranded DNA with an association constant of $10^3$ $M^{-1}$ or greater. This type of binding can be detected by well-established spectrophotometric methods such as ultraviolet (UV) and nuclear magnetic resonance (NMR) spectroscopy and also by gel electrophoresis. Shifts in UV spectra upon binding of a minor groove binder molecule and NMR spectroscopy utilizing the "Nuclear Overhauser" (NOESY) effect are particularly well known and useful techniques for this purpose. Gel electrophoresis detects binding of an MGB to double stranded DNA or fragment thereof, because upon such binding the mobility of the double stranded DNA changes.

A variety of suitable minor groove binders have been described in the literature. See, for example, Kutyavin, et al. U.S. Pat. No. 5,801,155; Wemmer, D. E., and Dervan P. B., Current Opinion in Structural Biology, 7:355-361 (1997); Walker, W. L., Kopka, J. L. and Goodsell, D. S., Biopolymers, 44:323-334 (1997); Zimmer, C.& Wahnert, U. Prog. Biophys. Molec. Bio. 47:31-112 (1986) and Reddy, B. S. P., Dondhi, S. M., and Lown, J. W., Pharmacol. Therap., 84:1-111 (1999) (the disclosures of which are herein incorporated by reference in their entireties). A preferred MGB in accordance with the present disclosure is $DPI_3$. Synthesis methods and/or sources for such MGBs, some of which may be commercially available, are also well-known in the art. (See, e.g., U.S. Pat. Nos. 5,801,155; 6,492,346; 6,084,102; and 6,727,356, the disclosures of which are incorporated herein by reference in their entireties).

As used herein, the term "MGB blocker probe," "MBG blocker," or "MGB probe" is an oligonucleotide sequence and/or probe further attached to a minor groove binder moiety at its 3' and/or 5' end. Oligonucleotides conjugated to MGB moieties form extremely stable duplexes with single-stranded and double-stranded DNA targets, thus allowing shorter probes to be used for hybridization based assays. In comparison to unmodified DNA, MGB probes have higher melting temperatures (Tm) and increased specificity, especially when a mismatch is near the MGB region of the hybridized duplex. (See, e.g., Kutyavin, I. V., et al., Nucleic Acids Research, 2000, Vol. 28, No. 2: 655-661).

In some embodiments, the nucleotide units, which are incorporated into the oligonucleotides acting as a probe, can include a minor groove binder (MGB) moiety. In some embodiments, such MGB moieties can have a cross-linking function (an alkylating agent) covalently bound to one or more of the bases, through a linking arm. Similarly, modified sugars or sugar analogues can be present in one or more of the nucleotide subunits of an oligonucleotide disclosed herein. Sugar modifications include, but are not limited to, attachment of substituents to the 2', 3' and/or 4' carbon atom of the sugar, different epimeric forms of the sugar, differences in the alpha- or beta-configuration of the glycosidic bond, and other anomeric changes. Sugar moieties include, but are not limited to, pentose, deoxypentose, hexose, deoxyhexose, ribose, deoxyribose, glucose, arabinose, pentofuranose, xylose, lyxose, and cyclopentyl. In some embodiments, the sugar or glycoside portion of some embodiments of oligonucleotides acting as a probe, e.g., one including an MGB moiety, can include deoxyribose, ribose, 2-fiuororibose, 2-O alkyl or alkenylribose where the alkyl group may have 1 to 6 carbons and the alkenyl group 2 to 6 carbons. In some embodiments, the naturally occurring nucleotides and in the herein described modifications and analogs the deoxyribose or ribose moiety can form a furanose ring, and the purine bases can be attached to the sugar moiety via the 9-position, the pyrimidines via the I-position, and the pyrazolopyrimidines via the I-position. And in some embodiments, especially in the oligonucleotides acting as a probe (e.g., the third and/or sixth oligonucleotide, target site-specific probe), the nucleotide units of the oligonucleotides can be interconnected by a "phosphate" backbone, as is well known in the art and/or can include, in addition to the "natural" phosphodiester linkages, phosphorothiotes and methylphosphonates. Other types of modified oligonucleotides or modified bases are also contemplated herein as would be understood by those of ordinary skill in the art.

When two different, non-overlapping (or partially overlapping) oligonucleotides anneal to different regions of the same linear complementary nucleic acid sequence, and the 3' end of one oligonucleotide points toward the 5' end of the other, the former may be called the "upstream" oligonucleotide and the latter the "downstream" oligonucleotide.

As used herein, the terms "target sequence," "target nucleic acid," "target nucleic acid sequence," and "nucleic acid of interest" are used interchangeably and refer to a desired region of a nucleic acid molecule which is to be either amplified, detected or both.

"Primer" as used herein can refer to more than one primer and refers to an oligonucleotide, whether occurring naturally or produced synthetically, which is capable of acting as a point of initiation of synthesis when placed under conditions in which synthesis of a primer extension product which is complementary to a nucleic acid strand is induced i.e., in the presence of nucleotides and an agent for polymerization such as DNA polymerase, at a suitable temperature for a sufficient amount of time and in the presence of a buffering agent. Such conditions can include, for example, the presence of at least four different deoxyribonucleoside triphosphates (such as G, C, A, and T) and a polymerization-inducing agent such as DNA polymerase or reverse transcriptase, in a suitable buffer ("buffer" includes substituents which are cofactors, or which affect pH, ionic strength, etc.), and at a suitable temperature. In some embodiments, the primer may be single-stranded for maximum efficiency in amplification. The primers herein are selected to be substantially complementary to the different strands of each specific sequence to be amplified. This means that the primers must be sufficiently complementary to hybridize with their respective strands. A non-complementary nucleotide fragment may be attached to the 5'-end of the primer (such as having a "tail"), with the remainder of the primer sequence being complementary, or partially complementary, to the target region of the target nucleic acid. Commonly, the primers are complementary, except when non-complementary nucleotides may be present at a predetermined sequence or sequence range location, such as a primer terminus as described. In some embodiments, such non-complementary "tails" can comprise a universal sequence, for example, a sequence that is common to one or more oligonucleotides. In certain embodiments, the non-complementary fragment or tail may comprise a polynucleotide sequence such as a poly (T) sequence to hybridize, for example, to a polyadenylated oligonucleotide or sequence.

The complement of a nucleic acid sequence as used herein refers to an oligonucleotide which, when aligned with the nucleic acid sequence such that the 5' end of one sequence is paired with the 3' end of the other, is in "antiparallel association." Complementarity need not be perfect; stable duplexes may contain mismatched base pairs or unmatched bases.

Stability of a nucleic acid duplex is measured by the melting temperature, or "$T_m$." The $T_m$ of a particular nucleic acid duplex under specified conditions is the temperature at which half of the base pairs have disassociated.

As used herein, the term "$T_m$" or "melting temperature" of an oligonucleotide refers to the temperature (in degrees Celsius) at which 50% of the molecules in a population of a single-stranded oligonucleotide are hybridized to their complementary sequence and 50% of the molecules in the population are not-hybridized to said complementary sequence. The $T_m$ of a primer or probe can be determined empirically by means of a melting curve. In some cases it can also be calculated using formulas well known in the art (See, e.g., Maniatis, T., et al., Molecular cloning: a laboratory manual/Cold Spring Harbor Laboratory, Cold Spring Harbor, N.Y.: 1982).

As used herein, the term "sensitivity" refers to the minimum amount (number of copies or mass) of a template that can be detected by a given assay. As used herein, the term "specificity" refers to the ability of an assay to distinguish between amplification from a matched template versus a mismatched template. Frequently, specificity is expressed as $\Delta C_t = Ct_{mismatch} - Ct_{match}$. In some embodiments, improvement in specificity or "specificity improvement" or "fold difference" is expressed as $2^{(\square Ct\_condition1-(\square Ct\_condition2)}$.

As used herein, the term "Ct" or "Ct value" refers to threshold cycle and signifies the cycle of a PCR amplification assay in which signal from a reporter that is indicative of amplicon generation (e.g., fluorescence) first becomes detectable above a background level. In some embodiments, the threshold cycle or "Ct" is the cycle number at which PCR amplification becomes exponential.

The term "complementary to" is used herein in relation to a nucleotide that can base pair with another specific nucleotide. Thus, for example, adenosine is complementary to uridine or thymidine and guanosine is complementary to cytidine.

The term "identical" means that two nucleic acid sequences have the same sequence or a complementary sequence.

"Amplification" as used herein denotes the use of any amplification procedures to increase the concentration of a particular nucleic acid sequence within a mixture of nucleic acid sequences.

"Polymerization", which may also be referred to as "nucleic acid synthesis", refers to the process of extending the nucleic acid sequence of a primer through the use of a polymerase and a template nucleic acid.

The term "label" as used herein refers to any atom or molecule which can be used to provide or aid to provide a detectable and/or quantifiable signal, and can be attached to a biomolecule, such as a nucleic acid or protein. Labels may provide signals detectable by fluorescence, radioactivity, colorimetry, gravimetry, magnetism, enzymatic activity or the like. Labels that provide signals detectable by fluorescence are also referred to herein as "fluorophores" or "fluors" or "fluorescent dyes." As used herein, the term "dye" refers to a compound that absorbs light or radiation and may or may not emit light. A "fluorescent dye" refers to a molecule that emits the absorbed light to produce an observable detectable signal (e.g., "acceptor dyes", "donor dyes", "reporter dyes", "big dyes", "energy transfer dyes", "on-axis dyes", "off-axis dyes", and the like). A "quencher dye" refers to a molecule that is designed to absorb emission from a corresponding fluorescent dye.

In some embodiments, the term "fluorophore," "fluor," or "fluorescent dye" can be applied to a fluorescent dye molecule that is used in a fluorescent energy transfer pairing (e.g., with a donor dye or acceptor dye). A "fluorescent energy transfer conjugate," as used herein typically includes two or more fluorophores (e.g., a donor dye and acceptor dye) that are covalently attached through a linker and are capable of undergoing a fluorescence energy transfer process under the appropriate conditions.

The term "quencher," "quencher compound," "quencher group," "quencher moiety" or "quencher dye" is used in a broad sense herein and refers to a molecule or moiety capable of suppressing the signal from a reporter molecule, such as a fluorescent dye.

The term "overlapping" as used herein (when used in reference to oligonucleotides) refers to the positioning of two oligonucleotides on its complementary strand of the template nucleic acid. The two oligonucleotides may be overlapping any number of nucleotides of at least 1, for example by 1 to about 40 nucleotides, e.g., about 1 to 10 nucleotides or 1, 2, 3, 4, 5, 6, 7, 8, 9, or 10 nucleotides. In other words, the two template regions hybridized by oligonucleotides may have a common region which is complementary to both the oligonucleotides.

The terms "thermally cycling," "thermal cycling," "thermal cycles," or "thermal cycle" refer to repeated cycles of temperature changes from a total denaturing temperature, to an annealing (or hybridizing) temperature, to an extension temperature, and back to the total denaturing temperature. The terms also refer to repeated cycles of a denaturing temperature and an extension temperature, where the annealing and extension temperatures are combined into one temperature. A total denaturing temperature unwinds all double stranded fragments into single strands. An annealing temperature allows a primer to hybridize or anneal to the complementary sequence of a separated strand of a nucleic acid template. The extension temperature allows the synthesis of a nascent DNA strand of the amplicon. The term "single round of thermal cycling" means one round of denaturing temperature, annealing temperature and extension temperature. In a single round of thermal cycling, for example, there may be internal repeating cycles of an annealing temperature and an extension temperature. For example, a single round of thermal cycling may include a denaturing temperature, an annealing temperature (i.e., first annealing temperature), an extension temperature (i.e., first extension temperature), another annealing temperature (i.e., second annealing temperature), and another extension temperature (i.e., second extension temperature).

The terms "reaction mixture," "amplification mixture," or "PCR mixture" as used herein refer to a mixture of components necessary to amplify at least one amplicon from nucleic acid templates. The mixture may comprise nucleotides (dNTPs), a thermostable polymerase, primers, and a plurality of nucleic acid templates (e.g., a target nucleic acid). The mixture may further comprise a Tris buffer, a monovalent salt, and/or Mg'. The working concentration range of each component is well known in the art and can be further optimized or formulated to include other reagents and/or components as needed by an ordinary skilled artisan.

The terms "amplified product" or "amplicon" refer to a fragment of a nucleic acid amplified by a polymerase using a pair of primers in an amplification method such as PCR or reverse transcriptase (RT)-PCR.

As defined herein, "5'→3' nuclease activity" or "5' to 3' nuclease activity" or "5' nuclease activity" refers to that activity of a cleavage reaction including either a 5' to 3' nuclease activity traditionally associated with some DNA polymerases, whereby nucleotides are removed from the 5' end of an oligonucleotide in a sequential manner, (i.e., *E. coli* DNA polymerase I has this activity whereas the Klenow fragment does not), or a 5' to 3' endonuclease activity wherein cleavage occurs to more than one phosphodiester bond (nucleotide) from the −5' end, or both, or a group of homologous 5'-3' exonucleases (also known as 5' nucleases) which trim the bifurcated molecules, the branched DNA structures produced during DNA replication, recombination and repair. In some embodiments, such 5' nuclease can be used for cleavage of the labeled oligonucleotide probe annealed to target nucleic acid sequence.

As used herein, the term "alkyl" refers to a straight or branched, saturated, aliphatic radical having the number of carbon atoms indicated. For example, $C_1$-$C_6$ alkyl includes, but is not limited to, methyl, ethyl, propyl, butyl, pentyl, hexyl, iso-propyl, iso-butyl, sec-butyl, tert-butyl, and the like. As used herein, the term "alkylene" refers to a straight or branched, saturated, aliphatic diradical having the number of carbon atoms indicated. For example, $C_1$-$C_6$ alkyl includes, but is not limited to, methylene, ethylene, propylene, butylene, pentylene, hexylene, and the like. It will be appreciated that alkyl and alkylene groups can be optionally substituted with one or more substituents by replacement of one or more hydrogen atoms on the alkyl and alkylene group.

As used herein, the term "alkenyl" refers to either a straight chain or branched hydrocarbon radical having the number of carbon atoms indicated, and having at least one double bond. For example, $C_2$-$C_6$ alkenyl, includes, but is not limited to, vinyl, propenyl, isopropenyl, butenyl, isobutenyl, butadienyl, pentenyl, hexadienyl, and the like. As used herein, the term "alkenylene" refers to either a straight chain or branched hydrocarbon diradical having the number of carbon atoms indicated, having at least one double bond. For example, $C_2$-$C_6$ alkenyl, includes, but is not limited to, vinyl, propenyl, isopropenyl, butenyl, isobutenyl, butadienyl, pentenyl, hexadienyl, and the like. It will be appreciated that alkenyl and alkenylene groups can be optionally substituted with one or more substituents by replacement of one or more hydrogen atoms on the alkenyl and alkenylene group.

As used herein, the term "alkoxy" refers to alkyl radical with the inclusion of at least one oxygen atom within the alkyl chain or at the terminus of the alkyl chain, for example, methoxy, ethoxy, and the like. "Halo-substituted-alkoxy" refers to an alkoxy where at least one hydrogen atom is substituted with a halogen atom. For example, halo-substituted-alkoxy includes trifluoromethoxy, and the like. As used herein, the term "oxy-alkylene" refers to alkyl diradical with the inclusion of an oxygen atom, for example, $—OCH_2$, $—OCH_2CH_2—$, $—OC_1$-$C_{10}$ alkylene-, $—C_1$-$C_6$ alkylene-O—$C_1$-$C_6$ alkylene-, poly(alkylene glycol), poly(ethylene glycol) (or PEG), and the like. "Halo-substituted-oxy-alkylene" refers to an oxy-alkylene where at least one hydrogen atom is substituted with a halogen atom. It will be appreciated that alkoxy and oxy-alkylene groups can be optionally substituted with one or more substituents by replacement of one or more hydrogen atoms on the alkoxy and oxy-alkylene group.

As used herein, the term "alkynyl" refers to either a straight chain or branched hydrocarbon radical having the number of carbon atoms indicated, and having at least one triple bond. For example, $C_2$-$C_6$ alkynyl, includes, but is not limited to, acetylenyl, propynyl, butynyl, and the like. As used herein, the term "alkynylene" refers to either a straight chain or branched hydrocarbon diradical having the number of carbon atoms indicated, and having at least one triple bond. Examples of alkynylene groups include, but are not limited to, $—C{\equiv}CCH_2CH_2—$, $—CH_2C{\equiv}CCH_2—$, and the like. It will be appreciated that alkynyl and alkynylene groups can be optionally substituted with one or more substituents by replacement of one or more hydrogen atoms on the alkynyl and alkynylene group.

As used herein, the term "aryl" refers to a cyclic hydrocarbon radical having the number of carbon atoms indicated, and having a fully conjugated π-electron system. For example, $C_6$-$C_{10}$ aryl, includes, but is not limited to, phenyl, naphthyl, and the like. As used herein, the term "arylene" refers to a cyclic hydrocarbon diradical having the number of carbon atoms indicated, and having a fully conjugated π-electron system. For example, $C_6$-$C_{10}$ arylene, includes, but is not limited to, phenylene, naphthylene, and the like. It will be appreciated that aryl and arylene groups can be optionally substituted with one or more substituents by replacement of one or more hydrogen atoms on the aryl and arylene group.

As used herein, the term "phosphodiester portion" refers to a linkage comprising at least one —O—P(O)(OH)—O— functional group. It will be appreciated that a phosphodiester portion can include other groups, such as alkyl, alkylene, alkenylene, oxy-alkylene, such as PEG, in addition to one or more —O—P(O)(OH)—O— functional groups. It will be appreciated that the other groups, such as alkyl, alkylene, alkenylene, oxy-alkylene, such as PEG, can be optionally substituted with one or more substituents by replacement of one or more hydrogen atoms on the group.

As used here, the term "sulfo" refers to a sulfonic acid, or salt of sulfonic acid (sulfonate).

As used here, the term "carboxy" refers to a carboxylic acid or salt of carboxylic acid.

As used here, the term "phosphate," refers to an ester of phosphoric acid, and includes salts of phosphate.

As used here, the term "phosphonate," refers to a phosphonic acid and includes salts of phosphonate.

As used herein, unless otherwise specified, the alkyl portions of substituents such as alkyl, alkoxy, arylalkyl, alkylamino, dialkylamino, trialkylammonium, or perfluoroalkyl are optionally saturated, unsaturated, linear or branched, and all alkyl, alkoxy, alkylamino, and dialkylamino substituents may be optionally substituted by carboxy, sulfo, amino, or hydroxy.

As used herein, "substituted" refers to a molecule wherein one or more hydrogen atoms are replaced with one or more non-hydrogen atoms, functional groups or moieties. Exemplary substituents include but are not limited to halogen, e.g., fluorine and chlorine, $C_1$-$C_8$ alkyl, $C_6$-$C_{14}$ aryl, heterocycle, sulfate, sulfonate, sulfone, amino, ammonium, amido, nitrile, nitro, lower alkoxy, phenoxy, aromatic, phenyl, polycyclic aromatic, heterocycle, water-solubilizing group, linkage, and linking moiety. In some embodiments, substituents include, but are not limited to, —X, —R, —OH, —OR, —SR, —SH, $—NH_2$, —NHR, $—NR_2$, $—NR_3^+$, $—N{=}NR_2$, $—CX_3$, —CN, —OCN, —SCN, —NCO, —NCS, —NO, $—NO_2$, $—N_2^+$, $—N_3$, —NHC(O)R, —C(O)R, $—C(O)NR_2$, $—S(O)_2O—$, $—S(O)_2R$, $—OS(O)_2OR$, $—S(O)_2NR$, —S(O)R, $—OP(O)(OR)_2$, $—P(O)(OR)_2$, $—P(O)(O)_2$, $—P(O)(OH)_2$, —C(O)R, —C(O)X, —C(S)R, —C(O)OR, —C(S)OR, —C(O)SR, —C(S)SR, $—C(O)NR_2$, $—C(S)NR_2$, $—C(NR)NR_2$, where each X is independently a halogen and each R is independently —H, $C_1$-$C_6$ alkyl, $C_6$-$C_{14}$ aryl, heterocycle, or linking group.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

The compounds disclosed herein may exist in unsolvated forms as well as solvated forms, including hydrated forms. In some embodiments, the compounds disclosed herein are soluble in an aqueous medium (e.g., water or a buffer). For example, the compounds can include substituents (e.g., water-solubilizing groups) that render the compound soluble in the aqueous medium. Compounds that are soluble in an aqueous medium are referred to herein as "water-soluble" compounds. Such water-soluble compounds are particularly useful in biological assays. These compounds may exist in multiple crystalline or amorphous forms. In general, all physical forms are equivalent for the uses described herein and are intended to be within the scope of the present disclosure. The compounds disclosed herein may possess asymmetric carbon atoms (i.e., chiral centers) or double bonds; the racemates, diastereomers, geometric isomers and individual isomers of the compounds described herein are within the scope of the present disclosure. The compounds described herein may be prepared as a single isomer or as a mixture of isomers.

Where substituent groups are specified by their conventional chemical formulae and are written from left to right, they equally encompass the chemically identical substituents, which would result from writing the structure from right to left, e.g., $—CH_2O—$ will be understood to also recite $—OCH_2—$.

It will be understood that the chemical structures that are used to define the compounds disclosed herein are each representations of one of the possible resonance structures by which each given structure can be represented. Further, it will be understood that by definition, resonance structures are merely a graphical representation used by those of skill in the art to represent electron delocalization, and that the present disclosure is not limited in any way by showing one particular resonance structure for any given structure.

Where a disclosed compound includes a conjugated ring system, resonance stabilization may permit a formal electronic charge to be distributed over the entire molecule. While a particular charge may be depicted as localized on a particular ring system, or a particular heteroatom, it is commonly understood that a comparable resonance structure can be drawn in which the charge may be formally localized on an alternative portion of the compound.

As used herein, the term "protecting group" or "PG" refers to any group as commonly known to one of ordinary skill in the art that can be introduced into a molecule by chemical modification of a reactive functional group, such as an amine or hydroxyl, to obtain chemoselectivity in a subsequent chemical reaction. It will be appreciated that such protecting groups can be subsequently removed from the functional group at a later point in a synthesis to provide further opportunity for reaction at such functional groups or, in the case of a final product, to unmask such functional group. Protecting groups have been described in, for example, Wuts, P. G. M., Greene, T. W., Greene, T. W., & John Wiley & Sons. (2006). *Greene's protective groups in organic synthesis*. Hoboken, N.J: Wiley-Interscience. One of skill in the art will readily appreciate the chemical process conditions under which such protecting groups can be installed on a functional group. In the various embodiments described herein, it will be appreciated by a person having ordinary skill in the art that the choice of protecting groups used in the preparation of the energy transfer dye conjugates described herein can be chosen from various alternatives known in the art. It will further be appreciated that a suitable protecting group scheme can be chosen such that the protecting groups used provide an orthogonal protection strategy. As used herein, "orthogonal protection" refers to a protecting group strategy that allows for the protection and deprotection of one or more reactive functional group with a dedicated set of reaction conditions without affecting other protected reactive functional groups or reactive functional groups.

As used herein, "PAG" refers to a poly(alkylene glycol) moiety, where alkylene can be a $C_2$-$C_6$ linear or branched alkylene chain. It will be appreciated that a poly(alkylene glycol) can be represented by $—(C_2$-$C_6$ alkylene-O—$C_2$-$C_6$ alkylene$)_n$-, where n is an integer from 1 to about 20, or the formula $—(C_2$-$C_6$ alkylene-O—$C_2$-$C_6$ alkylene$)_n$-, where n is an integer from 1 to about 100. Suitable PAG moieties taken together with the O-P linker bonds include but are not limited to penta(ethylene glycol) (a.k.a. PEG), penta(propylene glycol) (a.k.a. PPG), penta(1,2-butylene glycol), and the like.

As used herein, "water-solubilizing group" refers to a moiety that increases the solubility of the compounds in aqueous solution. Exemplary water-solubilizing groups include but are not limited to hydrophilic group, as described herein, polyether, polyhydroxyl, boronate, polyethylene glycol, repeating units of ethylene oxide ($—(CH_2CH_2O)—$), and the like.

As used herein, "hydrophilic group" refers to a substituent that increases the solubility of the compounds in aqueous solution. Exemplary hydrophilic groups include but are not limited to —OH, $—O^-Z^+$, —SH, $—S^-Z^+$, $—NH_2$, $—NR_3^+Z^-$, $—N{=}NR_2^+Z^-$, —CN, —OCN, —SCN, —NCO, —NCS, —NO, $—NO_2$, $—N_2^+$, $—N_3$, —NHC(O)R, —C(O)R, $—C(O)NR_2$, $—S(O)_2O—Z^+$, $—S(O)_2R$, $—OS(O)_2OR$, $—S(O)_2NR$, —S(O)R, $—OP(O)(OR)_2$, $—P(O)(OR)_2$, $—P(O)(O^-)_2Z^+$, $—P(O)(OH)_2$, —C(O)R, —C(S)R, —C(O)OH, —C(O)OR, $—CO_2^-Z^+$, —C(S)OR, $—C(S)O—Z^+$, —C(O)SR, $—C(O)S^-Z^+$, —C(S)SR, $—C(S)S^-Z^+$, $—C(O)NR_2$, $—C(S)NR_2$, $—C(NR)NR_2$, and the like, where R is H, $C_1$-$C_6$ alkyl, $C_1$-$C_6$ alkyl$C_6$-$C_{10}$ aryl, or $C_6$-$C_{10}$ aryl, and optionally substituted.

As used herein, "reactive functional group" or "reactive group" means a moiety on the compound that is capable of chemically reacting with a functional group on a different compound to form a covalent linkage, i.e., is covalently reactive under suitable reaction conditions, and generally represents a point of attachment for another substance. Typically the reactive group is an electrophile or nucleophile that can form a covalent linkage through exposure to the corresponding functional group that is a nucleophile or electrophile, respectively. In some embodiments, the "reactive functional group" or "reactive group" can be a hydrophilic group or a hydrophilic group that has been activated to be a "reactive functional group" or "reactive group." In some embodiments, a "reactive functional group" or "reactive group" can be a hydrophilic group such as a C(O)OR group. In some embodiments, a hydrophilic group, such as a —C(O)OH, can be activated by a variety of methods known in the art to become a reactive functional group, such as by reacting the —C(O)OH group with N,N,N,N-tetramethyl-O—(N-succinimidyl)uronium tetrafluoroborate (TSTU) to provide the NHS ester moiety —C(O)O—NHS (a.k.a. the active ester).

Alternatively, the reactive group is a photoactivatable group that becomes chemically reactive only after illumination with light of an appropriate wavelength.

Exemplary reactive groups include, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, alkynes (including strained alkynes, such as MO and DBCO), azo compounds, azoxy compounds, and nitroso compounds. Reactive functional groups also include those used to prepare bioconjugates, e.g., N-hydroxysuccinimide esters (or succinimidyl esters (SE)), maleimides, sulfodichlorophenyl (SDP) esters, sulfotetrafluorophenyl (STP) esters, tetrafluorophenyl (TFP) esters, pentafluorophenyl (PFP) esters, nitrilotriacetic acids (NTA), aminodextrans, cyclooctyne-amines and the like. Methods to prepare each of these functional groups are well known in the art and their application to or modification for a particular purpose is within the ability of one of skill in the art (see, for example, Sandler and Karo, eds., Organic Functional Group Preparations, Academic Press, San Diego, 1989). Exemplary reactive groups or reactive ligands include NHS esters, phosphoramidites, and other moieties listed in Table 1 below. Nucleotides, nucleosides, and saccharides (e.g., ribosyls and deoxyribosyls) are also considered reactive ligands due to at least their ability to form phosphodiester bonds through enzymatic catalysis. For the avoidance of doubt, saturated alkyl groups are not considered reactive ligands.

As used herein, the term "solid support," as used herein, refers to a matrix or medium that is substantially insoluble in liquid phases and capable of binding a molecule or particle of interest. Solid supports suitable for use herein include semi-solid supports and are not limited to a specific type of support. Useful solid supports include solid and semi-solid matrixes, such as aerogels and hydrogels, resins, beads, biochips (including thin film coated biochips), microfluidic chip, a silicon chip, multi-well plate (also referred to as a microtitre plate or microplate), array (such as a microarray), membranes, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as SEPHAROSE (GE Healthcare), poly(acrylate), polystyrene, poly(acrylamide), polyol, agarose, agar, cellulose, dextran, starch, FICOLL (GE Healthcare), heparin, glycogen, amylopectin, mannan, inulin, nitrocellulose, diazocellulose, polyvinylchloride, polypropylene, polyethylene (including poly(ethylene glycol)), nylon, latex bead, magnetic bead, paramagnetic bead, superparamagnetic bead, starch and the like.

A hydrolysis probe assay can exploit the 5' nuclease activity of certain DNA polymerases, such as a Taq DNA polymerase, to cleave a labeled probe during PCR. One specific example of a hydrolysis probe is a TaqMan probe. In some embodiments, the hydrolysis probe contains a reporter dye at the 5' end of the probe and a quencher dye at the 3' end of the probe. During the PCR reaction, cleavage of the probe separates the reporter dye and the quencher dye, resulting in increased fluorescence of the reporter. Accumulation of PCR products is detected directly by monitoring the increase in fluorescence of the reporter dye. When the probe is intact, the close proximity of the reporter dye to the quencher dye results in suppression of the reporter fluorescence primarily by Forster-type energy transfer (Förster, 1948; Lakowicz, 1983). During PCR, if the target of interest is present, the probe specifically anneals between the forward and reverse primer sites. The 5' to 3' nucleolytic activity of the Taq DNA polymerase cleaves the probe between the reporter and the quencher only if the probe hybridizes to the target. The probe fragments are then displaced from the target, and polymerization of the strand continues. In some embodiments, the 3' end of the probe is blocked to prevent extension of the probe during PCR. In general, hybridization and cleavage process occurs in sequential cycles and does not interfere with the exponential accumulation of the product.

Without being bound to these parameters, the general guideline for designing TaqMan probes and primers is as follows: design the primers as close as possible to, but without overlapping the probe; the $T_m$ of the probe should be about 10 °C higher than the $T_m$ of the primers; select the strand that gives the probe more C than G bases; the five nucleotides at the 3' end of the primer should have no more than two G and/or C bases, and the reaction should be run on the two-step thermal profile with the annealing and extension under the same temperature of 60 °C The following description of the fluorescent dyes, i.e., fluorophores, and quencher compounds provides general information regarding construction of the energy transfer conjugates and probes described herein. As described herein, the fluorescent dyes, e.g. donor dye and acceptor dye, can be covalently bound to one another through a linker to form an energy transfer dye conjugate (e.g. a reporter moiety). In some embodiments, an energy transfer dye or an energy transfer dye conjugate and a quencher compound can be covalently bound to one another through an analyte. In some embodiments the analyte is a probe, such as an oligonucleotide probe. The disclosed FRET conjugates and probes that include unique fluorophore/quencher combinations disclosed herein allow for increased multiplex reactions and detection through the additional spectral channels already available on some commercial instruments. Further, the new fluorophores, FRET conjugates and fluorophore/quencher and probe combinations provide unique optical properties that can facilitate even higher order multiplexing once instruments with additional channels and other related hardware and software improvements become available.

Energy Transfer Dyes

In some embodiments, the energy transfer dye conjugate described herein includes two or more fluorescent dyes. The two or more fluorescent dyes include a donor dye and an acceptor dye. Any fluorescent dye having the appropriate optical and physical properties can be utilized in construction of the dye conjugates disclosed herein. In some embodiments, the emission spectrum of the donor dye overlaps with the absorption spectrum of the acceptor dye. In some embodiments, the acceptor dye can have an emission maximum that is a longer wavelength than the emission maximum of the donor dye. It will be appreciated that the identity of either the donor dye or the acceptor dye is not particularly limited in the energy transfer dye conjugates described herein, provided that the donor dye and the acceptor dye pair and linker are selected such that the donor dye can transfer energy to the reporter dye.

Suitable fluorescent dyes, i.e. the donor dye and the acceptor dye, in an energy transfer dye conjugate as described herein can independently be a xanthene dye (e.g., a fluorescein or rhodamine dye), a silicon-rhodamine dye, a cyanine dye, a boron-dipyrrornethene (referred to herein as "BODIPY") dye, a pyrene dye, or a coumarin dye. In some embodiments, the cyanine dye included in the ET conjugate is an azaindole cyanine compound (i.e., a cyanine compound that includes at least one azaindole group). In some embodiments, the cyanine dye included in the ET conjugate is an azaindole (i.e., pyrrolopyridine) cyanine compound (i.e., a cyanine compound that includes at least one azaindole group). As used herein, "azaindole" and "pyrrolopyridine" are used interchangeably to refer to a heterocyclic aromatic organic compound having a bicyclic structure that includes a pyrrole ring fused to a pyridine ring. As used herein, "azaindole cyanine" and "pyrrolopyridine cyanine" are used interchangeably to refer to a cyanine compound that includes at least one azaindole group. Certain azaindole cyanine compounds can include one or two optionally substituted azaindole groups. For compounds including two azaindole groups, the azaindole groups can be the same or different. Examples of dyes that can be used in connection with the present disclosure include those described in U.S. Pat. Nos. 5,863,727, 6,448,407, 6,649,769, 7,038,063, 6,162,931, 6,229,055, 6,130,101, 5,188,934, 5,840,999, 7,179,906, 6,008,379, 6,221,604, 5,231,191, 5,366,860, 7,595,162, 7,550,570, 5,936,087, 8,030,096, 6,562,632, 5,846,737, 5,442,045, 6,716,994, 5,582,977, 5,321,130, 5,863,753, 6,977,305, 7,566,790, 7,927,830, 7,888,136, 4,774,339, 5,248,782, 5,187,288, 5,451,663, 5,433,896, 9,040,674, 9,783,560, 9,040,674, 6,255,476, 6,020,481, 6,303,775, and 6,020,481, the disclosure of each of which is incorporated herein by reference in its entirety as they relate to dyes and methods for conjugating dyes to oligonucleotides.

In some embodiments, the donor dye or acceptor dye can be a cyanine dye such as described in U.S. Pat. No. 6,974,873. Suitable cyanines include those having the Formula (I):

(I)

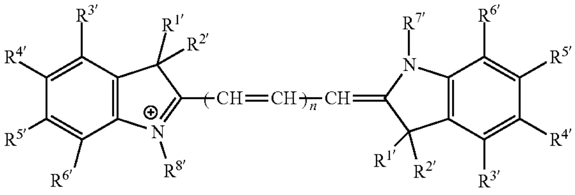

wherein, each $R^{1'}$ is independently H or $C_1$-$C_6$ alkyl, wherein each hydrogen atom in $C_1$-$C_6$ alkyl is independently optionally substituted with one or more hydrophilic groups or hydrophilic group containing moieties (e.g., —$C_1$-$C_6$ alkylOH, —$C_1$-$C_6$ alkyl$CO_2$H, or alkylaryl);

each $R^{2'}$ is independently H, $C_1$-$C_6$ alkyl, $C_1$-$C_6$ alkyl$C_6$-$C_{10}$ aryl, or $C_6$-$C_{10}$ aryl, wherein each hydrogen atom in $C_1$-$C_6$ alkyl, $C_1$-$C_6$ alkyl$C_6$-$C_{10}$ aryl, or $C_6$-$C_{10}$ aryl is independently optionally substituted with one or more hydrophilic groups or hydrophilic group containing moieties (e.g., —$C_1$-$C_6$ alkylOH, —$C_1$-$C_6$ alkyl$CO_2$H, or alkylaryl);

each $R^{3'}$, $R^{4'}$, $R^{5'}$, and $R^{6'}$ is independently H, $C_1$-$C_6$ alkyl, $C_6$-$C_{10}$ aryl, a hydrophilic group, a hydrophilic group containing moiety, or each pair of $R^{3'}$ and $R^{4'}$, $R^{4'}$ and $R^{5'}$, or $R^{5'}$ and $R^{6'}$, taken together with the carbon atoms to which they are attached, independently optionally form a fused six-membered aryl ring optionally substituted with one or more hydrophilic groups or hydrophilic group containing moieties; and each $R^{7'}$ or $R^{8'}$ is independently H, $C_1$-$C_6$ alkyl, —$C_1$-$C_6$ alkyl$SO_3$H, alkyl$SO_3$Z, alkylOH, or —$C_1$-$C_6$ alkyl$CO_2$H, wherein one of $R^{1'}$, $R^{2'}$, $R^{7'}$ or $R^{8'}$ comprises a linker ($L_1$, $L_2$, or $L_3$) as disclosed herein.

In some embodiments, the donor dye or acceptor dye can be a rhodamine dye or a derivative thereof such as described in U.S. Pat. No. 9,040,674 or PCT/US2019/067925 (now WO 2020/132487); a dichlororhodamine (e.g., 4,7-dichlororhodamine) such as described in U.S. Pat. No. 5,847,162; an asymmetric rhodamine such as described in Appl. No. PCT/US2019/068111No. (now WO 2020/132607); or a silicon rhodamine such as described in Appl. No. PCT/US2019/045697 (now WO 2020/033681).

A representative class of rhodamine dyes that can serve as the donor dye or acceptor dye is depicted in Formula (II):

(II)

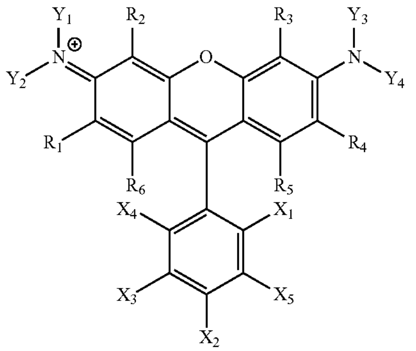

wherein, $R_1$-$R_6$ taken separately are selected from the group consisting of hydrogen, fluorine, chlorine, lower alkyl, lower alkene, sulfonate sulfone, amino amido, nitrile lower alkoxy, linking group and combinations thereof, or when taken together, R1 and R6 is benzo, or, when taken together R4 and R5 is benzo; Y1-Y4 taken separately are selected from the group consisting of hydrogen and lower alkyl or, when taken together, Y1 and R2 is propano or propenyl and Y2 and R1 is propano or propenyl, when taken together, Y3 and R3 is propano or propenyl and Y4 and R4 is propano or propenyl; X1-X5 taken separately are selected from the group consisting of hydrogen, chlorine, fluorine lower alkyl, carboxylate, sulfonic acid, and linking group;

X1 is carboxylate;

X2 and X3 is linking group;

X4 and X5 are chlorine; and

Y1-Y4 taken separately are selected from the group consisting of hydrogen, methyl and ethyl and taken together Y2 and R1 and Y4 and R4 are propano or propenyl.

In some embodiments, the donor dye or acceptor dye can be a rhodamine dye of the Formula (III):

(III)

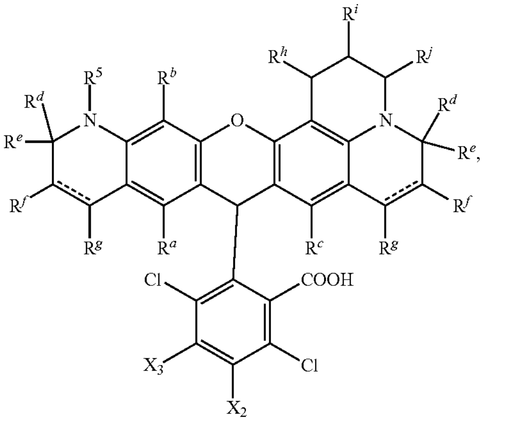

wherein, $R^a$, $R^b$, and $R^c$, are each independently of one another selected from hydrogen, $(C_1\text{-}C_4)$ alkyl, $(C_6\text{-}C_{14})$ aryl, $(C_7\text{-}C_{20})$ arylalkyl, 5-14 membered heteroaryl, 6-20 membered heteroarylalkyl, —$R^k$, or —$(CH_2)_{1\text{-}10}$—$R^k$; wherein each hydrogen atom in $(C_1\text{-}C_4)$ alkyl, $(C_6\text{-}C_{14})$ aryl, $(C_7\text{-}C_{20})$ arylalkyl, 5-14 membered heteroaryl, 6-20 membered heteroarylalkyl is independently optionally substituted with one or more hydrophilic groups or hydrophilic group containing moieties;

each $R^d$ and $R^e$, when taken alone, is independently selected from hydrogen, $(C_1\text{-}C_4)$ alkyl, $(C_6\text{-}C_{14})$ aryl, $(C_7\text{-}C_{20})$ arylalkyl, 5-14 membered heteroaryl, 6-20 membered heteroarylalkyl, —$R^b$, or —$(CH_2)_n$—$R^b$; wherein each hydrogen atom in $(C_1\text{-}C_4)$ alkyl, $(C_6\text{-}C_{14})$ aryl, $(C_7\text{-}C_{20})$ arylalkyl, 5-14 membered heteroaryl, 6-20 membered heteroarylalkyl is independently optionally substituted with one or more hydrophilic groups or hydrophilic group containing moieties;

each of $R^f$, $R^g$, $R^h$, $R^i$, and $R^j$, when taken alone, are each, independently of one another, selected from hydrogen, $(C_1\text{-}C_4)$ alkyl, $(C_6\text{-}C_{14})$ aryl, $(C_7\text{-}C_{20})$ arylalkyl, 5-14 membered heteroaryl, 6-20 membered heteroarylalkyl, —$R^b$, or —$(CH_2)_n$—Rb; wherein each hydrogen atom in $(C_1\text{-}C_4)$ alkyl, $(C_6\text{-}C_{14})$ aryl, $(C_7\text{-}C_{20})$ arylalkyl, 5-14 membered heteroaryl, 6-20 membered heteroarylalkyl is independently optionally substituted with one or more hydrophilic groups or hydrophilic group containing moieties;

each $R^k$ is independently selected from halogen, —$SR^a$—$NH_2$, —$NH_2$, perhalo lower alkyl, trihalomethyl, trifluoromethyl, —$P(O)(OH)_2$, —$OP(O)(OH)_2$, —$S(O)_2OH$, —C(O)H, —C(O)OH, —$C(O)NH_2$, —$C(S)NH_2$, and —$C(NH)NH_2$;

and $X_2$ and $X_3$ can be carboxylate, sulfonate, H, or a linking group.

In some embodiments, the donor dye or acceptor dye can be a silicon-rhodamine dye (also referred to as a "silyl rhodamine). An exemplary structure for a silicon-rhodamine dye has the Formula (IV):

(IV)

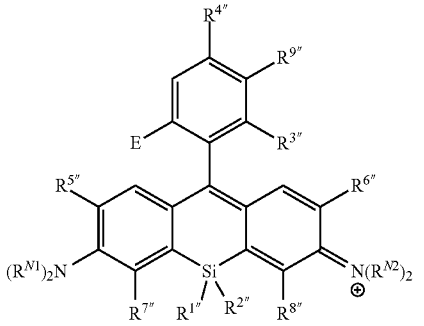

wherein, $R^{1''}$ and $R^{2''}$ are each independently $C_1\text{-}C_6$ alkyl optionally substituted with at least one at least one hydrophilic group or hydrophilic group containing moiety, a thioether or substituted thioether; or $R^{1''}$ and $R^{2''}$ form a ring together with the silicon to which they are attached;

$R^{3''}$ is H, —COOH, —$SO_3Z$, —$C(O)NR^{N3}R^{N4}$, each $R^{N1}$ is independently H, $C_1\text{-}C_4$ alkyl, —$C(O)R^{13''}$, or $R^{N1}$ taken together with the nitrogen atom to which it is attached forms a 5-7-membered heterocyclic ring with $R^{5''}$ and/or $R^{7''}$, wherein each hydrogen atom in $C_1\text{-}C_4$ alkyl or the 5-7-membered heterocyclic ring is independently optionally substituted with one or more hydrophilic groups or hydrophilic group containing moieties;

each $R^{N2}$ is independently H, $C_1\text{-}C_4$ alkyl, —$C(O)R^{13''}$, or $R^{N2}$ taken together with the nitrogen atom to which it is attached forms a 5-7-membered heterocyclic ring with $R^{6''}$ and/or $R^{8''}$, wherein each hydrogen atom in $C_1\text{-}C_4$ alkyl or the 5-7-membered heterocyclic ring is independently optionally substituted with one or more hydrophilic groups or hydrophilic group containing moieties;

each of $R^{N3}$ and $R^{N4}$ is independently H, $C_1\text{-}C_6$ alkyl, or $R^{N3}$ and $R^{N4}$, taken together with the nitrogen atom to which they are attached, form a 5- to 7-membered heterocyclic group, wherein each hydrogen atom in $C_1\text{-}C_4$ alkyl or the 5-7-membered heterocyclic ring is independently optionally substituted with one or more hydrophilic groups or hydrophilic group containing moieties, or $R^{N3}$ and $R^{N4}$ is independently a linker;

$R^{4''}$ is H, —$SO_3Z$, $C_1\text{-}C_6$ alkyl, chloro or a linker;

E is H, —$SO_3Z$, $C_1\text{-}C_6$ alkyl, chloro or a linker;

$R^{5''}$ is H, $C_1\text{-}C_6$ alkyl, or $R^{5''}$, taken together with the carbon atom to which it is attached, forms a 5-7-membered heterocyclic ring with $R^{N1}$, wherein each hydrogen atom in $C_1\text{-}C_4$ alkyl or the 5-7-membered heterocyclic ring is independently optionally substituted with one or more hydrophilic groups or hydrophilic group containing moieties;

$R^{6''}$ is H, $C_1\text{-}C_6$ alkyl, or $R^{6''}$, taken together with the carbon atom to which it is attached, forms a 5-7-membered heterocyclic ring with $R^{N2}$, wherein each hydrogen atom in $C_1\text{-}C_4$ alkyl or the 5-7-membered heterocyclic ring is independently optionally substituted with one or more hydrophilic groups or hydrophilic group containing moieties;

$R^{7''}$ is H, $C_1\text{-}C_6$ alkyl, or $R^{7''}$, taken together with the carbon atom to which it is attached, forms a 5-7-membered heterocyclic ring with $R^{N1}$, wherein each hydrogen atom in $C_1$-$C_4$ alkyl or the 5-7-membered heterocyclic ring is independently optionally substituted with one or more hydrophilic groups or hydrophilic group containing moieties;

$R^{8''}$ is H, $C_1$-$C_6$ alkyl, or $R^{8''}$, taken together with the carbon atom to which it is attached, forms a 5-7-membered heterocyclic ring with $R^{N2}$, wherein each hydrogen atom in $C_1$-$C_4$ alkyl or the 5-7-membered heterocyclic ring is independently optionally substituted with one or more hydrophilic groups or hydrophilic group containing moieties;

$R^{9''}$ is H, —$SO_3Z$, $C_1$-$C_6$ alkyl, chloro or a linker;

$R^{10''}$ is —$CF_3$ or —O—$CH_2$-$A^1$ where $A^1$ is an aryl or heteroaryl optionally substituted with at least one $R^{11''}$;

$R^{11''}$ is $C_1$-$C_6$ alkyl or —$OR^{12''}$;

$R^{12''}$ is H, methyl, acetyl (Ac), acetoxymethyl (AM), —$PO_3M_2$, —$PO_3(R^{14''})_2$, or a glycoside;

$R^{13''}$ is

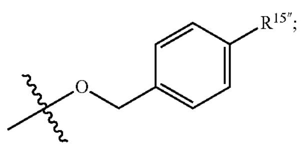

$R^{14''}$ is acetoxymethyl; and $R^{15''}$ is —OR', where R' is acetyl (Ac), AM, $PO_3M_2$, $PO_3(R^{14})_2$, or a glycoside.

Typically, $R^{1''}$, $R^{2''}$, or $R^{3''}$ includes a linker structure to the donor or acceptor dye.

In some embodiments, the donor dye or acceptor dye can be a fluorescein or a derivative thereof. An exemplary structure for a fluorescein dye has the Formula (V):

(V)

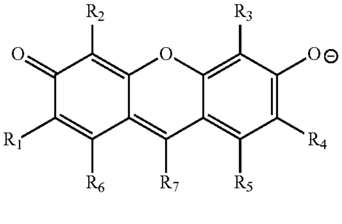

wherein, $R_1$-$R_6$ taken separately are selected from the group consisting of hydrogen, fluorine, chlorine, phenyl, lower alkyl, lower alkene, sulfonate sulfone, amino, amido, nitrile lower alkoxy, linking group and combinations thereof, or when taken together, $R_1$ and $R_6$ is benzo, or, when taken together $R_4$ and $R_5$ is benzo; and $R_7$ is selected from the group consisting of acetylene, lower alkyl, cyano, phenyl, and heterocyclic aromatic.

In some embodiments, $R_7$ is phenyl:

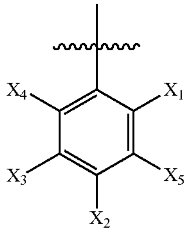

wherein, $X_1$-$X_5$ taken separately are selected from the group consisting of hydrogen, chlorine, fluorine, lower alkyl, carboxylate, sulfonic acid, or a linking group. In certain embodiments, independently, $X_1$ is carboxylate; $X_2$ or $X_3$ is a linking group; and $X_4$ and $X_5$ are chlorine.

The fluorescent dyes disclosed herein can be provided in a protected or unprotected form. Various dyes (e.g., rhodamines), as well as their unprotected counterparts, can be in a closed, spirolactone form. In certain embodiments, the dye is provided in a closed, spirolactone form. In certain embodiments, the dye is provided in an open, acid form of the compound. The open, acid form of certain rhodamine dyes disclosed herein can be fluorescent (or exhibit an increase in fluorescence) relative to the closed, spirolactone form of the compound. Thus, also provided herein are fluorescent compounds and fluorescently-labeled nucleic acid probes and primers that include compounds in deprotected, open lactone form.

The energy transfer dye conjugates described herein can include different combinations of donor dyes and acceptor dyes, depending on the desired excitation and/or emission profile. Representative classes of dyes that can be used in ET conjugates include those in which the donor or acceptor dye is a xanthene dye (e.g., a fluorescein or rhodamine), a cyanine dye, a BODIPY dye, a pyrene dye, a pyronine dye, or a coumarin dye, where the acceptor dye is a compound that emits at a longer wavelength than the donor dye. Although certain donor-acceptor dye combinations are described herein as being suitable for construction of FRET conjugates, many other examples of donor-acceptor combinations that are not explicitly described can be implemented to provide FRET conjugates using the chemistries disclosed herein.

One suitable combination includes a fluorescein as the donor dye (e.g., FAM or VIC) and a rhodamine as the acceptor dye. Another suitable combination includes a coumarin as the donor dye (e.g., Coumarin 343, ATTO 425, or Pacific Blue), and a rhodamine as the acceptor dye. Yet another suitable combination includes fluorescein as the donor dye and a cyanine as the acceptor dye. Examples of cyanine dyes suitable for use an acceptor dye in ET conjugates disclosed herein include, without limitation, those commercially available under the tradename ALEXA FLUOR from Thermo Fisher Scientific (e.g., AF-647, AF-680, AF-700, and AF-750). In yet another suitable combination, the donor dye is a rhodamine and the acceptor dye is a cyanine dye. In yet another suitable combination, the donor dye is a rhodamine, and the acceptor dye is a rhodamine that emits at a longer wavelength than the donor dye, e.g., TAMRA and ROX, a silyl rhodamine, or a pyronine dye. In some embodiments, the donor dye is a cyanine dye (e.g., AF-647) and the acceptor dye is a compound that emits at a longer wavelength than the donor, such as, a silyl rhodamine or cyanine. In some embodiments, the acceptor dye is a cyanine dye. For example, the donor dye can be FAM and the acceptor dye can be a cyanine dye, with substituents as described herein. In some embodiments, the acceptor dye is an NH-rhodamine, as described herein. For example, the donor dye can be FAM and the acceptor dye can be an NH-rhodamine. Additional examples of donor-acceptor dye pairs that can be utilized in the ET dye conjugates described herein are listed in Table 3.

In some embodiments, the donor dye or acceptor dye can have one or more hydrophilic groups, as described herein, at any of the positions shown in the dye structures described herein. In some embodiments, the donor dye or acceptor dye can have one of more hydrophilic group containing moieties, as described herein, at any of the positions shown in the dye structures described herein.

In some embodiments, each dye can have a structure including multiple sulfonate groups. Sulfonate groups are known in the art to improve the solubility of dye compounds in an aqueous medium. In some embodiments, the dye includes one or more reactive functional groups or a protected reactive functional groups for linking the dye to another substance. In some embodiments, the dye is provided as a phosphoramidite derivative which can be used to conjugate the dye to a molecule, such as an oligonucleotide during automated nucleic acid synthesis, as is known in the art.

In some embodiments, the water-solubilizing groups, hydrophilic groups, dyes and ET dyes described herein have an overall electronic charge. It is to be understood that when such electronic charges are shown to be present, they are balanced by the presence of an appropriate counterion, which may or may not be explicitly identified. Where the water-solubilizing group, hydrophilic group, dye or ET dye described herein is positively charged, the counterion is a negatively charged moiety, typically selected from, but not limited to, chloride, bromide, iodide, sulfate, alkanesulfonate, arylsulfonate, phosphate, perchlorate, tetrafluoroborate, tetraarylboride, nitrate and anions of aromatic or aliphatic carboxylic acids. Where the water-solubilizing group, hydrophilic group, dye or ET dye described herein is negatively charged, the counterion is a positively charged moiety, typically selected from, but not limited to, alkali metal ions, such as $Li^+$, $Na^+$, $K^+$, and the like, ammonium or substituted ammonium, such as $NMe_4^+$, $Pr_2NHEt^+$, and the like, or pyridinium ions. In some embodiments, the counterion is biologically compatible, is not toxic as used, and does not have a substantially deleterious effect on biomolecules. Counterions are readily changed by methods well known in the art, such as ion-exchange chromatography, or selective precipitation.

It is to be understood that the dyes as disclosed herein have been drawn in one or another particular electronic resonance structure. Every aspect discussed above applies equally to dyes that are formally drawn with other permitted resonance structures, as the electronic charge on the subject dyes are delocalized throughout the dye itself Linkers In some embodiments, the energy transfer dyes conjugates include a linker covalently attaching the donor dye to the acceptor dye.

The identity of the linker will depend, in part, upon the identities of the dyes being linked to one another. In general, the linkers include a spacing group that can include virtually any combination of atoms or functional groups stable to the synthetic conditions used for the synthesis of labeled biomolecules, e.g., oligonucleotides, such as the conditions commonly used to synthesize oligonucleotides by the phosphite triester method, and can be linear, branched, or cyclic in structure, or can include combinations of linear, branched and/or cyclic structures. The spacing group can be monomeric in nature, or it can be or include regions that are polymeric in nature. The spacing group can be designed to have specified properties, such as the ability to be cleaved under specified conditions, or specified degrees of rigidity, flexibility, hydrophobicity and/or hydrophilicity.

Representative examples of linkers that can be used to prepare ET conjugates as disclosed herein can include one or more of an alkyl portion, an amino-alkylene portion, and an oxy-alkylene portion, and amino-alkylene-dialkoxy portion, an alkenylene portion, an alkynylene portion, a polyether portion, an arylene portion, an amide portion, or a phosphodiester portion. Alternatively, the linker can be a covalent bond.

Figure 4:
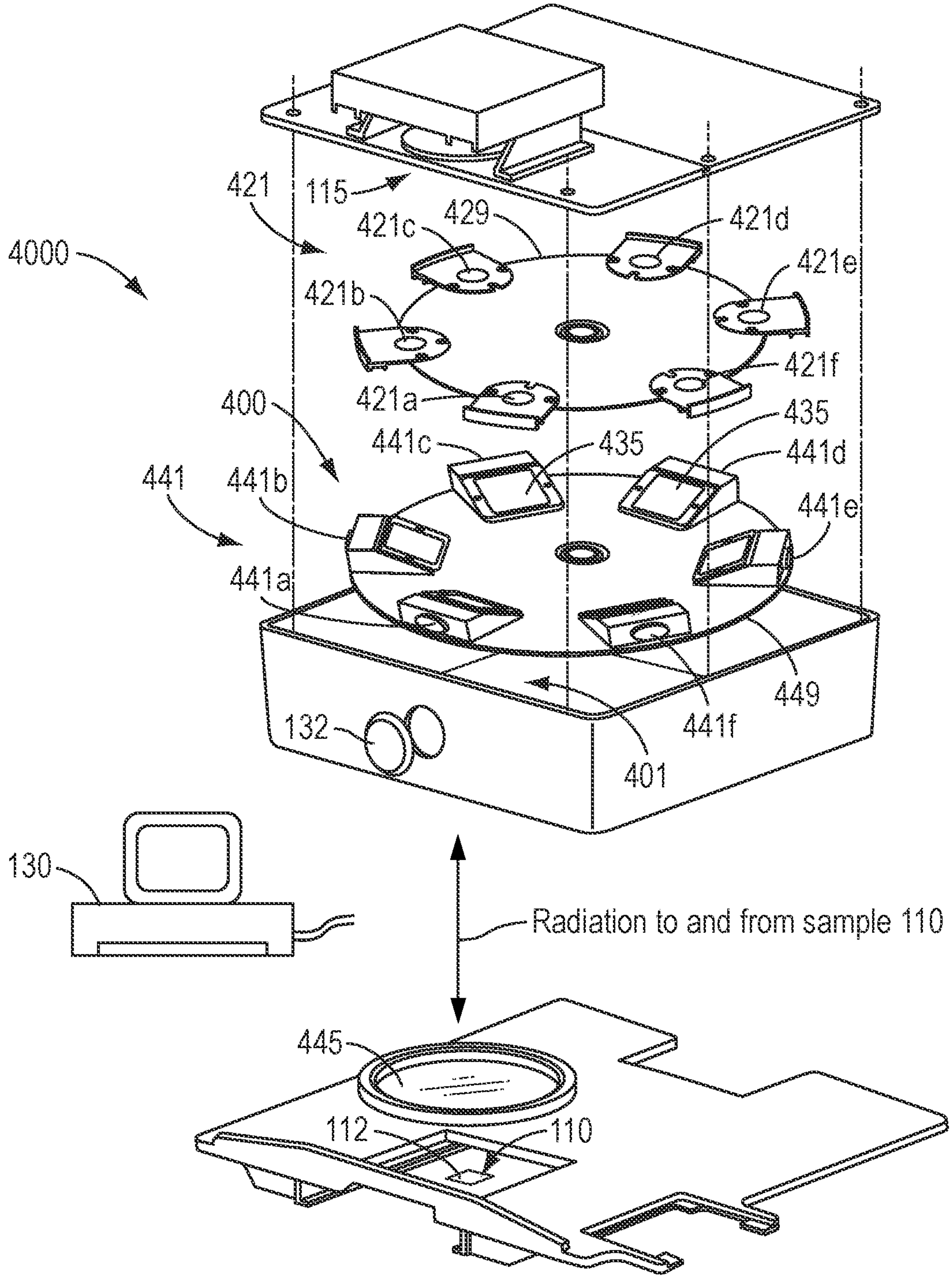
FIG. 4 is a perspective view of a system according to an embodiment of the present disclosure.

FIG. 4 show representative types of energy transfer dye conjugates that include a donor dye bound to an acceptor dye through a linker. For example, a donor dye can be bound to an acceptor dye through a linker, such as $L_1$ or $L_2$. In certain embodiments, the dye conjugate includes a linker (e.g., $L_3$) that attaches to a donor or acceptor dye (e.g., $D_1$) to the analyte and further includes an additional linker (e.g., $L_4$) for attachment to the acceptor or donor dye ($D_2$). Examples of donor and acceptor dyes that can be used in energy transfer conjugates, as described herein, include xanthene, cyanine, rhodamine, BODIPY, pyrene, pyronine, and coumarin dyes.

In some embodiments, the linker has one of the following structures:

(LI)

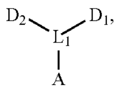

(LII)

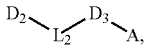 or (LIII)

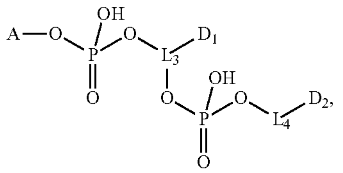

wherein $L_1$ is a first linker, wherein $L_1$ is attached to $D_1$, $D_2$ and A through a covalent bond or through a spacer comprising one or more intervening atoms;

$L_2$ is a second linker, wherein $L_2$ is attached to each of $D_2$ and $D_3$ through a covalent bond or through a spacer comprising one or more intervening atoms;

$L_3$ is a third linker, wherein $L_3$ is attached to each $PO_4H$ and $D_1$ through a covalent bond or through a spacer comprising one or more intervening atoms;

$L_4$ is a fourth linker, wherein $L_4$ is attached to $PO_4H$ and $D_2$ through a covalent bond or through a spacer comprising one or more intervening atoms; and A is the analyte;

each of $D_1$, $D_2$, and $D_3$ is interchangeably a donor dye or an acceptor dye; and wherein the combination of $D_1$ and $D_2$ in $L_I$ and $L_{III}$ and $D_2$ and $D_3$ in $L_{II}$ forms an energy transfer dye pair.

In certain embodiments, the $L_1$ linker includes an arylene portion of the formula

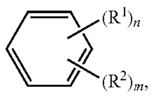

wherein each $R^1$ is independently $-C_1$-$C_{10}$ alkyl-N($R^3$)—*, $-C_2$-$C_{10}$ alkenyl-N($R^3$)—*, $-C_2$-$C_{10}$ alkynyl-N($R^3$)—*, $-OC_1$-$C_{10}$ alkyl-*, $-C_1$-$C_{10}$ alkyl-O—*, —N($R^3$)$C_1$-$C_6$ alkyl-*, —N($R^3$)$C_1$-$C_6$ alkyl-O—*, alkyl-N($R^3$)—*; or —N($R^3$)—*;

each $R^2$ is independently —C(O)N($R^4$), $-C_1$-$C_{10}$ alkyl-C(O)N($R^4$), $-C_2$-$C_{10}$ alkenyl-C(O)N($R^4$), $-C_2$-$C_{10}$ alkynyl-$R^4$, —C(O)N($R^4$), —N($R^3$)—C(O)N($R^4$), $C_1$-$C_6$ alkyl-O—C(O)N($R^4$), alkyl-C(O)N($R^4$), —N($R^4$), halogen, $-CO_2^-Z^+$, $-SO_3R_4$, or $-SO_3^-Z^+$;

each $R^3$ is independently H or $C_1$-$C_6$ alkyl;

each $R^4$ is independently H, $C_1$-$C_6$ alkyl, or a point of attachment to A, wherein the attachment to A is through a covalent bond or through a spacer comprising one or more intervening atoms;

each * represents a point of attachment to $D_1$ or $D_2$, wherein the attachment to $D_1$ or $D_2$ is through a covalent bond or through a spacer comprising one or more intervening atoms;

$Z^+$ is a cation(s) (e.g., $Na^+$, $K^+$, or $NH_4^+$);

n is 2, 3 or 4; and m is 0, 1, 2, 3, or 4, provided that n+m=3 to 6.

In some embodiments, $L_1$ linker includes an arylene portion and one or more of a bis-alkylamino portion or a bis-carboxyamidyl portion, wherein the $L_1$ linker further includes a point of attachment to A, wherein the attachment to A is through a covalent bond or through a spacer comprising one or more intervening atoms.

The $L^2$ linker can include an arylene portion of the formula

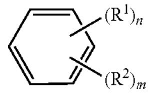

wherein each $R^1$ is independently $-C_1$-$C_{10}$ alkyl-N($R^3$)—*, $-C_2$-$C_{10}$ alkenyl-N($R^3$)—*, $-C_2$-$C_{10}$ alkynyl-N($R^3$)—*, $-OC_1$-$C_{10}$ alkyl-*, $-C_1$-$C_{10}$ alkyl-O—*, —N($R^3$)$C_1$-$C_6$ alkyl*-, —N($R^3$)$C_1$-$C_6$ alkyl-O—*, $-OC_1$-$C_6$ alkyl-N($R^3$)—*; or —N($R^3$)—*;

each $R^2$ is independently —C(O)N($R^3$)—*, $-C_1$-$C_{10}$ alkyl-C(O)N($R^3$)—*, $-C_2$-$C_{10}$ alkenyl-C(O)N($R^3$)—*, $-C_2$-$C_{10}$ alkynyl-($R^3$)—*, —C(O)N($R^3$)—*, —N($R^3$)—C(O)N($R^3$)—*, $C_1$-$C_6$ alkyl-O—C(O)N($R^3$)—*, $-OC_1$-$C_6$ alkyl-C(O)N($R^3$)—*, —N($R^3$)—*, halogen, $-CO_2^-Z^+$ or $-SO_3^-Z^+$;

each $R^3$ is independently H or $C_1$-$C_6$ alkyl;

each * represents a point of attachment to $D_2$ or $D_3$, wherein the attachment to $D_2$ or $D_3$ is through a covalent bond or through a spacer comprising one or more intervening atoms;

$Z^+$ is a cation(s) (e.g., $Na^+$, $K^+$, or $NH_4^+$);

n is 2, 3 or 4; and m is 0, 1, 2, 3, or 4, provided that n+m=2 to 6.

In certain embodiments, the linker includes a fragment of the formula

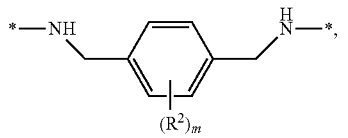

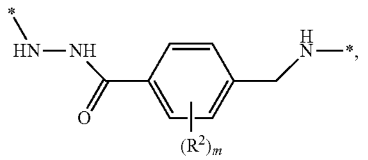

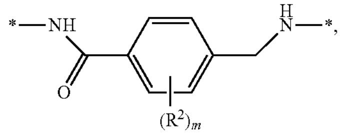

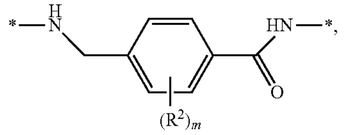

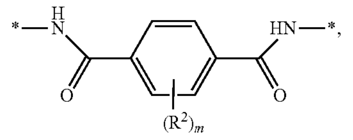

or

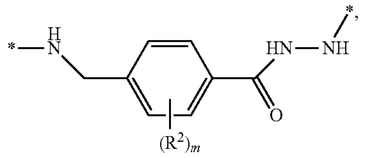

wherein each $R^2$, m and * is as defined above.

The $L_3$ linker can include a fragment of the formula.

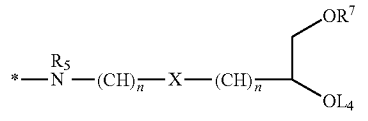

wherein $R^5$ is H or $C_1$-$C_6$ alkyl;

n is 2, 3 or 4; X is O or $CH_2$;

$L_4$ is an attachment to $D_2$, wherein $L_4$ is a covalent bond or a spacer comprising one or more intervening atoms;

$R^7$ is a point of attachment to POSH-A, wherein the attachment to $PO_3H$-A is through a covalent bond or through a spacer comprising one or more intervening atoms; and wherein * represents a point of attachment to $D_1$, wherein the attachment to $D_1$ is through a covalent bond or through a spacer comprising one or more intervening atoms.

In the energy transfer dye conjugate shown above, $L_4$ linker can include a phosphodiester portion of the formula

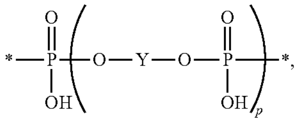

wherein Y includes one or more of an alkoxy portion, an alkyl portion, an arylene portion, or an oligonucleotide portion;

p is an integer from 0 to 10;

$D_2$ or A comprises an oxygen atom, wherein each * represents a point of attachment of the phosphodiester portion to the oxygen atom in $D_2$ or A, wherein the attachment of the phosphodiester to the oxygen atom in $D_2$ or A is through a covalent bond or through a spacer comprising one or more intervening atoms.

In certain embodiments, Y is $C_1$-$C_{10}$ alkyl or poly(alkylene glycol).

In certain embodiments, the combination of the $L_3$ and $L_4$ linker can include a structure having the formula:

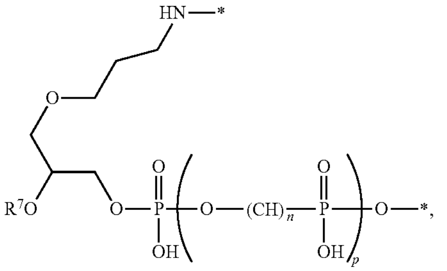

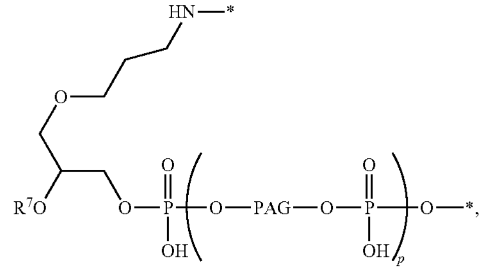

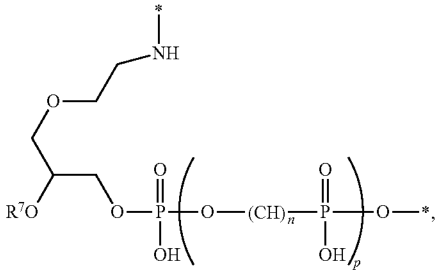

or

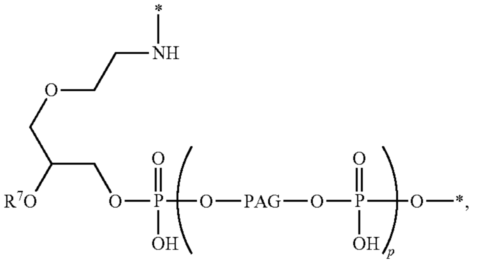

wherein $R^7$ comprises a phosphodiester group attached to A, wherein the phosphodiester group is attached to one or more of a phosphodiester portion, alkoxy portion, amino-alkyl portion, alkoxy portion, alkyl portion, polyether portion, or arylene portion, PAG is a poly(alkylene glycol), wherein the poly(alkylene glycol) is or comprises a $C_2$-$C_6$ linear or branched alkylene chain; n is 2-6; and p is 1-4.

In some embodiments, the PAG is pentaethylene glycol.

In any of the linker structures described above, the analyte (A) can be a biological molecule, such as, e.g., a nucleic acid molecule, a peptide, a polypeptide, a protein, and a carbohydrate.

The different linker structures provided herein each have their own particular advantages, and selection of an appropriate linker design depends on the particular dyes that are used to form the ET conjugate, as well as the type of analyte that will be coupled to the ET conjugate. Linker $L_1$ (also referred to as a "Y-linker") can be used in combination with a particularly large variety of potential donor and acceptor dyes, as $L_1$ does not require the use of a dual functional group containing dye to form a link to the analyte and to its ET partner, as required when using linker $L_2$. Because linker $L_1$ does not require that the dye bear a second functional group, any pair of dye NHS esters can be linked together with the Y-linker. The versatility of the Y-linker structure universalizes the use of different donor and acceptor dyes and thereby facilitates construction of a vast array of different donor-acceptor pair conjugates.

Another advantage of linker $L_1$ is that this linker includes a third functional group that can be attached to the probe or analyte after construction of the ET conjugate. As a result, ET conjugates can prepared and purified before addition to the oligonucleotide probe or analyte. While purification prior to probe attachment is also feasible with the $L_2$ linker (but not with linker $L_3$), purification of the ET conjugate prior to probe attachment can provide for significantly improved yield and purity of the final product. However, the $L_2$ linker having orthogonally reactive linkage sites to $D_1$ and $D_2$ precludes formation of regio-isomers that are produced with use of $L_1$ without use of additional selective protecting group derivatization.

Linker $L_3$ can be readily used to prepare ET conjugates using automated coupling chemistry. But for all practical purposes, linker $L_3$ requires at least one dye phosphoramidite coupling step. Thus, coupling of donor and acceptor dyes using linker $L_3$ requires that at least one dye, and preferably both dyes, be derivatized with a phosphoramidite group. Not all dye molecules can be readily made into phosphoramidite derivatives. Therefore, linker $L_3$ is less versatile as compared to $L_1$. Although it is feasible to first attach linkers $L_3$ and $L_4$ to a solid support before dye addition using protected phosphoramidite linker derivatives, the dyes must be separately added to the linker on the support in two secondary coupling steps using selective deprotection chemistry and NHS coupling chemistry. Such a multi-step synthetic scheme negates the advantages of automation (e.g., high yield and purity with less steps and labor) that can be achieved through use of at least one dye phosphoramidite in synthesis of the ET conjugate.

Conjugates of Energy Transfer Dyes

In one aspect, the present disclosure provides energy transfer dye conjugates that include one or more energy transfer dyes as described herein, covalently attached to an analyte. The analyte can be, e.g., an oligonucleotide probe, either directly or through an optional linker. In some embodiments, the energy transfer dye conjugates described herein can be further covalently attached to a quencher dye (Q), either directly or through an optional linker. In some embodiments, the quencher dye (Q) is covalently attached to an oligonucleotide portion of an energy transfer dye conjugate of the disclosure.

In some embodiments, a conjugation reaction between a donor dye and acceptor dye to form the energy transfer dye conjugate and the analyte or substance to be conjugated results a new linkages attaching the donor and acceptor dyes and the conjugated analyte through complementary Z and ZR groups. Suitable examples of complementary reactive groups and linkages are shown below in Table 1, where the reaction of an electrophilic group and a nucleophilic group yields a covalent linkage.

TABLE 1

Examples of routes to covalent linkages

| Electrophilic Group | Nucleophilic Group | Resulting Covalent Linkage |
|---|---|---|
| activated esters* | amines/anilines | carboxamides |
| aldehydes | amines/anilines | imines |
| aldehydes or ketones | hydrazines | hydrazones |
| aldehydes or ketones | hydroxylamines | oximes |
| anhydrides | alcohols/phenols | esters |
| anhydrides | amines/anilines | carboxamides |
| aziridines | thiols | thioethers |
| boronates | glycols | boronate esters |
| carbodiimides | carboxylic acids | N-acylureas or anhydrides |
| epoxides | thiols | thioethers |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | alcohols | ethers |
| sulfonyl halides | amines/anilines | sulfonamides |
| sulfonyl halides | phenols/alcohols | sulfonate esters |
| azide | alkyne | 1,2,3-triazole |

The covalent linkage binds the reactive group Z to form an energy transfer dye as described herein, either directly or through an optional linker portion. It will be appreciated that the optional linker portion covalently attaching an energy transfer dye conjugate to an analyte, such as an oligonucleotide probe, is not particularly limited by structure. The optional linker portion can be a combination of stable chemical bonds, optionally including single, double, triple or aromatic carbon-carbon bonds, as well as carbon-nitrogen bonds, nitrogen-nitrogen bonds, carbon-oxygen bonds, phosphorus-oxygen bonds. The optional linker portion can include functional moieties such as ether, thioether, carboxamide, sulfonamide, urea, urethane or hydrazine moieties. in some embodiment, the optional linker portion can include 1-20 non-hydrogen atoms selected from the group consisting of C, N, O, P, and S and are composed of any combination of ether, thioether, amine, carboxamide, sulfonamide, hydrazide bonds and aromatic or heteroaromatic bonds. In some embodiments, the optional linker portion can be a combination of single carbon-carbon bonds and carboxamide or thioether bonds.

In some embodiments, the energy transfer dye conjugate is covalently attached to an analyte, such as an oligonucleotide probe, through the linker portion of the energy transfer dye. In some embodiments, the energy transfer dye conjugate is covalently attached to an analyte, such as an oligonucleotide probe, through the linker portion of the energy transfer dye conjugate by an additional linker connecting the energy transfer dye linker portion to the analyte. In some embodiments, the energy transfer dye conjugate is covalently attached to an analyte, such as an oligonucleotide probe, by attachment of the analyte to the donor dye or the acceptor dye through an additional linker. In some embodiments, the energy transfer dye conjugate is covalently attached to an analyte, such as an oligonucleotide probe, by attachment of the analyte to the donor dye or the acceptor dye.

In some embodiments, the energy transfer dye conjugate is covalently attached to an analyte, such as an oligonucleotide probe, with a covalent bond to a reactive functional group on the analyte.

It will be appreciated that the choice of reactive groups used for attachment of the energy transfer dye conjugate to the analyte can be a function of the functional group present on the analyte to be conjugated and/or the type or length of covalent linkage desired.

Reactive groups for conjugating the ET dyes to an analyte are well-known to those skilled in the art. Typically, the reactive group will react with an amine, a thiol, an alcohol, an aldehyde or a ketone. In some embodiments, the reactive group reacts with an amine or a thiol functional group. In some embodiments, the reactive group is an acrylamide, a reactive amine (including a cadaverine or ethylenediamine), an activated ester of a carboxylic acid (typically a succinimidyl ester of a carboxylic acid), an acyl azide, an acyl nitrile, an aldehyde, an alkyl halide, an anhydride, an aniline, an aryl halide, an azide, an aziridine, a boronate, a carboxylic acid, a diazoalkane, a haloacetamide, a halotriazine, a hydrazine (including hydrazides), an imido ester, an isocyanate, an isothiocyanate, a maleimide, a phosphoramidite, a sulfonyl halide, or a thiol group.

In some embodiments, ET conjugates described herein can be attached to a nucleic acid base, nucleoside, nucleotide, or a nucleic acid polymer, including those that are modified to possess an additional linker or spacer for attachment of the energy transfer dye conjugate, such as an alkynyl linkage, an aminoallyl linkage, or a heteroatom-substituted linker, or other linkage.

In some embodiments, the additional linker portion connecting an energy transfer dye conjugate with the analyte, either through the linker portion on the energy transfer dye conjugate or through the donor dye or acceptor dye, comprises one or more of an alkyl portion, an amino-alkylene portion, and an alkoxy portion, and amino-alkylene-dialkoxy portion, an alkenylene portion, an alkynylene portion, a polyether portion, an amide portion, or an arylene portion.

Any donor dye and acceptor dye with appropriate functional groups can be attached to the linkers disclosed herein. However, in certain embodiments, the energy transfer dye conjugate does not include a fluorescein dye covalently attached to a rhodamine dye when the linker comprises an alkyl portion, a polyether portion, and a phosphodiester portion.

In some embodiments, the additional linker portion is a substituted or an unsubstituted polymethylene, arylene, alkylarylene, arylenealkyl, or arylthio. In some embodiments, the additional linker portion comprises a fragment of the formula

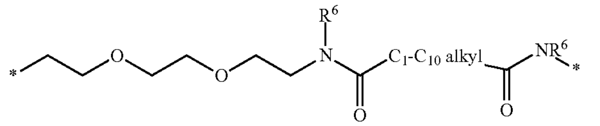

wherein $R^6$ is H or $C_1$-$C_6$ alkyl;

each * represents a point of attachment of the additional linker portion to the oligonucleotide and the rest of the energy transfer dye conjugate.

In some embodiments, the additional linker portion comprises a fragment of the formula $—(CH_2)_d(CONH(CH_2)_e)_{z'}—$, $—(CH_2)_d(CON(CH_2)_4NH(CH_2)_e)_{z'}—$, $—(CH_2)_d(CONH(CH_2)_eNH_2)_{z'}—$, or $—(CH_2)_d(CONH(CH_2)_eNHCO)_{z'}—$, where d is 0-5, e is 1-5, and z' is 0 or 1.

In another embodiment, the point of conjugation of the analyte can be a nucleoside or nucleotide analog that links a purine or pyrimidine base to a phosphate or polyphosphate moiety through a noncyclic spacer.

In some embodiments, the energy transfer dye conjugate can be further conjugated to the carbohydrate portion of a nucleotide or nucleoside, including, but not limited to, through a hydroxyl group, through a thiol, or through an amino group. In some embodiments, the conjugated nucleotide is a nucleoside triphosphate or a deoxynucleoside triphosphate or a dideoxynucleoside triphosphate. It will be appreciated that incorporation of methylene moieties or nitrogen or sulfur heteroatoms into the phosphate or polyphosphate moiety may also be useful. Purine and pyrimidine non-natural bases such as 7-deazapurines and nucleic acids containing such bases can also be coupled to energy transfer dye conjugates as described herein. Nucleic acid adducts prepared by reaction of depurinated nucleic acids (e.g., ribose derivatives) with amine, hydrazide or hydroxylamine derivatives provide an additional means of labeling and detecting nucleic acids.

In some embodiments, labeled nucleic acid polymer conjugates include single-, double-, or multi-stranded, natural or synthetic DNA or RNA, DNA or RNA oligonucleotides, or DNA/RNA hybrids, or incorporate a linker such as morpholine derivatized phosphates (AntiVirals, Inc., Corvallis, OR), or peptide nucleic acids such as N-(2-aminoethyl)glycine units. When the nucleic acid is a synthetic oligonucleotide, such as an oligonucleotide probe, the oligonucleotide can contain from about 5 to about 50 nucleotides. In some embodiments, the oligonucleotide contains from about 5 to about 25 nucleotides. In some embodiments, energy transfer dye conjugates of peptide nucleic acids (PNA) are provided. It will be appreciated that such energy transfer dye conjugates of peptide nucleic acids may be useful for some applications because of their generally faster hybridization rates.

In some embodiments, fluorescent nucleic acid polymers can be prepared from labeled nucleotides or oligonucleotides using oligonucleotide-primed DNA polymerization, such as by using the polymerase chain reaction or through primer extension, or by terminal-transferase catalyzed addition of a labeled nucleotide to a 3'-end of a nucleic acid polymer. In some embodiments, fluorescent RNA polymers are typically prepared from labeled nucleotides by transcription. In some embodiments, the energy transfer dye conjugate is attached via one or more purine or pyrimidine bases through an amide, ester, ether or thioether bond; or is attached to the phosphate or carbohydrate by a bond that is an ester, thioester, amide, ether or thioether. In some embodiments, an energy transfer dye conjugate may be simultaneously labeled with a hapten, such as biotin or digoxigenin, or to an enzyme such as alkaline phosphatase, or to a protein such as an antibody. In some embodiments, energy transfer dye nucleotide conjugates can be incorporated by DNA polymerase and can be used for in situ hybridization and nucleic acid sequencing.

Figures 5, 6:
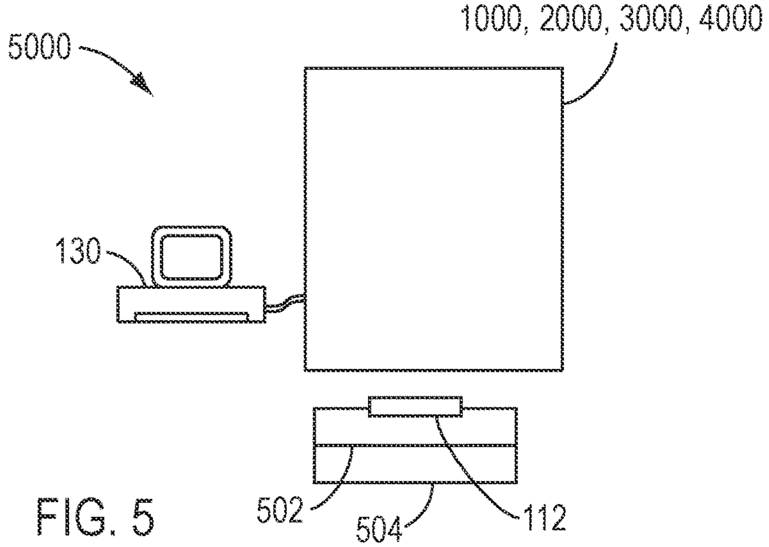
FIG. 5 is a schematic representation of system according to an embodiment of the present disclosure that may include any of the systems illustrated in FIGS. 1-4.
FIG. 6 is a tabular representation of a set of ex-em channels and dyes according to an embodiment of the present disclosure.

In some embodiments, biological polymers, such as oligonucleotides and nucleic acid polymers, are labeled with at least one energy transfer dye conjugate to form an energy-transfer probe. Referring to FIG. 5, an oligonucleotide probe 1000 is shown that includes an ET conjugate 1010 attached to an oligonucleotide 1050, where ET conjugate 1010 includes a donor dye 1020 attached through a linker 1030 to an acceptor dye 1040. Excitation of donor dye 1020 at an appropriate wavelength of light results in a transfer of the absorbed energy to an acceptor dye 1040 with subsequent emission of light by the acceptor dye at a different wavelength. Depending on the physical and optical properties of the donor dye and acceptor dye in the conjugate, the structure and composition of the linker 1030 (in regards to $L_1$, $L_2$, and $L_3$, described previously) can be uniquely tailored to maximize energy transfer efficiency, quantum yield, and fluorescence intensity.

In some embodiments, biological polymers, such as oligonucleotides and nucleic acid polymers, are labeled with at least one energy transfer dye conjugate and at least one non-fluorescent dye to form an energy-transfer probe. In some embodiments, the non-fluorescent dye is a quencher. FIG. 6 depicts an oligonucleotide probe bound to an ET conjugate 1000 as shown in FIG. 5, where oligonucleotide 1050 is further bound to a quencher molecule 1060. The oligonucleotide probe can be used, e.g., in a TaqMan assay where it can be referred to as a "detector probe." When the quencher is in proximity to the acceptor dye 1040 in ET conjugate 1010, excitation of donor dye 1020 at an appropriate wavelength of light results in a transfer of the absorbed energy (referred to as $ET_1$) to the acceptor dye 1040 that results in suppression (i.e., quenching) of fluorescence signal from acceptor dye 1040.

Figure 7:
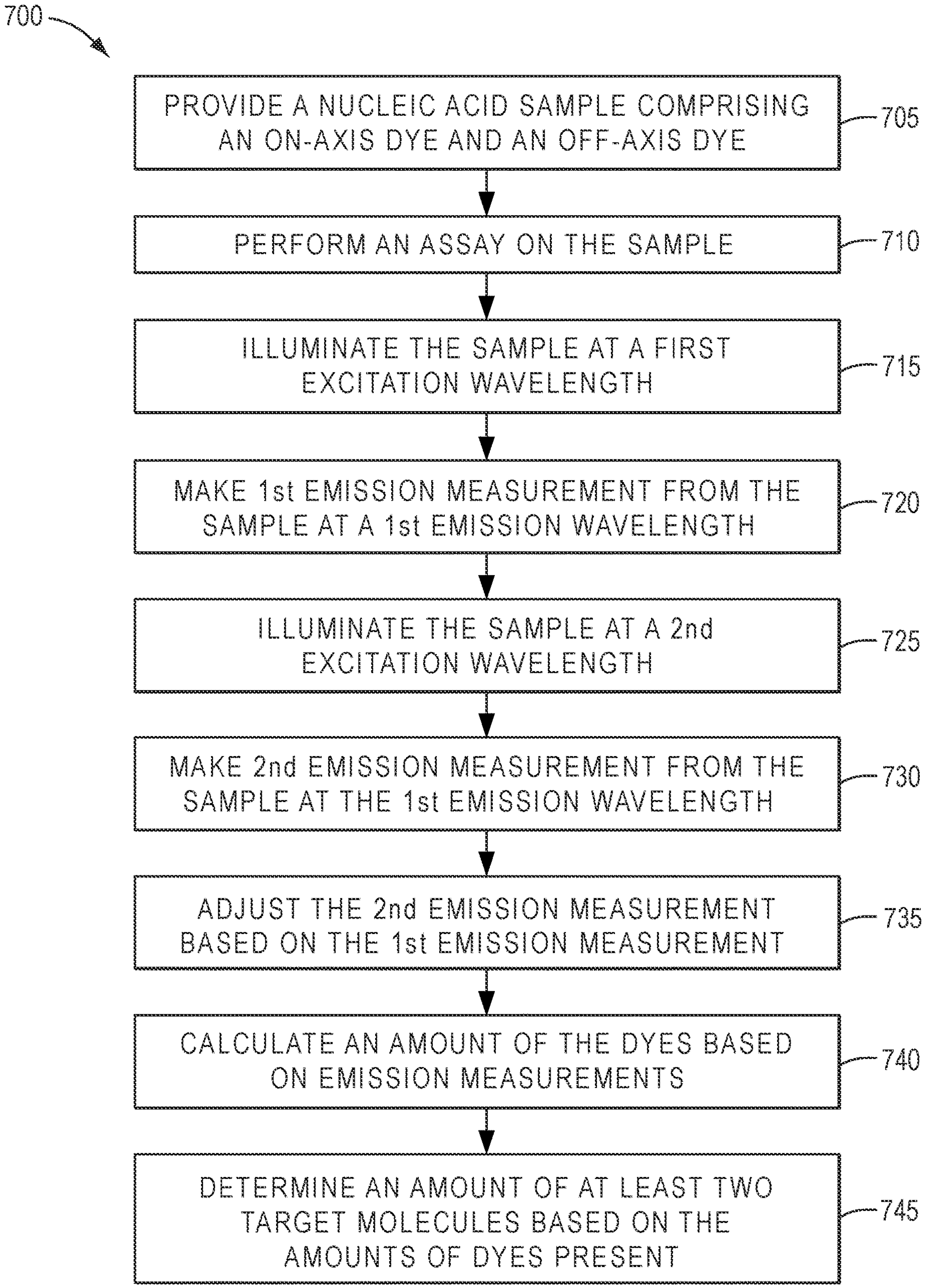
FIG. 7 is a method according to an embodiment of the present disclosure.

In some embodiments, the labeled probe functions as an enzyme substrate, and enzymatic hydrolysis disrupts the energy transfer between the energy transfer dye conjugate and the quencher. In some embodiments, the 5' to 3' nuclease activity of a nucleic acid polymerase cleaves the oligonucleotide, thus releasing the energy transfer dye conjugate and the quencher from their proximate location and thereby removing or substantially removing the quenching effect (referred to as $ET_2$) on the fluorescence produced by the energy transfer dye conjugate by the quencher. FIG. 7 shows the oligonucleotide probe depicted in FIG. 6 after probe displacement and cleavage (e.g., by a polymerase) of the oligonucleotide 1050. Once the quencher 1060 is displaced and no longer in proximity to acceptor dye 1040 of ET conjugate 1010, the fluorescence signal from acceptor dye 1040 that was previously suppressed by quencher 1060 is restored.

In some embodiments, an oligonucleotide is covalently attached to a first reporter moiety, wherein the reporter moiety is an ET dye conjugate. In some embodiments, the ET dye conjugate comprises a first donor dye and a first acceptor dye. In some embodiments, the first donor dye is a first fluorophore and the acceptor dye is a second fluorophore. In some embodiments, an oligonucleotide comprises a first fluorophore, a second fluorophore, and a first quencher. In some embodiments, the first fluorophore and the second fluorophore are covalently linked by any of the linkers described herein. In some embodiments, the first and second fluorophores are different. In some embodiments, the reporter moiety comprising the first donor dye and the first acceptor dye are located at one terminus of the oligonucleotide and the first quencher moiety is located at the opposite terminus. In some embodiments, the reporter moiety is located within about 5 nucleotides from one terminal end of the oligonucleotide and the first quencher moiety is located within 5 nucleotides from the opposing terminal end of the oligonucleotide. In some embodiments, the reporter moiety is located at or within 5 nucleotides from the 5'-end and the quencher moiety is located at or within 5 nucleotides from the 3'-end of the oligonucleotide. In some embodiments, the reporter moiety is located at or within 5 nucleotides from the 3'-end and the quencher moiety is located at or within 5 nucleotides from the 5'-end of the oligonucleotide.

Quenchers

In some embodiments, a quencher is a derivative of 3- and/or 6-amino xanthenes that are substituted at one or more amino nitrogen atoms by an aromatic or heteroaromatic quenching moiety, Q. In some embodiments, a quencher is a derivative of dabcyl. In some embodiments, a quencher is dabcyl. In some embodiments, a quencher is of the Formula (Q1):

(Q1)

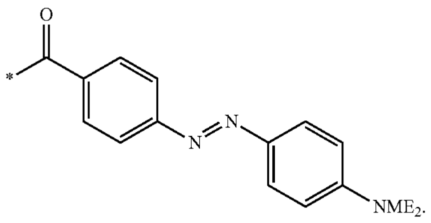

In some embodiments, the described quenching compounds typically have absorption maxima above 530 nm, have little or no observable fluorescence and efficiently quench a broad spectrum of fluorescence, such as is emitted by the fluorophores as disclosed herein. In some embodiments, the quenching compound is a substituted rhodamine. In another embodiment, the quenching compound is a substituted rhodol. In yet another embodiment, the quencher is a chemically reactive compound. Chemically reactive quenching compounds possess utility for labeling a wide variety of substances, including biomolecules, such as nucleic acids. These labeled substances are highly useful for a variety of energy-transfer assays and applications, particularly when used in combination with a fluorophore.

As used herein, each quenching moiety, Q, is an aromatic or heteroaromatic ring system, having 1-4 fused aromatic or heteroaromatic rings, attached to the amino nitrogen by a single covalent bond. Where the Q moiety is fully aromatic and contains no heteroatom, Q comprises 1-4 fused six-membered aromatic rings. Where the Q moiety is heteroaromatic, Q incorporates at least one 5- or 6-membered aromatic heterocycle that contains at least 1 and as many as 4 heteroatoms that are selected from the group consisting of O, N, and S in any combination, that is optionally fused to an additional six-membered aromatic ring, or is fused to one 5- or 6-membered heteroaromatic ring that contains at least 1 and as many as 3 heteroatoms that are selected from the group consisting of O, N, and S in any combination.

In some embodiments, each Q moiety is bound to the xanthene compounds at a 3- or 6-amino nitrogen atom via a single covalent bond. In some embodiments, the amino nitrogen substituents, taken in combination, form a 5- or 6-membered heterocycle that is a piperidine, a morpholine, a pyrrolidine, a pyrazine, or a piperazine, and the Q moiety is fused to the resulting heterocycle adjacent to the xanthene nitrogen, so as to be formally bound to the amino nitrogen via a single bond. The Q moiety may be bound to the amino nitrogen atom at either an aromatic or heteroaromatic ring, provided it is attached at a carbon atom of that ring.

Typically, the Q moieties are substituted or unsubstituted phenyl, naphthyl, anthracenyl, benzothiazole, benzoxazole, or benzimidazole. Where the amino nitrogen substituents form a 5- or 6-membered heterocycle and the Q moiety is fused to the resulting heterocycle, the heterocycle is typically a pyrrolidine ring and the Q moiety is typically a fused six-membered aromatic ring. In some embodiments, Q is a phenyl or substituted phenyl.

In various embodiments, each Q moiety is optionally and independently substituted by hydrogen, halogen, cyano, sulfo, alkali or ammonium salt of sulfo, carboxy, alkali or ammonium salt of carboxy, nitro, alkyl, perfluoroalkyl, alkoxy, alkylthio, amino, monoalkylamino, dialkylamino or alkylamido.

In various embodiments, the quenching compounds have the Formula (Q2)

(Q2)

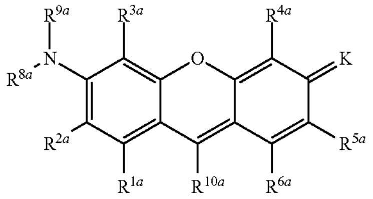

wherein the K moiety is O or $N^+R^{18a}R^{19a}$.

In various embodiments of quenching compounds described herein, at least one of $R^{8a}$, $R^{9a}$, $R^{18a}$, and $R^{19a}$ is a Q moiety. Alternatively, either $R^{8a}$ taken in combination with $R^{9a}$, or $R^{18a}$ taken in combination with $R^{19a}$, forms a saturated 5- or 6-membered heterocycle that is a piperidine, or a pyrrolidine that is fused to a Q moiety. Typically one of $R^{8a}$ and $R^{9a}$ and one of $R^{18a}$ and $R^{19a}$ are each a Q moiety, which are the same or different. In another embodiment, each of $R^{8a}$, $R^{9a}$, $R^{18a}$ and $R^{19a}$ is a Q moiety, which may be the same or different.

The remainder of $R^{8a}$, $R^{9a}$, $R^{18a}$, and $R^{19a}$ are independently H, $C_1$-$C_6$ alkyl, $C_1$-$C_6$ carboxyalkyl, $C_1$-$C_6$ sulfoalkyl, a salt of $C_1$-$C_6$ carboxyalkyl, or a salt of $C_1$-$C_6$ sulfoalkyl, wherein the alkyl portions are optionally substituted by amino, hydroxy, carboxylic acid, a salt of carboxylic acid, or a carboxylic acid ester of a $C_1$-$C_6$ alkyl. Alternatively, where Rea in combination with $R^{9a}$, or $R^{18a}$ in combination with Riga, or both, forms a saturated 5- or 6-membered heterocyclic ring that is a piperidine, a morpholine, a pyrrolidine, a pyrazine, or a piperazine, that is optionally substituted by methyl, sulfonic acid, a salt of sulfonic acid, carboxylic acid, a salt of carboxylic acid, or a carboxylic acid ester of a $C_1$-$C_6$ alkyl. Alternatively, one or more of $R^{8a}$ in combination with $R^{8a}$, $R^{9a}$ in combination with $R^{3a}$, $R^{18a}$ in combination with $R^{4a}$, or $R^{19a}$ in combination with $R^{5a}$, forms a 5- or 6-membered ring that is saturated or unsaturated, and that is optionally substituted by one or more $C_1$-$C_6$ alkyls or $CH_2SO_3X^a$, where $X^a$ is H or a counterion.

In some embodiments, $R^{1a}$ and $R^{6a}$ are H, or one or more of $R^{1a}$ in combination with $R^{2a}$, or $R^{6a}$ in combination with $R^{5a}$, is a fused six-membered aromatic ring.

In some embodiments, substituents $R^{2a}$, $R^{3a}$, $R^{4a}$, and $R^{5a}$ are independently H, F, Cl, Br, I, CN; or $C_1$-$C_{18}$ alkyl, or $C_1$-$C_{18}$ alkoxy, where each alkyl or alkoxy is optionally further substituted by F, Cl, Br, I, a carboxylic acid, a salt of carboxylic acid, or a carboxylic acid ester of a $C_1$-$C_6$ alcohol; or —$SO_3X^a$.

In some embodiments, the pendant group $R^{10a}$ is H, CN, a carboxylic acid, a salt of carboxylic acid, or a carboxylic acid ester of a $C_1$-$C_6$ alcohol. Alternatively $R^{10a}$ is a saturated or unsaturated, branched or unbranched $C_1$-$C_{18}$ alkyl that is optionally substituted one or more times by F, Cl, Br, carboxylic acid, a salt of carboxylic acid, a carboxylic acid ester of a $C_1$-$C_6$ alcohol, —$SO_3X^a$, amino, alkylamino, or dialkylamino, the alkyl groups of which have 1-6 carbons. In another embodiment, $R^{10a}$ has the formula

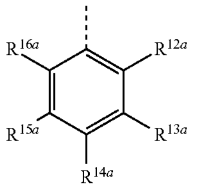

where $R^{12a}$, $R^{13a}$, $R^{14a}$, $R^{15a}$ and $R^{16a}$ are independently H, F, Cl, Br, I, —$SO_3X^a$, a carboxylic acid, a salt of carboxylic acid, CN, hydroxy, amino, hydrazino, azido; or $C_1$-$C_{18}$ alkyl, $C_1$-$C_{18}$ alkoxy, $C_1$-$C_{18}$ alkylthio, $C_1$-$C_{18}$ alkanoylamino, $C_1$-$C_{18}$ alkylaminocarbonyl, $C_2$-$C_{36}$ dialkylaminocarbonyl, $C_1$-$C_{18}$ alkyloxycarbonyl, or $C_7$-$C_{18}$ arylcarboxamido, the alkyl or aryl portions of which are optionally substituted one or more times by F, Cl, Br, I, hydroxy, carboxylic acid, a salt of carboxylic acid, a carboxylic acid ester of a $C_1$-$C_6$ alcohol, —$SO_3X^a$, amino, alkylamino, dialkylamino or alkoxy, the alkyl portions of each having 1-6 carbons. Alternatively, a pair of adjacent substituents $R^{13a}$ and $R^{14a}$, $R^{14a}$ and $R^{15a}$, or $R^{15a}$ and $R^{16a}$, taken in combination, form a fused 6-membered aromatic ring that is optionally further substituted by carboxylic acid, or a salt of carboxylic acid.

The compounds are optionally substituted by a reactive group ($R_x$) or conjugated analyte or substance ($S_c$) that is attached to the compound by a covalent linkage, L, as described in detail above. Typically, the compound is substituted by an -L-$R_x$ or -L-$S_c$ moiety at one or more of $R^{8a}$, $R^{9a}$, $R^{12a}$, $R^{13a}$, $R^{14a}$, $R^{15a}$, $R^{16a}$, $R^{18a}$, or $R^{19a}$, e.g., at one of $R^{12a}$-$R^{16a}$, or at $R^{12a}$, $R^{14a}$ or $R^{15a}$, or as a substituent on a Q moiety. Alternatively, an -L-$R^x$ or -L-$S_c$ moiety is present as a substituent on an alkyl, alkoxy, alkylthio or alkylamino substituent. In some embodiments, exactly one of $R^{8a}$, $R^{9a}$, $R^{12a}$, $R^{13a}$, $R^{14a}$, $R^{15a}$, $R^{16a}$, $R^{18a}$, or $R^{19a}$ is an L $R_x$ or -L-$S_c$ moiety. In another embodiment, exactly one of $R^{12a}$, $R^{13a}$, $R^{14a}$, $R^{15a}$, or $R^{16a}$ is an -L-$R_x$ or -L-$S_c$ moiety. In some embodiments, one of $R^{12a}$, $R^{14a}$, and Rica is an -L-$R_x$ or an -L-$S_c$ moiety.

In embodiments where the K moiety is $N^+R^{18a}R^{19a}$, the compounds are rhodamines, and have the Formula (Q3):

(Q3)

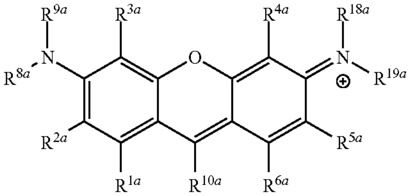

wherein at least one of $R^{8a}$, $R^{9a}$, $R^{18a}$ and $R^{19a}$ is a Q moiety. In some embodiments, at least one of $R^{8a}$ and $R^{9a}$ is a Q moiety and at least one of $R^{18a}$ and $R^{19a}$ is a Q moiety, which may be the same or different.

In embodiments where the K moiety is 0, the compounds are rhodols, and have the Formula (Q4):

(Q4)

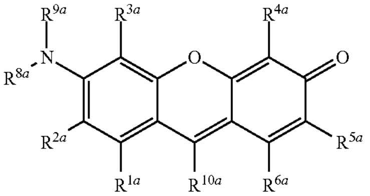

wherein at least one of $R^{8a}$ and $R^{9a}$ is a Q moiety.

In some embodiments, the instant compounds have the Formula (Q5):

(Q5)

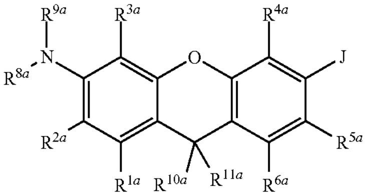

wherein J is O—$R^{7a}$ or $NR^{18a}R^{19a}$ and each of $R^{1a}$-$R^{19a}$ is as defined above.

The precursors to the quenching compounds typically do not function as quenchers unless or until the aromaticity of the ring system is restored, as for the quenching compounds described above. In these precursors $R^{7a}$ is H, $C_1$-$C_6$ alkyl, $C_1$-$C_6$ carboxyalkyl, $C_1$-$C_6$ sulfoalkyl, a salt of $C_1$-$C_6$ carboxyalkyl, or a salt of $C_1$-$C_6$ sulfoalkyl, wherein the alkyl portions are optionally substituted by amino, hydroxy, carboxylic acid, a salt of carboxylic acid, or a carboxylic acid ester of a $C_1$-$C_6$ alkyl. Alternatively, $R^7$ is a monovalent radical formally derived by removing a hydroxy group from a carboxylic acid, a sulfonic acid, a phosphoric acid, or a mono- or polysaccharide, such as a glycoside.

In some embodiments, $R^{10a}$ is as defined previously, and $R^{11a}$ is H, hydroxy, CN or alkoxy having 1-6 carbons. Alternatively, $R^{11a}$ in combination with $R^{11a}$ forms a 5- or 6-membered spirolactone ring, or $R^{11a}$ in combination with $R^{12a}$ forms a 5- or 6-membered spirolactone ring, or a 5- or 6-membered sultone ring.

These precursor compounds are readily converted to the fully conjugated quenching compounds by chemical, enzymatic, or photolytic means. Typically, the colorless precursors are substituted by an -L-$R_x$ moiety, or are conjugated to an analyte or substance ($S_c$).

Exemplary quencher compounds include, but are not limited to, the following:
(Q6)
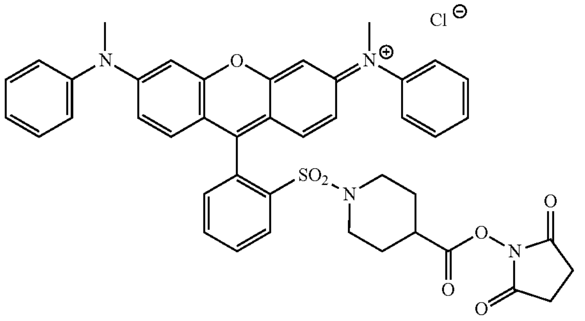
(Q7)
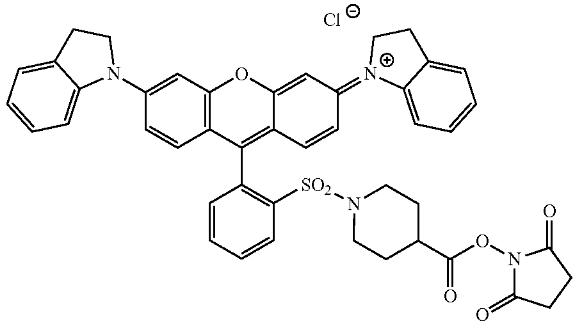
(Q8)
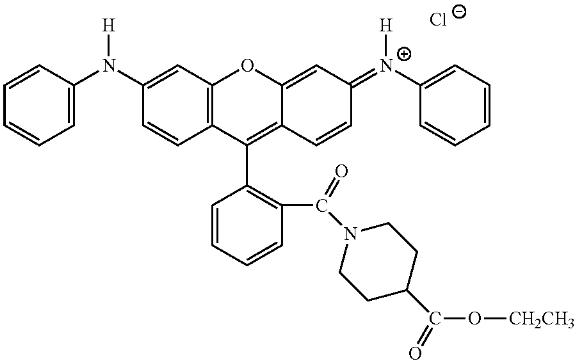
(Q9)
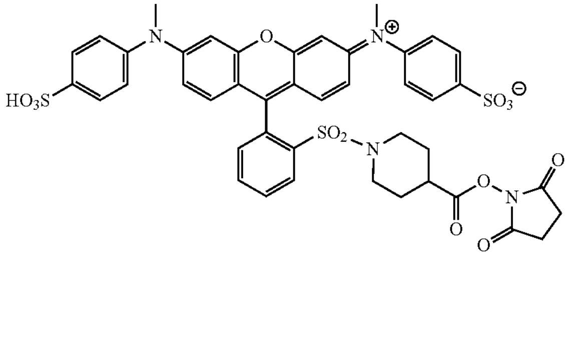
-continued
(Q10)
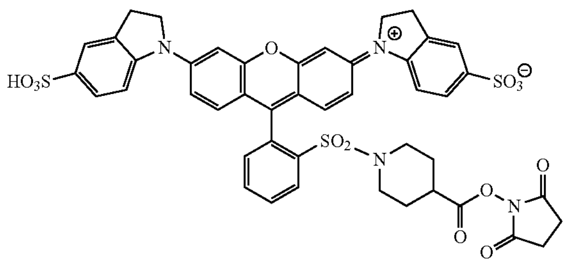
(Q11)
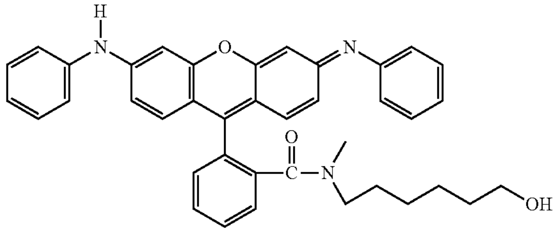
(Q12)
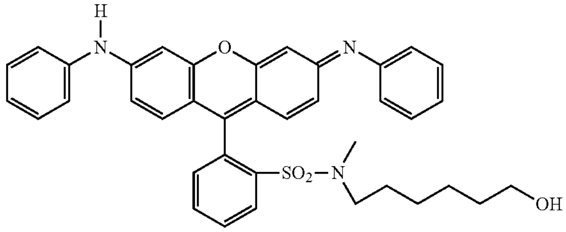
In some embodiments, the quencher is
(Q13)
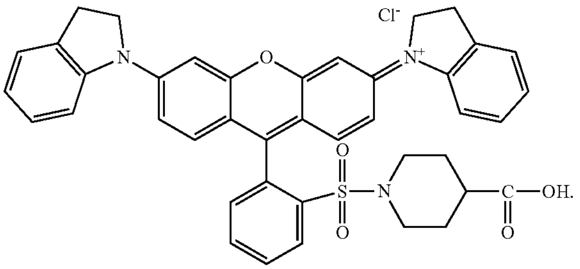
In some embodiments, the quencher includes one or more sulfonate or $SO_3H$ substituents, such as, e.g.,
(Q14)
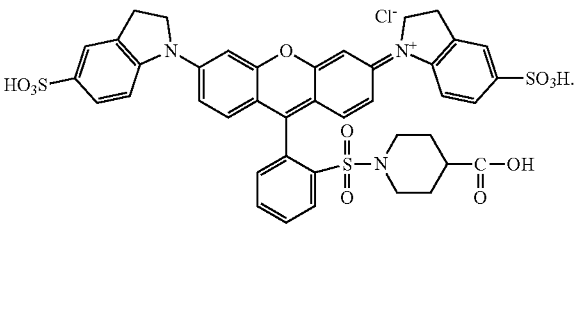

Also provided herein is an oligonucleotide probe coupled to an ET conjugate, as disclosed herein, that is further coupled to a quencher, wherein the quencher is a dibenzoxanthene compound. In certain embodiments, the dibenzoxanthene compound is an imino-dibenzoxanthene compound, such as a substituted 3-imino-3H-dibenzo[c,h]xanthen-11-amine compound.

Specific examples of quenchers that can used to prepare oligonucleotide probes that are coupled to the ET conjugates described herein are provided in Table 2.

TABLE 2

| Examples of Quencher Compounds | | | | | |
|---|---|---|---|---|---|
| Dabcyl | QSY7 | BHQ1 | BBQ | Iowa Black FQ | DYQ-1 |
| Dabsyl | QSY21 | BHQ2 | QC-1 | Iowa Black RQ | DYQ-2 |
| Eclipse | IRDye QC-1 | BHQ3 | DYQ-660 | QYQ-700 | DYQ-3 |

Conjugates of Reactive Compounds

In some embodiments, the compound (quenching compound or precursor compound) is substituted by at least one group -L-$R_x$, where $R_x$ is the reactive group that is attached to the compound by a covalent linkage L, as described in detail above for the dyes. The compounds with a reactive group ($R_x$) label a wide variety of organic or inorganic substances that contain or are modified to contain functional groups with suitable reactivity, resulting in chemical attachment of the conjugated analyte or substance ($S_c$), represented by -L-$S_c$.

In some embodiments, the conjugated analyte or substance ($S_c$) is a natural or synthetic nucleic acid base, nucleoside, nucleotide or a nucleic acid polymer, including those that are protected, or modified to possess an additional linker or spacer for attachment of the compounds, such as an alkynyl linkage, an aminoallyl linkage, or other linkage. In some embodiments, the conjugated nucleotide is a nucleoside triphosphate or a deoxynucleoside triphosphate or a dideoxynucleoside triphosphate.

Exemplary nucleic acid polymer conjugates are labeled, single-, double-, or multi-stranded, natural or synthetic DNA or RNA, DNA or RNA oligonucleotides, or DNA/RNA hybrids, or incorporate an unusual linker such as morpholine derivatized phosphates or peptide nucleic acids such as N-(2-aminoethyl)glycine units. When the nucleic acid is a synthetic oligonucleotide, it typically contains fewer than 50 nucleotides, more typically fewer than 25 nucleotides. Larger nucleic acid polymers are typically prepared from labeled nucleotides or oligonucleotides using oligonucleotide-primed DNA polymerization, such as by using the polymerase chain reaction or through primer extension, or by terminal-transferase catalyzed addition of a labeled nucleotide to a 3'-end of a nucleic acid polymer. Typically, the compound is attached via one or more purine or pyrimidine bases through an amide, ester, ether or thioether bond; or is attached to the phosphate or carbohydrate by a bond that is an ester, thioester, amide, ether or thioether. Alternatively, the compound is bound to the nucleic acid polymer by chemical post-modification, such as with platinum reagents, or using a photoactivatable molecule such as a conjugated psoralen. In some embodiments, the quenching moiety is attached to the nucleotide, oligonucleotide or nucleic acid polymer via a phosphoramidite reactive group, resulting in a phosphodiester linkage.

The quenching compounds can accept energy from a wide variety of fluorophores, provided that the quenching compound and the fluorophore are in sufficiently close proximity for quenching to occur, and that at least some spectral overlap occurs between the emission wavelengths of the fluorophore and the absorption band of the quenching compound. This overlap may occur with emission of the donor occurring at a lower or even higher wavelength emission maximum than the maximal absorbance wavelength of the quenching compound, provided that sufficient spectral overlap exists. In some embodiments, the quenching compound is only dimly fluorescent, or essentially non-fluorescent, so that energy transfer results in little or no fluorescence emission. In one aspect, the quenching compound is essentially non-fluorescent and has a fluorescence quantum yield of less than about 0.05. In another aspect, the quenching compound has a fluorescence quantum yield of less than about 0.01. In yet another aspect, the quenching compound has a fluorescence quantum yield of less than about 0.005.

It should be readily appreciated that the degree of energy transfer, and therefore quenching, is highly dependent upon the separation distance between the reporter moiety (e.g., fluorophore) and the quenching moiety. In molecular systems, a change in fluorescence quenching typically correlates well with a change in the separation distance between the fluorophore molecule and the quenching compound molecule. A fluorophore with sufficient spectral overlap and proximity with a quenching compound is generally a suitable donor for the various applications contemplated herein. The greater the degree of overlap and proximity, the greater the potential for overall quenching.

In some embodiments, the disassembly, cleavage or other degradation of a molecular structure comprising the described fluorophore and quencher is detected by observing the partial or complete restoration of fluorescence of a fluorophore. In some embodiments, the initially quenched fluorescence of a fluorophore associated with the structure becomes dequenched upon being removed from the close proximity to a quenching compound by changes to secondary structure, disassembly, cleavage, or degradation of the molecular structure. The quenching compound is optionally associated with the same molecular structure as the fluorophore, or the donor and acceptor are associated with adjacent but distinct subunits of the structure. The following systems, among others, can be analyzed using the described energy transfer pairs to detect and/or quantify structural disassembly: detection of protease activity using fluorogenic substrates (for example HIV protease assays); detection of enzyme-mediated protein modification (e.g. cleavage of carbohydrates/fatty acids, phosphates, prosthetic groups); immunoassays (via displacement/competitive assays); detection of DNA duplex unwinding (e.g. helicase/topoisomerase/gyrase assays); nucleic acid strand displacement; ds DNA melting; nuclease activity; lipid distribution and transport; and TaqMan assays.

Structure disassembly is typically detected by observing a partial or complete restoration of fluorescence, as a conjugated analyte is exposed to a degradation conditions of interest for a period of time sufficient for degradation to occur. A restoration of fluorescence indicates an increase in separation distance between the fluorophore and quenching compound, and therefore a degradation of the conjugated analyte. Structure changes can be monitored during a biological assay (e.g., using a polymerase or other enzymatic disassembly cleavage mechanism), and the extent of disassembly can provide valuable information about the biological system under study.

Probe

In some embodiments, the energy transfer dye conjugates described herein can be reporter dyes for detection in PCR implementing multiple excitation and multiple emission (i.e., detection) channels, such as those involving excitation at about 480+/−10 nm (blue) and a detection channel at about 587+/−10 nm (yellow/orange), excitation at about 480+/−10 nm (blue) and a detection channel at about 623+/−14 nm (orange/red), excitation at about 550+/−10 nm (green) and a detection channel at about 682+/−14 nm (red), or excitation at about 550+/−10 nm (green) and a detection channel at about 711+/−12 nm (red). In some embodiments, the energy transfer dye conjugates described herein can be reporter dyes for detection in PCR implementing $7^{th}$, $8^{th}$, $9^{th}$, $10^{th}$, etc. reporter dyes. In some embodiments, additional reporter dyes, such as $7^{th}$, $8^{th}$, $9^{th}$, $10^{th}$, etc. reporter dyes, can be provided as a phosphoramidite precursor. It will be appreciated that phosphoramidite precursors of reporter dyes can facilitate synthesis of PCR probes in high quality and at reduced cost. In some embodiments, the described probe(s) are included in a multiplex PCR assay as the higher wavelength, such as 5th, 6th, 7th, 8th, etc., probes. In some embodiments, the assay can also include probes having dye/quencher combinations where the quencher can be any of those known to those of skill in the art, include, for example Dabcyl, Dabsyl, Eclipse™ Quencher, QSY7, QSY21, and Black Hole Quenchers 1, 2, and 3 (see also Table 2 for additional examples). In some embodiments, the described probes include a minor groove binder (MGB) moiety at the 3' end that increases the melting temperature (Tm) of the probe and stabilizes probe-target hybrids. In some embodiments, the use of a MGB or a locked nucleic acid (LNA) in the probe allows the probe to be shorter than traditional probes, which can provide better sequence discrimination and flexibility to accommodate more targets.

In some embodiments, the described probe comprises one of the energy transfer dye conjugates as described herein (as the fluorophore) and one of the quenchers described herein, where the fluorophore and the quencher are each covalently conjugated to an oligonucleotide. Examples of probes suitable for multiplex PCR applications can include an energy transfer dye conjugate, as described herein, that emits in the spectral region for detection in one or more emission channels of a PCR instrument that includes multiple excitation and emission channels. In some embodiments, such a probe comprising an energy transfer dye conjugate as described herein is a detector probe which can be used for the detection of a complementary target nucleic acid molecule.

The described probe can be synthesized according to methods known in the art. For example, in some embodiments, the fluorophore and the quencher are covalently conjugated to the termini of an oligonucleotide using the conjugation chemistries and reactive groups described above. In another example, the quencher or probe may be conjugated to a solid support and the oligonucleotide is synthesized from the attached quencher or probe using standard oligonucleotide synthesis methods, such as a DNA synthesizer, and then the other of the quencher or probe is covalently attached to the terminus of the synthesized oligonucleotide.

Methods and Kits

Figure 21:
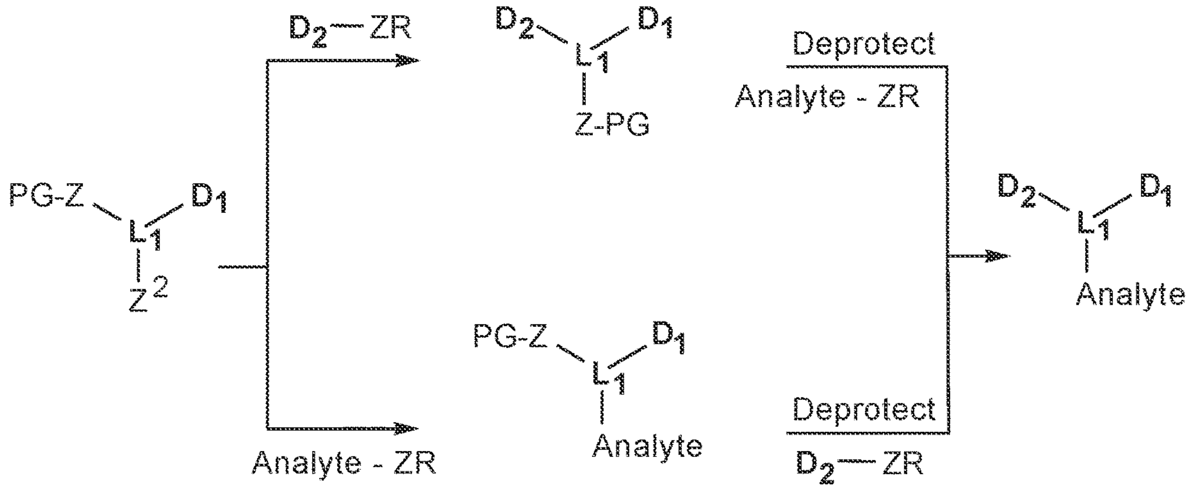
FIG. 21 is a reaction scheme (Scheme 1) for preparing an energy transfer dye conjugate with a linker $L_1$, where $D_1$ and $D_2$ refer to Dye 1 and Dye 2, respectively.
Figure 22:
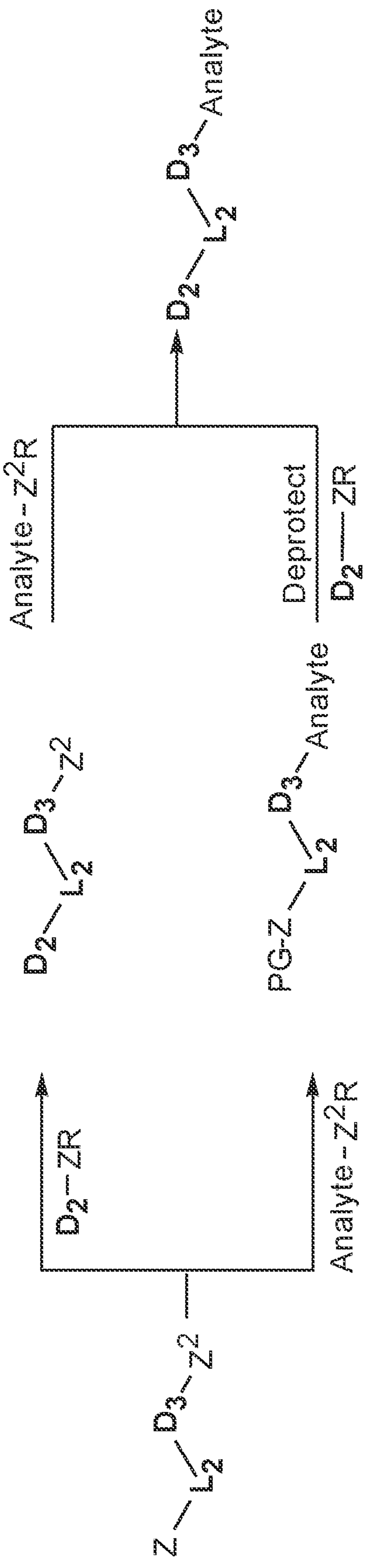
FIG. 22 is a reaction scheme (Scheme 2) for preparing an energy transfer dye conjugate with a linker $L_2$, where $D_2$ and $D_3$ refer to Dye 2 and Dye 3, respectively.
Figure 23:
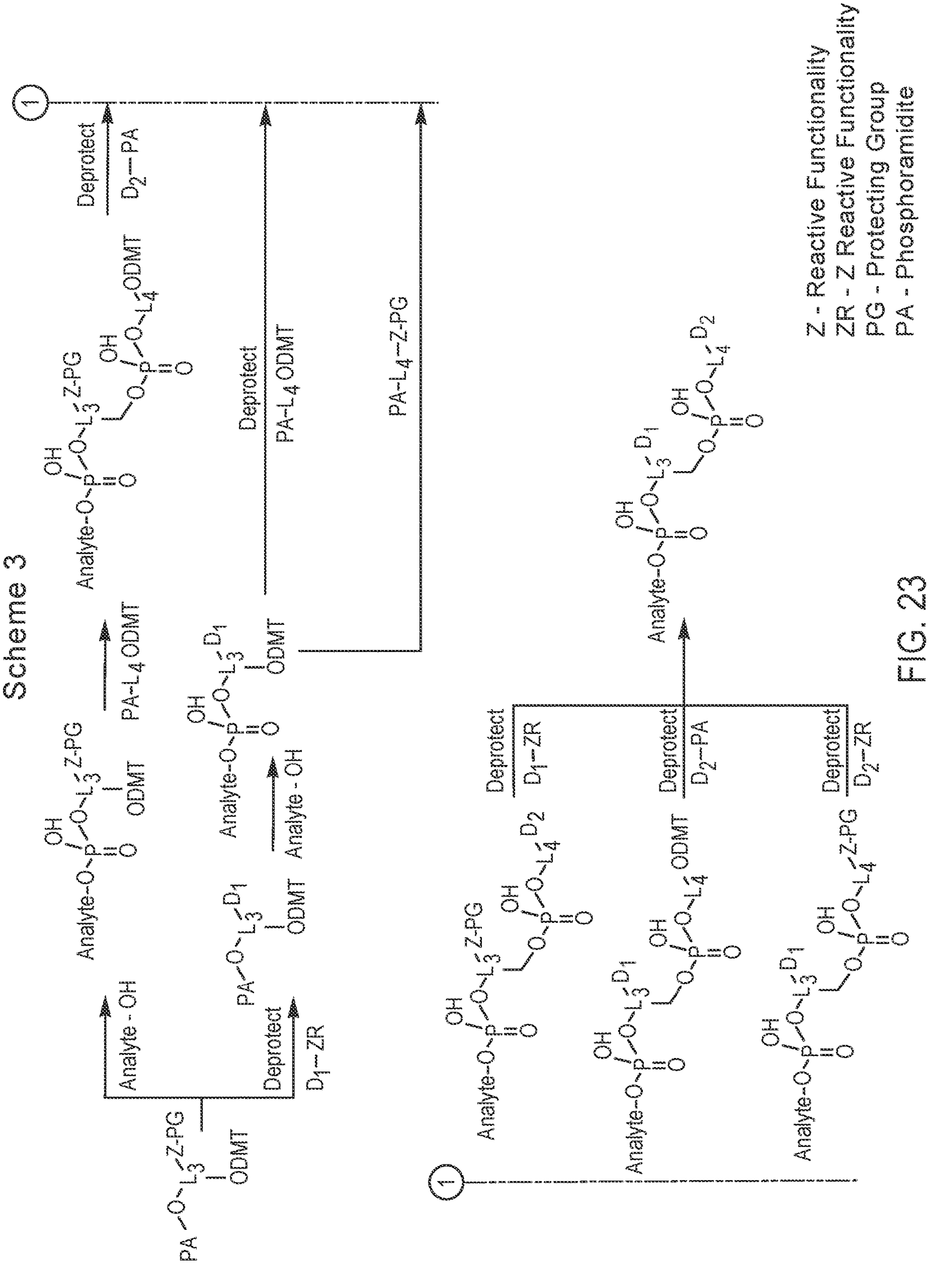
FIG. 23 is a reaction scheme (Scheme 3) for preparing an energy transfer dye conjugate with two linkers, $L_3$ and $L_4$, where $D_1$ and $D_2$ refer to Dye 1 and Dye 2, respectively.
Figure 24:
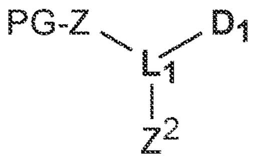
FIG. 24 is a listing of precursors containing a linker and energy transfer dye conjugates prepared using each type of precursor.
Figure 24:
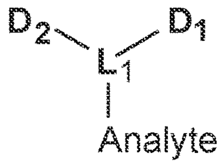
Figure 24:
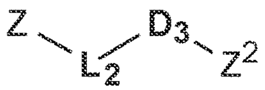
Figure 24:
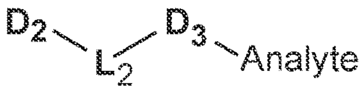
Figure 24:
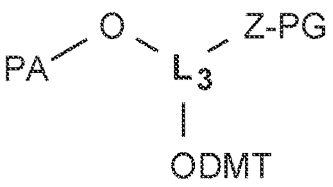
Figure 24:
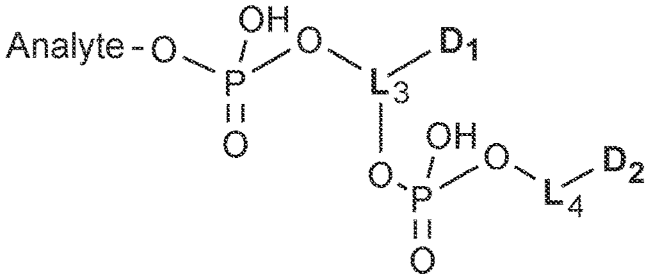
Figure 25:
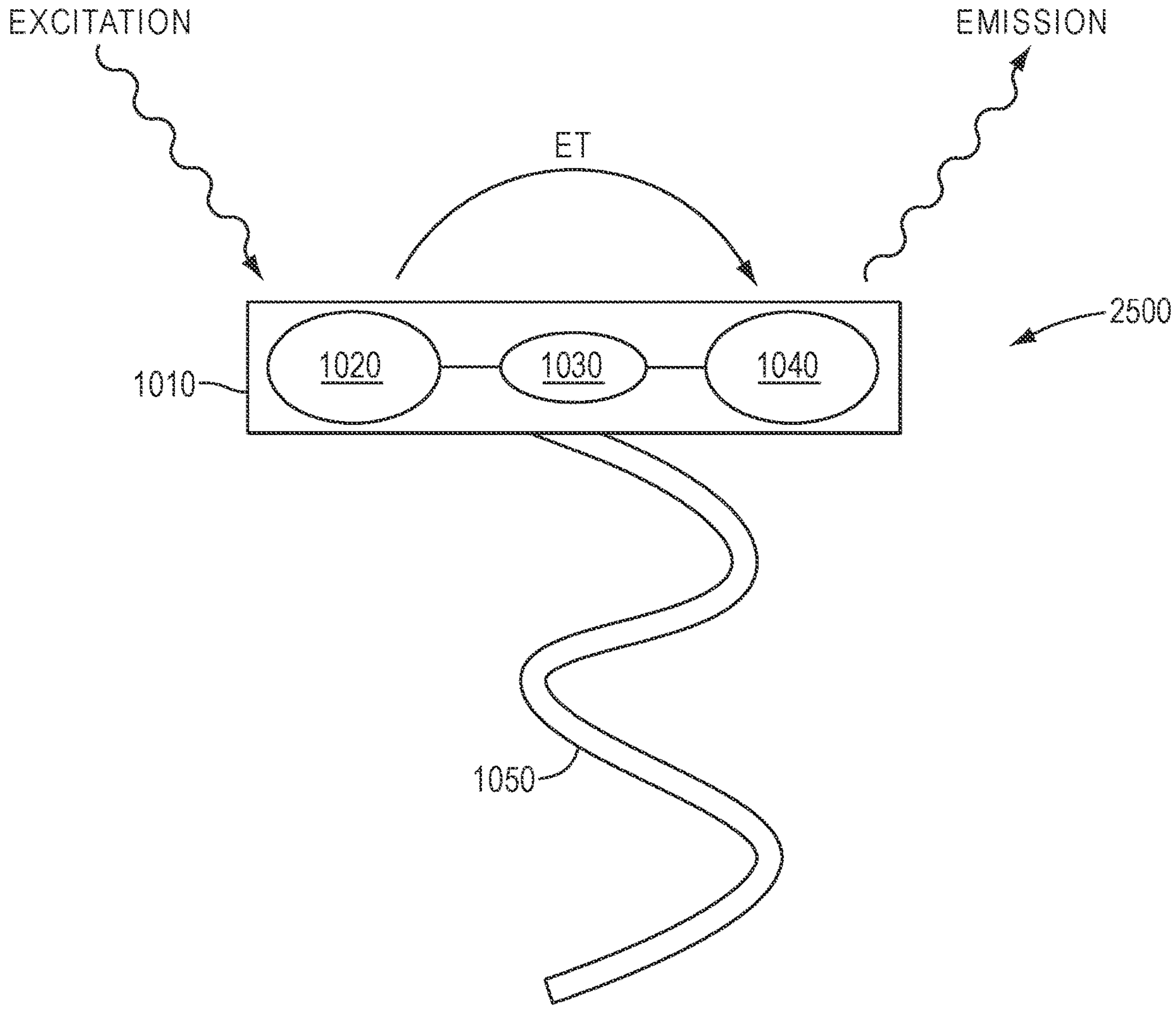
FIG. 25 is a diagram of an energy transfer conjugate attached to an oligonucleotide probe.
Figure 26A:
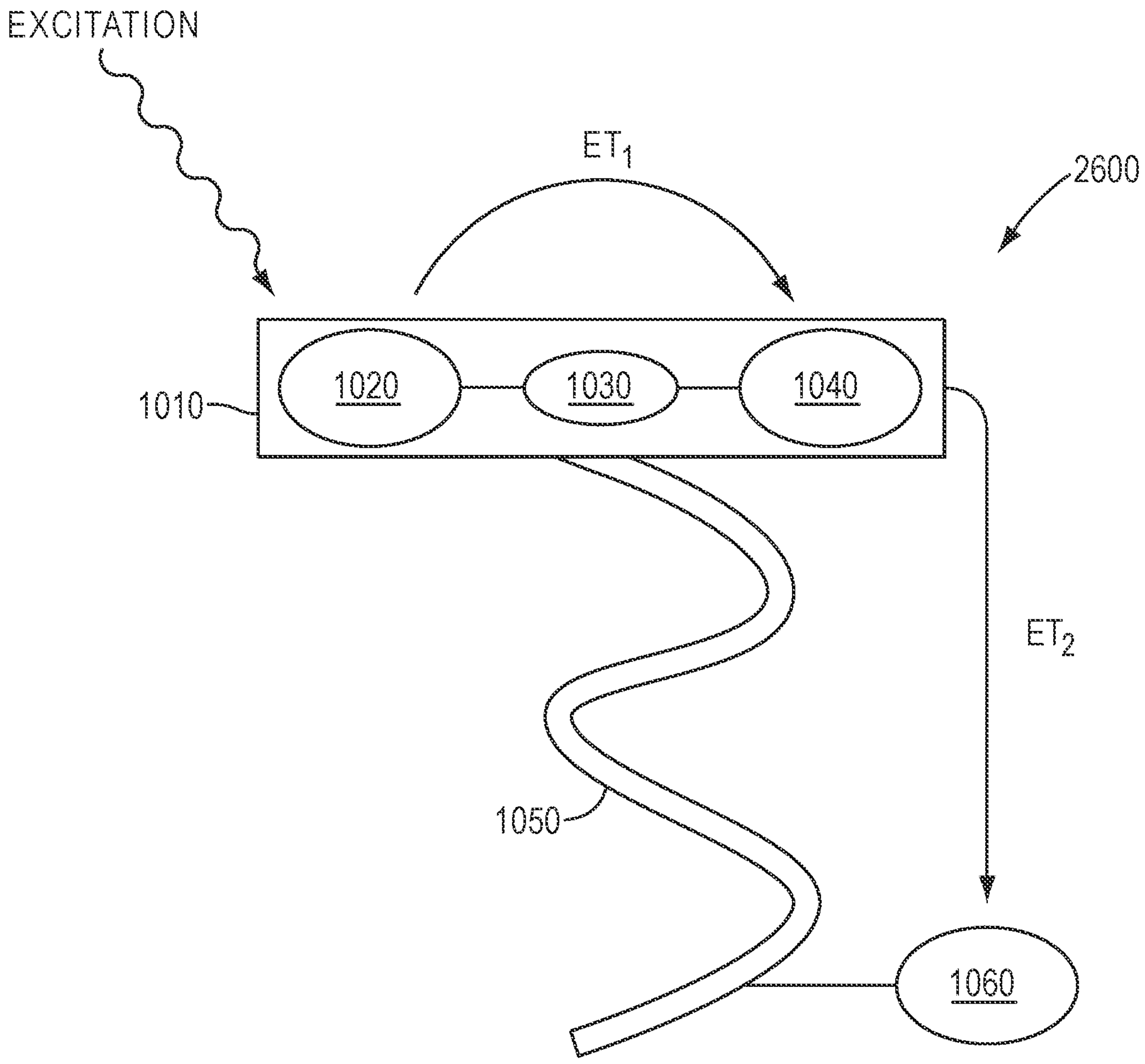
FIG. 26A is a diagram of an energy transfer conjugate attached to an oligonucleotide probe, where the probe is attached to a quencher.
Figure 26B:
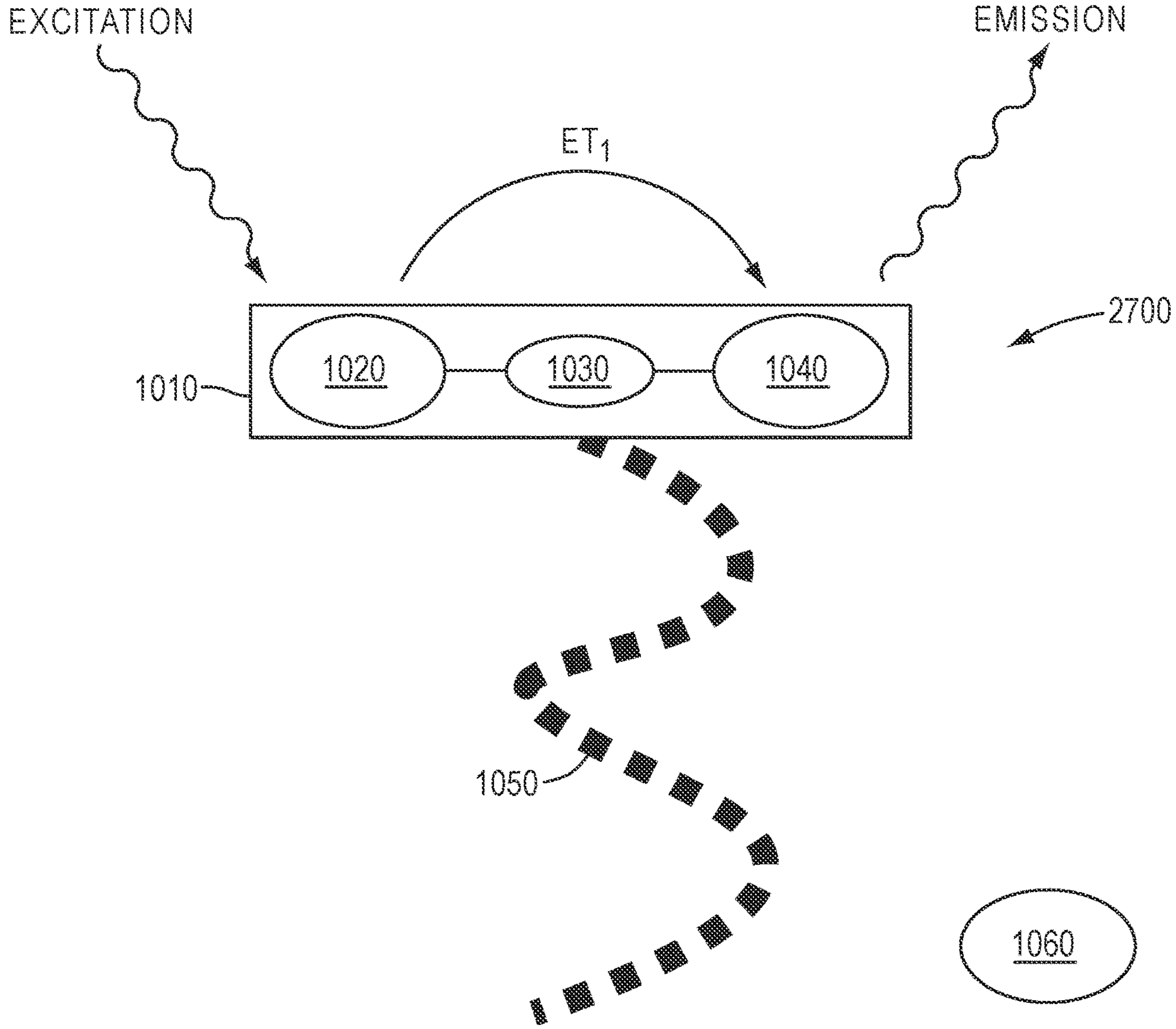
FIG. 26B is a diagram of the energy transfer conjugate of FIG. 26A after displacement and cleavage of the oligonucleotide probe during a qPCR reaction.

Also provided herein are methods of making energy transfer conjugates and linking of such conjugates to biological molecules (e.g., oligonucleotides). Examples of synthetic routes for preparing energy transfer conjugates including linkers $L_1$-$L_4$ are depicted in FIG. 21, FIG. 22, and FIG. 23. The present disclosure provides reagents that can be used to chemically synthesize oligonucleotides linked to an ET conjugate. In certain embodiments, the unique linker strategies described herein allow for attachment of an ET conjugate to an oligonucleotide using automated solid phase synthesis techniques that are well-known in the art and can be purified without the use of HPLC.

Also provided herein are methods for using the fluorescent energy transfer conjugates in biological assays and kits for performing such assays. For example, the energy transfer dye conjugates provided herein can be used in real-time and end-point PCR assays. Fluorescent ET conjugates can be prepared that can be excitable and emit across a wide range of wavelengths. By adjusting the type and length of linker between donor dye, acceptor dye and analyte, the optical properties of the resulting conjugate can be tuned to offer precise excitation and emission profiles. Because the conjugates can be tailored to suit the desired excitation and emission profile, the conjugates are particularly useful in the construction of oligonucleotide probes for use in multiplex biological assays (e.g., qPCR assays), either alone or in combination with one or more other fluorophores.

Thus, in another aspect, ET transfer dye conjugates described herein can be used in the practice of multiplex assays. Any fluorescent ET conjugate with the appropriate excitation and emission profile can be used in the practice of such multiplex assays. Various manufacturers provide instruments capable of detecting multiplex PCR assays. As one example, Thermo Fisher Scientific (Waltham, MA) provides 4-plex TaqMan assays for real time detection of nucleic acids targets on Thermo Fisher Scientific instruments, such as, Vii7, Quant Studio, and the like, where certain real time qPCR instruments have the optical capability to run up to a 6-plex TaqMan assay.

The unique ET conjugates provided herein allow for expansion of qPCR assays beyond 6-plex, e.g., 7-plex, 8-plex, 9-plex, 10-plex, etc Thus, in a further aspect, methods of performing singleplex or multiplex PCR, such as qPCR or end-point PCR, using the described ET conjugates are provided. End point PCR is the analysis after all cycles of PCR are completed. Unlike qPCR, which allows quantification as template is doubling (exponential phase), end point analysis is based on the plateau phase of amplification.

In particular, a method for amplifying and detecting multiple target DNA sequences comprising providing a composition or reaction mixture comprising the described probe, subjecting the reaction mixture to a thermocyling protocol such that amplification of said multiple target sequences can take place, and monitoring amplification by detecting the fluorescence of the described probe at least once during a plurality of amplification cycles. In some embodiments, the method comprises a 5-plex or 6-plex multiplex qPCR assay where the described probes allow for detection of the 5th and/or 6th nucleic acid target. In some embodiments, the method comprises a 7-plex or 8-plex multiplex qPCR assay where the probes use the ET reporters described herein that allow for detection of the 7th and/or 8th nucleic acid targets. In some embodiments, the method comprises a 9-plex or 10-plex multiplex qPCR assay where the described probes allow for detection of the 9 or 10 nucleic acid targets. ET conjugates described herein can be used in higher order multiplex assays. For example, multiplex assays for evaluation of 6-20 (e.g., 6, 7, 8, 9, 10, 11, 12, 13, 14, 15, 16, 17, 18, 19, and 20) or more nucleic acid targets can be facilitated using the ET conjugates described herein. In some embodiments, the method comprises up to a 6-plex multiplex qPCR assay where the described probes allow for detection of 6 nucleic acid targets. In some embodiments, the method comprises up to a 10-plex multiplex qPCR assay where the described probes allow for detection of 10 nucleic acid targets. In some embodiments, the method comprises up to a 20-plex multiplex qPCR assay where the described probes allow for detection of 20 nucleic acid targets. In some embodiments, the method comprises enough assays for a 5-plex up to a 30-plex multiplex qPCR assay (or any plexy in between) where the described probes are provided in a manner that allows for detection of between 5 to 30, or any number in between, nucleic acid targets.

The ET transfer dye conjugate described herein can be used in the practice of multiplex assays. Any fluorescent ET conjugate with the appropriate excitation and emission profile can be used in the practice of such multiplex assays. In certain embodiments, the donor dye has an excitation maximum from about 450 nm to about 580 nm, and the acceptor dye has an emission maximum from about 580 nm to about 750 nm. Representative examples of donors and reporters that can be used to prepare ET dye conjugates using the linkers described herein for use in the practice of a multiplex qPCR assay, with their associated excitation and emission wavelengths, are shown in Table 3

TABLE 3

Examples of Donor and Reporter Dyes

| Excitation (nm) | Emission (nm) | Donor Dye | Acceptor Dye | Example Dyes |
|---|---|---|---|---|
| 480 +/− 10 | 587 +/− 10 | Fluorescein, Rhodamine | Rhodamine, Cyanine | FAM-TAMRA, FAM-ABY, FAM-NED |
| 480 +/− 10 | 623 +/− 14 | Fluorescein, Rhodamine | Rhodamine, Cyanine | FAM-PET, FAM-ROX, FAM-JUN, FAM-Texas Red, TET-Alexa Fluor 594 |
| 480 +/− 10 | 682 +/− 14 | Fluorescein, Rhodamine | Cyanine, Pyronine | FAM-AF647 |
| 480 +/− 10 | 711 +/− 12 | Fluorescein, Rhodamine | Cyanine | FAM-AF676 |
| 550 +/− 10 | 682 +/− 14 | Fluorescein, Rhodamine | Cyanine, Pyronine | ABY-Alexa Fluor 647, NED-Alexa Fluor 647, ABY-Cy5 ®, ABY-ATTO 647 ™, ABY-DyLight 650 ™ |
| 550 +/− 10 | 711 +/− 12 | Fluorescein, Rhodamine | Cyanine | ABY-Alexa Fluor 676, NED-Alexa Fluor 676, NED DyLight 680 ™, NED-Cy5.5 ® |
| 580 +/− 10 | 711 +/− 12 | Fluorescein, Rhodamine | Cyanine | JUN-AF676 |

An appropriate linker can be chosen to maximize energy transfer efficiency between the donor dye and the acceptor dye. In certain embodiments, the donor dye is a fluorescein or rhodamine dye covalently linked through a linker having the structure (LI) to a rhodamine acceptor dye, pyronine or cyanine acceptor dye. In yet other embodiments, the donor dye is a fluorescein or rhodamine dye covalently linked through a linker having the structure (LII) to a rhodamine, pyronine or cyanine acceptor dye. In yet other embodiments, the donor dye is a fluorescein or rhodamine dye covalently linked through a linker having the structure (LIII) to a rhodamine acceptor dye. In yet other embodiments, the donor dye is a fluorescein or rhodamine dye covalently linked through a linker having the structure (LIII) to a pyronine or cyanine acceptor dye. In any of these embodiments, linker (LI), (LII), or (LIII) can be the donor and acceptor dye can be further linked to an analyte (e.g., an oligonucleotide or a protein).

The detection of the signal may be accomplished using any reagents or instruments that detect a change in fluorescence from a fluorophore. For example, detection may be performed using any spectrophotometric thermal cycler. Examples of spectrophotometric thermal cyclers include, but are not limited to, Applied Biosystems (AB) PRISM® 7000, AB 7300 real-time PCR system, AB 7500 real-time PCR system, AB PRISM® 7900HT, Bio-Rad Cycler IQ™, Cepheid SmartCycler® II, Corbett Research Rotor-Gene 3000, Idaho Technologies R.A.P.I.D.™, MJ Research Chromo 4™, Roche Applied Science LightCycler®, Roche Applied Science LightCycler®2.0, Stratagene Mx3000P™, and Stratagene Mx4000™.

Representative examples of dyes that can used to expand the dye set to beyond 10-plex include without limitation: the donor dye is Coumarin 343 and the acceptor dye is FAM. In some embodiments, the donor dye is ATTO 425 (ATTO-Tec, GmbH) and the acceptor dye is FAM. In some embodiments, the donor dye is Pacific Blue (Thermo Fisher Scientific) and the acceptor dye is FAM. In some embodiments, the donor dye is ATTO 425 and the acceptor dye is FAM. In some embodiments, the donor dye is ALEXA FLUOR 405 and the acceptor dye is FAM. In some embodiments, the donor dye is Coumarin 343 and the acceptor dye is VIC. In some embodiments, the donor dye is ATTO 425 and the acceptor dye is VIC. In some embodiments, the donor dye is Pacific Blue and the acceptor dye is VIC. In some embodiments, the donor dye is ATTO 425 and the acceptor dye is VIC. In some embodiments, the donor dye is Alexa Fluor 405 and the acceptor dye is VIC. Similarly, the dye matrix can be expanded to include reporter dyes that include an acceptor that emits above the m6 emission channel, such as cyanine dyes such as Cy 7 (GE Healthcare), azaindoline cyanine dyes, Alexa Fluor 750, or a silylrhodamine. In certain embodiments, the donor dye is a rhodamine or a cyanine dye, and the reporter dye is a cyanine dye (e.g., an azaindoline cyanine) that emits in the far-red or near-IR region of the spectrum.

The nucleic acid target(s) of the described method may be any nucleic acid target known to the skilled artisan. Further, the targets may be regions of low mutation or regions of high mutation. For example, one particularly valuable use of the methods disclosed herein involves targeting highly mutated nucleic acids, such as RNA viral genes, or regions of high genetic variability, such a single nucleotide polymorphisms (SNPs). In some embodiments, the targets may be fragmented or degraded, such as material from forensic samples and/or fixed (e.g., by formalin) tissues. The targets may be any size amenable to amplification. One particularly valuable use of the methods and compositions provided herein involves the identification of short fragments, such as siRNA and miRNA. Another particularly valuable use is for samples that may have fragmented and/or degraded nucleic acid, such as fixed samples or samples that have been exposed to the environment. Thus, the methods may be used to biopsy tissues and forensic DNA samples for example. The targets may be purified or unpurified. The targets may be produced in vitro (for example, a cDNA target) or can be found in biological samples (for example, an RNA or a genomic DNA (gDNA) target). The biological sample may be used without treatment or the biological samples may be treated to remove substances that may interfere with the methods disclosed herein.

Samples in which nucleic acid targets may exist include, for instance, a tissue, cell, and/or fluid (e.g., circulating, dried, reconstituted) sample obtained from a mammalian or non-mammalian organism (e.g., including but not limited to a plant, virus, bacteriophage, bacteria, and/or fungus). In some embodiments, the sample may be derived from, for example, mammalian saliva, buccal epithelial cells, cheek tissue, lymph, cerebrospinal fluid, skin, hair, blood, plasma, urine, feces, semen, a tumor sample (e.g., cancer cells/tissue), cultured cells, and/or cultured tumor cells. The target polynucleotide may be DNA in genomic form, or it may be cloned in plasmids, bacteriophage, bacterial artificial chromosomes (BACs), yeast artificial chromosomes (YACs), and/or other vectors. Other types of samples may also be useful in the methods described herein which may be related, for example, to diagnostic or forensic assays. In some embodiments, the probes described herein may be used for detection of viral DNA sequences.

The probes provided herein may be used in methods of diagnosis, e.g., SNP detection, identification of specific biomarkers, etc., whereby the probes are complementary to a sequence (e.g., genomic) of an infectious disease agent, e.g., of human disease including but not limited to viruses, bacteria, parasites, and fungi, thereby diagnosing the presence of the infectious agent in a sample having nucleic acid from a patient. The target nucleic acid may be a genomic DNA (gDNA), cDNA, or RNA, such as mRNA, siRNA, or miRNA; or synthetic DNA, human or animal; or of a microorganisms, etc. In other embodiments, the probes may be used to diagnose or prognose a disease or disorder that is not caused by an infectious agent. For example, the probes may be used to diagnose or prognose cancer, autoimmune diseases, mental illness, genetic disorders, etc. by identifying the presence of an infective agent, such as a virus, or a host, a mutation, polymorphism, or allele in a sample from a human or animal. In some embodiments, the probe comprises the mutation or polymorphism. Additionally, the probes may be used to evaluate or track progression of treatment for an infection, a disease or disorder.

Also provided are compositions, such as a reaction mixture or master mix, comprising the described probe. In some embodiments, the composition for PCR, such as for real-time or quantitative PCR or end-point PCR, comprises at least one of the described probes. In some embodiments, the composition or reaction mixture or master mix for PCR (e.g., qPCR or end-point PCR) comprises probes for allowing for detection of at least 4 target nucleic acids and the described probe(s) allowing for detection of at least one of a 5th and/or a 6th target nucleic acid, at least one of the described probes consisting of an ET donor dye and an ET acceptor dye, where the fluorophore has an emission maximum between about 650 and 720 nm. The absorbance maximum of the acceptor as described herein is between 660-668 nm. The absorbance range of the quencher as described herein is 530-730 nm. In an alternate embodiment, labeling reagents are provided for conjugating the described fluorophore and quencher to an oligonucleotide of choice.

In addition, such a composition or reaction mixture or master mix may comprise one or several compounds and reagents selected from the following list: Buffer, applicable for a polymerase chain reaction, deoxynucleoside triphosphates (dNTPs), DNA polymerase having 5' to 3' exonuclease activity, at least one pair or several pairs of amplification primers and/or additional probes, a uracil DNA glycosylase, PCR inhibitor blocking agents (such as a combination of a gelatin and albumin mixture), a hot start component and/or modification, at least one salt, such as magnesium chloride and/or potassium chloride, a reference dye, and at least one detergent. Other compounds and reagents suitable for inclusion in the compositions, reaction mixtures, and master mixes as disclosed herein may be contemplated by those of skill in the art.

In some embodiments, the compositions or master mixes as described herein can comprise components, including probes as described herein, that are appropriate for lyophilization (e.g., "lyo-ready"), are already in lyophilized form, and/or are otherwise stabilized (e.g., freeze-dried), dried down, or prepared as an evaporated composition or component.

In certain embodiments, kits are provided that may be used to carry out hybridization, extension and amplification reactions using the oligonucleotides provided herein. Preferred kits may comprise one or more containers, such as vials, tubes and the like, configured to contain the reagents used in the methods described herein and optionally may contain instructions or protocols for using such reagents. The kits described herein may comprise one or more components selected from the group consisting of one or more oligonucleotides described herein, including but not limited to, one or more probes described herein, and a polymerase. In other embodiments, the kits may also include one or more primers.

In yet another aspect, a kit comprising at least one of the described probe(s) is provided. In addition, a kit may comprise one or several other compounds and reagents selected from the following list: Buffer, applicable for a polymerase chain reaction, deoxynucleoside triphosphates (dNTPs), DNA polymerase having 5' to 3' exonuclease activity, at least one or multiple pairs of amplification primers. The kit may also comprise an internal control DNA or standard. Each of the components disclosed above may be stored in a single storage vessel and packaged separately or together. Yet, any combination of components for storage within the same vessel is possible as well. In some embodiments, the probe(s) and/or other components included in the kit may be lyophilized or otherwise stabilized for storage and/or shipment, and reconstituted as desired by the user. Instructions for use of the kit can also be included.

Another aspect provided herein is a method of detecting or quantifying a target nucleic acid molecule in a sample by polymerase chain reaction (PCR), such as by quantitative real-time polymerase chain reaction (qPCR). In some embodiments, the method includes: (i) contacting a sample comprising one or more target nucleic acid molecules with a) at least one probe, such as those described herein, being sequence specific for the target nucleic acid molecule, where the at least one probe undergoes a detectable change in fluorescence upon amplification of the one or more target nucleic acid molecules; and with b) at least one oligonucleotide primer pair; (ii) incubating the mixture of step (i) with a DNA polymerase under conditions sufficient to amplify one or more target nucleic acid molecules; and (iii) detecting the presence or absence or quantifying the amount of the amplified target nucleic acid molecules by measuring fluorescence of the probe. In some embodiments, the probe is a hydrolysis probe, such as a TaqMan probe.

Another aspect provided herein is a kit for PCR, such as quantitative real-time polymerase chain reaction (qPCR). In some embodiments the kit includes a probe, such as those described herein, instructions for conducting the PCR, and one or more of the following: a buffering agent, deoxynucleotide triphosphates (dNTPs), an organic solvent, an enzyme, enzyme cofactors, and an enzyme inhibitor. In yet further aspects provided herein are compositions, such as a "master mix" for PCR comprising the described probe along with other components that are used in PCR. The term "amplification reaction mixture" and/or "master mix" as used herein refers to an aqueous solution comprising the various (some or all) reagents used to amplify a target nucleic acid. Such reactions may also be performed using solid supports (e.g., an array). The reactions may also be performed in single or multiplex format as desired by the user. These reactions typically include enzymes, aqueous buffers, salts, amplification primers, target nucleic acid, and nucleoside triphosphates. Depending upon the context, the mixture can be either a complete or incomplete amplification reaction mixture. The method used to amplify the target nucleic acid may be any available to one of skill in the art. Any in vitro means for multiplying the copies of a target sequence of nucleic acid may be utilized. These include linear, logarithmic, and/or any other amplification method. While this disclosure may generally discuss PCR as the nucleic acid amplification reaction, it is expected that the modified detergents describe herein should be effective in other types of nucleic acid amplification reactions, including both polymerase-mediated amplification reactions (such as helicase-dependent amplification (HDA), recombinase polymerase amplification (RPA), and rolling circle amplification (RCA)), as well as ligase-mediated amplification reactions (such as ligase detection reaction (LDR), ligase chain reaction (LCR), and gap-versions of each), and combinations of nucleic acid amplification reactions such as LDR and PCR (see, for example, U.S. Pat. No. 6,797,470). For example, the modified detergents may be used in, for example, various ligation-mediated reactions, where for example ligation probes are employed as opposed to PCR primers. Additional exemplary methods include polymerase chain reaction (PCR; see, e.g., U.S. Pat. Nos. 4,683,202; 4,683,195; 4,965,188; and/or 5,035,996), isothermal procedures (using one or more RNA polymerases (see, e.g., PCT Publication No. WO 2006/081222), strand displacement (see, e.g., U.S. Pat. No. RE39007E), partial destruction of primer molecules (see, e.g., PCT Publication No. WO 2006/087574)), ligase chain reaction (LCR) (see, e.g., Wu, et al., Genomics 4: 560-569 (1990)), and/or Barany, et al. Proc. Natl. Acad. Sci. USA 88:189-193 (1991)), Q~ RNA replicase systems (see, e.g., PCT Publication No. WO 1994/016108), RNA transcription-based systems (e.g., TAS, 3SR), rolling circle amplification (RCA) (see, e.g., U.S. Pat. No. 5,854,033; U.S. Patent Application Publication No. 2004/265897; Lizardi et al. Nat. Genet. 19: 225-232 (1998); and/or Barrer et al. Nucleic Acid Res., 26: 5073-5078 (1998)), and strand displacement amplification (SDA) (Little, et al. Clin. Chem. 45:777-784 (1999)), among others. These systems, along with the many other systems available to the skilled artisan, may be suitable for use in polymerizing and/or amplifying target nucleic acids for use as described herein.

In some embodiments, the master mix is prepared such that it requires less than a 3× dilution prior to use in PCR, e.g., 2× dilution, 1.5× dilution, 1.2× dilution, etc. In some embodiments, the compositions or master mixes as described herein include stabilizing components or are able to be processed to provide stabilization for storage and/or shipment. For example, the master mixes can be prepared as compositions that are stable for approximately two years at −20 °C; approximately one year at 4 °C; approximately three to six months at room temperature; and/or approximately one to two months at a temperature higher than room temperature. In some embodiments the compositions or master mixes provided herein are dry (e.g., lyophilized) or in a solution of water or TE buffer. Kits, described herein, may also include a buffer or the like for reconstitution of lyophilized or otherwise stabilized compositions (e.g., by addition of water or a buffer such as TE or Tris.

Polymerases

As disclosed herein, the compositions, reaction mixtures and kits can also comprise at least one polymerase (e.g., a DNA polymerase) and at least one source of nucleotides (e.g., dNTPs). The polymerase can be a DNA polymerase with 5' to 3' exonuclease activity. In some embodiments, the polymerase can be a "thermostable polymerase," which refers to an enzyme that is heat-stable, heat-resistant, and/or not irreversibly inactivated when subjected to elevated temperatures for the time necessary to effect destabilization of single-stranded nucleic acids or denaturation of double-stranded nucleic acids during amplification (e.g., will not irreversibly denature at about 90° to about 100 °C under conditions such as is typically required for amplification (e.g., in a polymerase chain reaction (PCR)) and catalyzes polymerization of deoxyribonucleotides to form primer extension products that are complementary to a target polynucleotide strand. Thermostable polymerases may be obtained, for example, from a variety of thermophilic bacteria that are publically available (for example, from American Type Culture Collection, Rockville, Md.) using methods that are well-known to one of ordinary skill in the art (See, e.g., U.S. Pat. No. 6,245,533). Bacterial cells may be grown according to standard microbiological techniques, using culture media and incubation conditions suitable for growing active cultures of the particular species that are well-known to one of ordinary skill in the art (See, e.g., Brock, T. D., and Freeze, H., J. Bacteriol. 98(1):289-297 (1969); Oshima, T., and Imahori, K, Int. J. Syst. Bacteriol. 24(1): 102-112 (1974)). Suitable for use as sources of thermostable polymerases are the thermophilic bacteria *Thermus aquaticus, Thermus thermophilus, Thermococcus litoralis, Pyrococcus furiosus, Pyrococcus woosii*, and other species of the *Pyrococcus* genus, *Bacillus stearothermophilus, Sulfolobus acidocaldarius, Thermoplasma acidophilum, Thermus flavus, Thermus ruber, Thermus brockianus, Thermotoga neapolitana, Thermotoga maritima*, and other species of the *Thermotoga* genus, and *Methanobacterium* thermoautotrophicum, and mutants of each of these species. Exemplary thermostable polymerases can include, but are not limited to, any of the SuperScript, Platinum, TaqMan, MicroAmp, AmpliTaq, and/or fusion polymerases. Exemplary polymerases can include but are not limited to (*Thermus aquaticus*) Taq DNA polymerase, AmpliTaq™ DNA polymerase, AmpliTaq™ Gold DNA polymerase, DreamTaq™ DNA Polymerase, recombinant, modified form of the (*Thermus aquaticus*) Taq DNA polymerase gene expressed in *E. coli* (Thermo Fisher Scientific), iTaq™ (Bio-Rad), Platinum Taq DNA Polymerase High Fidelity, Platinum™ II Taq™ Hot-Start DNA Polymerase, Platinum SuperFi DNA Polymerase, AccuPrime Taq™ DNA Polymerase High Fidelity, Tne DNA polymerase, Tma DNA polymerase, Phire Hot Start II DNA polymerase, Phusion U Hot Start DNA Polymerase, Phusion Hot Start II High-Fidelity DNA Polymerase, iProof High Fidelity DNA Polymerase (Bio-Rad); HotStart Taq Polymerase (Qiagen)), a chemically modified polymerase that for instance blocks its activity at a particular temperature such as room temperature, and/or mutants, derivatives and/or fragments thereof. In some embodiments, an oligonucleotide or aptamer may also be used as a hot start agent, and/or the hot start function may result from a chemical modification to a polymerase that blocks its activity at a particular temperature (e.g., room temperature) (e.g., TaqGold, FlashTaq, Hot-Start Taq). In some embodiments, the hot start component may be one or more antibodies directed to (i.e., have binding specificity for) a thermostable polymerase in the mixture (as available from Thermo Fisher Scientific in, e.g., Platinum™ II Hot-Start Green PCR Master Mix; DreamTaq™ Hot Start Green PCR Master Mix, Phusion U Green Muliplex PCR Master Mix, Phire Green Hot Start II Master Mix, or AmpliTaq® Gold 360 Master Mix (Thermo Fisher Scientific)). In some embodiments, a dual hot start mechanism may be used. For example, a first hot start component, such as an oligonucleotide may be used as a hot start agent in conjunction with a second hot start component, such as one or more antibodies. In some embodiments, the first and second hot start components of the dual hot start mechanism, may be the same type or different (oligo-based; antibody-based; chemical-based, etc.). In some embodiments, the first and second hot start components of the dual hot start mechanism may be inhibitory to the same polymerase (e.g., a dual hot start mechanism which employs an inhibitory antibody directed to Taq DNA polymerase and an inhibitory oligonucleotide specific to Taq DNA polymerase). In some embodiments, the polymerase can be a fusion or chimeric polymerase which refers to an enzyme or polymerase that is comprised of different domains or sequences derived from different sources. For example, a fusion polymerase may comprise a polymerase domain, such as a *Thermus aquaticus* (Taq) polymerase domain, fused with a DNA binding domain, such as a single- or double-stranded DNA binding protein domain. Fusion or chimeric polymerases may be obtained, for example, using methods that are well-known to one of ordinary skill in the art (See, e.g., U.S. Pat. No. 8,828,700), the disclosure of which is incorporated by reference in its entirety. In some embodiments, such fusion or chimeric polymerases are thermostable. In some embodiments, the mixtures can comprise a mixture that is a master mix and/or a reaction mixture (e.g., TaqPath™ ProAmp™ Master Mix (Applied Biosystems™), TaqPath™ ProAmp™ Multiplex Master Mix (Applied Biosystems™), TaqMan™ PreAmp Master Mix (Applied Biosystems™), TaqMan™ Universal Master Mix II with UNG (Applied Biosystems™), TaqMan™ Universal PCR Master Mix II (no UNG) (Applied Biosystems™), TaqMan™ Gene Expression Master Mix II with UNG (Applied Biosystems™), EXPRESS qPCR Supermix, universal (Invitrogen), TaqMan™ Fast Advanced Master Mix (Applied Biosystems™, TaqMan™ Multiplex Master Mix (Applied Biosystems™), TaqMan™ PreAmp Master Mix Kit (Applied Biosystems™), TaqMan™ Universal PCR Master Mix, no AmpErase™ UNG (Applied Biosystems™), PowerUp SYBR Green Master Mix (Applied Biosystems™), or FlashTaq HotStart 2× MeanGreen Master Mix (Empirical Biosciences)). In some embodiments, the mixtures can further comprise one or more of at least one detergent; glycerol; PCR inhibitor blocking agents, including combinations of gelatin and albumin; uracil DNA glycosylase (UDG), and at least one reference dye (e.g., ROX™, Mustang Purple™). In some embodiments, the reaction mixture further can comprise an amplicon(s) comprising the target polynucleotide sequence (e.g., first sequence) of the target polynucleotide strand. In some embodiments, the mixture does not include an amplicon that includes a sequence of a second polynucleotide strand (e.g., of a major allelic variant).

Reverse Transcriptases

In some embodiments, the compositions, reaction mixtures, and kits as disclosed herein can also comprise at least one reverse transcriptase (RT) and related components, such as for reverse transcription PCR (RT-PCR). RT-PCR may be performed using the compositions, reaction mixtures and kits described herein, when, for example, RNA is the starting material for subsequent analysis. In some embodiments, the RT-PCR may be a one-step procedure using one or more primers and one or more probes as described herein. In some embodiments, the RT-PCR may be carried out in a single reaction tube or reaction vessel, such as in 1-step or 1-tube RT-PCR. Suitable exemplary RTs can include, for instance, a Moloney Murine Leukemia Virus (M-MLV) Reverse transcriptase, SuperScript Reverse Transcriptases (Thermo Fisher Scientific), SuperScript IV Reverse Transcriptases (Thermo Fisher Scientific), or Maxima Reverse Transcriptases (Thermo Fisher Scientific), or modified forms of any such RTs. The compositions, reaction mixtures, and kits may also comprise any other components necessary for carrying out such RT-PCR reactions, such as may be found in SuperScript IV VILO Master Mix (Thermo Fisher Scientific), or any other suitable RT-PCR master mixes (including those described above).

As used herein, the terms "wavelength range", "wavelength band", or the like, may mean a "full width at half maximum" (FWHM) wavelength range or wavelength band. As used herein, the terms FWHM wavelength range or FWHM wavelength band means a wavelength range or wavelength band having an extent equal to a difference between maximum and minimum wavelength values at which the radiation through, from, or off an optical element (e.g., a source of radiation or a spectral filter, mirror, beamsplitter, grating, or the like) is equal to one half a maximum value within the wavelength range or wavelength band of that element.

For a spectrum defined by a spectral function (e.g., an absorption, excitation, or emission spectral function) over a wavelength range, as used herein, a "peak wavelength" or "maximum wavelength" (e.g., "maximum absorption wavelength", "maximum excitation wavelength", "maximum emission wavelength") means a wavelength at which the spectrum function decreases as the wavelength increases or decreases about the maximum or peak wavelength (e.g., the absorption, excitation, or emission decreases as the wavelength increases or decreases from the maximum or peak wavelength—for example, increases or decreases by 2 nanometers). As used herein, the peak or maximum wavelength may be a local peak or maximum over a predetermined portion of a total spectrum or may be an "absolute peak" or "absolute maximum" in which the value of the spectral function is greater than at any other wavelength over an entirety of the spectrum.

As used herein, the peaks or maximums of two or more spectra (e.g., an absorption, excitation, or emission spectra of two or more dyes) may be considered "equal", "near", or "substantially equal" to one another when the difference between the peaks or maximums of two or more spectra is less than or equal to 15 nanometers. As used herein, a peak or maximum of a spectrum (e.g., an absorption, excitation, or emission spectrum of a dye) may be considered "near" a referenced wavelength band (e.g., of an excitation or emission channel, spectral element, or filter) when the peak or maximum of the spectrum is within 15 nanometers of a minimum or maximum limit of the referenced wavelength band. As used herein, a peak or maximum of a spectrum (e.g., an absorption, excitation, or emission spectrum of a dye) may be considered "nearest" or "closest" to a referenced wavelength band belonging to a set of available wavelength bands (e.g., the wavelength bands of a set of excitation or emission channels, spectral elements, or filters) when the integrated value of the spectrum over the referenced wavelength band is greater than the integrated value of the spectrum over any of other wavelength band of the set of available wavelength bands.

As used herein a "radiant generator" or "generator" means a source capable of producing electromagnetic radiation. The radiant generator may comprise a single source of light, for example, an incandescent lamp, a gas discharge lamp (e.g., Halogen lamp, Xenon lamp, Argon lamp, Krypton lamp, etc.), a light emitting diode (LED), a white light LED, an organic LED (OLED), a laser (e.g., chemical laser, excimer laser, semiconductor laser, solid state laser, Helium Neon laser, Argon laser, dye laser, diode laser, diode pumped laser, fiber laser, pulsed laser, continuous laser), or the like. Alternatively, the radiant generator may comprise a plurality of individual radiant generators (e.g., a plurality of LEDs or lasers) each configured to produce a different wavelength range or band that may be non-overlapping or partially overlapping with the other individual radiant generators. The radiant generator may be characterized by electromagnetic radiation that is primarily within the visible light range (e.g., a "light source" emitting electromagnetic radiation within a wavelength in the range of 400 nanometers to 700 nanometers or in the range of 380 nanometers and 800 nanometers), near infrared range, infrared range, ultraviolet range, or other ranges within the electromagnetic spectrum. The radiant generator may provide continuous or pulsed illumination, and may comprise either a single beam or a plurality of beams that are spatially and/or temporally separated.

Referring to FIG. 1, in certain embodiments a system 1000 comprises a first radiant source 101*a* that is configured to illuminate a nucleic acid sample 110 located in or on a sample holder or container 112, the sample 110 being disposed to receive radiation from a first radiant source 101*a*. Sample 110 comprises a first dye configured to bind to a first target molecule and a second dye configured to bind to a second target molecule. Radiant source 101*a* is configured to produce excitation beams that are directed along an excitation optical path 125 to sample 110. System 1000 further comprises a sensor or detector 115 configured to measure emissions from sample 110, a first emission spectral element 121*a* characterized by a first average emission wavelength, and a second emission spectral element 121*b* characterized by a second average emission wavelength that is different than first average emission wavelength. An optical element or lens 123 may be used in combination with detector 115, for example, to reimage sample holder 112, sample 110, and/or emissions therefrom. Optical element 123 may be in the form of a transmissive and/or reflected optical element configured to focus or image light or radiation from sample holder 112 and/or sample 110.

Each emission spectral element 121*a*, 121*b* may be further characterized by wavelength band or range. The wavelength band or range of emission spectral elements 121*a*, 121*b* may be selected so that the wavelength band or range of emission spectral elements 121*a* does not overlap, or only partially overlaps, that of emission spectral element 121*b*. When the first target molecule and/or second target molecules are present in sample 110, emissions from corresponding first and/or second dyes are directed from sample 110 to detector 115 along an emission optical path 126. Emission spectral elements 121*a*, 121*b* may comprise respective filters passing or reflecting a wavelength band suitable for detecting and/or measuring a respective dye.

System 1000 may be configured to perform an amplification assay on sample 110. Optionally, the amplification assay may be performed on a separate system and further processed and/or examined using system 1000. System 1000 may also comprise at least one computer or processor 130 comprising at least one memory (not shown) including instructions to perform an amplification assay on sample 110. During and/or after the amplification assay, system 1000 is configured to illuminate sample 110 using radiant source 101*a* and to detect and/or measure emissions from any target molecules present using detector 115 in combination with emission spectral elements 121*a*, 121*b*. The memory associated with processor 130 may include instructions to, at least once during or after an amplification assay, illuminate sample 110 with first radiant source 101*a* and, in response, (1) to measure emissions from sample 110 using detector 115 and emission spectral element 121*a* and (2) to measure emissions from sample 110 using detector 115 and second emission spectral element 121*b*. As discussed in further detail below, the memory may comprise instructions to determine an amount of any target molecule present in sample 110, for example, by correlating measured emissions from sample 110 using first and second emission spectral elements 121*a*, 121*b* with an amount of the first and second target molecules, respectively.

Figure 2:
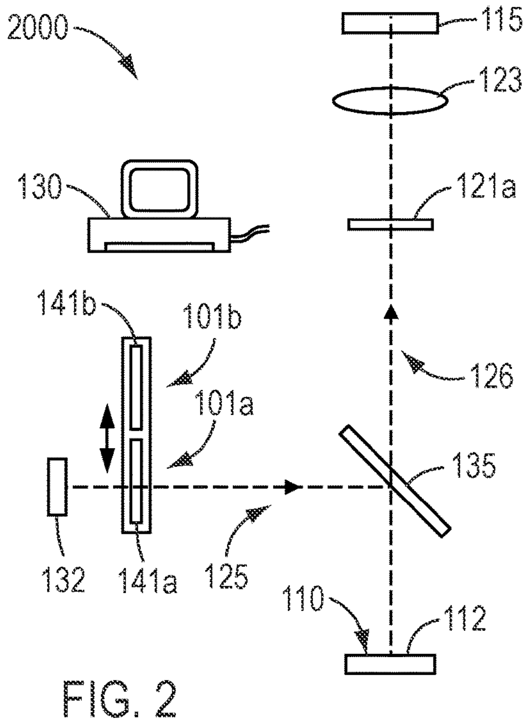
FIG. 2 is a schematic representation of another system according to an embodiment of the present disclosure.

Referring to FIG. 2, in another embodiment, a system 2000 comprises first radiant source 101*a* and a second radiant source 102, wherein first radiant source 101*a* is characterized by a first average excitation wavelength and second radiant source 102 is characterized by a second average excitation wavelength that is different than the first average excitation wavelength. Radiant sources 101*a*, 102 for systems 1000, 2000 may each be further characterized by wavelength band or range. The wavelength band or range of radiant sources 101*a*, 101*b* may be selected so that the wavelength band or range of radiant sources 101*a* does not overlap that of radiant sources 101*b*. Sample 110 comprises a first dye configured to bind to a first target molecule and a second dye configured to bind to a second target molecule, where either or both dyes may be different than the first and second dyes discussed above regarding system 1000. System 2000 may optionally include first emission spectral element 121*a*, which may be the same as or different from first emission spectral element 121*a* used in system 1000. Radiant sources 101*a*, 101*b* of systems 1000, 2000 may comprise a radiant emitter or radiant generator 132 in combination of a respective excitation spectral element 141*a*, 141*b*, which may, for example, be respective excitation filters passing or reflecting a wavelength band suitable for exciting a respective dye.

System 2000 may be configured to perform an amplification assay on sample 110. Optionally, the amplification assay may be performed on a separate system and subsequently processed and/or examined using system 2000. During and/or after the amplification assay, system 2000 is configured to illuminate sample 110 using radiant sources

101*a*, 101*b* and to detect and/or measure emissions from any target molecules present using detector 115 in combination with first emission spectral element 121*a*, when present. The memory associated with processor 130 in system 2000 may include instructions to perform an amplification assay on sample 110. The memory associated with processor 130 may include instructions to, at least once during or after an amplification assay, (1) illuminate sample 110 with first radiant source 101*a* and, in response, measure emissions from sample 110 using detector 115 and, optionally, first emission spectral element 121*a* and (2) illuminate sample 110 with second radiant source 101*b* and, in response, measure emissions from sample 110 using detector 115 and, optionally, first emission spectral element 121*a*. As discussed in further detail below, the memory may further comprise instructions to determine an amount of the first target molecule and/or an amount of the second target molecule when present in sample 110, for example, by correlating measured emissions from sample 110 when illuminating with first and second radiant sources 101*a*, 101*b* with an amount of the first and second target molecules, respectively. Where applicable, system 2000 may incorporate any of the elements or features discussed above herein regarding system 1000. Where applicable, processor 130 and associated memory of system 2000 may incorporate any of the elements or features of the processor 130 discussed above herein regarding system 1000.

Figure 3:
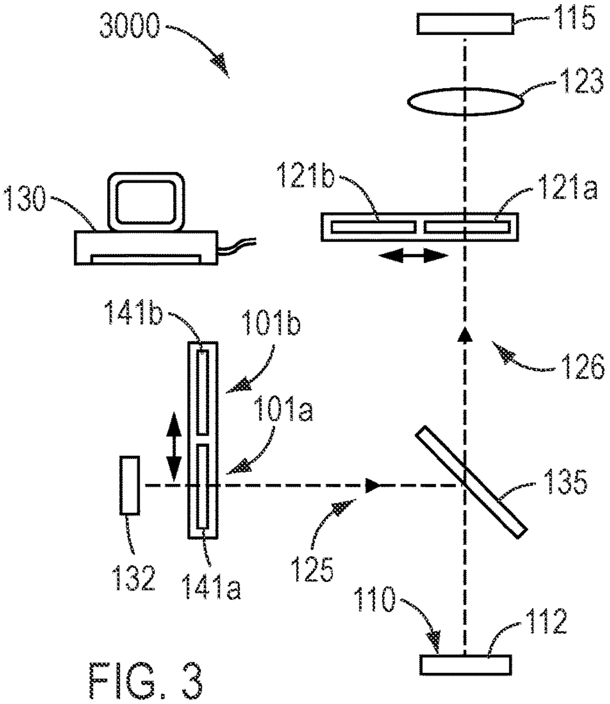
FIG. 3 is a schematic representation of another system according to an embodiment of the present disclosure.

With further reference to FIG. 3, in some embodiments, a system 3000 comprises both the first and second radiant sources 101*a*, 101*b* and both first and second emission spectral elements 121*a*, 121*b*. In such embodiments, sample 110 comprises a first dye configured to bind to a first target molecule, a second dye configured to bind to a second target molecule, and a third dye configure to bind to a third target molecule. As discussed above, first radiant source 101*a* is characterized by a first average excitation wavelength and second radiant source 101*b* is characterized by a second average excitation wavelength that is different than the first average excitation wavelength, while first emission spectral element 121*a* is characterized by a first average emission wavelength and second emission spectral element 121*b* is characterized by a second average emission wavelength that is different than the first average emission wavelength.

System 3000 may be configured to perform an amplification assay on sample 110. Optionally, the amplification assay may be performed on a separate system and further processed and/or examined using system 3000. During and/or after the amplification assay, system 1000 is configured to illuminate sample 110 using radiant sources 101*a*, 101*b* and to detect and/or measure emissions from any target molecules present using detector 115 in combination with emission spectral elements 121*a*, 121*b*. System 3000 may be configured to perform an amplification assay on sample 110. Optionally, the amplification assay may be performed on a separate system and further processed and/or examined using system 3000. During and/or after the amplification assay, system 3000 is configured to, at least once during or after the amplification assay, (1) illuminate sample 110 at least once with first radiant source 101*a* and, in response, detect or measure emissions from sample 110 using detector 115 and first emission spectral element 121*a* and detect or measure emissions from sample 110 using detector 115 and second emission spectral element 121*b* and (2) illuminate sample 110 with second radiant source 101*b* and, in response, detect or measure emissions from sample 110 using detector 115 and second emission spectral element 121*b*. As discussed in further detail below, the memory may comprise instructions to determine an amount of the first target molecule, the second target molecule, and/or the third target molecule when present in sample 110, for example, by correlating measured emissions from sample 110 when illuminating with first or second radiant sources 101*a*, 101*b* with an amount of the first, second, and third target molecules, respectively.

Where applicable, system 3000 may incorporate any of the elements or features discussed above herein regarding systems 1000, 2000. Where applicable, processor 130 of system 3000 may incorporate any of the elements or features of the processor 130 and associated memory discussed above herein regarding systems 1000, 2000. The embodiments of spectral elements 121*a*, 121*b*, 141*a*, 141*b* and sources 101*a*, 101*b* discussed above in relation to FIG. 1 and FIG. 2 may also apply to those elements and sources of system 3000. Any of systems 1000, 2000, or 3000 may include a filter wheel, translation stage, or the like, for example, to selectively move excitation spectral elements 141*a*, 141*b* into and out of excitation optical path 125. Any of systems 1000, 2000, or 3000 may include filter wheel, translation stage, or the like, for example, to selectively move emission spectral elements 121*a*, 121*b* into and out of emission optical path 126.

In certain embodiments, any of systems 1000, 2000, or 3000 may comprise at least one beam steering optical element 135 that steers or fold radiation from radiant sources 101*a*, 101*b* to sample 110. Alternatively, any of systems 1000, 2000, 3000 may be configured so that emissions from sample 110 are steered or directed to detector 115 using at least one beam steering optical element 135. Using that beam steering optical element 135, excitation and emission optical paths 125, 126 may comprise a common path portion where optical paths 125, 126 overlap from beam steering optical element 135 to sample 110. In other embodiments, excitation and emission optical paths 125, 126 do not overlap or have a common path portion except at sample 110. For example, emission beam optical path 126 may disposed normal or perpendicular to surface of sample holder 112, while excitation optical path 125 may be disposed at an off-axis angle from the surface that is not normal or perpendicular to the surface of sample holder 112. Systems 1000, 2000, 3000 may additionally or alternatively incorporate other optical configurations known in the art. For example, rather than in the reflective arrangement shown in FIG. 1-3, in which excitation and emission optical paths 125,126 are located on a common side or surface of sample holder 112, excitation and emission optical paths 125,126 may be configured in a transmissive arrangement in which the excitation optical path 125 is located on one side or surface of sample holder 112 and emission optical path 126 is located on an opposite side or surface of sample holder 112. Systems 1000, 2000, or 3000 may further comprise other optical elements for conditioning radiation or light from radiant sources 101*a*, 101*b* and/or emissions from sample 112.

Referring to FIG. 4, in certain embodiments, a system 4000 comprises a plurality of radiant sources 401 and plurality of emission spectral elements 441 (441*a*-441*f* in the illustrated embodiment). In the illustrated embodiment, each radiant source 401 comprise radiant generator 132 and one of the six excitation spectral elements 441. In certain embodiments, each radiant source 401 may be characterized by a respective average excitation wavelength, wherein one or more of the six average excitation wavelengths is different from the remaining average excitation wavelengths. Each radiant source 401 may be characterized by a respective excitation wavelength band or range, wherein at least some of the excitation wavelength bands or ranges do not overlap the excitation wavelength band or range of any of the remaining radiant sources 401. In certain embodiments, any of radiant sources 401*a-f* may comprise one or more radiant generators 132 in combination with an excitation spectral element 401 (e.g., with a respective one of excitation spectral elements 401*a-f*).

System 4000 further comprises detector 115 and a plurality of emission spectral elements 421 (421*a*-421*f* in the illustrated embodiment) for use in combination with radiant sources 421*a-f*. Sample 110 may comprise three dyes associated with three target molecules, as discussed regarding system 3000. Because of the additional number radiant sources 401 and emission spectral elements 421, system 4000 is configured to detect and/or measure more than three dyes. Using six radiant sources 401 and six associated emission spectral elements 421, prior art systems are only able to detect and deconvolve at most six dyes to determine amounts of at most six corresponding target molecules. As discussed in further detail below herein, system 4000 is configured to detect and deconvolve more than six dyes so as to determine amounts of more than six corresponding target molecules. In certain embodiments, system 4000 may include a field lens 445 or other optical elements suitable for conditioning radiation from radiant generator 132 and/or emissions from sample 112.

While FIG. 4 illustrates a system 4000 comprising six radiant sources 401*a-f* and six emission spectral elements 421*a-f*. It will be appreciated that system 4000 may contain fewer than six of radiant sources and/or fewer than six emission spectral elements (e.g., like systems 1000, 2000, or 3000). In certain embodiments, system 4000 may contain more than six radiant sources and/or more than six emission spectral elements, for example, to increase the number of target molecules that may be detected or measured by system 4000 and/or to increase the accuracy or sensitivity of system 4000 to detect or measure a selected number of target molecules. For example, system 4000 may comprise seven, eight, or more radiant sources 401 and/or seven, eight, or more emission spectral elements 421. In certain embodiments, each emission spectral element 421 comprises a specific wavelength band or range from a chromatically dispersive optical element such as a prism, diffractive optical element, spectrometer, or spectrophotometer that is illuminated by emissions from sample 110. Additionally or alternatively, each excitation spectral element 441 comprises a specific wavelength band or range from a chromatically dispersive optical element such as a prism or diffractive optical element from the spectrum provided by one or more radiant generators 132.

Where applicable, the elements or components of system 4000 may take the form of embodiments of any corresponding element discussed above regarding any of systems 1000, 2000, 3000. For example, the radiant generator 132, sample 110, sample holder 112, and processor(s) 130 and associated memory(ies) may take the form of those same elements or components discussed above with regard to any of systems 1000, 2000, 3000. Any or all of excitation spectral elements 441 may take the form of any of the embodiments discussed above regarding excitation spectral element 141*a* or excitation spectral element 141*b*. Any or all emission spectral elements 421 may take the form of any of the embodiments discussed above regarding emission spectral element 121*a* or excitation spectral element 121*b*. Any or all radiant sources 401*a-f* may take the form of any of the embodiments discussed above regarding radiant source 101*a* or radiant source 101*b*.

Systems 1000, 2000, 3000, 4000 may incorporate other lenses, filters, mirror, prisms, diffractive optical element, or the like, that known in the biological instruments and systems art. In certain embodiments, further lenses or other imaging optical elements may be included along the excitation and emission optical paths of systems 1000, 2000, 3000, 4000 (e.g., optical paths 125, 126). For example, a field lens may be located proximal sample holder 112 (e.g., field lens 445 shown proximal sample holder 112 in FIG. 4). In some embodiments, further imaging optics are located along the optical path between the sample holder 112 and detector 115 to relay an image or otherwise condition emissions from sample 110. Embodiments of 1000, 2000, 3000, 4000 may incorporate any of the optical elements or configurations disclosed in U.S. Pat. No. 6,818,437, US2004/0009586, U.S. Pat. No. 9,702,823, or US2016/0230210, which are herein incorporated by reference in their entirety.

Optical element 123 or any other imaging optical elements along the excitation and/or emission optical paths of systems 1000, 2000, 3000, 4000 may comprise one or more of a refractive lens, a mirror, a diffractive or holographic optical element, or the like. One or more of spectral elements 121, 141, 421, 441 may comprise one or more of a colored substrate, a dichroic element such as a filter, mirror, or beamsplitter, or a dispersive optical element such as a prism, diffractive grating, or holographic grating. For any of the systems 1000, 2000, 3000, 4000, detector 115 may comprise may comprise one or more individual photodetectors including, but not limited to, photodiodes, photomultiplier tubes, bolometers, cryogenic detectors, quantum dots, light emitting diodes (LEDs), semiconductor detectors, HgCdTe detectors, or the like. Additionally or alternatively, detector 115 may comprise an array sensor including an array of sensors or pixels. The array sensor may comprise one or more of a complementary metal-oxide-semiconductor sensor (CMOS), a charge-coupled device (CCD) sensor, a plurality of photodiodes detectors, a plurality of photomultiplier tubes, or the like. In certain embodiments, detector 115 comprises two or more array sensors.

System 4000 may include a plurality of beam steering optical elements 435 to direct excitation beams along excitation optical path from radiant generator 132 to sample 110 and/or to direct emissions along an emission optical path from sample 110 to detector 115. In the illustrated embodiment, each excitation spectral element 441 if coupled on a rotation 449. Beam steering optical elements 135, 435 may take the form of any of the embodiments discussed above regarding beam steering optical elements 135 discussed above regarding systems 1000, 2000, 3000. In the illustrated embodiment shown in FIG. 4, system 4000 comprises six beam steering optical elements 435, one for each of the six excitation spectral elements 441. One or more of the beam steering optical elements 135, 435 may comprise one or more spectrally selective optical elements (e.g., a dichroic mirror, filter, or beamsplitter) characterized by a spectrum corresponding to or complementing the spectrum of one of the radiant sources 401 and/or one of the emission spectral elements 421. In certain embodiments, one or more of the beam steering optical elements 135, 435 may comprise a neutral density filter having a constant, or essentially constant, transmission over a broad band of wavelengths (e.g., having constant transmission over the visible, infrared, and/or UV wavelength bands, over the wavelength band of some or all the spectral elements 421, 441, and/or over some or all of the wavelength band of radiant source 400). For example, one or more of the beam steering optical elements 135, 435 may comprise one or more neutral density filter having a transmission of 1%, 5%, 10%, 20%, 25%, 50%, 75%, 80%, 90%, 95%, or 99% over a given wavelength band. In the illustrated embodiment, beam steering optical elements 435 are coupled to filter wheel 449. Alternatively, beam steering optical elements 435 may be coupled to filter wheel 429 such that each beam steering optical element 435 corresponds to a respective one of the emission spectral elements 421*a-f*. In yet other embodiments, beam steering optical elements 135, 435 may be moved independently of radiant sources 401, excitation spectral elements 441, and emission spectral elements 421. The number of beam steering optical elements 135, 435 may be less than or greater than the total number of radiant sources 401 or the total number of emission spectral elements 421, for example, to increase the number of wavelength bands provide by the excitation spectral elements 441 or the total number of emission spectral elements 421.

Spectral elements 121 (e.g., 121*a*, 121*b*), 141 (e.g., 141*a*, 141*b*), 421 (e.g., 421*a-f*), 441 (e.g., 441*a-f*) illustrated in FIG. 1 to FIG. 4 may comprise a spectral filter, wherein each filter is characterized by a transmission wavelength band or range and/or an average transmission wavelength. Any of the spectral elements 121, 141, 421, 441 may comprise a transmissive or reflective optical filter configured to filter emissions from the sample into a desired or predetermined wavelength range or band. For example, any of the spectral elements 121, 141, 421, 441 may comprise one or more of a colored filter, a dichroic filter, a dichroic mirror, or a dichroic beamsplitter. In certain embodiment, spectral elements 121, 141, 421, 441 may comprise emission from sample 110 that have passed through a dispersive optical element, such as a prism or diffractive grating, spectrometer, or spectrophotometer. In such embodiments, each spectral element 121, 141, 421, 441 comprises a different portion of the spectrum produced by the dispersive optical element. Emission spectral elements 121, 421 may be attached to a filter wheel (e.g., filter wheel 429 in FIG. 4) or similar motion device to move different ones of elements 121, 421 into and out of an optical path between detector 115 and sample 110.

Any of radiant sources 101 (e.g., 101*a* and/or 101*b*), 401 illustrated in FIG. 1 to FIG. 4 may comprises one or more radiant generators 132 (e.g., one or more light sources or other broadband sources of light and/or UV radiation) in combination with a respective one from a plurality of excitation spectral elements 141*a*, 141*b*. Additionally or alternatively, one or more of the radiant sources 101, 401 may comprise a radiant generator 132 having a relatively narrow wavelength range or band, such as a colored or narrow band LED, laser, discharge tube, or the like, having a spectrum or wavelength band of light or other electromagnetic radiation selected to excite a dye that may be associated with a respective target molecule. In such embodiments, one or more of the excitation spectral elements 141 (e.g., 141*a*, 141*b*), 441 (e.g., any of 441*a-f*) may be optionally included, for example, to further narrow or otherwise condition the spectrum of radiation directed to sample 110. As illustrated in FIG. 4, excitation spectral elements 441 may be attached to a filter wheel 449 or similar motion device to move different ones of elements 441 into and out of an optical path between radiant generator 132 and sample 110. In some embodiments, radiant sources 101, 401 may each comprise a radiant generator and chromatically dispersive optical element configured to transmit or reflect radiation from the radiant generator, each radiant source including a different portion of a spectrum from the chromatically dispersive optical element.

Sample holder 112 in systems 1000, 2000, 3000, 4000 may comprise a plate or surface in which sample 110 is disposed on sample holder 112 or disposed within sample holder 112, for example, within a sample well, through-hole, or surface region. In embodiments, sample 110 comprises a plurality of spatially separated sample portions, for example, a sample solution separated into a plurality of spatially separated sample sites such as a plurality of sample wells, through-holes, or surface regions. Each sample portion may contain an identical, or substantially identical, amount of one or more target molecules, may contain different amounts or types of one or more target molecules, or contain no target molecules (e.g., dPCR sample portions). Sample holder 112 may comprise a strip or microtiter plate (e.g., a strip of 4, 6, or 8 wells or a microtiter plate comprising 24 wells, 48 well, 96 wells, 384 wells, 1536 wells, or 3456 wells). Alternatively, sample holder 112 may comprises a card or plate comprising an array of reaction sites or chambers that each contain a portion of sample 110 (e.g., a card or plate comprising 384 or 9,216 sample chambers or reaction sites). In some embodiments, sample holder 112 comprises a plate or chip including an array of spatially separated through-holes that each contain a portion of sample 110 (e.g., a through-hole plate or chip containing 3,072 through-holes, 20,000 through-holes, 50,000 through-holes, 100,000 through-holes, or more than 100,000 through-holes). In certain embodiments, sample holder 112 comprises a tube, channel, or capillary comprising a plurality of sample droplets or slugs containing a portion of sample 110 and, optionally, an immiscible fluid or oil disposed between the droplets. Each droplet or slug may contain an identical, or substantially identical, amount of one or more target molecules, may contain different amounts or types of one or more target molecules, or contain no target molecules (e.g., dPCR sample droplets or slug).

Where applicable, processor 130 and associated memory of system 4000 may incorporate any of the elements or features of the processor 130 discussed above herein regarding systems 1000, 2000, 3000. In the illustrated embodiment shown in FIG. 4, processor 130 and associated memory may be configured to comprise any of the instructions discussed above in relation to FIG. 1 to FIG. 3, for example, in performing an amplification assay, illuminating sample 110 with any of the radiant sources 401*a-f*, and/or detecting or measuring emissions from sample 110 with any of emission spectral elements 421*a-f*. In certain embodiments of systems 1000, 2000, 3000, 4000, all or portions of processor 130 and/or the associated memory may be integrated into a single instrument that may be enclosed into a housing. In some embodiments, all or portions of processor 130 and/or the associated memory may be separately located from the rest of system 1000, wherein they physically connected to one another via a physical cable, a local area network, a wide area network, or the like. Additionally or alternatively, they may be wirelessly connection to one another via a Wi-Fi connection, a Bluetooth connection, a cloud connection, or the like.

In certain embodiments, any of systems 1000, 2000, 3000, 4000 may comprise a single system or instrument having one or more processors 130 and associated memory containing instructions discussed above herein for the respective system. Alternatively, any of systems 1000, 2000, 3000, 4000 may comprise a second system or instrument configured to perform one or more of these tasks. In such embodiments, systems 1000, 2000, 3000, 4000 may comprise two or more systems or instruments that each perform some of these tasks. Each such system or instrument may have its own processor and/or memory or, alternatively, share a common processor and/or memory, for example using a centralized storage system, such as a cloud storage system, and/or a centralized processor or processor system, such as a cloud computing processor or system.

Systems 1000, 2000, 3000, 4000 may be an end-point system or instrument configured to provide measure emissions from one or more dyes in sample 110 after the conclusion of an amplification assay, such as a PCR assay (e.g., a qPCR or dPCR system or instrument or a system or instrument configured to perform a melt assay). Referring to FIG. 5, in certain embodiments, an amplification system 5000, comprises the optical components of systems 1000, 2000, 3000, or 4000 (e.g., radiant sources, spectral elements, detectors, beam steering optical elements, and the like), processor 130, sample holder 112, and a thermal controller or system including a thermal block 502 configured to receive sample holder 112 and a temperature controller or thermal cycler 504 configured to perform a PCR or other amplification assay. System 5000 may further include a heated cover (not shown) that is located opposite thermal block 502 and configured to further control the temperature and/or environment of sample holder 112 and/or sample 110. Processor 130 is configured to control system 5000 during performance of the amplification assay and to operate the optical components to detect or measure emissions from one or more dyes present in sample 100 one or more times during the amplification assay. System 5000 may be further configured to detect or measure emissions from one or more dyes after completion of the amplification assay, for example, for use in determining an amount of one or more molecules associated with the one or more dyes or for detecting or measuring emissions from the dyes during a melt assay performed after the amplification assay. In certain embodiments, system 5000 performs an amplification assay on sample 110 without the use of thermal cycling. In such embodiment, system 5000 may be configured without thermal block 502 and/or without thermal cycler 504.

Referring to FIG. 6, an example is given for a selection of radiant sources 401 (e.g., radiant generator 132 in combination with excitation spectral elements 441*a-f*) and emission spectral elements 421 in accordance with an embodiment of system 4000 and/or 5000. Each entry in the column labeled "Ex" is an excitation "channel" of system 4000, where each Ex or excitation channel indicates wavelength range or band for illumination of sample 110. The number shown for each excitation channel is an average or central excitation wavelength for a respective one of radiant sources 401*a-f*. The wavelength band for each excitation channel is indicated by a "±" numerical value in nanometers about the average or central transmission wavelength for that excitation or Ex channel (e.g., the wavelength band of excitation or Ex channel x1 in the illustrated embodiment is 480±10 nanometers, or 470 nanometers to 490 nanometers). In certain embodiments, the selection of the average or central excitation wavelength may be vary from that shown in FIG. 6, for example, to accommodate a particular set of dyes, selection of target molecules, and/or assay chemistry. For example, the average or central wavelength for Ex channels x1-x6 may select to be within a range of ±5 nanometers about the values shown in the table of FIG. 6 (e.g., the average or central wavelength for Ex channel x1 may select to be 480 nanometers ±5 nanometers, the average or central wavelength for Ex channel x2 may select to be 520 nanometers ±5 nanometers, etc.). In addition, the width of the Ex channels may be wider or narrower than the widths indicated in FIG. 6. For example, the width for any of the Ex channels may less than or equal to ±5 nanometers, ±10 nanometers, ±12 nanometers, ±15 nanometers, ±18 nanometers, ±20 nanometers, about average or central value for a given channel.

Each entry in the row labeled "Em" is an emission "channel" of system 4000, where each Em or emission channel represents emissions (e.g., fluorescent emissions) from sample 110 that are received by detector 115 after being transmitted, reflected, and/or diffracted by a respective one of the emission spectral elements 421 (e.g., 421*a-f*). The number shown for each emission channel is an average or central emission wavelength for a respective one of emission spectral element 421. The wavelength band for each emission channel is indicated by a "±" numerical value in nanometers about the average or central transmission wavelength for that emission or Em channel (e.g., the wavelength band of emission or Em channel m1 in the illustrated embodiment is 520±15 nanometers, or 505 nanometers to 535 nanometers). In certain embodiments, the selection of the average or central emission wavelength may be vary from that shown in FIG. 6, for example, to accommodate a particular set of dyes, selection of target molecules, and/or assay chemistry. For example, the average or central wavelength for Em channels m1-m6 may select to be within a range of ±5 nanometers about the values shown in the table of FIG. 6 (e.g., the average or central wavelength for Em channel m1 may select to be 480 nanometers ±5 nanometers, the average or central wavelength for Em channel m2 may select to be 520 nanometers ±5 nanometers, etc.). In addition, the width of the Em channels may be wider or narrower than the widths indicated in FIG. 6. For example, the width for any of the Em channels may less than or equal to ±5 nanometers, ±10 nanometers, ±12 nanometers, ±15 nanometers, ±18 nanometers, ±20 nanometers, about average or central value for a given channel.

The remaining elements to the right of the Ex column and below the Em role in FIG. 6 represent various excitation/emission channel combinations or pairs (herein referred to as ex-em channel combinations or pairs, or simply channel combinations or pairs) suitable for detecting or measuring emissions from one or more dyes in sample 110 over a particular emission wavelength range for a particular excitation wavelength range. In certain embodiments, a channel combination may correspond to a dye with a maximum absorption (or excitation) wavelength that is within or near the wavelength band of the corresponding excitation channel of the combination and a maximum emission wavelength that is within or near the wavelength band of the emission channel of the corresponding excitation channel of the combination. For example, the x1, m1 channel combination (designated x1/m1 herein and represented by "A1") may be used to detect or measure a dye having (1) a maximum absorption wavelength that is within or nearest the 480±10 nanometer wavelength band of the x1 channel and (2) a maximum emission wavelength that is within or nearest the 520±15 nanometer band of the corresponding m1 channel. As another example, the x1, m3 channel combination (x1/m3 and represented by "B13") may be used to detect or measure any dye having (1) maximum absorption wavelength that is within or near the 480±10 nanometer band of the x1 channel and (2) a maximum emission wavelength that is within or near the 587±10 nanometer band of the corresponding m3 channel. Such dyes may be referred to by the excitation/emission channel to which they are readily detected or measured (e.g., as an "A1 dye" and a "B13 dye" for the current examples). It will be appreciated that a given dye may have an absorption and/or emission spectrum that extends outside the excitation/emission channel combination for which that dye has been designed.

The excitation/emission channel combinations labeled A1-A6 may be referred to as "on-axis channels" or "on-axis channel combinations", where dyes having a corresponding maximum excitation wavelength and maximum emission wavelength may be referred to as "on-axis dyes". All other excitation/emission channels combinations that are not on-axis channels in FIG. 6 may be referred to as "off-axis channels" or "off-axis channel combinations", where dyes having a corresponding maximum excitation wavelength and maximum emission wavelength may be referred to as "on-axis dyes". The off-axis channel combinations starting with the letter B (i.e., B12 to B56) are suitable for dyes also producing a Stokes shift, but these dyes may have a Stokes shift that is greater than dyes more suitable for use with on-axis channel combinations. Thus, off-axis dyes will generally produce a larger shift between a maximum absorption wavelength and a corresponding maximum emission wavelength (e.g., Stokes shift) than an on-axis dye. The off-axis channels starting with the letter C (i.e., C12 to C56) are suitable for so called "anti-Stokes" or "up-converting" fluorescent dyes, which are dyes that that produce shifted emissions in which the dye has a maximum emission wavelength or wavelength band that is less than their maximum absorption wavelength or wavelength band.

As used herein, an "on-axis channel combination" or "on-axis ex-em channel pair" is a pair of ex-em channels in which an average or central wavelength of the Em channel is shifted by an amount that is less than or equal to 60 nanometers from the corresponding Ex channel. Alternatively, for a set of Ex and Em channels, an "on-axis channel combination" or "on-axis ex-em channel pair" comprises a given Ex channel and the Em channel that has the smallest average or central wavelength shift from average or central wavelength of the given Ex channel. Under these definitions, an "off-axis channel combination" or "off-axis ex-em channel pair" is any pair of ex-em channels that is not an "on-axis channel combination" or "on-axis ex-em channel pair".

Figure 16:
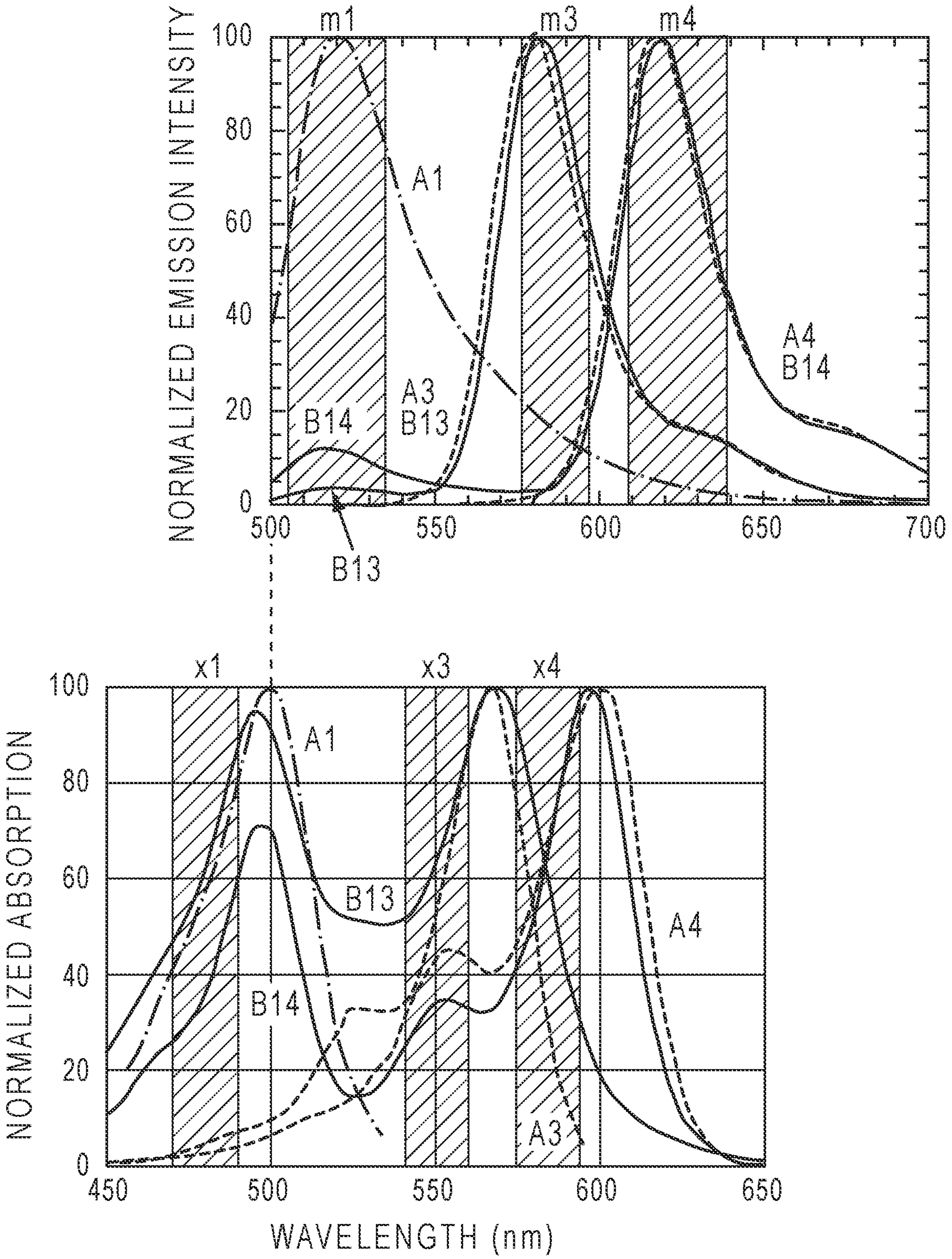
FIG. 16 is an absorption or excitation spectrum and associated emission spectrum for five dyes according to an embodiment of the present disclosure.

Unless otherwise noted, as used herein in the context of a system or instrument comprising one or more on-axis/off-axis channel combinations and one or more on-axis/off-axis ex-em channel combinations, an "off-axis dye" is defined as a dye having a first maximum absorption or excitation wavelength that is an absolute maximum over an entire spectrum of the dye and having a second maximum absorption or excitation wavelengths that is a local maximum and is separated from the first maximum absorption or excitation wavelength by at least 60 nanometers (e.g., see FIG. 16, in which B13 has two maximum wavelength separated by about 68 nanometers and B4 has two maximum wavelength separated by about 100 nanometers). Using this definition of an off-axis dye, an "on-axis dye" is any dye that is not an off-axis dye.

Some on-axis dyes may be a "broadened dye". As used herein, a "broadened dye" is defined as an on-axis dye having a first maximum absorption or excitation wavelength that is an absolute maximum over an entire spectrum of the dye and having a second maximum absorption or excitation wavelengths that is a local maximum and is separated from the first maximum absorption or excitation wavelength by less than 60 nanometers. A broadened dye may be used in combination with another on-axis dyes to increase the number of dyes that can be detected or measured using a combination of on-axis and off-axis channel combinations. For example, a first, on-axis dye may be selected that produces a maximum signal using an on-axis channel combination (e.g., the A1 channel combination) and used in combination with second, broadened dye that produces a higher signal in an adjacent off-axis channel combination (e.g. the B12 channel combination) than that produced by the first dye for an equal concentration of both dyes.

In certain embodiments, an "off-axis dye" is comprises a "big dye" or "energy transfer dye conjugate", where the off-axis dye comprises two "on-axis dyes": a "donor dye" and an "acceptor dye" (e.g., see U.S. Pat. No. 5,800,996, herein incorporated by reference in its entirety) covalently attached via a linker. This definition of an off-axis dye may be irrespective of the amount of shift between any pair of local maximum absorption or excitation wavelengths. The donor dye and the acceptor dye are linked by linker, wherein the donor dye is a dye capable of absorbing light at a first wavelength to produce excitation energy and the acceptor dye is dye which is capable of absorbing at least a portion of the excitation energy produced by the donor dye and, in response, fluorescing at a second wavelength that is equal to or substantially equal to a maximum emission wavelength of the acceptor dye by itself (i.e., when not linked to the donor dye).

In certain embodiments, a pair of dyes may be considered an "on-axis dye" or an "off-axis dye" in terms of their spectral characteristic as compared to one another. For example, a first dye within a sample may be considered an "on-axis dye" and a second dye may be considered an "off-axis dye" when the first and second dyes have the same or nearly the same maximum absorption or excitation wavelength (e.g., absorption or excitation maximums that are within 5 nanometers of one another or absorb a maximum amount of radiations from a common excitation channel of an instrument or system), but a maximum emission wavelength of the second dye that is at least 50 nanometers greater than that of the first dye (e.g., referring to FIG. 16, dyes A1, B13 or B14 all have maximum absorptions wavelengths that are nearly the same, but "off-axis dyes" B13, B14 each have maximum emission wavelengths that are more than 50 nanometers greater than "on-axis dye" A1). Additionally or alternatively, a first dye within a sample may be considered an "on-axis dye" and a second dye may be considered an "off-axis dye" when the first and second dyes have the same or nearly the same maximum emission wavelengths (e.g., emission maximums that are within 2 nanometers of one another or produce maximum emissions over the wavelength band of a common emission channel of an instrument or system), but a maximum absorption or excitation wavelength of the second dye is at least 60 nanometers less than that of a maximum absorption or excitation wavelength of the first dye (e.g., referring to FIG. 16, for the dye pairs A3, B13 or A4, B14, each dye pair has nearly the same maximum absorptions wavelengths (~565 nanometers and –600 nanometers, respectively), but "off-axis dyes" B13, B14 each have a maximum absorption/excitation wavelength that is at least 60 nanometers less than that of the "on-axis dye" A1).

In the case of six excitation channels and six corresponding emission channels, as shown in FIG. 6, the inventors have found that it is possible to obtain or multiplex all 21 different emission signals from a sample (i.e., for the channel combinations A1-A6 and B12-B56). In certain embodiment, the inventors have found that it is possible to obtain or multiplex 18 to 20 different emission signals from a sample (e.g., using all channel combination except B56 and/or another channel combination in which the difference between the central wavelength of adjacent ex and/or em channels is small; e.g. a difference that is less than or equal to 30 nanometers or is less than or equal to 25 nanometers). As discussed below herein, the inventors have found at least 10 dyes (e.g., six on-axis dyes and four off-axis dyes) can be selected to determine or measure the amounts of 10 different target molecules contained in the same sample solution during a single PCR assay.

The combination of six excitation channels x1-x6 and six emission channels m1-m6 shown in FIG. 6 provides an exemplary embodiment suitable for illustrating various embodiments of the current disclosure. The central wavelengths and wavelength bands for each of the ex/em channels x1-x6 and m1-m6 may be modified to accommodate various system or assay configurations, for example, to provide improved measurements of a particular set of dyes and/or probes and target molecules being considered. The number of ex/em channels may be increased by increasing the number of emission channels and/or the number of emission channels, for example, by using 7, 8, or more excitation channels and/or by 7, 8, or more emission channels. Additionally or alternatively, excitation channels may be configured to cover a broader range of wavelengths, for example, extending into the UV, near UV, infrared, or near-infrared wavelength bands of the electromagnetic spectrum (e.g., including an excitation channel with a central wavelength is less than or equal to 450 or 500 nanometers, or including an excitation channel with a central wavelength that is greater than or equal to 720 or 750 nanometer). Additionally or alternatively, emission channels may be configured to cover a broader range of wavelengths, for example, extending into the UV, near UV, infrared, or near-infrared wavelength bands of the electromagnetic spectrum (e.g., including an excitation channel with a central wavelength is less than or equal to 400 or 450 nanometers, or including an excitation channel with a central wavelength that is greater than or equal to 670 or 700 nanometer). In certain embodiments, as compared to the emission channels shown in FIG. 6, the number of emission channels may be increased and/or the spectral distance between adjacent emission channels may be decreased through the use of a spectrally dispersive optical element such as a prism, diffractive grating, spectrometer, or spectrophotometer. In certain embodiments, as compared to the excitation channels shown in FIG. 6 the number of excitation channels may be increased and/or the spectral distance between adjacent excitation channels may be decreased through the use of a spectrally dispersive optical element such as a prism or diffractive grating.

The inventors have identified various combinations of dyes for which it is possible to detect and/or quantify amounts of one or more off-axis dye and, as a consequence, detect and/or quantify amounts target nucleic acids associated with respective ones of the on-axis/off-axis dyes. Various methods and dye combinations including at least one off-axis dye will now be discussed for identifying three dyes, five dyes, and ten dyes in a sample or in each sample of an array of samples.

Referring to FIG. 7, in certain embodiments, a method 700 includes an element 705 comprising providing sample 110 comprising a first on-axis dye and a second off-axis dye. The method 700 also includes an element 710 comprising performing an assay on the sample. The method 700 also includes an element 715 comprising illuminating the sample with a first radiant source characterized by a first excitation wavelength and/or wavelength band. The method 700 also includes an element 720 comprising, in response to illumination in element 715, making a first emission measurement from the sample at a first emission wavelength and/or over a first wavelength band. The method 700 also includes an element 725 comprising illuminating the sample with a second radiant source characterized by a second excitation wavelength and/or wavelength band that is different than that of the first. The method 700 also includes an element 730 comprising, in response to illumination in element 725, making a second emission measurement from the sample at a second emission wavelength and/or over a second wavelength band. The method 700 may optionally include an element 735 comprising adjusting the second emission measurement based on the first emission measurement to provide an adjusted second emission measurement. The method 700 may optionally include an element 740 comprising calculating an amount of the first and second dyes based on at least some of the emission measurements. The method 700 may optionally include an element 745 comprising determining an amount of the two target molecules based on at least some of the emission measurements.

Systems 2000, 3000, 4000, or 5000 may be used to perform method 700, in which case the radiant sources may be any of those discussed herein with regard to radiant sources 101, 401, for example, radiant generator 132 in combination with excitation spectral elements 141 or 441. The first and second emission measurements from the sample may be made using one or more detectors 115 in combination with emission spectral elements 121 or 421. Referring to element 710, the assay may be a PCR assay such as a qPCR assay, a dPCR assay, a post PCR assay such as melt curve analysis, or the like.

Figure 8:
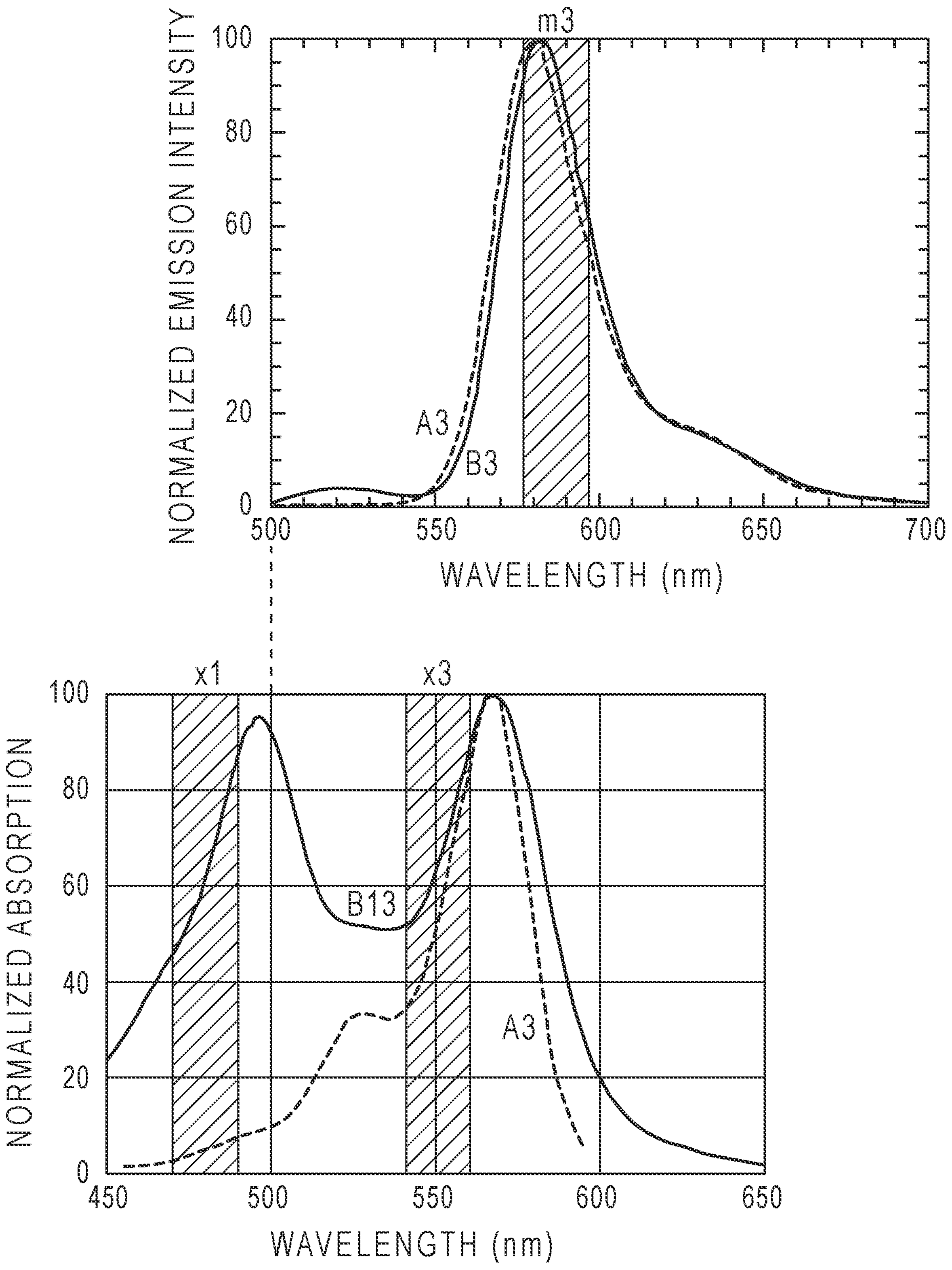
FIG. 8 is an absorption or excitation spectrum and associated emission spectrum for a pair of dyes according to an embodiment of the present disclosure.
Figure 9:
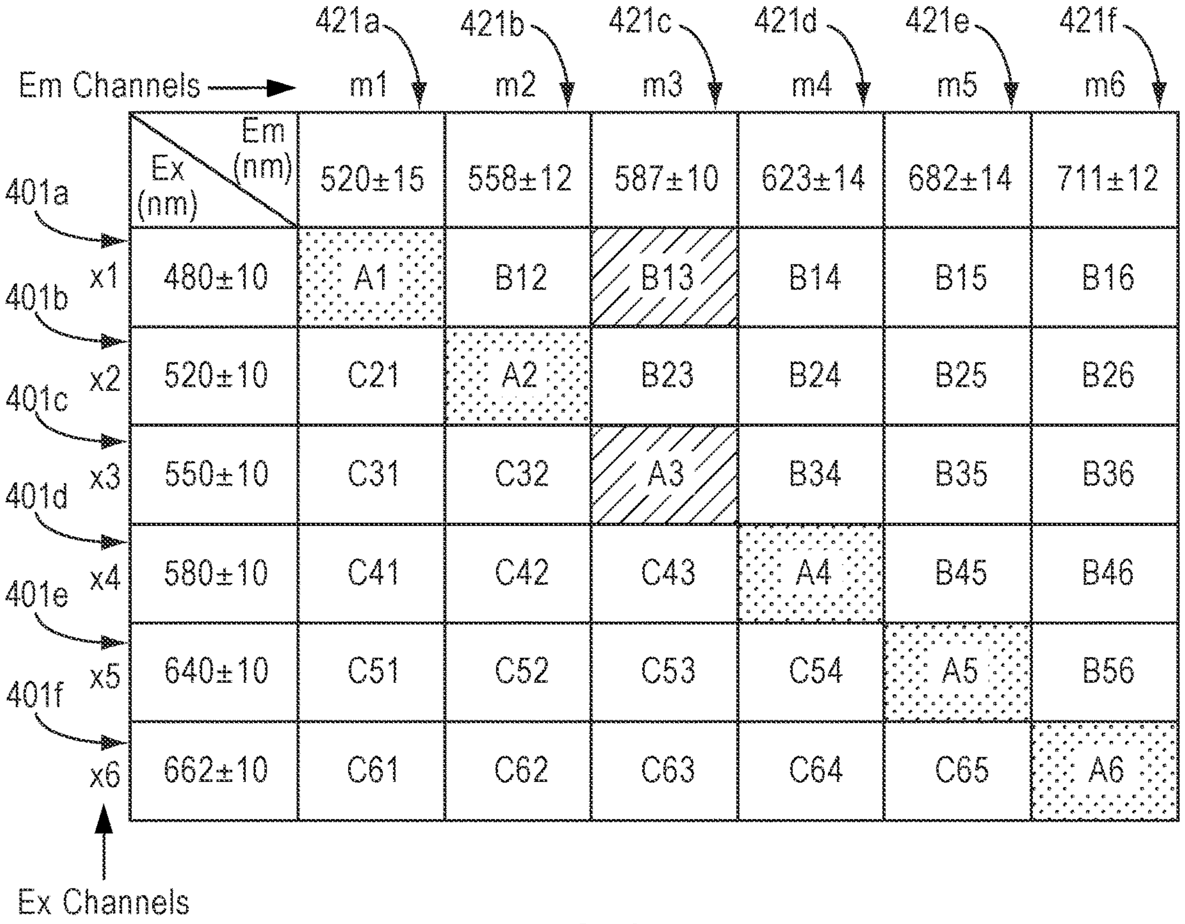
FIG. 9 is a tabular representation of a set of ex-em channels and dyes according to an embodiment of the present disclosure including the dyes shown in FIG. 8.

FIG. 8 shows the normalized absorption or excitation spectrum (lower plot) and the normalized emission spectra (upper plot) of two dyes suitable for use with method 700 (e.g., dyes A3 and B13). The features discussed here regarding plots in FIG. 8 are also generally applicable to the other such plots for other dyes discussed herein. The plots in FIG. 8 show normalized data for an off-axis dye referred to as B13 and an on-axis dye referred to as A3. The wavelength bands for excitation channels x1, x3 and emission channel m1, m3 from FIG. 6 are also indicated in the grayed-out area in the two plots. FIG. 9 shows the dyes A3 and B13 within the ex-em channel pair grid introduced in FIG. 6. The ex-em channel combination associated with these dyes correspond to absorption/excitation maximums and emission maximums for these two dyes. FIG. 9 shows ex-em channel combinations that may be correlated with the amount of each dye individually.

Using method 700 the amounts of the A3 and B13 may be determined using the excitation channels x1, x3 and emission channel m3 (i.e., channel combinations x1/m3 and x3/m3). Method 700 may also be used with other two dye combinations, such as disclosed herein or otherwise, that have a common or similar maximum emission wavelength (e.g., maximum emission wavelengths that are equal to one another, are within ±1 nanometer of one another, within ±2 nanometers of one another, within ±5 nanometers of one another, or within ±10 nanometers of one another) and with other ex-em channel combinations having spectral bandwidths that contains or is near to the maximum excitation and emission wavelengths of the two dyes. In the current example, the off-axis dye B13 comprises a maximum emission wavelength that is equal to or substantially equal to the maximum emission wavelength of the on-axis dye A3. In some embodiments, the dyes may comprise maximum emission wavelengths that are within 2 nanometers of one another, within 5 nanometers of one another, within 10 nanometers of one another, or within 15 nanometers of one another. In embodiments with more complex sample mixtures having more than two dyes, the selection of the emission channel m3 is selected such that the integrated energy of either or both of the two target dyes over the m3 channel bandwidth is greater than that of any other dyes within the sample solution when illuminated by the x1 channel and/or x3 channel.

Referring to the nominal absorption plot shown in FIG. 8, the on-axis dye is seen to have a maximum excitation wavelength that is near the x3 excitation channel spectral bandwidth. However, the off-axis dye B13 is seen to have two local maximum excitation wavelengths, one that is near the bandwidth of excitation channel x1 and another that is near the bandwidth of excitation channel x3. Alternatively, the x1 and/or x3 channel bandwidths may be selected such that any or all of the maximum excitation wavelengths of the two dyes are within the spectral bandwidth of the x1 and/or x3 excitation channels. In embodiments with more complex sample mixtures having more than two dyes, the bandwidth of the excitation channel is selected such that integrated energy of the on-axis and/or off-axis dyes over the corresponding ex channels is greater than that for other dyes contained in the same sample.

Figure 10:
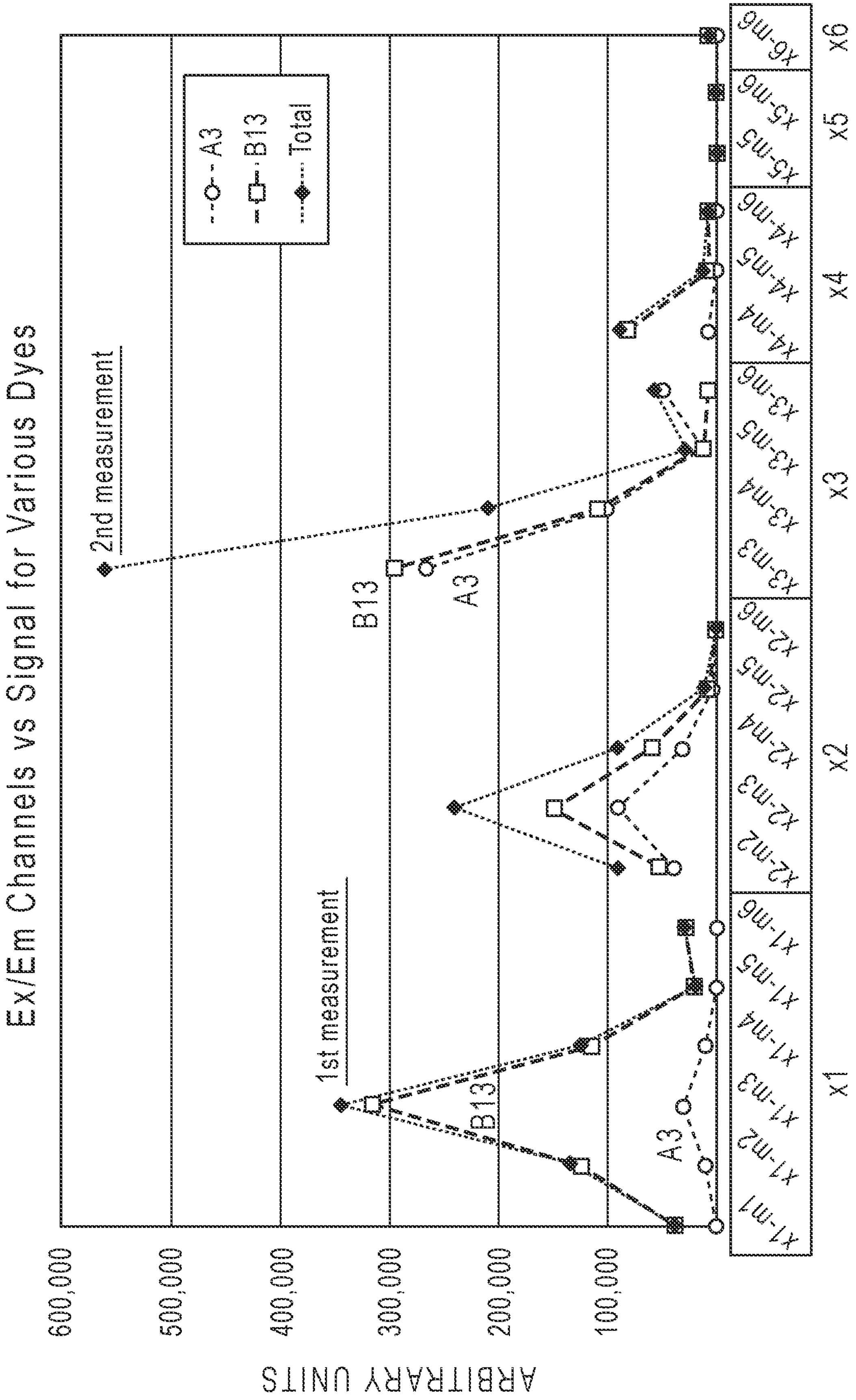
FIG. 10 is a graph of an ex-em channel space of the dyes shown in FIG. 8.

FIG. 10 shows the "ex-em channel space" or "ex-em filter space" (herein referred to as the "ex-em space") in the current example of method 700 and is based on the spectral characteristic of the dyes shown in FIG. 8 and the selected excitation and emission bands for each channel shown in FIG. 9 (i.e., for channels x1-x6 and m1-m6). FIG. 10 also shows the summation of the signals from the individual dyes at each ex-em channel combination, which is labeled as "Total". The lines between each of the data points in the plots are for clarity purposes in order to make it easier to see how the signal changes from one ex-em channel combination to the next (e.g., from x1-m1 to x1-m2, from x1-m2 to x1-m3, etc.). As can be seen, there is a break in the lines between different excitation channels (e.g., between x1-m6 and x2m2, between x2-m6 and x3-m3, etc.) so that each set of excitation channel can be distinguished from the next. As can be seen, each dye has a unique and distinctive signature, fingerprint, or pattern in the ex-em space, which the inventors have discover allows an off-axis dye to be distinguished from an on-axis dye and/or enables correction of signal interference or cross-talk between dyes when multiple dyes simultaneously produce signals that are above an ambient noise or threshold level.

The illustrated ex-em space for the A1 and B13 dyes in the current example are for a sample containing equivalent amounts of these dyes and using an instrument configured like system 4000 and the selected ex-em channel bandwidths shown. The detected signals for the first and second emission measurements in method 700 are values labeled "Total" in FIG. 10. The data in FIG. 10 for A1 and B13 are based on known amounts of these dyes in the sample for this example and on the known, distinctive dye signature, fingerprint, or pattern in the ex-em space for each dye. In general, the amount of some or all of the individual dyes is unknown and the amount of each dye and associated target molecules is determined using the method 700 or other deconvolution methods based on the first and second emission measurements in method 700.

Referring to elements 720, 730, 735 and with reference to FIG. 10, the contribution to the total signal in the second emission measurement (channel combination x3-m3) includes significant emission signals from both the off-axis dye, B13, and the on-axis dye, A3; however, the first emission measurement (channel combination x1-m3) includes emission signals almost entirely from the off-axis dye, B13. Therefore, the first emission measurement correlates well with the amount of B13 dye contained in the sample and provides a good estimate of the amount of B13 present in the sample. Based on the estimated amount of B13 from the first emission measurement, the contribution of dye B13 to the second measurement (total x3-m3 signal) can be estimated, since the spectral characteristic of the dyes are known from the ex-em data shown in FIG. 8. Thus, an adjusted second measurement can be calculated by subtracting the estimated emission of dye B13 in x3-m3 from the second measurement. The adjusted second emission measurement, therefore, correlates to the amount of A3 dye in the sample, since the contribution of the emission signal from B13 the second signal has been removed.

In certain embodiments, the adjusted second measurement can be used to provide an adjusted first measurement, since the contribution of the dye A3 signal in the x1-m3 channel can now be approximated and subtracted from the first measurement. Further iterations can also be implemented to, for example, provide a further adjusted second measurement based on the adjusted first measurement. In other embodiments, the method 700 may be modified to incorporate a system of equations that are simultaneously solved to determine or measure amounts of the A3 and B13 dyes and the associated target molecules. In any of these embodiments of the method 700, ex-em space data (FIG. 10) from any or all of the other ex-em channel combinations may be incorporated to provide more accurate estimates of the amounts of the A3 and B13 dyes, and the associated target molecules (e.g. any or all of: measurements of m1-m6 when the sample is illuminated with x1, measurements of m2-m6 when the sample is illuminated with x2, measurements of m3-m6 when the sample is illuminated with x3, measurements of m4-m6 when the sample is illuminated with x4, measurements of m5-m6 when the sample is illuminated with x5, measurements of m6 when the sample is illuminated with x6). Solving simultaneous equations using measurements from selected or all available ex-em channel combinations increased the accuracy for determining the amounts the A3 and B13 dyes when only these two dyes are present in the sample. Solving simultaneous equations using measurements from selected or all available ex-em channel combinations can also be used to determine the amount of additional dyes when 10 or more dye are present in the sample.

Figure 12:
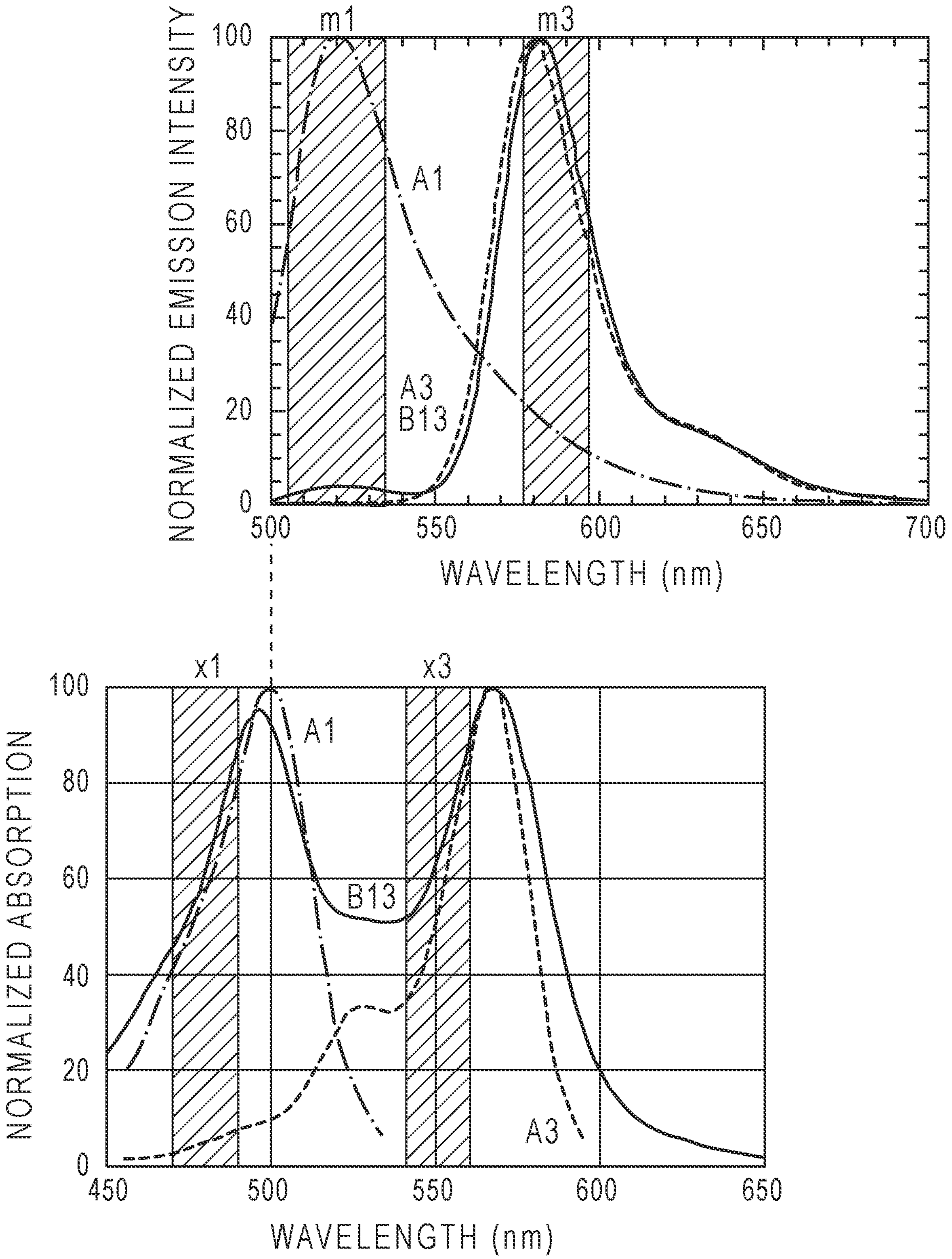
FIG. 12 is an absorption or excitation spectrum and associated emission spectrum for three dyes according to an embodiment of the present disclosure.

The following paragraphs explain advantages of the current teachings in terms of plots shown in FIG. 12. In prior art systems, a sample containing two or more on-axis dyes may be multiplexed to quantify an amount of the two or more corresponding target molecules to which the respective dyes are configured to bind. For example, on-axis dyes A1, A3 discussed above may both be placed in a sample containing two corresponding target molecules to which A1 and A3 are configured to bind (and may later be released to produce an emission signal). By illuminating the sample with channel x1 illumination, a large about of energy is absorbed by the A1 dye (as evidenced by the large integrated area under the absorption spectrum for A1 shown in FIG. 12 over the x1 excitation channel bandwidth). As seen in FIG. 12, most of resulting emitted energy of the A1 dye is contained in the m1 emission channel. By contrast, very little energy in the x1 channel is absorbed by the A3 dye, and most of this energy will be re-emitted in the m3 emission channel, not the m1 emission channel. Thus, the signal in emission channel m1 may be highly correlated with the amount A1 dye present in the sample. By similar review of the plots in FIG. 12, it can be seen that the combination of the x3 excitation channel with the m3 may be highly correlated with the amount A3 dye present in the sample.

However, these correlations are not exact. For example, the A1 dye has a small but measurable amount of emission in the m3 emission channel, which therefore can reduce the correlation to the A3 dye. This type of unwanted signal contribution is referred to as "cross-talk" or "signal interference". While the cross-talk is relatively small in the present example, it can be more significant when there are more than two on-axis dyes in a sample (e.g., A1, A2, and A4, or A1, A2, A3, and A4) and/or when, for a particular assay, there is a large amount of one target molecule and much less of another target molecule. These effects may be minimized by proper assay design, the use of calibration plates, and deconvolution algorithms for processing the raw emission data from each channel. The use of various off-axis channel combinations may also be used to enhance deconvolution, and thus improve the accuracy.

To compensate and/or correct for signal interference or cross-talk and other such effects, calibration plates may be used. A calibration plate contains known amounts multiple dyes. Thus, when illuminated with radiation from one or more excitation channels, the resulting fluorescent signal from each dye can be determined and the system can be corrected for cross-talk between the dyes under various illumination conditions. The calibration plate may comprise the known dye combinations in one or more reaction sites (e.g., the wells or vials of a 96 or 384 well microtiter plate), which correspond to one or more reaction sites of a test plate containing unknown amounts of a combination of target molecules. One commercially available example of a calibration plate is the Thermo Fisher calibration plate A26337. The A26337 establishes a pure dye spectra and multicomponent values for ABY™ JUN™ and MUSTANG PURPLE™ dyes on Applied Biosystems's QuantStudio™ 3 and 5, 96-well 0.1-mL real-time PCR systems. The formulations of the dyes in this plate improve results with multiplexing by more accurately representing the fluorescent spectra of the respective probes in your real-time PCR experiments.

The inventors have discovered that the off-axis channels may be used not only to improve deconvolution algorithms to improve the accuracy of multiple on-axis dyes, but that added information from these off-axis channels can be used to include additional, off-axis dyes into a sample, without the need to increase the number of excitation or emission channel. For example, six on-axis dyes may be identified in a sample using the six Ex channels x1-x6 and the six Em channels m1-m6 discussed herein. In order to increase the number of on-axis dyes that may be detected beyond six, additional Ex and Em channels would be needed using prior art techniques. Not only does this increase system costs and complexity, but there may be technical issues that, for example, make it difficult to increase the number of wavelength bands that can be provided utilizing optical components that are suitable for operation within the visible wavelength band.

The inventors have discovered that additional off-axis dyes may be included in sample 110 to increase the number of dyes and corresponding target molecules that can be measured with the same set of excitation and emission channels. This result was unexpected, since the introduction of additional off-axis dyes increases the problem of cross-talk discussed above in regard to multiplexing multiple on-axis dyes in the same sample. To appreciate, reference is again made to FIG. 12. For example, it can be seen that there is a large amount of cross-talk between the dyes A3 and B13, since both dyes A3 and B13 absorb significant energy in x3 excitation channel and both re-emit this energy in the m3 emission channel. Based on these observations, it would not appear possible to determine how much of the signal in the x3, m3 channel combination is from each of dyes A3, B13.

However, it has been discovered that the data from both the on-axis and off-axis channel combinations can be used to help mitigate such problems. For example, in the present case, the B13 channel combination may be used to help determine the amount dye B13 present in the sample 110. With this information, the contribution of dye B13 to the signal in the A3 channel combination may be calculated and used to modify the m3 signal to determine the amount of dye A3. This can be explained as follows. As seen in the absorption plot in FIG. 12, dye B13 absorbs a significant amount of energy over the excitation channel x1 band, while the dye A3 absorbs very little energy over excitation channel x1 band. Also, a significant amount of the x1 energy absorbed by dye B13 is emitted in the m3 channel. Thus, the x1 excitation channel can be used to determine the amount of both the A1 and B13 dyes by measuring the signals in the m1 emission channel and m3 emission channel, respectively, since dye A1 emits primarily in emission channel m1 and dye B13 emits primarily in emission channel m3 when both are illuminating using excitation channel x1. With this information for the amount of dye B13, the amount of the dye A3 may be determined using the x3 excitation channel, by adjusting the m3 emission signal for the known amount the B13 dye.

Figure 11:
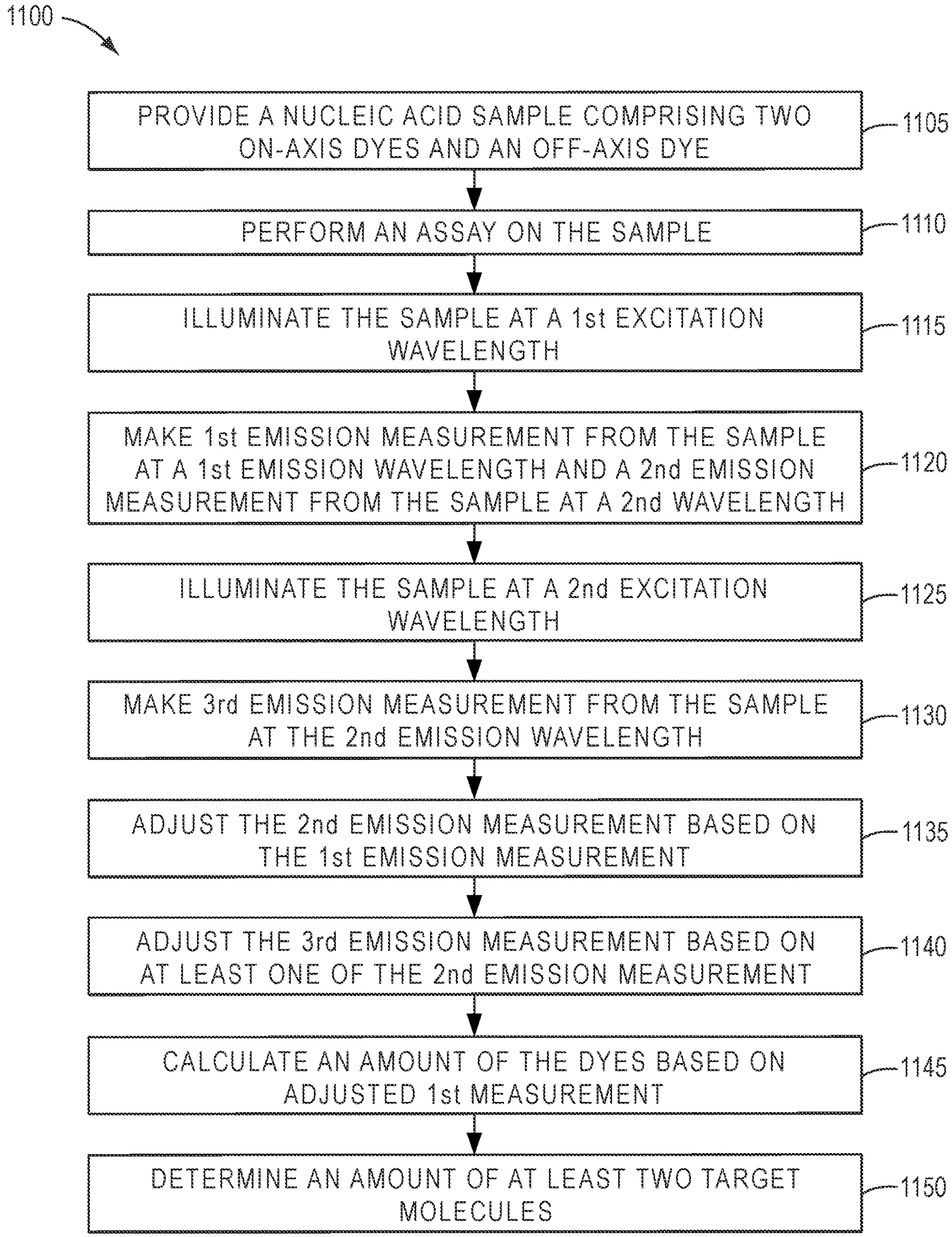
FIG. 11 is a method according to an embodiment of the present disclosure.

Referring to FIG. 11, in certain embodiments, a method 1100 includes an element 1105 comprising providing sample 110 comprising a first and second on-axis dye and a third off-axis dye. The method 1100 also includes an element 1110 comprising performing an assay on the sample. The method 1100 also includes an element 1115 comprising illuminating the sample with a first radiant source characterized by a first excitation wavelength and/or wavelength band. The method 1100 also includes an element 1120 comprising, in response to illumination in element 1115, making a first emission measurement from the sample at a first emission wavelength and/or over a first wavelength band and making a second emission measurement from the sample at a second emission wavelength and/or over a first wavelength band. The method 1100 also includes an element 1125 comprising illuminating the sample with a second radiant source characterized by a second excitation wavelength and/or wavelength band that is different than that of the first. The method 1100 also includes an element 1130 comprising, in response to illumination in element 1125, making a third emission measurement from the sample at the second emission wavelength and/or over the second wavelength band. The method 1100 may optionally include an element 1135 comprising adjusting the second emission measurement based on the first emission measurement to provide an adjusted second emission measurement. The method 1100 may optionally include an element 1140 comprising adjusting the third emission measurement to provide an adjusted second emission measurement that is based on at least one of the first emission measurement, the second emission measurement, and/or the adjusted second emission measurement. The method 1100 may optionally include an element 1145 comprising calculating an amount of the first, second, and third dyes based on at least some of the emission measurements. The method 1100 may optionally include an element 1145 comprising determining an amount of the three target molecules based on the amounts of the dyes present in the sample.

Systems 2000, 3000, 4000, or 5000 may be used to perform method 1100, in which case the radiant sources may be any of those discussed herein with regard to radiant sources 101 or 401, for example, radiant generator 132 in combination with excitation spectral elements 141 or 441. The emission measurements from the sample may be made using one or more detectors 115 in combination with, respectively, emission spectral elements 101*a*, 101*b* or two of the emission spectral elements 421*a-f*. Referring to element 1110, the assay may be a PCR assay such as a qPCR assay, a dPCR assay, a post PCR assay such as melt curve analysis, or the like. Where appropriate, any aspects of method 700 discussed above herein may also apply to method 1100, for example, regarding dyes, radiant sources, and/or emission filtering characteristics or methods of use.

FIG. 12 shows the normalized absorption spectrum and the normalized emission spectra three dyes suitable for use with method 1100 (two on-axis dyes A1, A3, and one off-axis dye B13). The features discussed here regarding plots in FIG. 12 are also generally applicable to the other such plots for other dyes discussed herein. The plots in FIG. 12 show normalized data for an off-axis dye B13 and an on-axis dyes A1 and A3. These three dyes are suitable for the ex-em channel combinations x1-m3, x1-m1 and x3-m3, respectively, shown in FIG. 6.

Using method 1100 the amounts of the A1, A3 and B13 may be determined using the excitation channels x1, x3 and emission channels x1, m3 (i.e., channel combinations x1/m3, x1/m1, and x3/m3). Method 1100 may also be used with other three dye combinations, such as disclosed herein or otherwise, where one of the on-axis dyes has a common or similar maximum emission wavelength with the off-axis dye and the other on-axis dye has a common or similar maximum excitation wavelength with the off-axis dye. Method 1100 may also be used with other ex-em channel combinations having a spectral bandwidth that contain or are near to the maximum emission and excoriation wavelengths of the three dyes. In the current example, the off-axis dye B13 comprises a maximum emission wavelength that is equal to or substantially equal to the maximum emission wavelength of the on-axis dye A3. Additionally, the off-axis dye B13 comprises a maximum excitation wavelength that is equal to or substantially equal to the maximum emission wavelength of the on-axis dye A1. In some embodiments, the dyes may comprise maximum emission wavelengths that are within 2 nanometers of one another, within 5 nanometers of one another, within 10 nanometers of one another, or within 15 nanometers of one another. In embodiments with more complex sample mixtures having more than three dyes, the selection of the emission channel m1 and m3 are selected such that the integrated energy of the three target dyes over each of the x1, x3, m1, and m3 channel bandwidths is greater than that of any other dyes within the sample when illuminated by the x1 channel and/or x3 channel and/or emitting energy in the m1 and/or m3 channels.

Figure 13:
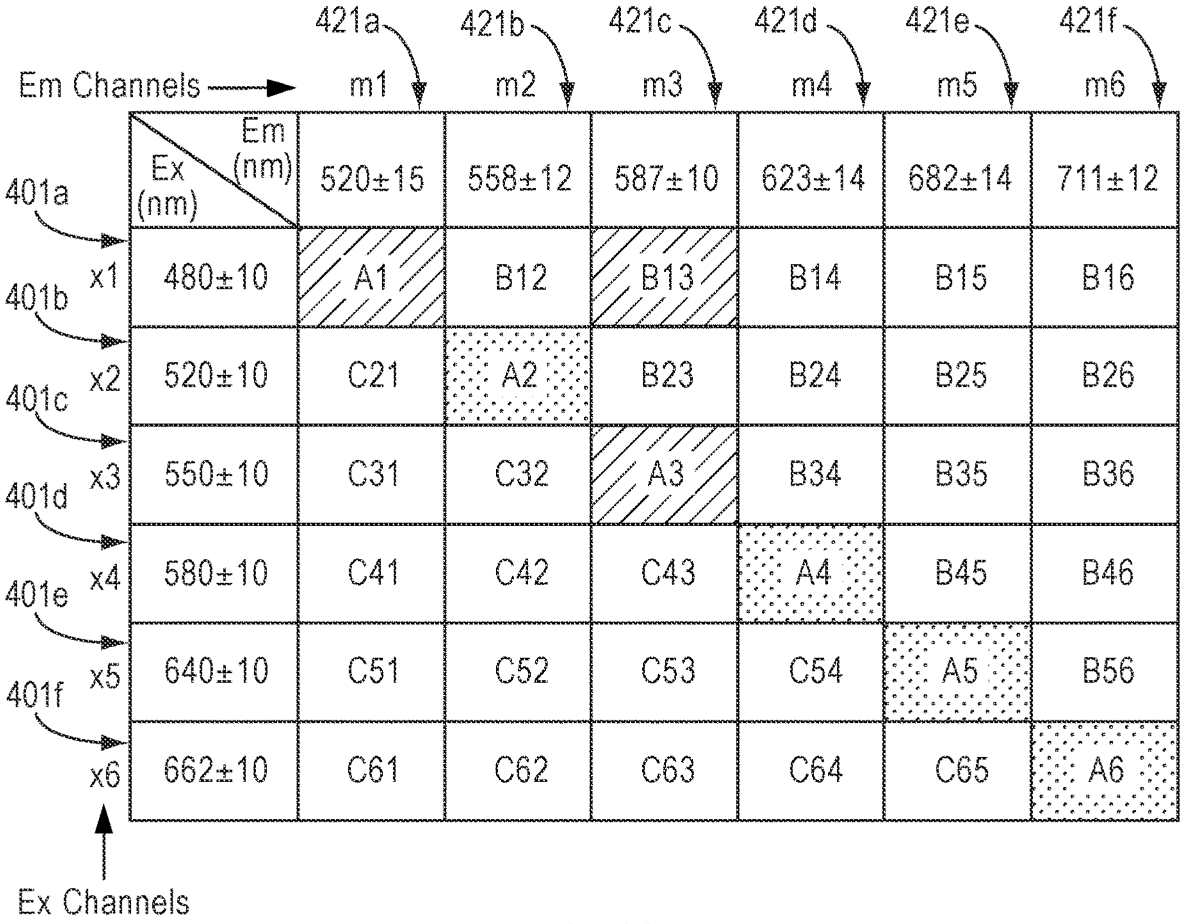
FIG. 13 is a tabular representation of a set of ex-em channels and dyes according to an embodiment of the present disclosure including the dyes shown in FIG. 12.

Referring to the nominal absorption plot shown in FIG. 12, the A1 on-axis dye is seen to have a maximum excitation wavelength that is near the x1 excitation channel spectral bandwidth, while the A3 on-axis dye is seen to have a maximum excitation wavelength that is near the x3 excitation channel spectral bandwidth. However, the off-axis dye B13 is seen to have two local maximum excitation wavelengths, one that is near the bandwidth of excitation channel x1 and another that is near the bandwidth of excitation channel x3. Alternatively, the x1 and/or x3 channel bandwidths may be selected such that any or all of the maximum excitation wavelengths of the three dyes are within the spectral bandwidth of the x1 and/or x3 excitation channels. In embodiments with more complex sample mixtures having more than three dyes, the bandwidth of the excitation channel is selected such that integrated energy of the on-axis and/or off-axis dyes over the corresponding ex channels is greater than that for other dyes contained in the same sample. FIG. 13 shows the dyes A1, A3, and B13 within the ex-em channel pair grid introduced in FIG. 6. The ex-em channel combination associated with these dyes correspond to absorption/excitation maximums and emission maximums for these three dyes. FIG. 13 shows ex-em channel combinations that may be correlated with the amount of each dye individually.

Figure 14:
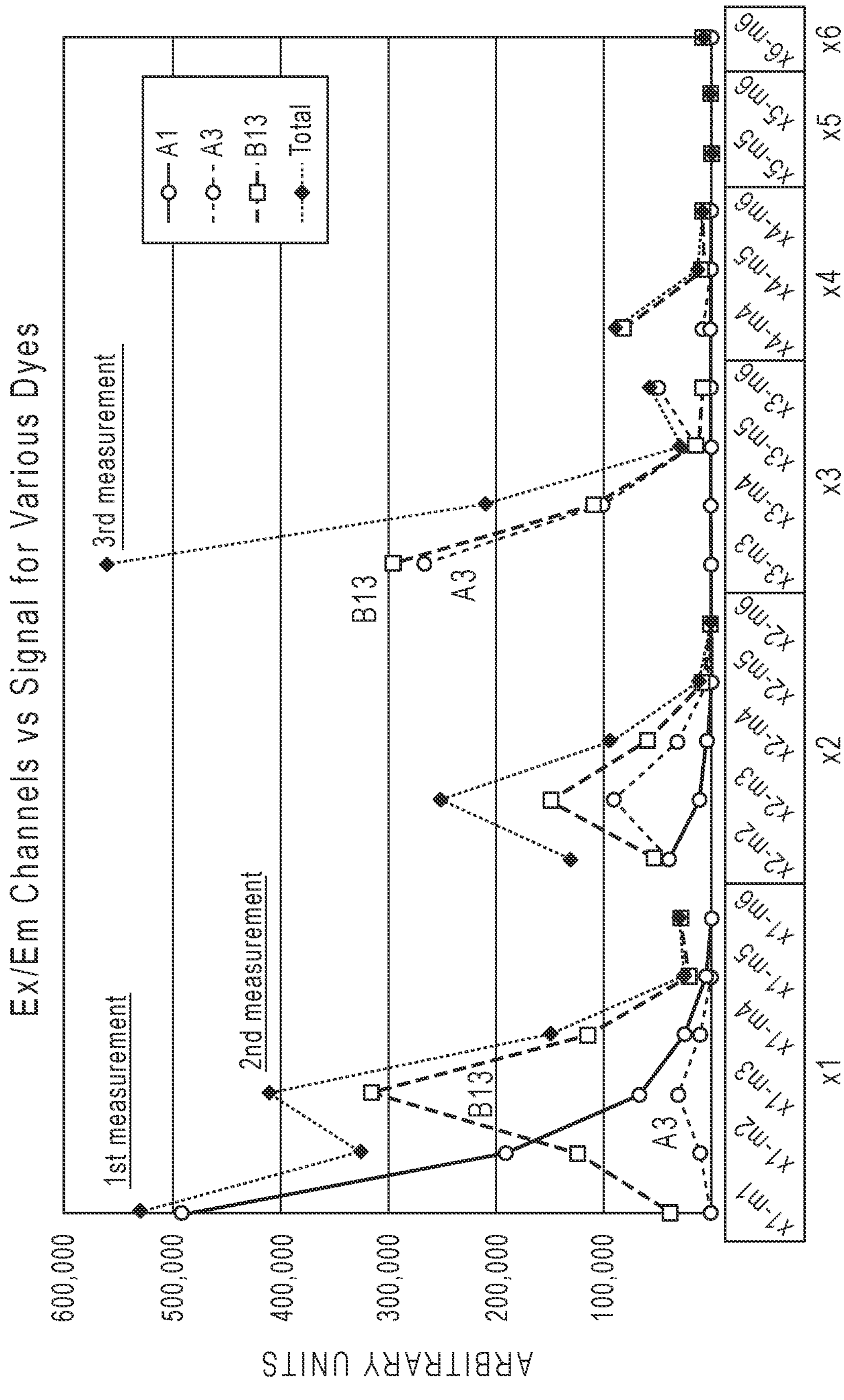
FIG. 14 is a graph of an ex-em channel space of the dyes shown in FIG. 12.

FIG. 14 shows the ex-em space for the three selected dyes used in the current example of method 1100 and is based on the spectral characteristic of the dyes shown in FIG. 12 and the selected excitation and emission bands for each channel shown in FIG. 13 (i.e., for channels x1-x6 and m1-m6). FIG. 14 also shows the summation of the signals from the individual dyes at each ex-em channel combination, which is labeled as "Total". As can be seen, each dye has a unique and distinctive signature or fingerprint in the ex-em space, which the inventors have discover allows an off-axis dye to be distinguished from an on-axis dye and/or enables correction of cross-talk between dyes when multiple dyes simultaneously produce signals that are above an ambient noise or threshold level.

The illustrated ex-em space for the A1, A3, B13 dyes in the current example are for a sample containing equivalent amounts of these dyes and using an instrument configured like system 4000 and the selected ex-em channel bandwidths shown. The detected signals for the first, second, and third measurements in method 1100 are values labeled "Total" in FIG. 14. The data in FIG. 14 for A1, A3, and B13 are based on known amounts of these dyes in the sample for this example and on the known, distinctive dye signature or fingerprint in the ex-em space for each dye. In general, the amount of some or all of the individual dyes is unknown and the amount of each dye and associated target molecules is determined using the method 1100 or other deconvolution methods based on the first, second, and third measurements in method 1100. The inventors have found that for more complex samples with greater numbers of on-axis and off-axis dyes and associated target molecules, the unique signature or fingerprint of each dye in the ex-em space, represented in FIG. 14 of this example, can be utilized to multiplex ten or more on-axis/off-axis dyes simultaneously in a common sample.

Referring to elements 1120, 1130, 1135, 1140 and to the ex-em space plots in FIG. 14, the contribution to the total signal in the second emission measurement (channel combination x1-m3) includes significant emission signals from both on-axis dyes, A1 and A3, as well as from off-axis dye, B13; however, the first emission measurement (channel combination x1-m1) includes emission signals primarily from the on-axis dye, A1. Therefore, the first emission measurement correlates well with the amount of A1 dye contained in the sample and provides a good estimate of the amount of A1 present in the sample. Based on the estimated amount of A1 from the first emission measurement, the contribution of dye A1 to the second measurement (total x1-m3 signal) can be estimated, since the spectral characteristic of the dyes are known from the ex-em data shown in FIG. 12. Thus, an adjusted second measurement can be calculated by subtracting the estimated emission of dye A1 in the x1-m3 from the second measurement. The adjusted second emission measurement, therefore, correlates to the amount of B13 dye in the sample, since the contribution of the emission signal from A3 the second signal has been removed.

In similar fashion, the contribution to the total signal in the third emission measurement (channel combination x3-m3) includes significant emission signals from off-axis dye, B13, as well as from on-axis dye, A3; however, the adjusted second emission measurement (channel combination x1-m3) provides a good estimate of the amount of B13 dye present in the sample. Based on the estimated amount of B13 from the adjusted second emission measurement, the contribution of dye B13 to the third measurement (total x3-m3 signal) can be estimated, since the spectral characteristic of the dyes are known from the ex-em data shown in FIG. 12. Thus, an adjusted third measurement can be calculated by subtracting the estimated emission of dye B13 in the x3-m3 from the third measurement. The adjusted third emission measurement, therefore, correlates to the amount of A3 dye in the sample, since the contribution of the emission signal from B13 the second signal has been removed. While the contribution of the A1 dye in the x3-m3 channel combination is insignificant in the present example, in general, method 1100 can also be used to subtract the amount of signal from the A1 dye in the x3-m3 channel combination to provide a more accurate adjusted third signal, leading to even better correlation of the adjusted third signal to the amount of the A3 dye and of the target molecule to which it is associated.

In certain embodiments, the adjusted second measurement and/or the adjusted third measurement can be used to provide an adjusted first measurement, since the contribution of the B13 dye signal and the A3 dye signal in the x1-m1 channel can now be approximated and subtracted from the first measurement (since these spectral characteristics of these dyes in any emission channel can be determined from the data in FIG. 12). Additionally or alternatively, the adjusted third measurement can be used to provide more accurate adjusted second measurement, since the contribution of the A3 dye signal in the x1-m3 channel can now be approximated and subtracted from the second measurement (since these spectral characteristics of the A3 in any emission channel can be determined from the data in FIG. 12). Further iterations can also be implemented to, for example, provide further adjusted third measurement based on the adjusted first and/or second measurements. In other embodiments, the method 1100 may be modified to incorporate a system of equations that are simultaneously solved to determine or measure the amounts of the A1, A3, and B13 dyes and the associated target molecules. In any of these embodiments of the method 1100, ex-em space data (FIG. 14) from any or all of the other ex-em channel combinations may be incorporated to provide more accurate estimates of the amounts of the A1, A3, and B13 dyes, and the associated target molecules (e.g. any or all of: measurements of m1-m6 when the sample is illuminated with x1, measurements of m2-m6 when the sample is illuminated with x2, measurements of m3-m6 when the sample is illuminated with x3, measurements of m4-m6 when the sample is illuminated with x4, measurements of m5-m6 when the sample is illuminated with x5, measurements of m6 when the sample is illuminated with x6). Solving simultaneous equations using measurements from selected or all available ex-em channel combinations increased the accuracy for determining the amounts of the A1, A3, and B13 dyes when only these three dyes are present in the sample. Solving simultaneous equations using measurements from selected or all available ex-em channel combinations can also be used to determine the amount of additional dyes when 10 or more dye are present in the sample.

Referring to element 1150, in certain embodiments, the first and second dyes are associated with and/or configured to bind or attach to different target molecules, such as first and second target polynucleotides, first and second proteins, or the like.

Referring to again to FIGS. 2-4, method 700 may be performed using any of system 3000, 4000, 5000 to measure an amount of at least a first dye and a second. Method 700 may be used to further measure or calculate an amount of a first target molecule configured to bind to the first dye and/or an amount of a second target molecule configured to bind to the second dye. In such embodiments, elements 715, 725 include illuminating sample 110 with radiant sources 101*a*, 101*b* or with first and second of radiant sources radiant sources 401*a-f*, where each of the two radiant sources is characterized by an average excitation wavelength that is different from that of the other (e.g., different by at least 60 nanometers). In the current embodiment, each emission spectral element 121*a*, 121*b* or two emission spectral elements 141*a-f* is characterized by an average emission wavelength from that is different from that of the other (e.g., different by at least 60 nanometers). In response to the illuminations, elements 720, 730 of method 700 includes:

- measuring an emission from sample 110 using detector 115 and emission spectral element 121*a* or a first of emission spectral elements 421 in response to illuminating the sample with radiant source 101*a* or the first of radiant sources 401, and
- measuring an emission from sample 110 using detector 115 and emission spectral element 121*b* or a second of emission spectral elements 421 in response to illuminating the sample with radiant source 101*b* or the second of radiant sources 401

In certain embodiments, the first dye comprises a first emission spectrum comprising a first maximum emission wavelength and the second dye comprises a second emission spectrum comprising a second maximum emission wavelength that is equal to or substantially equal first maximum emission wavelength. For example, the first dye may be an on-axis dye and the second dye may be an off-axis dye, where the maximum emission wavelength is the same or approximately the same (e.g., within 2 nanometers of one another or within 5 nanometers of one another).

Referring to again to FIGS. 3 and 4, method 1100 may be performed using any of system 3000, 4000, 5000 to measure an amount of at least a first dye, a second, and a third dye. Method 700 may be used to further measure or calculate an amount of a first target molecule configured to bind to the first dye, an amount of a second target molecule configured to bind to the second dye, and/or an amount of a third target molecule configured to bind to the third dye. In such embodiments, elements 1115, 1125 include illuminating sample 110 with radiant sources 101*a*, 101*b* or with first and second of radiant sources radiant sources 401*a-f*, where each of the two radiant sources is characterized by an average excitation wavelength that is different from that of the other (e.g., different by at least 60 nanometers). In the current embodiment, each emission spectral element 121*a*, 121*b* or two emission spectral elements 141*a-f* is characterized by an average emission wavelength from that is different from that of the other (e.g., different by at least 60 nanometers). In response to the illuminations, elements 1120, 1130 of method 1100 includes:

measuring an emission from sample 110 using detector 115 and emission spectral element 121*a* or a first of emission spectral elements 421 in response to illuminating the sample with radiant source 101*a* or the first of radiant sources 401, measuring an emission from sample 110 using detector 115 and emission spectral element 121*b* or a second of emission spectral elements 421 in response to illuminating the sample with radiant source 101*a* or the first of radiant sources 401, and measuring an emission from sample 110 using detector 115 and emission spectral element 121*b* or a second of emission spectral elements 421 in response to illuminating the sample with radiant source 101*b* or the second of radiant sources 401

In certain embodiments:

the first dye comprises a first absorption spectrum comprising a first maximum absorption wavelength the second dye comprises a second absorption spectrum comprising a second maximum absorption wavelength that is equal to or substantially equal first maximum absorption wavelength (e.g., within 2 nanometers of one another or within 5 nanometers of one another); and the second dye comprises a second emission spectrum comprising a second maximum emission wavelength and he third dye comprises a third emission spectrum comprising a third maximum emission wavelength that is equal to or substantially equal second maximum emission wavelength (e.g., within 2 nanometers of one another or within 5 nanometers of one another).

For example, the first and third dyes may be on-axis dyes having maximum absorption wavelengths over different excitation channels of a system or instrument.

In various embodiments, method 700 or method 1100 may further comprises performing an amplification assay on sample 110 using any of systems 1000, 2000, 3000, 4000, 5000. In such embodiments, method 700, 1100 may be performed using the various embodiments discussed herein for these systems. Embodiments of method 700, 1100 may include performing elements 715-70, 1115-1130 either during the amplification assay. For example, the amplification assay may be a real-time polymerase chain reaction (qPCR) assay in which sample 110 heated and cool over various cycles using a thermal cycler. At one or more points during one or more of the cycles, any or all of elements 715-70, 1115-1130 may be performed on sample 110. Additionally or alternatively, method 700, 1100 may be performed after the conclusion of PCR or other amplification assay. For example, after the last cycle of a PCR assay, during a melt assay after an amplification assay, or digital PCR (dPCR) assessment after an amplification assay.

Figure 15:
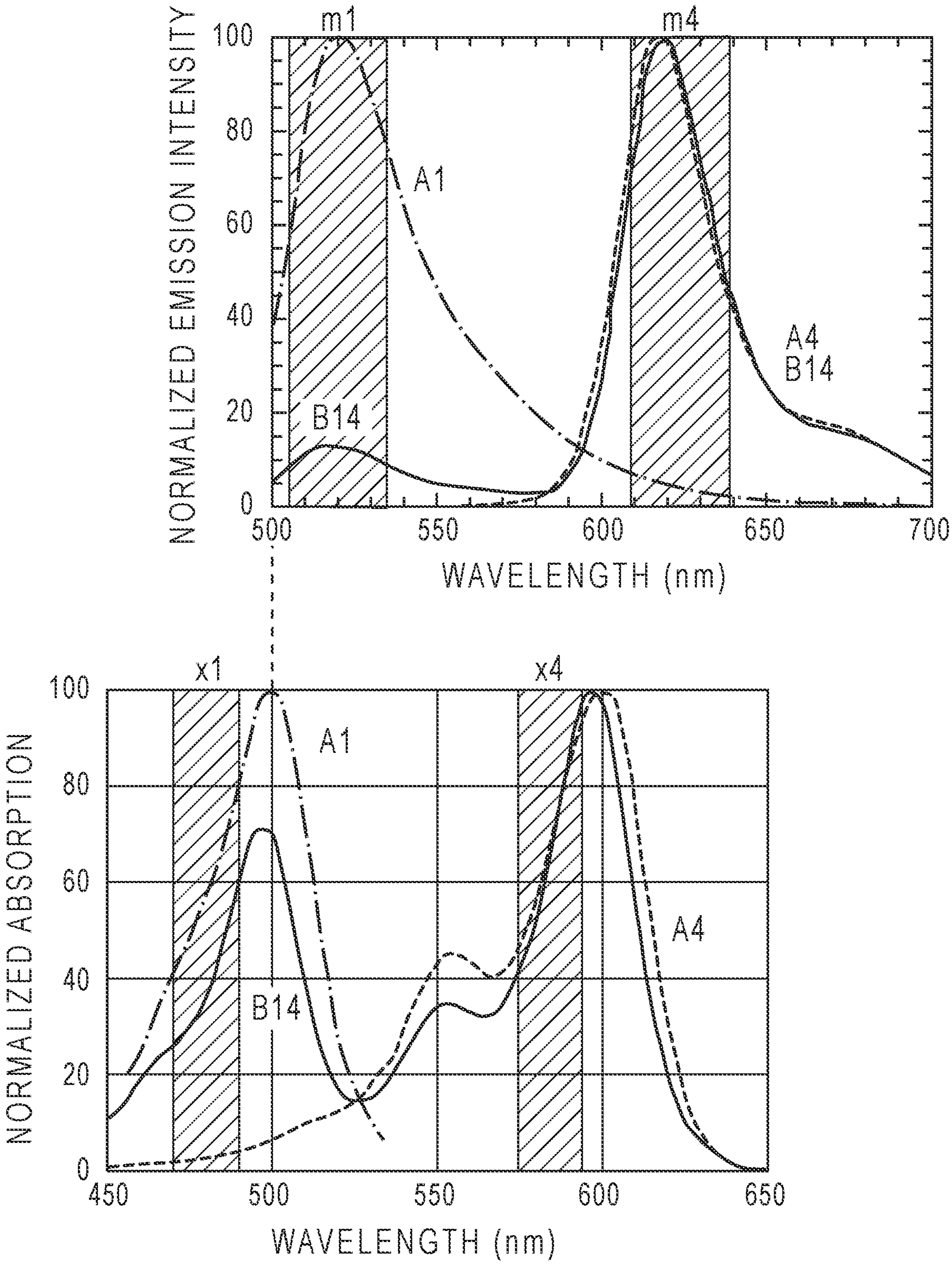
FIG. 15 is an absorption or excitation spectrum and associated emission spectrum for three dyes according to an embodiment of the present disclosure.

Referring to FIG. 15, the absorption or excitation spectral characteristic and the emission spectral characteristics of another triad combination of dyes is shown (dyes A1, A4, and B14). The amounts of A4 and B14 can also be determined or measured using methods 700 and/or 1100, where the same process is used as described above, but substituting channels combination x1-x4 and x4-m4 for channels combination x1-x3 and x3-m3. FIG. 16 shows the combined spectral characteristics of all five dyes discussed above (A1, A3, A4, B13, B14).

FIG. 17 shows the dyes A1, A3, A4, B13, B14 within the ex-em channel pair grid introduced in FIG. 6. The ex-em channel combination associated with these dyes correspond to absorption/excitation maximums and emission maximums for these five dyes. FIG. 17 shows ex-em channel combinations that may be correlated with the amount of each dye individually. Due to cross-talk when all five dyes are present, each dye's signature or fingerprint in the ex-em space shown in FIG. 18 may be used to reduce or eliminate the effects of cross-talk. For example, method 700, and the variations discussed above, may be used to correct for cross-talk between dyes A3, B13 and/or dyes A4, B14 contained in a sample. Additionally or alternatively, method 1100, and the variations discussed above, may be used to correct for cross-talk between dyes A1, A3, B13 and/or dyes A1, A4, B14 contained in a sample.

Figure 18:
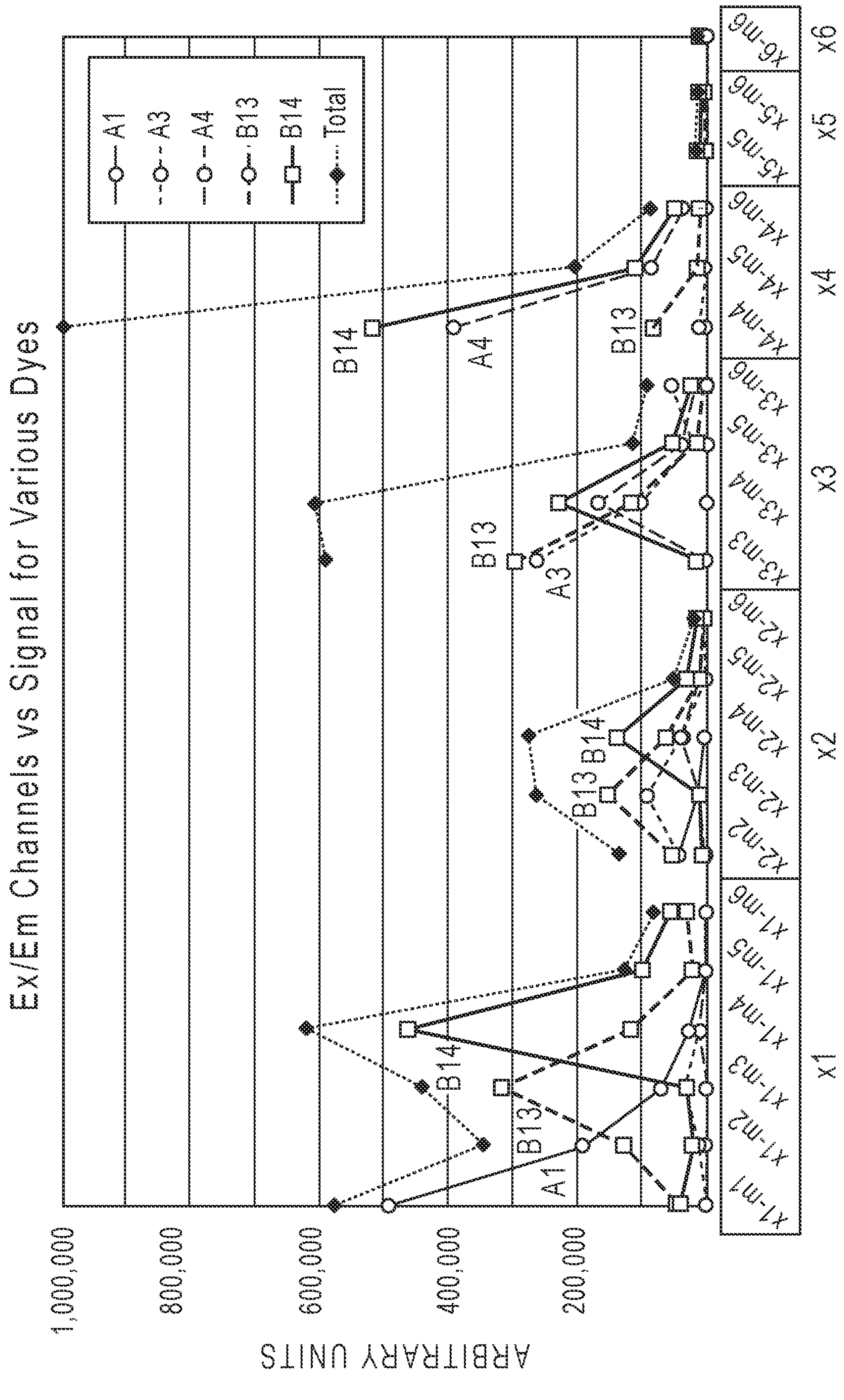
FIG. 18 is a graph of an ex-em channel space of the dyes shown in FIG. 16.

As seen in FIG. 18, the signatures or patterns of the A4 and B14 dyes are quite different from those of A3 and B13 dyes. For example, the contribution to the total signal from A3 and B13 is low in the x1-m4 and x4-m4 channel combinations. Therefore, in some embodiments, the A1, A4, B14 triad can be processed using method 1100 without considering the contribution of the signals from A3, B13. Alternatively, as discussed above with regard to a variation on method 1100 discussed above, a system of equations may be incorporated that are simultaneously solved determine or measure the amounts of the A1, A3, A4, B13, and B14 dyes and the associated target molecules. In certain embodiments, method 1100 may be modified to incorporate a system of equations including some or all 21 ex-em channel combinations of the "A" and "B" channel combinations shown in FIG. 6. Some or all of the ex-em space data in FIG. 18 may be incorporated to provide accurate estimates of the amounts of all five dyes and associated target molecules. In certain embodiments, the dyes A1, A3, A4, B13, B14 may various combinations of the dyes listed below in Table A. In certain embodiments, the assay performed may be a PCR assay such as a qPCR assay, a dPCR assay, a post PCR assay such as melt curve analysis, or the like.

TABLE 1 dyes for 2-plex, 3-plex, and 5-plex assays using x1, x3, x4, m1, m3, m4 channels

| Dye type | ex-em channels | Ex band (nm) | Em band (nm) | Suitable dyes |
|---|---|---|---|---|
| A1 | x1-m1 | 480 ± 10 | 520 ± 15 | 5-FAM, 6-FAM, Oregon Green, TET, R110 |
| A3 | x3-m3 | 550 ± 11 | 587 ± 10 | NED, TAMRA, ABY, DY-555 |
| A4 | x4-m4 | 580 ± 10 | 623 ± 14 | PET, ROX, JUN, Texas Red, Alexa Fluor 594 |
| B13 | x1-m3 | 480 ± 10 | 587 ± 10 | FAM-TAMRA, FAM-ABY, FAM-NED |
| B14 | x1-m4 | 480 ± 10 | 623 ± 14 | FAM-PET, FAM-ROX, FAM-JUN, FAM-Texas Red, TET-Alexa Fluor 594 |

FIG. 19 shows the dyes A1-A6, B13, B14, B35, and B36 within the ex-em channel pair grid introduced in FIG. 6. The ex-em channel combination associated with these dyes correspond to absorption/excitation maximums and emission maximums for these 10 dyes. FIG. 19 shows ex-em channel combinations that may be correlated with the amount of each dye individually. The inventors have discovered various dye combinations that may be used with these ten ex-em channel combinations to permit the amount of all ten dyes and associated target molecules to be simultaneously detected and/or measured. Table 2 below shows various dyes that may be used in each of these ten ex-em combinations.

TABLE 2 dyes for 10-plex assays using six excitation and six emission channels

| Dye type | ex-em channels | Ex band (nm) | Em band (nm) | Suitable dyes |
|---|---|---|---|---|
| A1 | x1-m1 | 480 ± 10 | 520 ± 15 | 5-FAM, 6-FAM, Oregon Green, TET, R110 |
| A2 | x2-m2 | 520 ± 10 | 558 ± 11 | VIC, HEX, JOE, Yakima Yellow, R6G |
| A3 | x3-m3 | 550 ± 11 | 587 ± 10 | NED, TAMRA, ABY, DY-555 |
| A4 | x4-m4 | 580 ± 10 | 623 ± 14 | PET, ROX, JUN, Texas Red, Alexa Fluor 594 |
| A5 | x5-m5 | 640 ± 10 | 682 ± 14 | Alexa Fluor 647, Cy5 ®, ATTO 647 ™, DyLight 650 ™ |
| A6 | x6-m6 | 662 ± 10 | 711 ± 13 | Alexa Fluor 676, DyLight 680 ™, Cy5.5 ® |
| B13 | x1-m3 | 480 ± 10 | 587 ± 10 | FAM-TAMRA, FAM-ABY, FAM-NED |
| B14 | x1-m4 | 480 ± 10 | 623 ± 14 | FAM-PET, FAM-ROX, FAM-JUN, FAM-Texas Red, TET-Alexa Fluor 594 |
| B35 | x3-m5 | 550 ± 11 | 682 ± 14 | ABY-Alexa Fluor 647, NED-Alexa Fluor 647, ABY-Cy5 ®, ABY-ATTO 647 ™, ABY-DyLight 650 ™ |
| B36 | x3-m6 | 550 ± 11 | 711 ± 13 | NED-Alexa Fluor 676, NED DyLight 680 ™, NED-Cy5.5 ®, ABY-Alexa Fluor 676, ABY DyLight 680 ™, ABY-Cy5.5 ® |

Comparing FIG. 19 with FIG. 17, it is seen that dyes A2, A5, A6, B35, and B36 have been added to the 5 dyes shown in FIG. 17. In certain embodiments, amounts of the on-axis dyes A2, A5, A6 in the sample may be at least be approximately determined or measured by correlation to the signal received at a detector by using on-axis, ex-em channel combinations x2-m2, x5-m5, and x6-m6. As seen in FIG. 18, the signatures or patterns of the A1, A3, A4, B13, B14 dyes have relatively low emissions in the ex-em channel combinations x2-m2, x5-m5, and x6-m6. Therefore, the cross-talk from the dyes A1, A3, A4, B13, B14 is relatively small. The amounts of the dyes A1, A3, A4, B13, B14 may be determined or measured using method 700 and/or method 1100 discussed above for these dyes. Similarly, the off-axis dyes B35 and B36, can be determined or measured with method 700 using the vertical ex-em channel combinations x5-m5 and x3-m5 for dyes B35 and A5, and ex-em using the channel combinations x6-m6 and x3-m6 for dyes B36 and A6. Additionally or alternatively, the off-axis dyes B35 and B36, can be determined or measured with method 1100 using the triad ex-em channel combinations x3-m3, x5-m5, and x3-m5 for dyes B35 and A5, and using the triad ex-em channel combinations x3-m3, x6-m6, and x3-m6 for dyes B36 and A6. Alternatively, as discussed above with regard to a variation on method 1100 discussed above, a system of equations may be incorporated that are simultaneously solved determine or measure the amounts of the A1, A2, A3, A4, A5, A6, B13, B14, B35, and B36 dyes and the associated target molecules. In certain embodiments, method 1100 may be modified to incorporate a system of equations including some or all 21 ex-em channel combinations of the "A" and "B" channel combinations shown in Table 2. Some or all of the ex-em space data in FIG. 18 may be incorporated to provide accurate estimates of the amounts of all ten dyes and their associated target molecules.

The inventors have found that for more complex samples having ten or more dyes (e.g., combinations six on-axis dyes and four off-axis dyes from Table 2) and their associated target molecules, the unique ex-em space signature or fingerprint of each dye in the ex-em space can be utilized to multiplex all the on-axis/off-axis dyes simultaneously in a common sample. FIG. 18 shows the different ex-em space signature or fingerprint of each the specific dyes A1, A3, A4, B13, B14 discussed above. As seen in comparing the signature or fingerprint for these dyes, A1 has a uniquely strong signal in the x1-m1 channel combination and a signal in the x1-m2 channel combination that is approximately two-fifths the signal in x1-m3 channel combination. By contrast, A3 and A4 have almost no signal in the x1-m1 or x1-m2 channel combinations, but instead have strong signals in the x3-m3 and x4-m4 channel combinations, respectively. Dyes B13 and B14 also have strong signal in the x3-m3 and x4-m4 channel combinations, respectively, but differ from the A3 and A4 dyes in that B13 and B14 also have relatively strong signals in the x2-m3 and x2-m4 channel combinations, respectively. While not shown in FIG. 18, similarly distinct characteristics exist for the dyes A2, A5, A6, B35, and B36. It may be noted that the dyes A2, A5, A6, B35, and B36 dyes in general have high emission in emission channels m5 and m6, while, referring to again to FIG. 18, the dyes A1, A3, A4, B13, and B14 have very little to essentially no emissions in the m5 or m6 emission channels, especially when excited by the x5 or x6 channels.

The inventors have found that for assays including both on-axis and off-axis dyes (e.g., the 8 dyes shown in FIG. 17 or the 10 dyes shown in FIG. 19), standard calibration plates, such the Thermo Fisher calibration plate A26337 discussed above herein, do not adequately correct for signal interference or cross-talk between the various dye and thus reduce the accuracy in determining the amount of each dye and a corresponding target molecule in a sample. To increase the accuracy of such determinations, the inventors have discovered that known amounts of one or more off-axis dyes should be included a calibration plate used during calibration of an instrument. For example, in embodiments using 10 dyes in a common sample or sample solution, as illustrated in FIG. 19, the inventors have found that use of a calibration plate containing four on-axis dyes plus two off-axis dyes or two on-axis dyes plus four off-axis dyes can improve the accuracy in determining or measuring the amount of each of the 10 dyes and/or the corresponding target molecules to which they are associated. For example, a calibration plate comprising FAM and VIC plus four off-axis dyes have been found to improve the accuracy determining or measuring the amount of each of the 10 dyes and/or the corresponding target molecules to which they are associated. The four off-axis dyes may include:

one of FAM-TAMRA, FAM-ABY, or FAM-NED, and one of FAM-PET, FAM-ROX, FAM-JUN, FAM-Texas Red, or TET-Alexa Fluor 594, and one of ABY-Alexa Fluor 647, NED-Alexa Fluor 647, ABY-Cy5®, ABY-ATTO 647™, or ABY-DyLight 650™, and one of NED-Alexa Fluor 676, NED DyLight 680™, NED-Cy5.5®, ABY-Alexa Fluor 676, ABY-DyLight 680™, or ABY-Cy5.5®.

Systems 4000 and/or 5000 may be used to perform methods discussed here for 10-plex sample assays of conducting a multiplex assay on a sample containing three on-axis dyes and two off-axis dyes and to analyze the resulting data to simultaneously determine or measure the amounts of ten or more dyes and their associated target molecules. In certain embodiments, such 10-plex or higher-plex assays comprise a PCR assay such as a qPCR assay, a dPCR assay, a post PCR assay such as melt curve analysis, or the like.

Figure 20:
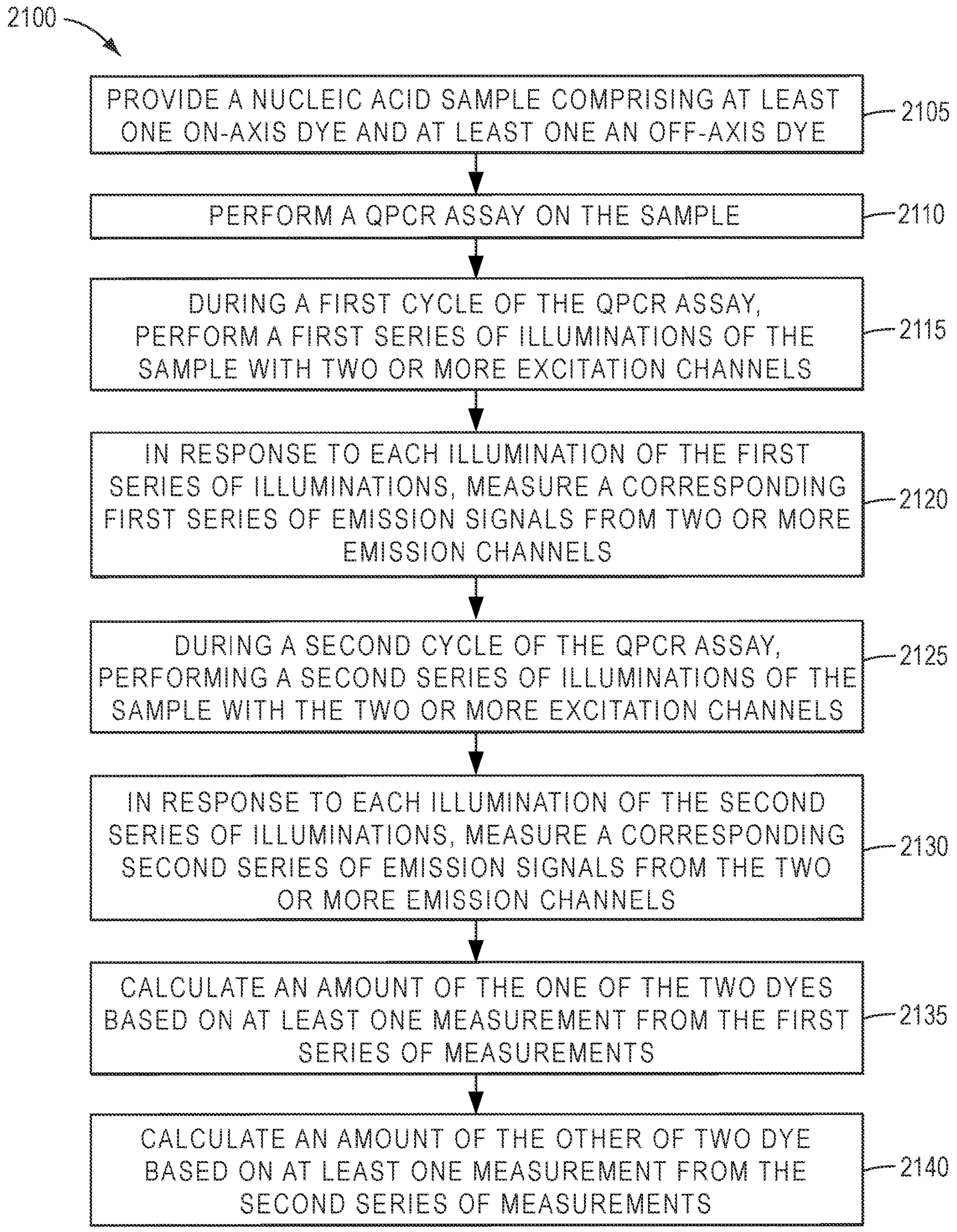
FIG. 20 is a method according to an embodiment of the present disclosure

Referring to FIG. 20, in certain embodiment, systems 2000, 3000, 4000, 5000 may be used with a method 2100 of conducting or performing an amplification assay, such as a qPCR assay. Method 2100 includes an element 2105 comprising providing an off-axis dye and an on-axis dyes. Method 2100 also includes an element 2110 comprising performing an amplification assay on the sample. Method 2100 also includes an element 2115 comprising, during a first cycle of the of the amplification assay, performing a first series of illuminations of the sample with two or more excitation channels. Method 2100 also includes an element 2120 comprising, in response to each illumination of the first series of illuminations, measuring a corresponding first series of emission signals from the two or more emission channels. Method 2100 also includes an element 2125 comprising, during a second cycle of the of the amplification assay, performing a second series of illuminations of the sample with the two or more excitation channels. Method 2100 also includes an element 2130 comprising, in response to each illumination of the second series of illuminations, measuring a corresponding second series of emission signals from the two or more emission channels. Method 2100 also includes an element 2135 comprising, calculating an amount of the off-axis dye or the on-axis dye based on at least one of the measurements from the first series of measurements. Method 2100 also includes an element 2140 comprising, calculating an amount of the other of the off-axis dye and the on-axis dye based on at least one of the measurements from the second series of measurements.

The inventors have discovered that the unique signature or fingerprint of off-axis dyes, as discussed above herein, may be used increase the accuracy of measuring or calculating amounts of various dyes in a sample and/or their associated target molecules in assays in which one or more dyes produce a fluorescence signal exceeding a background fluorescence in fewer cycles than other dyes within the same sample (e.g., where one or more dyes have a lower threshold cycle, Ct, or crossing point, Cp). It will be recalled that the ex-em space plots shown in FIGS. 10, 14, and 18 represent data from samples containing equal amounts or concentrations of each dye. In some assays, a sample contains target molecules of varying number or concentration. Thus, during a qPCR or related amplification assay, dyes associated with target molecules of greater number or concentration, the signals from these dyes will be detected during earlier cycles in the amplification assay and, therefore, prior to any detectable signal being generated from other dyes, so that these less abundant dyes produce no cross-talk when measuring fluorescence signals from the more abundant target molecules.

For example, referring to FIG. 18, if the one or both off-axis dyes B13 and/or B14 are associated with target molecules that are much more abundant than those associated with the on-axis dyes A3 and A4, then during early cycles within an amplification assay the detected signal in the with be primarily from the B13 dye in the x3-m3 channel combination and/or from the B14 dye in the x4-m4 channel combination. Therefore, the signal produced by the x3-m3 and/or x4-m4 channel combinations will be predominately due to the signal generated by the B13 and/or B14 dyes, respectively, which allow calculating an amount of B13 and/or B14 present in the solution during the early cycles. Based on this calculated value of B13 and/or B14, the amount of these dyes present during later amplification cycles may also be calculated during later cycles, since the performance of the associated target molecule based on, for example, an estimated value of Ct or Cp. Thus, once the molecules associated with A3 and/or A4 begin to fluoresce during subsequent cycles in the amplification assay, a calculated signal from B13 and/or B14 may be subtracted from the detected signal from x3-m3 and/or x4-m4. The adjusted signal(s) may be used to calculate an amount of the molecules associated with the A3 and/or A4 dyes. In similar fashion, the contribution of the B13 and/or B14 in one or more of the other ex-em channel combinations may be used to more accurately calculate the amount of A3 and/or A4 in later amplification cycles.

EXAMPLES

Example 1: Synthesis of t-Boc-F-Dye 1 NHS Ester (5)

Fluorescein donor dyes were synthesized according to the general procedure in Scheme 1 shown for 2,7-difluoro-sulfo-fluorescein 3. A resorcinol derivative, such as 1, is heated with a 2-sulfo-terephthalic acid derivative, such as 2, in methanesulfonic acid and isolated by normal phase chromatography. The fluorescein dye is O-protected, such as shown for conversion of Dye 3 to t-BOC protected Dye 4, and converted to the corresponding NHS ester 5 by standard procedures.

Scheme 1

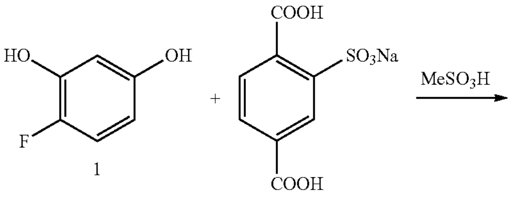

1

2

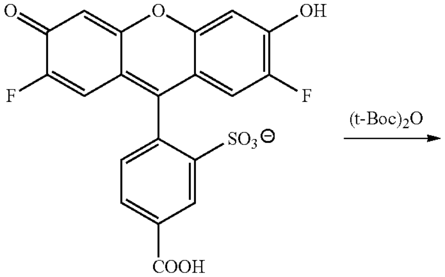

3

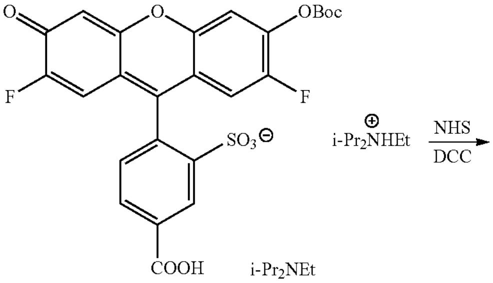

4

-continued

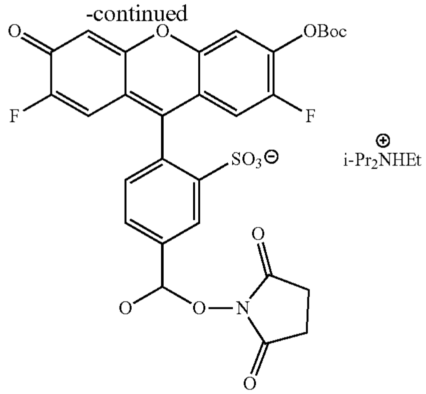

5

Step 1: Synthesis of F-Dye 1 (3)

A mixture of 4-fluororesorcinol (1, 490 mg, 3.825 mmol) and 2-sulfo-terephthalic acid sodium salt (2, 513 mg, 1.913 mmol) in methanesulfonic acid (5 mL) was heated at 110 °C for 6 h. The reaction mixture was cooled to room temperature and stirring was continued for 3 days. Ice-$H_2O$ (100 mL) was added and the resulting suspension was filtered. The filter cake was washed with portions of ice-$H_2O$ and then was suspended in 5 mL of MeOH. The suspension was diluted with 50 mL of $Et_2O$ and filtered. The solid product was washed with $Et_2O$ and dried in vacuo to give 555 mg (65%) of 3 as a yellowish solid.

Step 2: Protection of 3 with a t-Boc Group

F-Dye 1 (3, 184 mg, 0.410 mmol) was suspended in 10 mL of MeCN and treated with diisopropylethylamine (0.644 mL) and di-t-butyl dicarbonate (537 mg, 2.46 mmol) at room temperature for 3 days. $H_2O$ (0.5 mL) was added and stirring was continued for 30 min. The reaction mixture was loaded directly onto a silica (Iatrobeads 6RS-8060) column (2×22 cm) and the column was eluted with 10% to 30% MeOH/DCM. Evaporation of the appropriate fractions gave 216 mg (65%) of 4 as brown foam.

Step 3: Synthesis of t-Boc-F-Dye 1 NHS Ester (5)

A mixture of 4 (210 mg, 0.260 mmol), N-hydroxysuccinimide (150 mg, 1.3 mmol), and dicyclohexylcarbodiimide (107 mg, 0.52 mmol) in DCM (5 mL) was stirred at room temperature for 3 h. The reaction was quenched with $H_2O$ (0.1 mL) and stirred for additional 15 min. The resulting suspension was filtered and the filtrate was loaded directly onto a silica (Iatrobeads 6RS-8060) column (2×15 cm). The column was eluted with 1:0:20:80 to 1:30:20:50 AcOH/MeOH/EtOAc/DCM. The fractions containing the desired product were evaporated to give 185 mg (92%) of 5 as brown foam.

Example 2: Synthesis of Sulfo-Fluorescein Dyes 8 and 9

By employing the general procedure of Example 1 for synthesis of sulfo-fluorescein 3 from the fluororesorcinol 1, resorcinol 6 and the pyridyl resorcinol (U.S. Pat. No. 6,221,604) 7, were used to make the corresponding sulfo-fluorescein dyes 8 and 9, as shown in Scheme 2 from sulfo-terphthalate 2.

Scheme 2

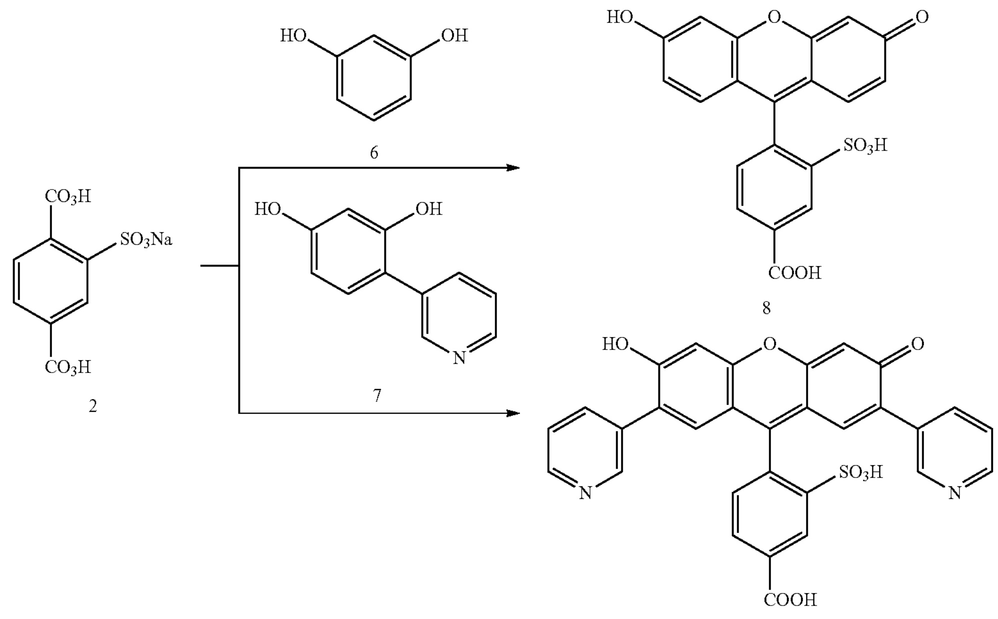

6

7

2

8

9

Compound 9 is excitable at 520 nm and emits at 544 nm due to the presence of the pyridyl substituents, making this dye compatible for use in the X2/m2 (green) channel of a real-time PCR instrument. The structures of sulfo FAM and pyridyl FAM products were confirmed by MS analysis (data not shown)

Example 3: Synthesis of DPC-Dipyridyl-Dichloro-Fluorescein NHS Ester (17)

Dichloro sulfoterephalate 13 was synthesized and used to make the sulfo-fluorescein 15, as shown in Scheme 3, employing the general procedure of Example 1 for synthesis of sulfo-fluorescein 3. The dye 15 was O-protected and converted to the NHS ester 17.

Scheme 3

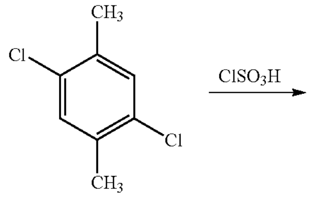

10

-continued

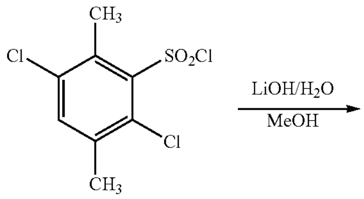

11

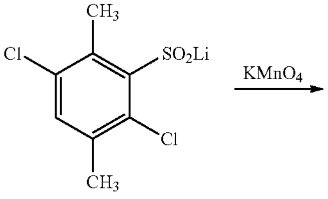

12

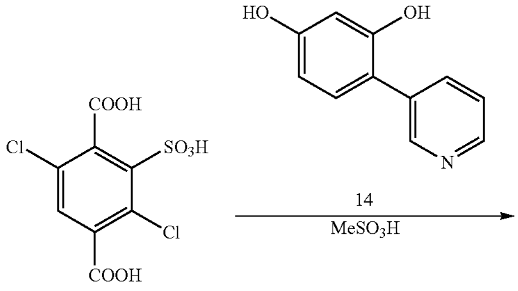

14

13

-continued

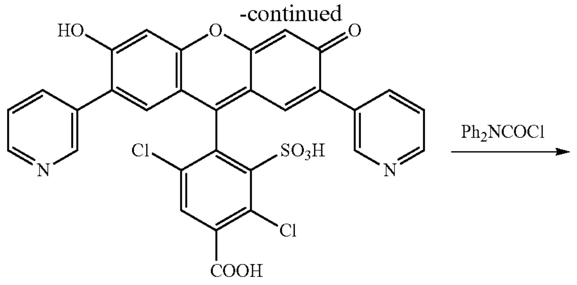

15

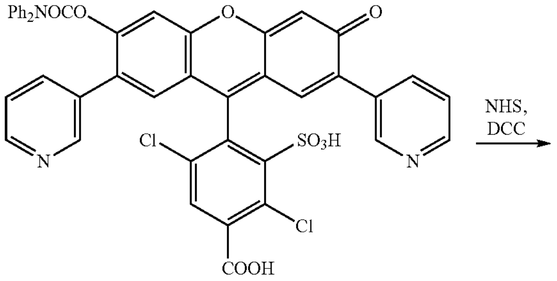

16

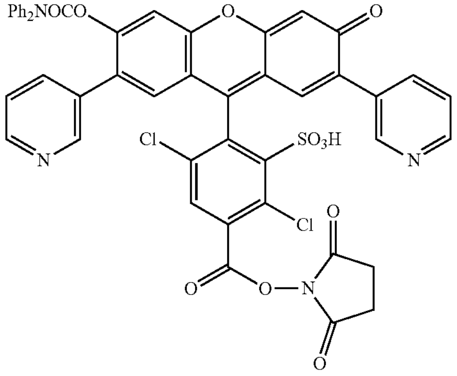

17

Step 1: 2,5-Dichloro-3,6-dimethyl-benzenesulfonyl chloride (11)

To 17.5 g (0.1 mol) of 2,5-dichloro-p-xylene 10, was added 53.2 mL (0.8 mol) of chlorosulfuric acid. The reaction mixture was stirred at room temperature for 3 days and then diluted with 350 mL of DCM. The DCM solution was added very slowly to 350 g of ice and stirred for 1 h. The mixture was transferred to a separatory funnel and the organic layer was separated, dried ($Na_2SO_4$), evaporated, and dried in vacuo to give 25.56 g (93%) of 11 as white solid. $^1H$ NMR ($CDCl_3$) □ 7.63 (s, 1, 4-H), 2.84, 2.46 (2×s, 6, 2×$CH_3$). MS (ion trap MS) m/z 273.0 (calcd. $MH^+$=272.9).

Step 2: 2,5-Dichloro-3,6-dimethyl-benzenesulfonic Acid Lithium Salt (12)

To a solution of 15.307 g (60 mmol) of 11 in 200 mL of MeOH, was added slowly 75 mL (150 mmol) of 2 N LiOH. The reaction mixture was stirred at room temperature for 18 h. MeOH was removed by evaporation and the resulting suspension of the product in $H_2O$ was filtered. The filter cake was washed with 20 mL of cold $H_2O$ and then air-dried to give 14.5 g of 12 as a white crystalline compound. A second crop of product was isolated from the filtrate. The total yield of 3× was 15.24 g (97%). $^1H$ NMR ($CD_3OD$) □ 7.42 (s, 1, 4-H), 2.76, 2.38 (2×s, 6, 2×$CH_3$). MS m/e 253.0 (calcd. $[M-Li]^-$=253.0).

Step 3: 2,5-Dichloro-3-sulfo-terephthalic Acid (13)

To a solution of 25.286 g (160 mmol) of $KMnO_4$ in 400 mL of $H_2O$, was added 5.221 g (20 mmol) of 12. The reaction mixture was stirred and heated at gentle reflux for 22 h. Excess $KMnO_4$ was destroyed by slow addition of 100 mL of MeOH while maintaining refluxing and stirring for 30 min. The reaction mixture was filtered while hot. The filter cake was again suspended in a mixture of $H_2O$/MeOH (200 mL/50 mL), heated to boil and filtered while hot. The combined filtrate was evaporated to dryness and re-dissolved in 50 mL of $H_2O$. The $H_2O$ solution was filtered and the filtrate was evaporated. The residue was purified on a Dowex 50W-X8 $H^+$ column (4×34 cm, 450 mL of resin, eluted with 350 mL of $H_2O$). Evaporation of the $H_2O$ solution gave 4.6 g (73%) of 13 as white solid. $^1H$ NMR ($CD_3OD$) □ 7.80 (s, 1, 6-H). MS m/e 313.0 (calcd. $[M-H]^-$= 312.9).

Step 4: Dye Compound (15)

A mixture of 473 mg (1.5 mmol) of 13 and 561 mg of pyrido-resorcinol 14 in 6 mL of $MeSO_3H$ was stirred at 170 °C-180 °C for 28 h., then cooled to room temperature, and precipitated in 160 mL of $Et_2O$. The solid was collected by centrifugation and then re-dissolved in 30 mL of $H_2O$. The pH value of the $H_2O$ solution was adjusted to ~5 with 20% NaOH. The resulting suspension was centrifuged and the supernatant was decanted. The solid was re-suspended in 30 mL of water, sonicated, centrifuged and the $H_2O$ washing process was repeated one more time. The crude solid product was re-suspended in 20 mL of MeOH, sonicated, diluted with 40 mL of EtOAc, vortexed, and centrifuged. The solid product was air-dried, then dried in vacuo to give 502 mg (53%) of 15 as dark red solid. $^1H$ NMR ($CD_3OD$) □ 8.73 (d, 2), 8.46 (dd, 2), 7.96 (m, 2), 7.64 (s, 1), 7.45 (m, 2), 7.17 (s, 2), 6.84 (s, 2). MS m/z 635.0 (calcd. $[MH]^+$=635.0).

Step 5: DPC-Dye Acid (16)

A mixture of 64 mg (0.1 mmol) of 15 and 46 mg (0.2 mmol) of $Ph_2NCOCl$ in 6 mL of pyridine was stirred at room temperature for 2 h. $H_2O$ (0.1 mL) was added and stirring was continued for 1 h. Volatile materials were removed by evaporation and co-evaporation with 1:50:50 i-$Pr_2Net$/DCM/$PhCH_3$ (2×). The residue was dissolved in 10% MeOH/DCM (25 mL) and washed with $H_2O$ (25 mL). The $H_2O$ solution was extracted with 10% MeOH/DCM (25 mL×4). The organic layer and extracts were combined and evaporated. The residue was purified by silica (Iatrobeads 6RS-8060 from Shell-USA) column chromatography using 0-20% $H_2O$/MeCN as eluant. Evaporation of the appropriate fractions gave 39 mg (47%) of 16. MS m/z 830.0 (calcd. $[MH]^+$=830.0).

Step 6: DPC-Dye-NHS Ester (17)

To a solution of 39 mg (0.047 mmol) of 16 and 27 mg (0.235 mmol) of N-hydroxysuccinimide (NHS) in 1.5 mL of DCM, was added 19 mg (0.094 mmol) of dicyclohexylcarbodiimide (DCC). The reaction mixture was stirred at room temperature for 3 h and then quenched with 10% HCl (0.1 mL). Volatile materials were removed by evaporation and the residue was dissolved in 5% MeOH/DCM (5 mL) and purified by silica (Iatrobeads 6RS-8060 from Shell-USA) column chromatography using a gradient (1:5:95-1:30:70) of AcOH/MeOH/DCM as eluant. Evaporation of the appropriate fractions gave 31 mg (71%) 17.

Example 4: Synthesis of FRET-Linker (24)

A synthetic approach to prepare an L1 type energy transfer linker 24 (referred to herein as a "Y-linker") is outlined below in Scheme 4. Bromination of methyl 2,5-dimethylbenzoate 18 with N-bromosuccinimide gave the dibromide 19. Subsequent treatment of 19 with sodium azide was followed by saponification of the intermediate diazide 20. The resulting acid 21 was activated with N,N,N',N'-tetramethyl-O—(N-succinimidyl)uronium tetrafluoroborate (TSTU) and then quenched with a large excess of 2,2'-(ethylenedioxy)bis(ethylamine) to afford the amine derivative 22. Further reaction of 22 with glutaric anhydride gave the carboxylic acid derivative 23, which was converted to the desired Y-linker 24 by hydrogenation in the presence of Raney-Nickel.

Scheme 4

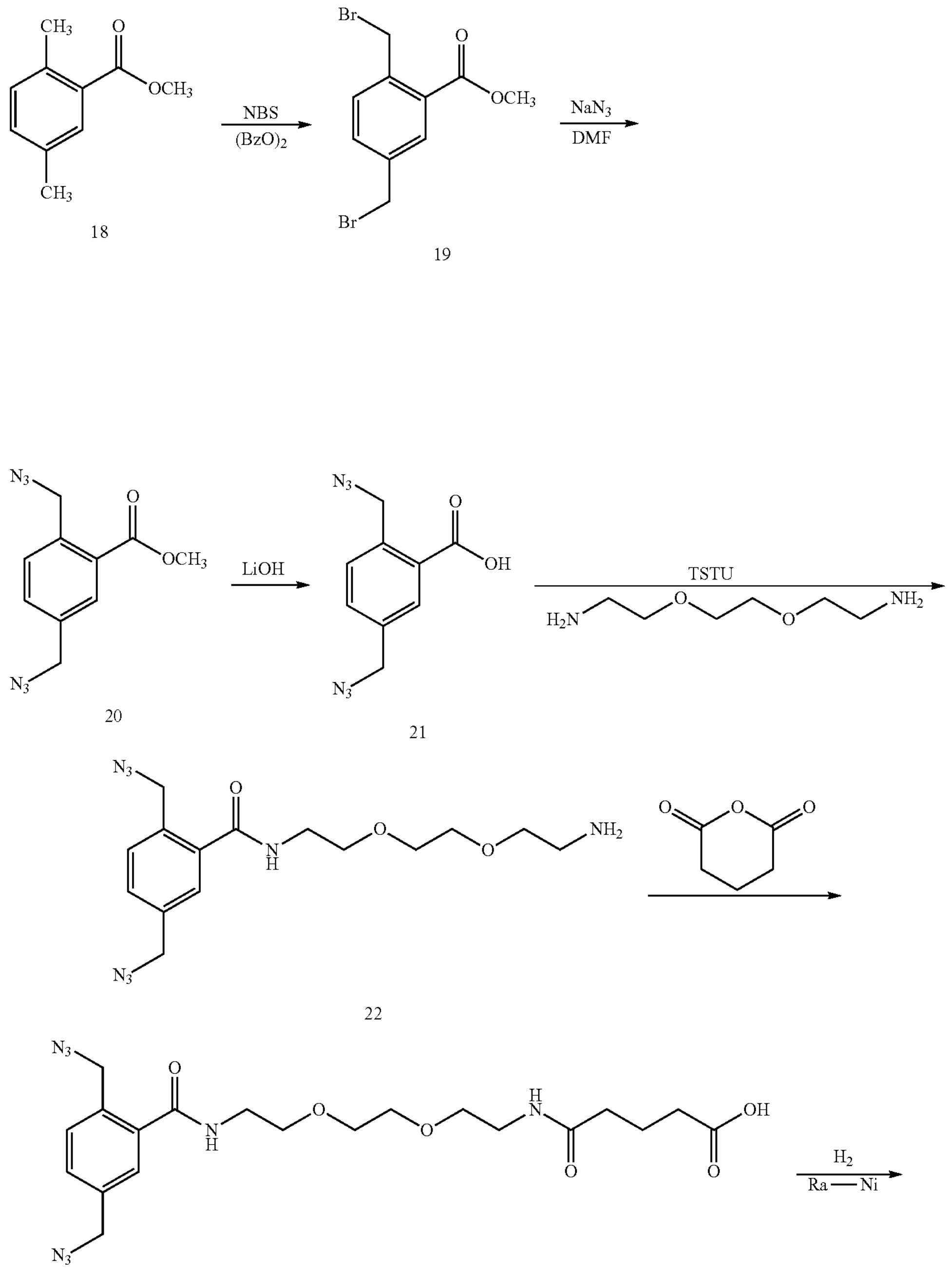

18

19

20

21

22

23

-continued

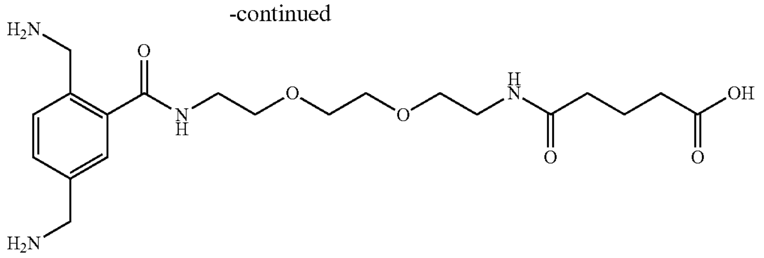

24

Step 1: Synthesis of the Dibromide (19)

To a solution of 18 (11.5 g, 70 mmol) in carbon tetrachloride (100 mL), were added N-bromosuccinimide (23.7 g, 133.2 mmol) and benzoyl peroxide (1.7 g, 7 mmol). The reaction mixture was stirred at 80 °C for 6 h. It was cooled to room temperature and diluted with hexane (50 mL). The resulting suspension was filtered and the filtrate was evaporated. Fractional re-crystallization of the residue from hexane gave 6.7 g (31%) of 19 as a white crystalline compound.

Step 2: Displacement of the Dibromide (19)

A solution of 19 (6.7 g, 20.8 mmol) in DMF (40 mL) was treated with sodium azide (6.8 g, 104.0 mmol) at room temperature for 16 h. The reaction mixture was diluted with DCM (50 mL) and filtered. The filtrate was evaporated and the residue was re-dissolved in DCM (150 mL). The DCM solution was washed with $H_2O$ (100 mL), Brine solution (100 mL), dried ($Na_2SO_4$), and filtered. Evaporation of the filtrate and drying of the residue in vacuo gave 5.06 g (99%) of 20 as syrup.

Step 3: Saponification of Compound (20)

To a solution of 20 (5.05 g, 20.5 mmol) in MeOH (80 mL) was added a solution of LiOH/$H_2O$ (1.72 g, 41.0 mmol). The reaction mixture was stirred at room temperature for 16 h and then was acidified with a solution of 10% HCl (14.8 mL). Volatile materials were removed by evaporation and the residue was dissolved in DCM (150 mL). The DCM solution was washed with $H_2O$ (100 mL), Brine solution (100 mL), dried ($Na_2SO_4$), and filtered. The filtrate was evaporated and the residue was re-crystallized from EtOAc/hexane to give 4.17 g (2 crops, 88%) of 21 as white crystalline needles.

Step 4: Synthesis of the Amine (22)

A solution of 21 (929 mg, 4.0 mmol), diisopropylethylamine (1.394 mL, 8.0 mmol), and TSTU (1.806 g, 6.0 mmol) in DCM (20 mL) was stirred at room temperature for 1 h. This reaction mixture was then added slowly to a solution of 2,2'-(ethylenedioxy)bis(ethylamine)/DCM (2.929 mL/20 mL) and stirred for additional 3 h. DCM (100 mL) was added and the DCM solution was washed with brine solution (100 mL×2), dried ($Na_2SO_4$), and filtered. The filtrate was evaporated and the residue was purified on a silica (Iatrobeads 6RS-8060) column (2.5×17 cm) using 1:10:90 to 1:35:65 $Et_3N$/MeOH/DCM as eluants. Evaporation of the appropriate fractions gave 1.15 g (79%) of 22 as syrup.

Step 5: Synthesis of the Acid (23)

To a solution of 22 (1.142 g, 3.151 mmol) in DCM (15 mL), were added diisopropylethylamine (1.098 mL, 6.302 mmol) and glutaric anhydride (0.539 g, 4.727 mmol). The reaction mixture was stirred at room temperature for 17 h. $H_2O$ (0.2 mL) was added and stirring was continued for 15 min. Volatile materials were removed by evaporation and the residue was re-dissolved in DCM (120 mL). The DCM solution was washed with 0.1 N HCl (100 mL), dried ($Na_2SO_4$), and filtered. The filtrate was evaporated and the residue was purified on a silica (Iatrobeads 6RS-8060) column (2×20 cm) using 1:5:95 to 1:10:90 $Et_3N$/MeOH/DCM as eluants. Evaporation of the appropriate fractions gave 1.43 g (95%) of 23 as syrup.

Step 6: Synthesis of Dimethylamino-FRET-Linker 24

A suspension of 23 (300 mg, 0.630 mmol) and Raney-Nickel (— 200 mg, wet weight) in MeOH (15 mL) was stirred under $H_2$ for 20 h. The reaction mixture was then filtered through Celite and the filtrate was evaporated. The residue was co-evaporated with MeOH and dried in vacuo to afford 260 mg (97%) of 24 as foam.

Example 5: Synthesis of the Dye Linker Intermediate

The synthesis of a dye linker intermediate follows in general the procedure outlined below in Scheme 5 for formation of t-BOC-protected Sulfo-FAM-ET-linker NETS ester 28. The ET-linker, such as 24, is coupled to the t-Boc-protected Dye NHS ester, such as 25, to give the Dye Linker intermediate, such as 26 as a mixture of regioisomers. After silica column purification, the pure regioisomer amino group could be protected with a trifluoroacetyl group for use in stepwise analyte labeling or used directly for labeling with the second Dye NHS to create the ET dye. To create the Dye-linker intermediate NHS, the free amino is protected, such as shown below with a TFA group, and the carboxylic acid group activated to give the t-Boc-Dye-ET-linker NHS ester 28.

Scheme 5
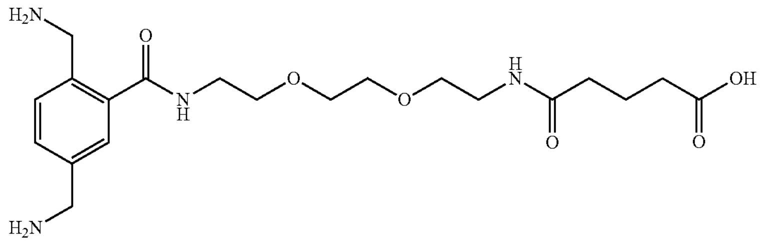
24
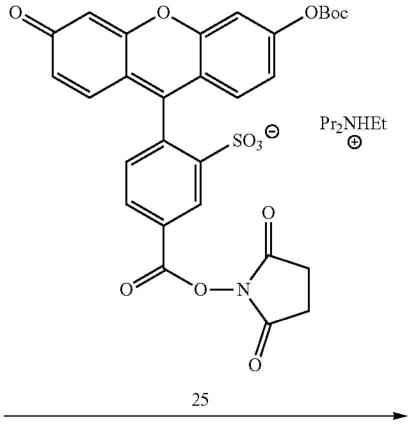
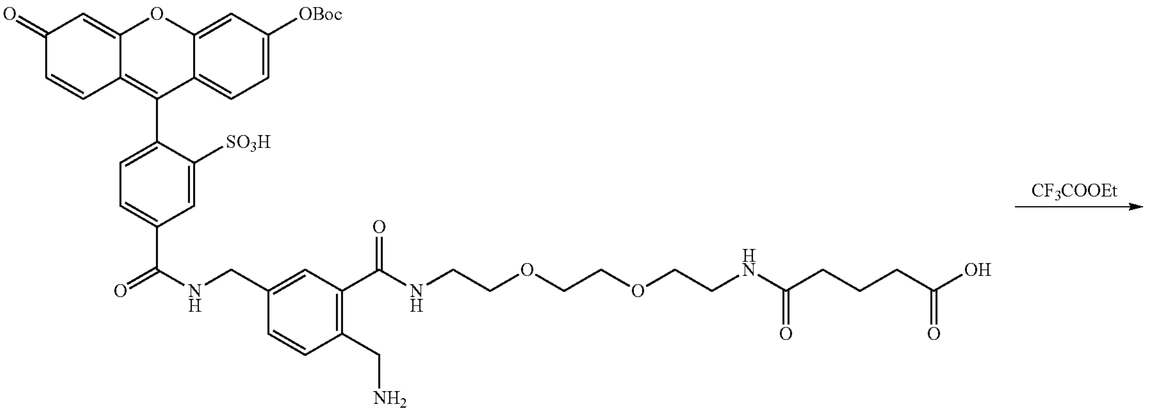
26
(mix Regio-isomers)
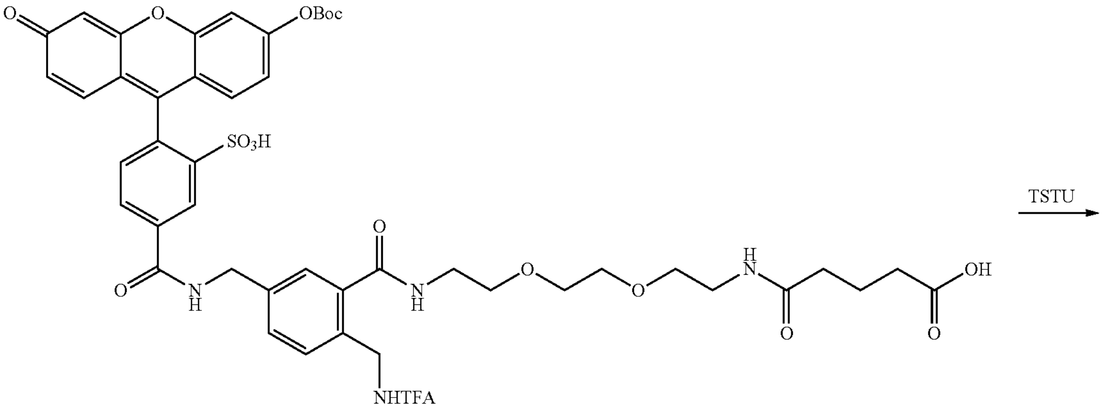
27

-continued

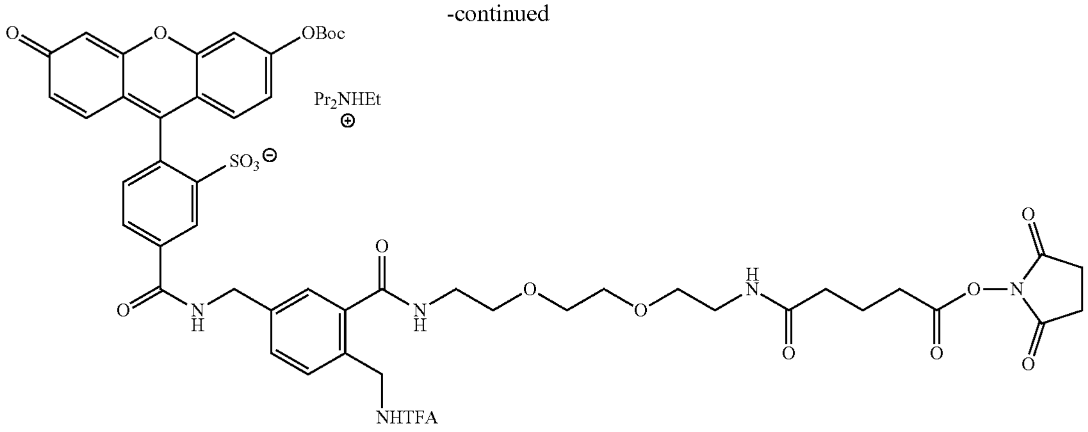

28

Step 1: Coupling of t-Boc-Dye NHS Ester (25) with Linker (24)

To a mixture of linker (24, 130 mg, 0.306 mmol) and diisopropylethylamine (0.07 mL) in DCM (5 mL), was added t-Boc-Dye NHS ester (25, 148 mg, 0.2 mmol). The reaction mixture was stirred at room temperature for 2 h. Volatile materials were removed by evaporation and the residue was purified on a silica (Iatrobeads 6RS-8060) column (2×26 cm) using 5% to 20% $H_2O$/MeCN as eluants. Evaporation of the appropriate fractions afforded 80 mg (44%) of 26 as regioisomers.

Step 2: Protection of 26 with a Trifluoroacetyl Group

A mixture of 26 (77 mg, 0.084 mmol), diisopropylethylamine (0.2 mL), and ethyl trifluoroacetate (0.3 mL) in MeOH (3 mL) was stirred at room temperature for 18 h. Volatile materials were removed by evaporation and the residue was co-evaporated with MeCN and DCM to give the carboxylic acid 27. This material was used directly in the subsequent reaction without further purification.

Step 3: Synthesis of t-Boc-Dye-linker NHS ester (28). To a solution of 27 (from the previous reaction) in DCM (10 mL), were added diisopropylethylamine (0.1 mL) and TSTU (50 mg, 0.167 mmol). The reaction mixture was stirred at room temperature for 2.5 h. Solvents were removed by evaporation and the residue was purified on a silica (Iatrobeads 6RS-8060) column (2×16 cm) using 1:5:95 to 1:20:80 AcOH/MeOH/DCM as eluants. Evaporation of the appropriate fractions afforded 81 mg (87% overall) of Dye-linker NHS intermediate 28 as a solid.

Example 6: Synthesis of Dye Linker Intermediate (32)

The synthesis of the a dye linker intermediate follows in general the procedure outlined below in Scheme 6 for formation of Cy3-FRET-linker NHS ester 32. The linker, such as 24, is coupled to the Cy3 Dye NHS ester, such as 29, to give the Dye Linker intermediate, such as 30 as a mixture of regio-isomers. After silica column purification, the pure regioisomer amino group could be protected with a trifluoroacetyl group for use in stepwise analyte labeling or used directly for labeling with the second Dye NHS to prepare the ET dye. To prepare the Dye-linker intermediate NHS 28, the free amino in 26 is protected, such as shown below with a TFA group to provide 27, and the carboxylic acid group activated to Cy3-FRET-linker NHS ester 28.

Scheme 6

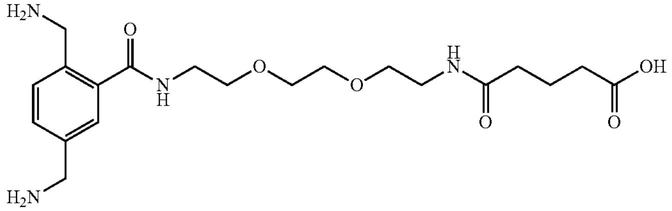

24

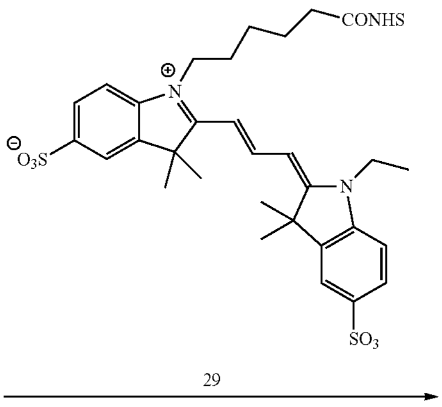

29

-continued
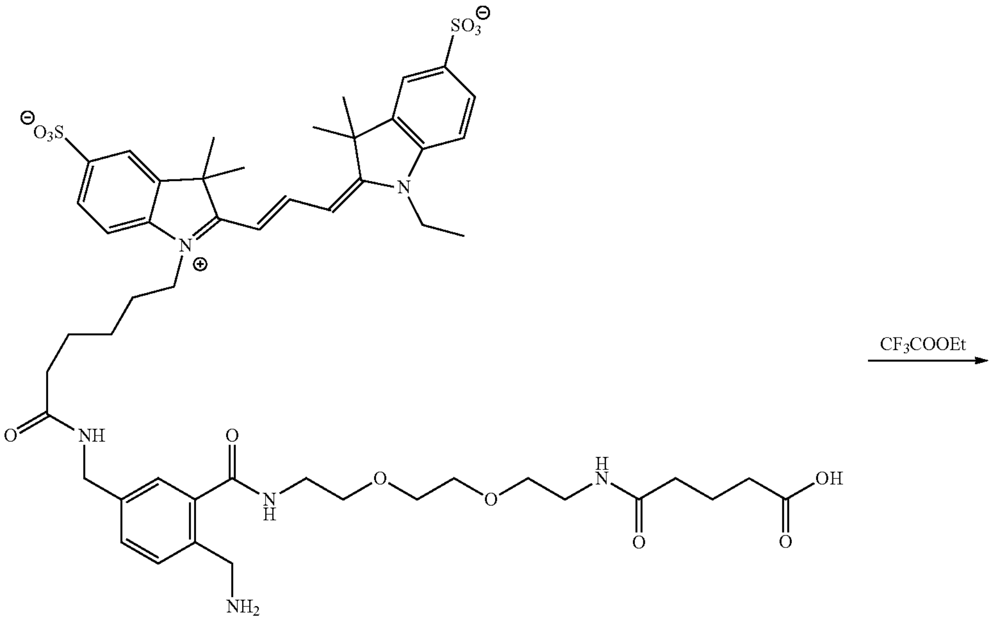
30
(mix Regio-iosmers)
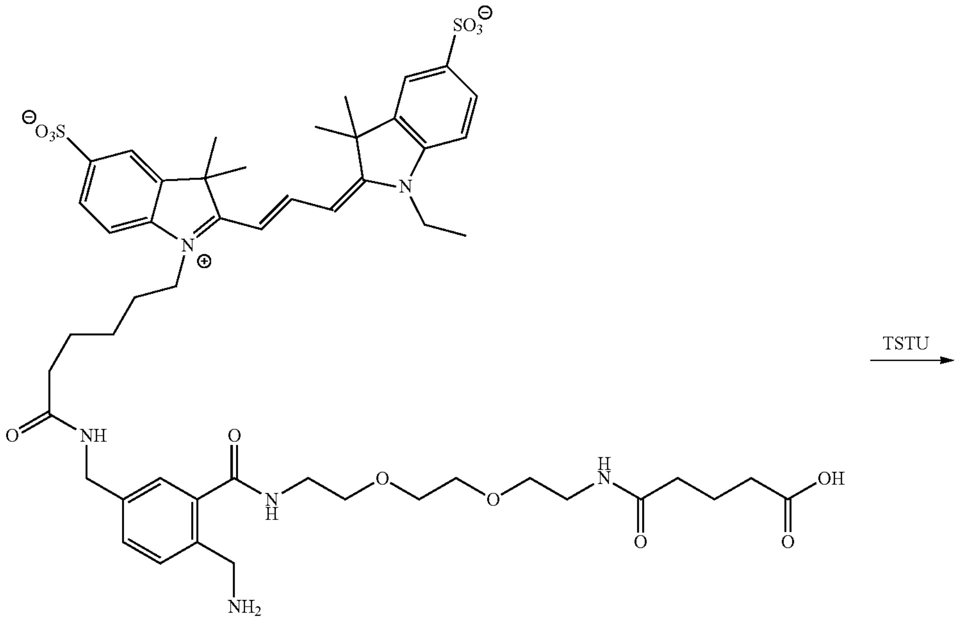
31

-continued

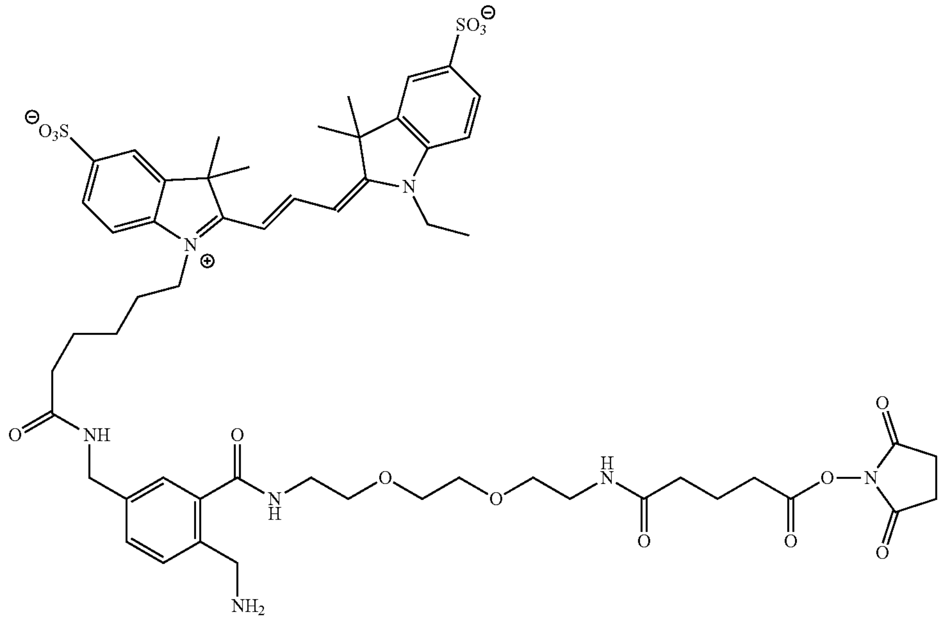

32

Step 1: Coupling of Cy3 NHS Ester (29) with the ET-Linker (24)

To a mixture of the ET-linker (24, 130 mg, 0.306 mmol) and diisopropylethylamine (0.07 mL) in DMF (5 mL), was added Cy3 NHS ester (29, 0.2 mmol). The reaction mixture was stirred at room temperature for 2 h. The reaction solution was added to 20 mL of diethyl ether. The mother liquors were decanted from the resulting oily precipitate and the precipitate suspended in 10% $MeOH/CH_2Cl_2$ purified by normal phase chromatography eluting with 10% $MeOH/CH_2Cl_2$/1% AcOH. Evaporation of the appropriate fractions afforded 30 as a mixture of regioisomers.

Step 2: Protection of 30 with a trifluoroacetyl group. A mixture of 30 (77 mg), diisopropylethylamine (0.2 mL), and ethyl trifluoroacetate (0.3 mL) in MeOH (3 mL) was stirred at room temperature for 18 h. Volatile materials were removed by evaporation and the residue was co-evaporated with MeCN and DCM to give the carboxylic acid 31. This material was used directly in the subsequent reaction without further purification.

Step 3: Synthesis of Cy3-ET-Linker NHS Ester (32)

To a solution of 31 (from the previous reaction) in DCM (10 mL), were added diisopropylethylamine (0.1 mL) and TSTU (50 mg, 0.167 mmol, 2 equivalents). The reaction mixture was stirred at room temperature for 2.5 h. Solvents were removed by evaporation and the residue was purified on a silica (Iatrobeads 6RS-8060) column (2×16 cm) using 1:5:95 to 1:20:80 AcOH/MeOH/DCM as eluants. Evaporation of the appropriate fractions afforded of Cy3-linker NHS intermediate 32 as a solid.

Example 7: Cy3-Cy5.5 ET Dye NHS (35) Synthesis

Pure isomer Cy3-Linker intermediate 30 (10 mgs) was suspended in 3 mL of anhydrous DMF and 6 equivalents of diisopropylethylamine (11 μL). Cy5.5-NHS ester 33 from GE Healthcare (1.2 equiv, 12 mg) suspended in 2 mL DMF was added and the reaction stirred at room temp for 5 hours. The crude product was isolated by addition of acetonitrile/diethyl ether and collection of the precipitated solid. The ET dye carboxylic acid product 34 was isolated by normal phase column chromatography (Iatrobeads 6RS-8060) using 5% to 20% $H_2O$/MeCN/1% $NEt_3$ as eluants. ET dye 34 was suspended in DMF with 6 equivalents DIPEA. Solid TSTU (3 equiv) was added and the mixture stirred for 3 hour at room temperature. Crude bichromophoric Cy3-Cy5.5 ET dye NHS 35 was precipitated by addition of ethyl acetate. The resulting solid precipitate was collected and resuspended in AcCN and the residue collected and used without further purification. The procedure of Scheme 7 can be implemented with other types of dyes provided in NHS form in place of Cy3, such as, e.g., AF 555, FAM, BODIPY 530/550, BODIPY R6G, and BODIPY TMR, which are all available from Thermo Fisher Scientific (Waltham, MA). Other dyes that can be utilized in place of Cy3 in the procedure shown in Scheme 7 include NHS derivatives of fluorescein and rhodamine dyes, such as, e.g., NED, VIC, HEX, or JOE. In Scheme 7, other cyanine dyes in NHS form that can be utilized instead of Cy5.5 include, e.g., AF647, AF660, and AF680, available from Thermo Fisher Scientific.

Scheme 7
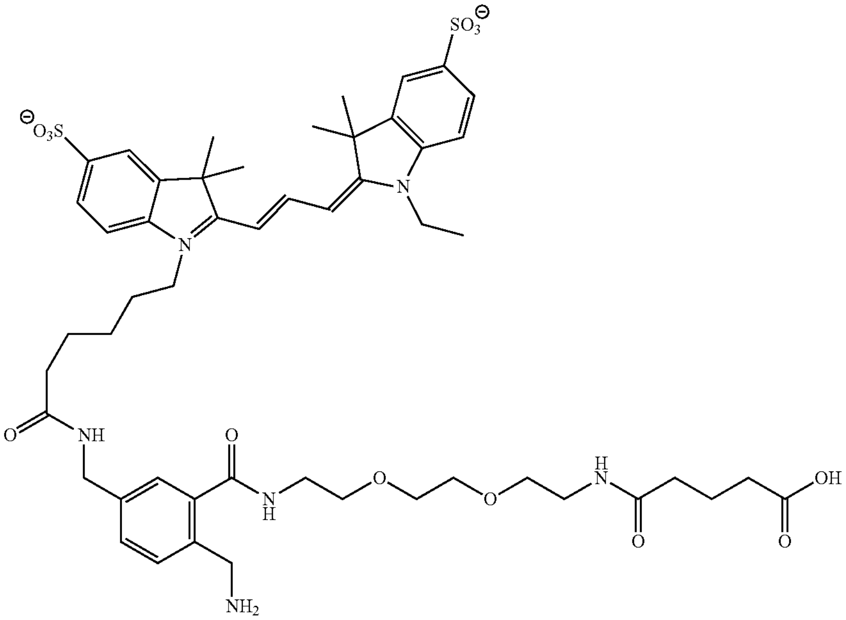
30
+
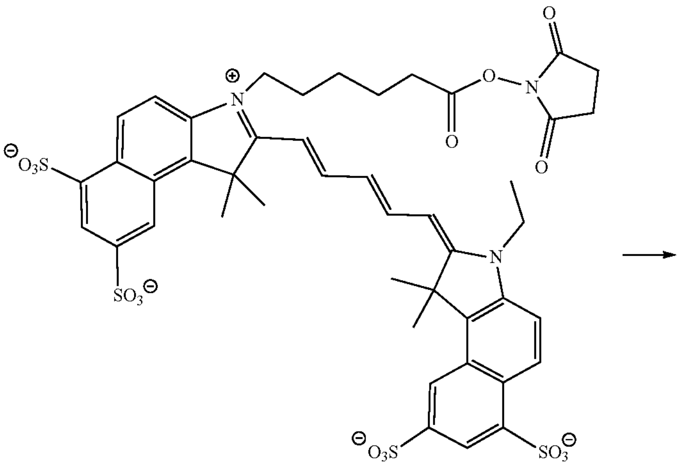
33

-continued
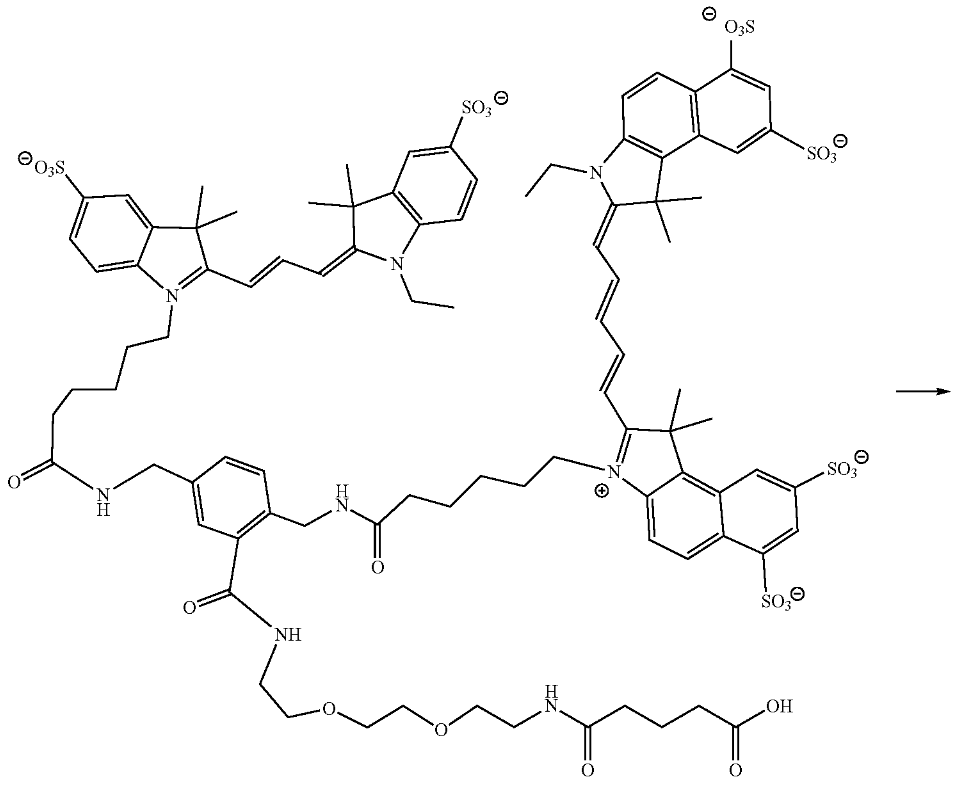
34
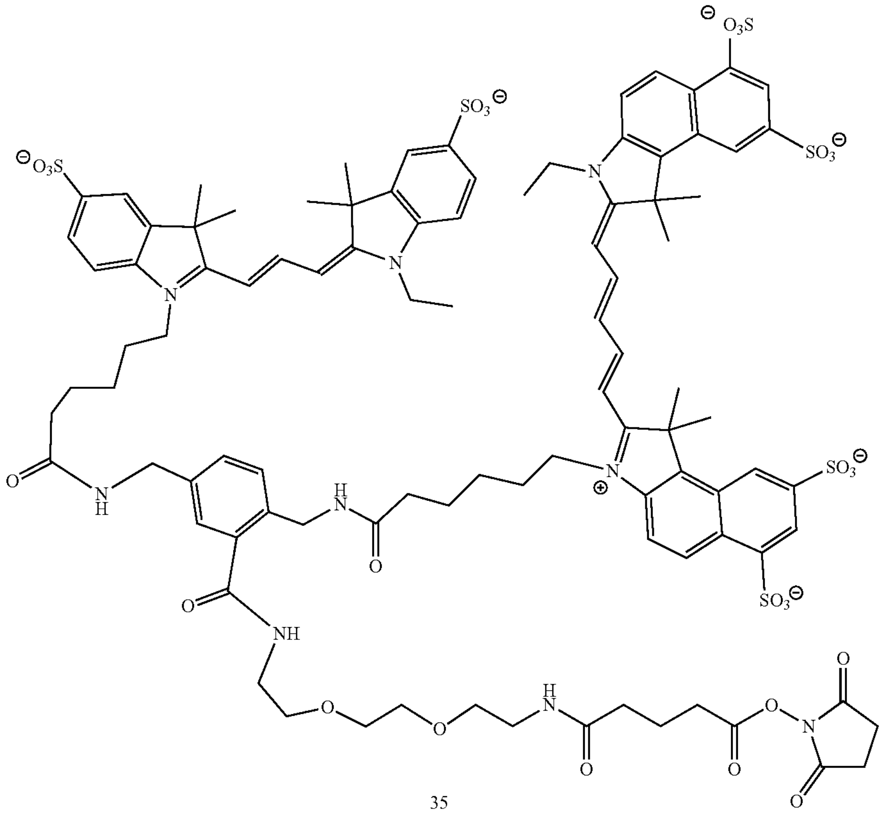
35

Example 8. ET Dye Synthesis and Analyte Labeling

Labeling of the desired target analyte follows either a single step or two step labeling procedure depending on the substrate where an analyte amine is coupled to a preformed donor/acceptor ET dye NHS ester to directly give the desired ET dye labeled analyte, or the amino protected Dye-linker intermediate NHS can be added in a first step, the analyte-linker-dye labeled intermediate isolated, N-deprotected, and subsequently labeled in a second step with the complementary dye NHS to generate the ET dye labeled analyte (see, FIG. 1).

Example 8a: Single-Step ET Dye Labeling of Analyte

Single-step oligonucleotide labeling was performed following the general procedure outlined in Scheme 9 for labeling of an amino group derivatized oligonucleotide with preformed ET dye, such as dye 35. Amino group derivatized oligomer (30,000 pM) is suspended in 250 μL of 100 molar $NaHCO_3$DI water. 3 equivalents (0.2 mg) of 35 suspended in 5 μL DMSO is added. The reaction is stirred for 5 hours, loaded onto an LH-20 size exclusion column equilibrated with 1×TEAA and the faster moving oligo-Dye labeled band collected 40. The pure product was isolated by RP HPLC purification eluting with from 5 to 60% AcCN in 1×TEAA.

Scheee 9

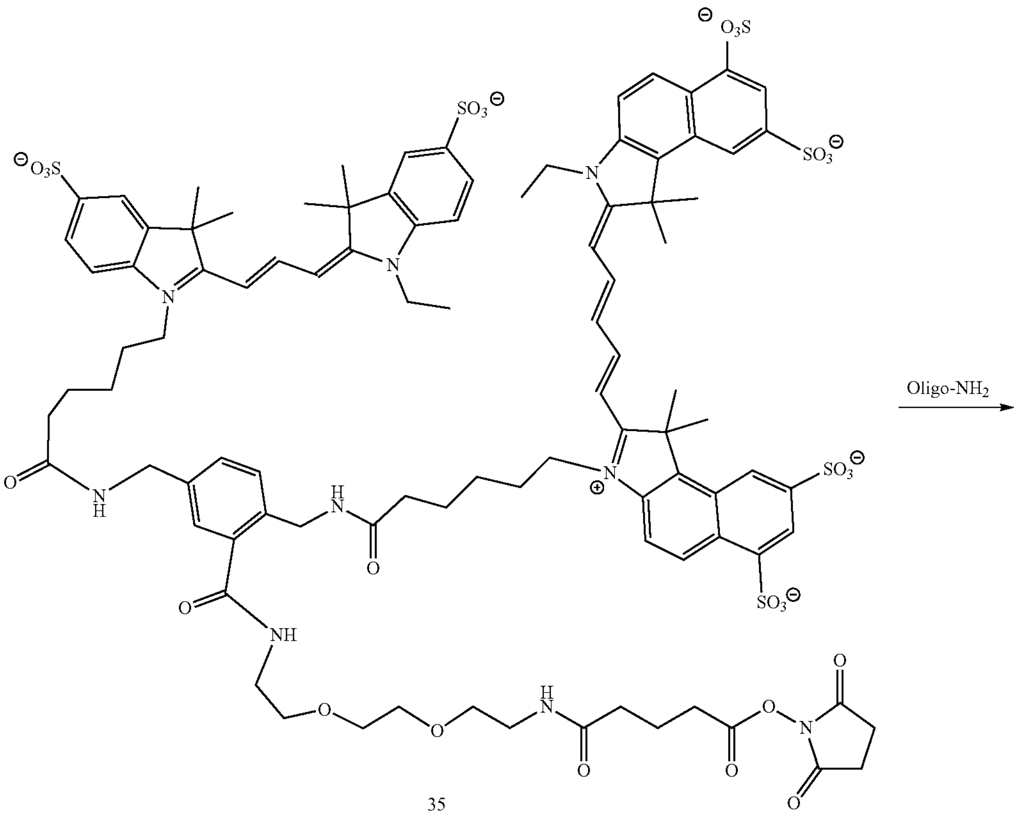

35

-continued

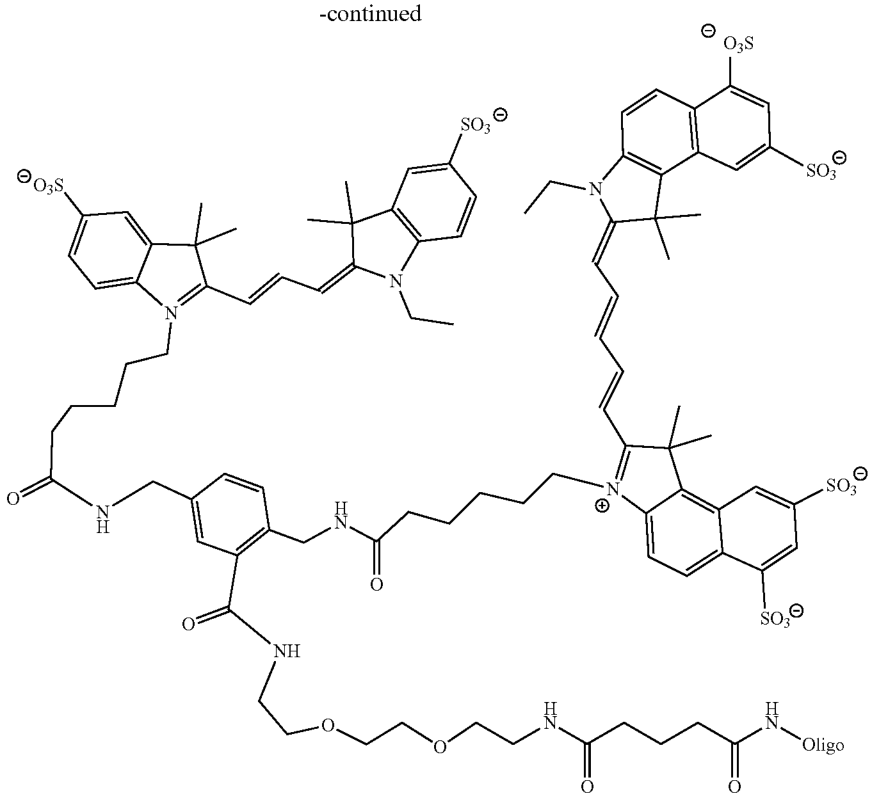

40

Example 8b: Two Step ET Dye Labeling of Analyte

Using a two-step labeling process, a series of ET dyes were synthesized employing fluorescein-linker NETS intermediate 28 or Cy3-linker NHS intermediate 32 in combination with an appropriate reporter dye NHS ester to yield the series of ET dyes shown below in Scheme 10. A method for preparing the dye-labeled oligonucleotides shown in Scheme 10 is shown in Scheme 11.

Scheme 10

36

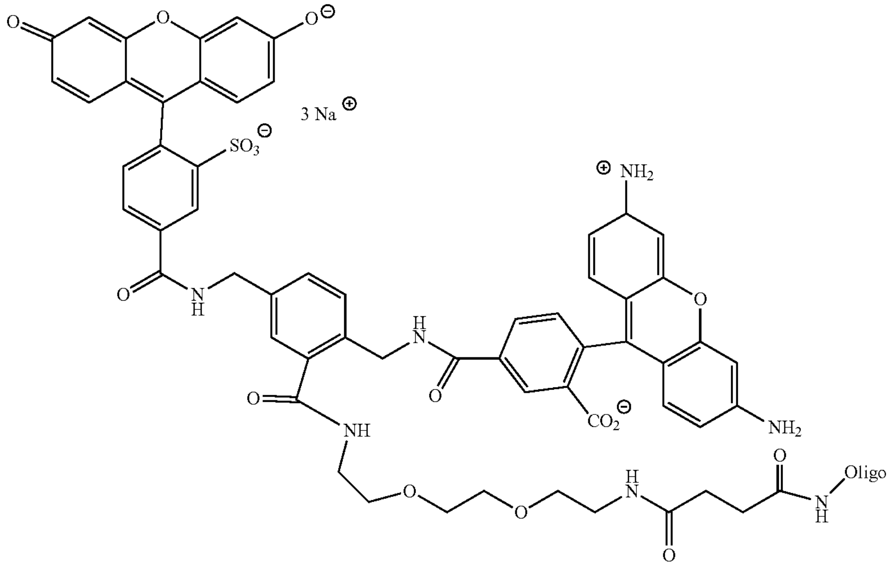

-continued
37
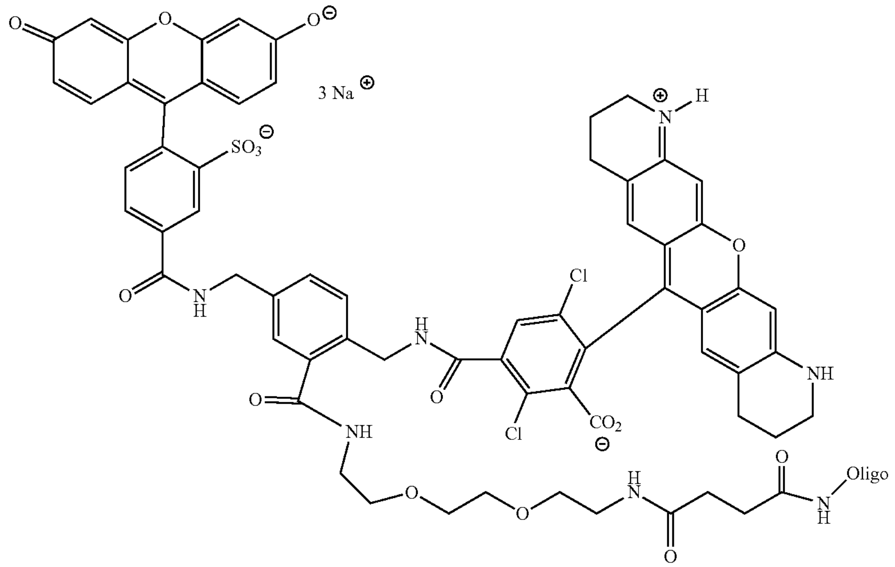
38
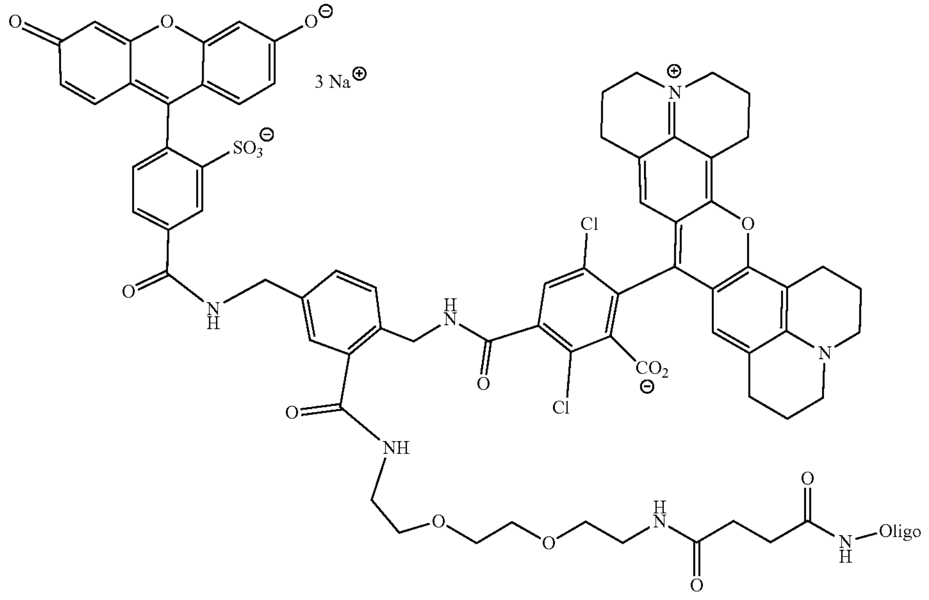

-continued
39
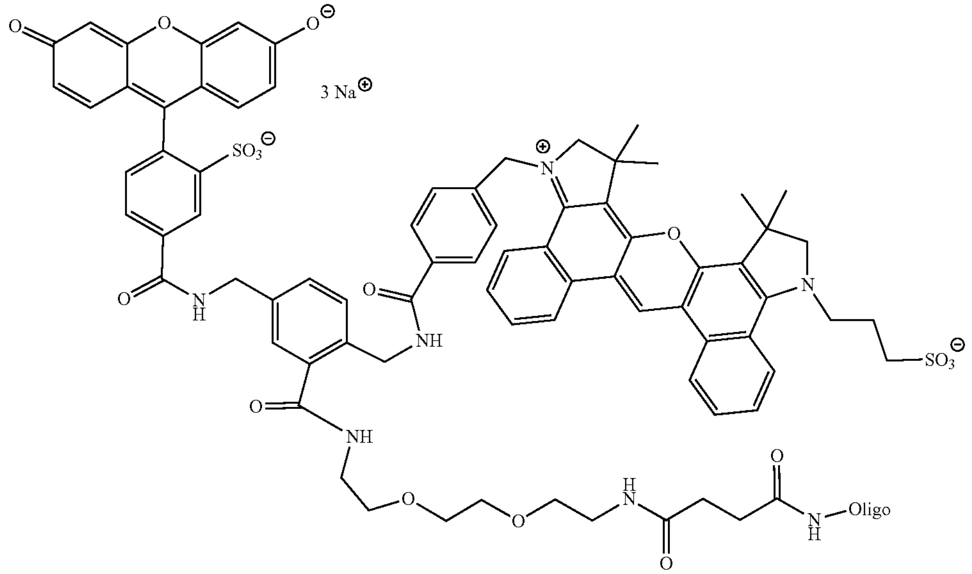
Scheme 11
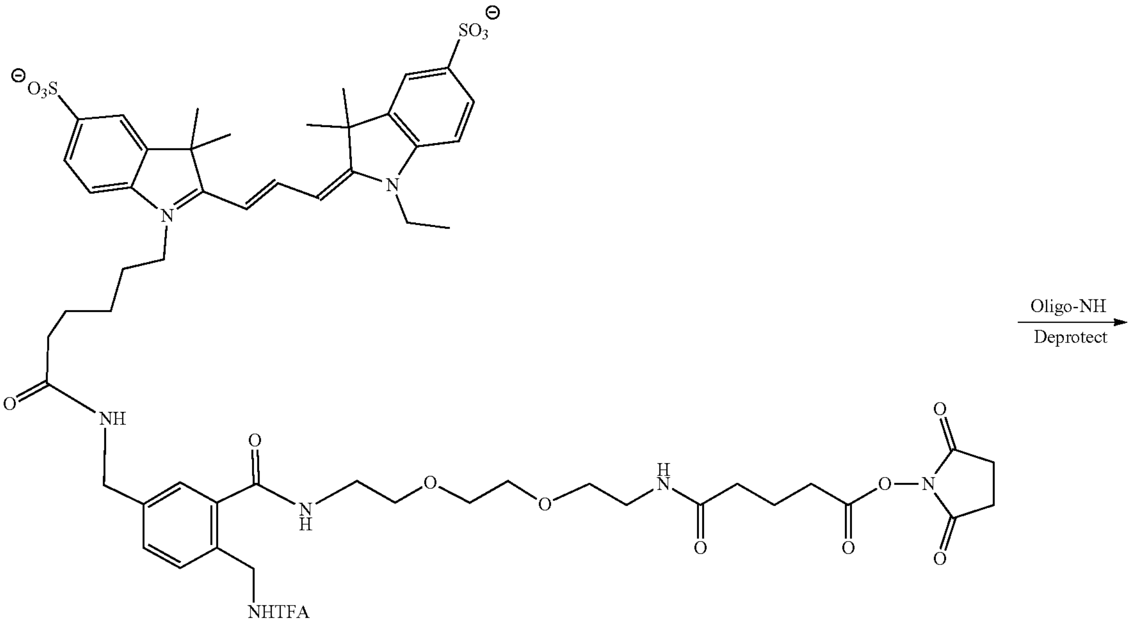
32

-continued
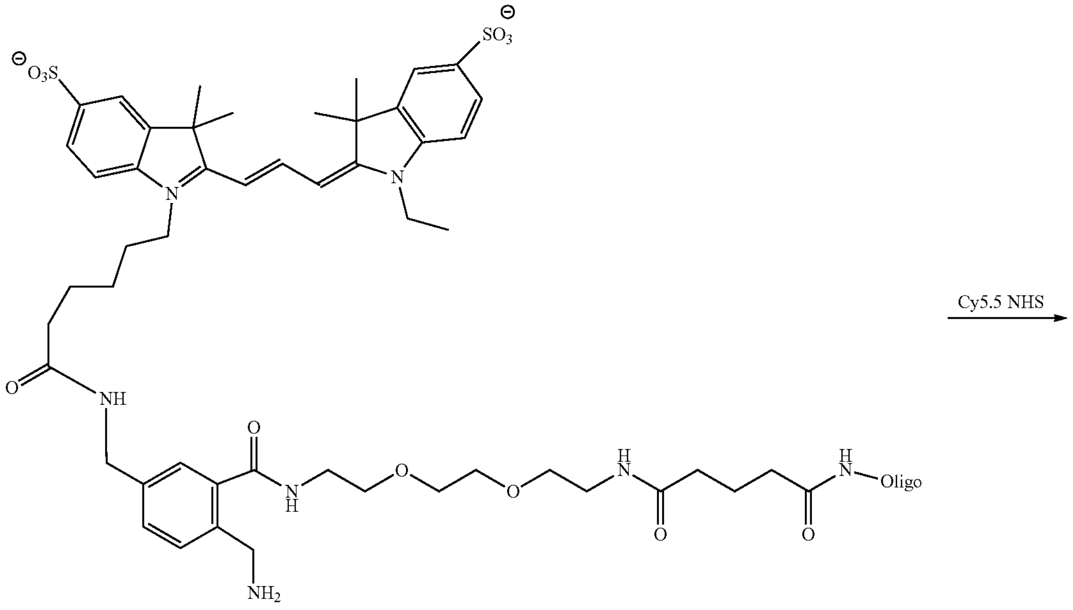
41
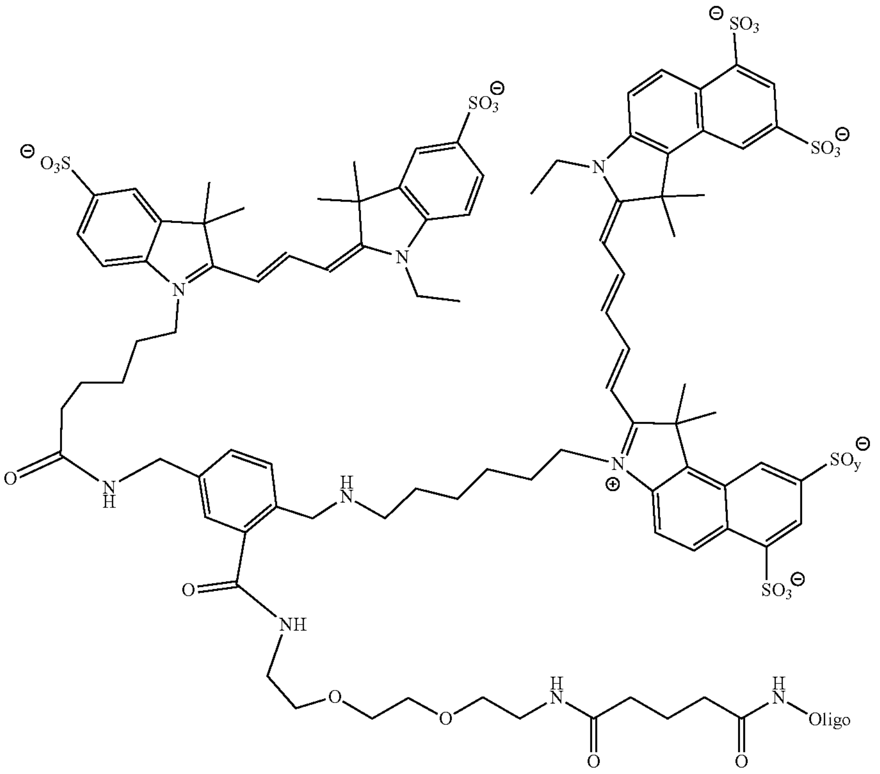
42

First the substrate is labeled with a Dye-linker NHS intermediate, such as Cy3-linker NHS intermediate 32 to give dye-linker labeled oligonucleotide intermediate 41 which is purified by reverse phase HPLC and subsequently labeled with a Cy5.5 dye NHS in DMF and DIPEA to give the ET dye labeled oligonucleotide 42.

Example 9: Quencher Attachment

The quencher compound may be attached to a solid support, e.g., a bead, to provide a substrate for construction of a probe using an oligonucleotide synthesizer, in accordance with the following reaction in Scheme 12.

Scheme 12

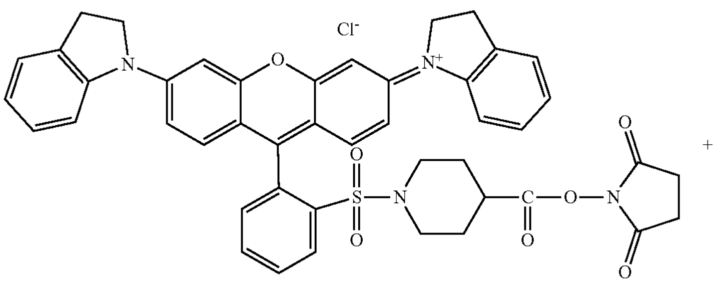

43

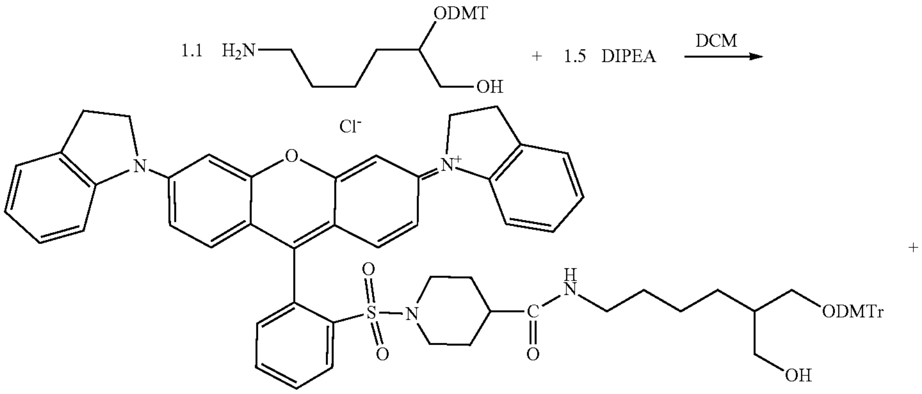

44

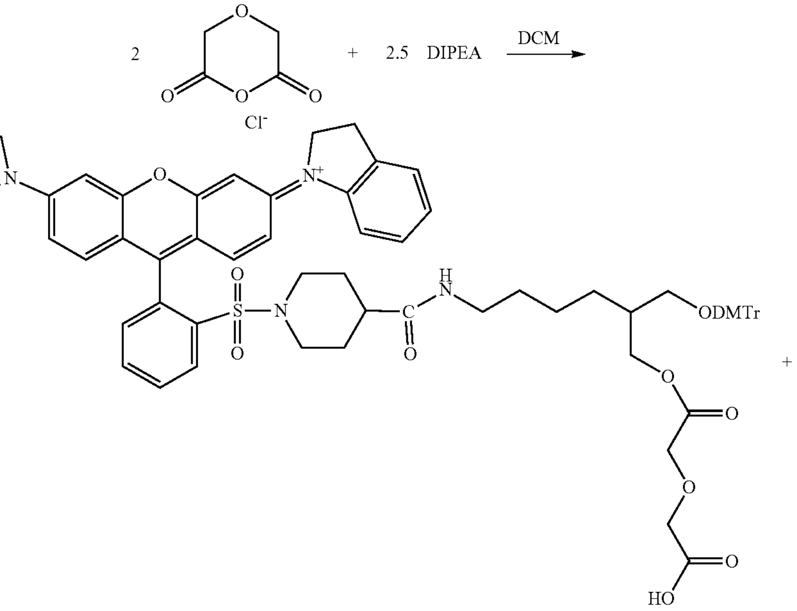

45

-continued

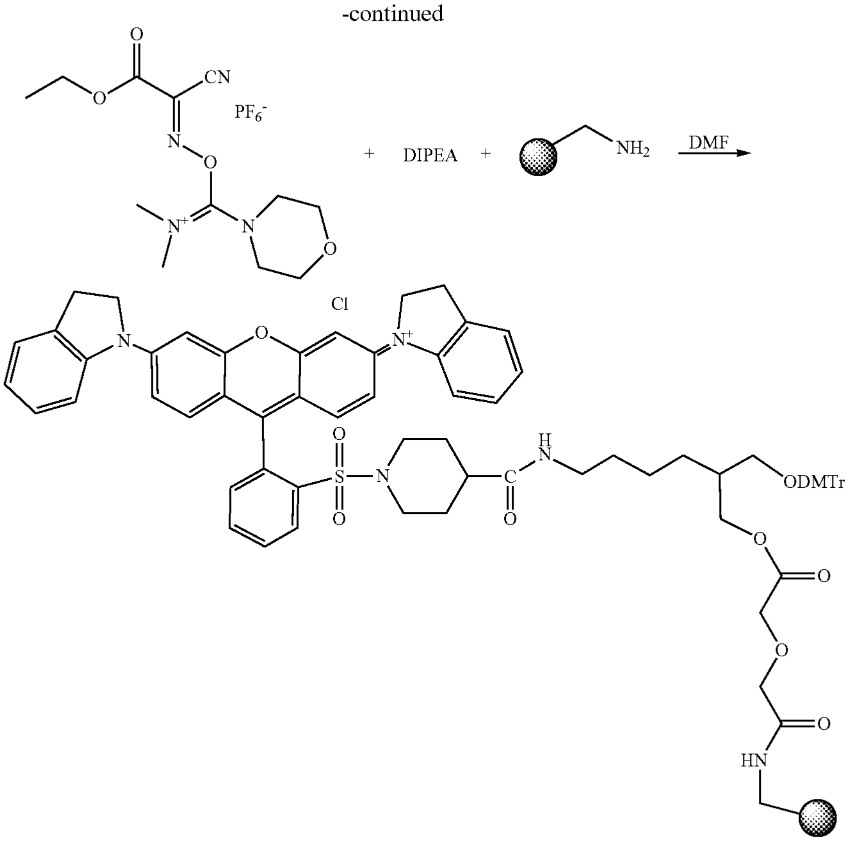

46

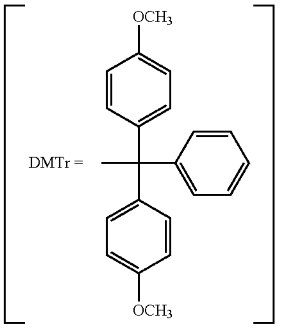

The following exemplary synthetic procedure may be easily generalized to any of the quenchers described above.

In some embodiments, a representative derivatized quencher 44 can be synthesized according to the following procedure. Representative quencher 43 NHS ester (100 mg, 0.123 mmol) was dissolved in 1 mL of anhydrous DCM. 1-O-DMT-2-(4-Aminobutyl)-1,3-propanediol (61 mg, 0.14 mmol) dissolved in 1213 μL of DCM (a 5% solution) was mixed with diisopropylethylamine (32 μL, 0.19 mmol). This was added dropwise to representative quencher 43 NHS ester at room temperature and stirred for 30 min under nitrogen. The crude representative quencher 44 in DCM solution was diluted with DCM (50 mL) and washed with 1% citric acid, water, and then brine. The organic layer was dried over $Na_2SO_4$ and evaporated to dryness. Further high vacuum drying overnight provided 125 mg (88% yield) of 44 as a dark blue solid. The product was used in the next step without further purification. $^1H$ NMR (400 MHz, $CD_2Cl_2$): δ 8.14 (1H, d), 7.83 (2H, m), 7.60 (2H, d), 7.50-7.10 (22H, m), 6.80 (4H, m) 4.40 (2H, m), 4.25 (2H, m), 3.75 (6H, s), 3.62-3.50 (4H, m), 3.30 (6H, m), 3.05 (2H, m), 2.51 (2H, t), 2.40 (1H, t), 1.72 (2H, d), 1.50-1.20 (7H, m). LC/HRMS (Ho Calcd for [$M^+$] 1113.48; found 1113.47. Elutions were done with a 20 minute linear gradient from 40 to 100% acetonitrile (against 0.1 M triethylammonium acetate). 1.0 ml/min flow rate. Detection at 285 nm and 655 nm.

In another embodiment, a representative quencher including a diglycolic linker 45 can be synthesized according to the following procedure. Representative quencher 44 (125 mg, 0.109 mmol) was dissolved in 3 mL of anhydrous DCM. DIPEA (47 μL, 0.27 mmol) was added, followed by diglycolic anhydride (25 mg, 0.22 mmol). The solution was stirred for 30 min under nitrogen. The reaction solution was concentrated and the residue re-dissolved in 1% TEA/DCM and purified on silica gel column chromatography (pre-equilibrated in 10%-1% TEA/DCM) using 5-15% MeOH/DCM/1% TEA eluent. The purified pool was concentrated and then washed with 1% citric acid, water, and brine. The organic layer was dried over anhydrous $Na_2SO_4$, evaporated to dryness, and then further dried under high vacuum to yield representative quencher diglycolic linker (45) (96 mg, 69% yield) as a dark blue solid. $^1$H NMR (400 MHz, $CD_2Cl_2$): δ 8.14 (1H, d), 7.85 (2H, m), 7.60 (2H, d), 7.52-7.10 (22H, m), 6.79 (4H, d), 4.35 (2H, m), 4.25 (2H, m) 4.05 (3H, s/m), 3.80 (2H, s), 3.72 (6H, s), 3.28 (6H, m), 3.00 (2H, m), 2.90 (2H, m), 2.50 (2H, t), 2.32 (1H, t), 1.65 (2H, m), 1.50-1.10 (7H, m). LC/HRMS ($ESI^+$) Calcd for [$M^+$] 1229.49; found 1229.49. Elutions were done with a 20 minute linear gradient from 40 to 100% acetonitrile (against 0.1 M triethylammonium acetate). 1.0 ml/min flow rate. Detection at 285 nm and 655 nm.

Representative quencher 45 can be linked to a solid support, e.g., polystyrene bead, according to the following procedure to provide 46. Representative quencher diglycolic linker 45 (357 mg, 0.20 mmol) was dissolved in 50 mL of anhydrous DMF. To this was added aminomethyl polystyrene (6.77 g, 0.223 mmol, 33 □mol/g amine), DIPEA (194 □L, 1.12 mol), and COMU or 1-cyano-2-ethoxy-2-oxoethylidenaminooxy)dimethylamino-morpholino-carbenium hexafluorophosphate (287 mg, 0.669 mmol). The mixture was shaken for 3 hr. The solvent was removed and the resin was washed 3 times each with 50 mL of DMF, MeCN, and DCM. Any remaining amine groups on the resin were then capped by reacting with 50 mL acetic anhydride/pyridine in THF mixed with 50 mL of 1-N-methylimidazole in THF and shaken for 1 hr. The solvent was removed and the resin washed 3 times each with THE, MeCN, and DCM. The resin was then dried overnight under high vacuum to yield 6.60 g of light blue powder representative quencher 46. The resin support was tested for any residual amine groups using the ninhydrin test and found to be 0.94 □mol/g amine (negligible). The amount of representative quencher coupled to the support was determined by cleaving off the DMT group of a weighed aliquot of the representative quencher PS sample with a known volume of 0.1M toluenesulfonic acid in MeCN. The absorbance at 498 was obtained and using the extinction coefficient (76,500$M^{-1}cm^{-1}$), mass, and volume, the loading of representative quencher per g of polystyrene was found to be 22 μmol/g. The typical range found for this coupling condition was 20-27 μmol/g.

Example 10: Quencher Solid Support Amino Probe Synthesis

The quencher compound and ET dye may be attached to a solid support, e.g., a bead, to provide a substrate for construction of a probe using an oligonucleotide synthesizer, to provide a quencher-ET dye oligonucleotide probe construct in accordance with the following reaction scheme which utilize an L3 (i.e., 47)-L4 (i.e., 49) type linker (see, FIG. 3):

Pack a 0.25 μmole QSY21 3900 column by weighing out 11 mg of QSY21 Bulk Solid Support (22 μmole/g loading) and pour into 3900 column body. Prepare Biolytics 3900 Synthesizer with all standard reagents including the Dye phosphoramidite 50, and linker phosphoramidites (47 and 49) according to 3900 Synthesis standard protocol. Install 28% DIPA/Acetonitrile reagent in Position 6 on 3900. Prepare specialty reagents at 0.1M concentration in anhydrous acetonitrile. Open 3900. Sequence Template in Microsoft Excel, and type in the relevant oligonucleotide sequence information for each oligonucleotide sequence. Load QSY21 columns into DNA synthesizer by placing them into each bank in the column positions designated on the synthesis page. Prime the reagents lines. Start the oligonucleotide synthesis. Once oligonucleotide synthesis steps are complete dry down the QSY support completely to remove any residual acetonitrile by placing synthesis columns on vacuum plate and placing vacuum plate on vacuum manifold and turn on vacuum for 5 minutes. Add 50/50 amine/methanol/water cleavage solution to column and wait for 10 minutes. Drain out all of the wash solution. Repeat. Place capped column vials into savant or equivalent set at 65 °C, and heat for 4-5 hours. Remove vials and place in freezer for 10 minutes to cool down. After cool remove cap from vial and place in savant or equivalent and dry oligonucleotide under vacuum. Ethanol precipitate the dried QSY-dye labeled oligonucleotide 51 by diluting oligonucleotide in nuclease free water in Eppendorf tube and vortexing. Add 50 mM sodium acetate in ethanol and vortex. Put oligonucleotide in freezer to cool. Centrifuge tube at 2500 rpm for 5 minutes to pellet crude Remove supernatant out of oligonucleotide tube into waste beaker. Repeat three times and dry down oligonucleotide pellet in vacuum savant.

The dried amino QSY oligonucleotide 52 is removed from the savant and suspended in 0.25M sodium bicarbonate in water (pH 8.5) with vortexing and mild heating. A solution of Dye NHS ester Alexa Fluor 647 (53) solution is prepared in DMSO at 60 mM. The dye DMSO solution (5 equivalents) is added to the oligonucleotide and the solution is vortexed. The reaction is run for 1-2 hours at room temperature with intermittent agitation. The reaction is monitored by collecting a mass spectrum of the reaction mixture and when the labeled product reaches 80% conversion the reaction is stopped ethanol precipitated by adding 50 mM sodium acetate in ethanol, cooling and collecting the pelleted material by centrifugation and drying the pellet under vacuum. The pure QSY labeled probe 53 is isolated by reverse phase HPLC employing 0.1M TEAA and 0.1M TEAA in 50/50 acetonitrile/water.

The procedure of Scheme 13 can be implemented with other types of dyes provided in phosphoramidite form in place of FAM, such as, e.g., VIC, NED, and HEX. Other dyes that can be utilized instead of AF647 in Scheme 13 include NHS derivatives of cyanine dyes, such as, e.g., AF660, and AF680 or rhodamine dyes, such as, TAMRA or ROX.

Scheme 13
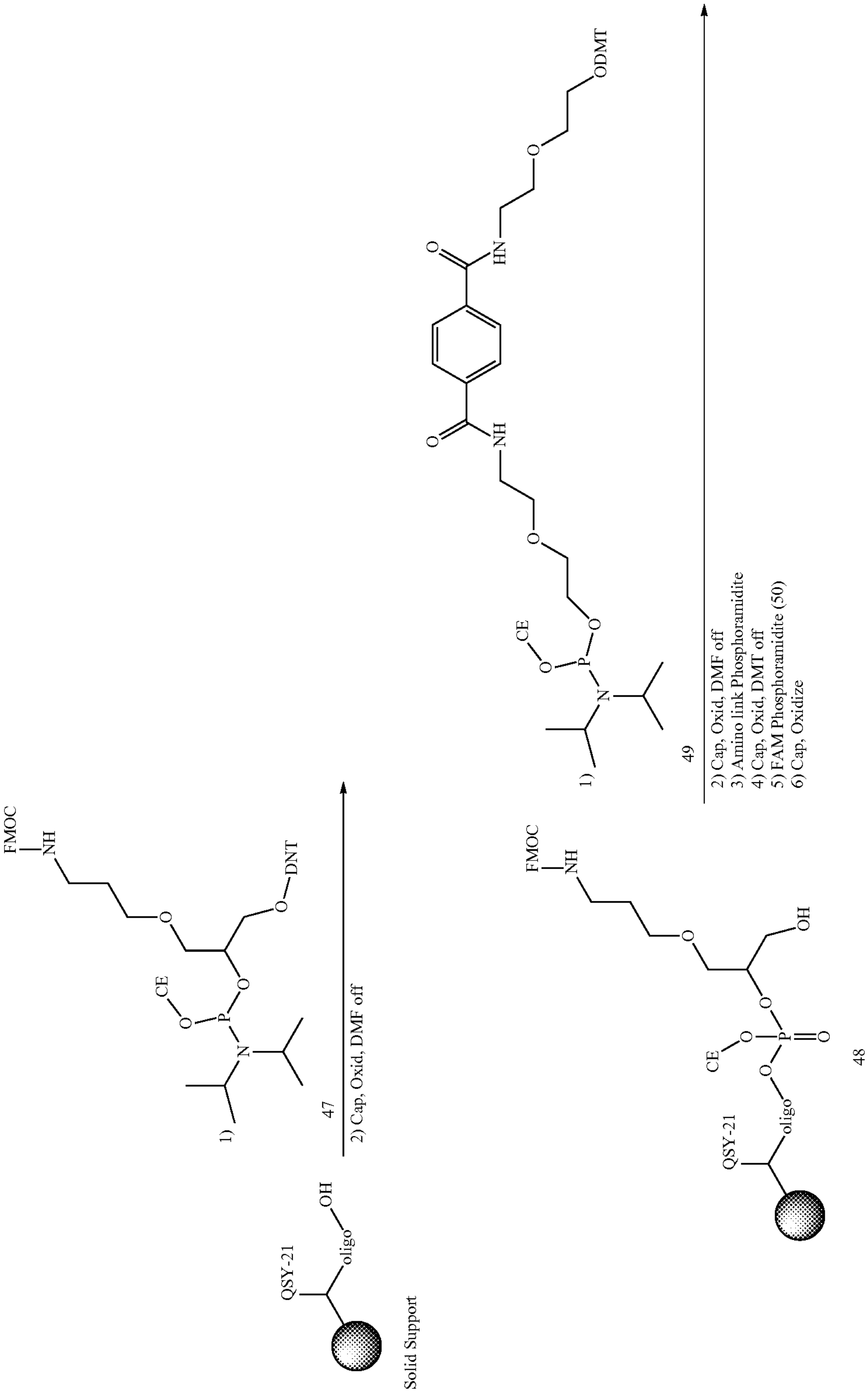
Scheme 13
Solid Support
1) 47
2) Cap, Oxid, DMF off
48
1) 49
2) Cap, Oxid, DMF off
3) Amino link Phosphoramidite
4) Cap, Oxid, DMT off
5) FAM Phosphoramidite (50)
6) Cap, Oxidize -continued
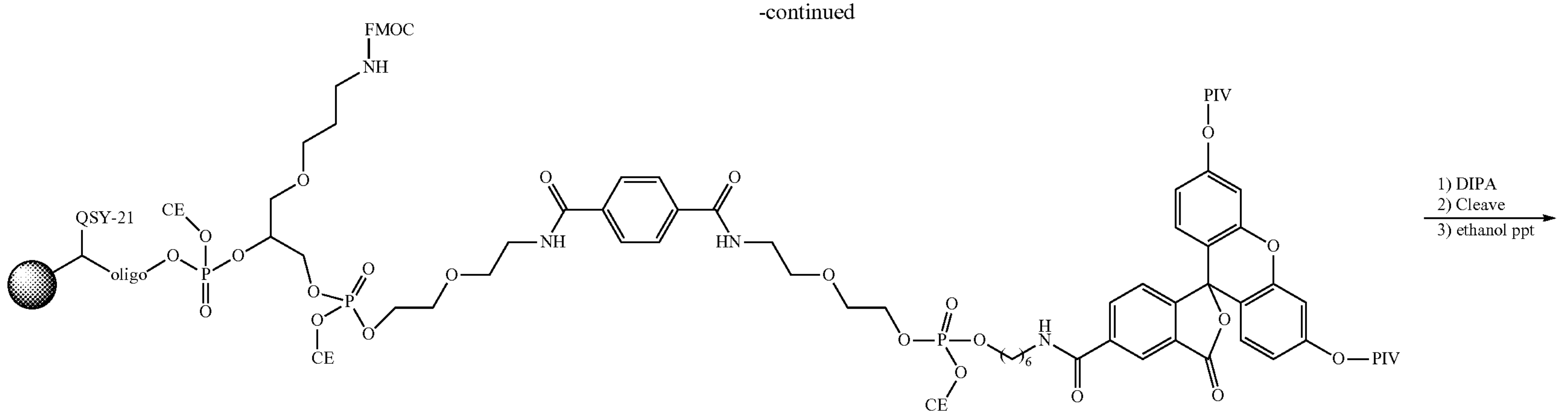
51
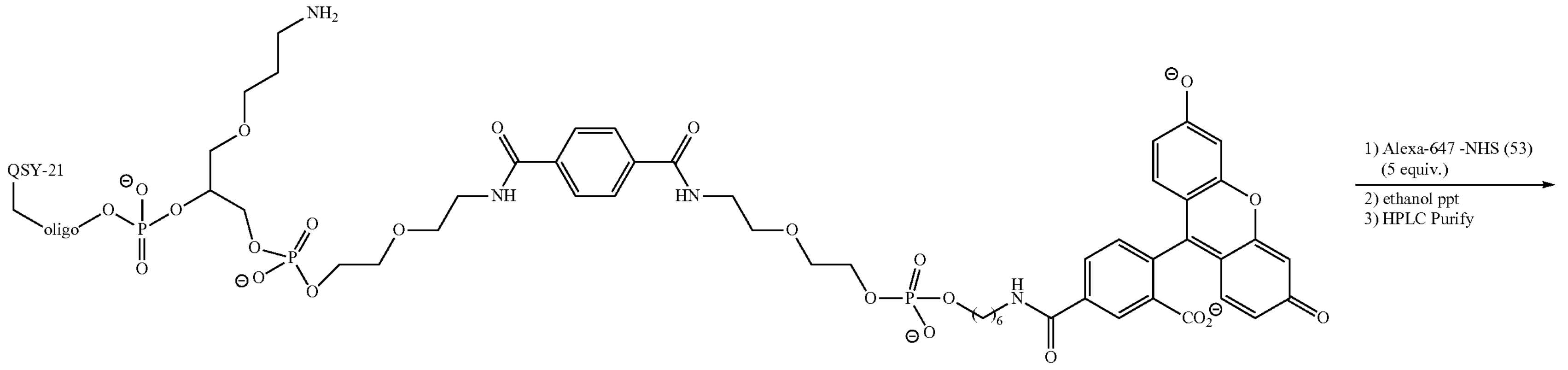
52

-continued
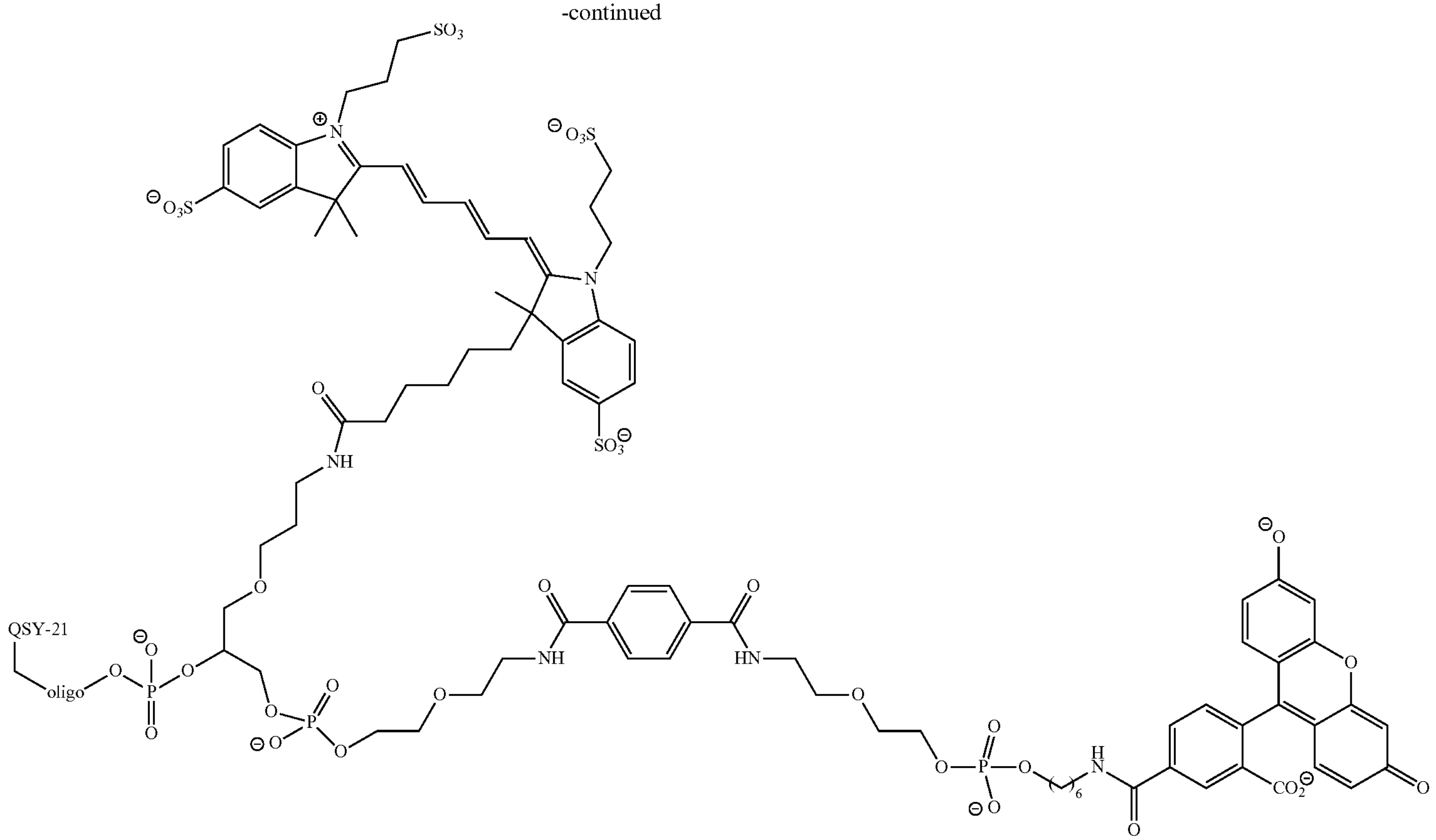
53
CE = Cyanoethyl. QSY-21 Molecular Probes Quencher. PIV = Pivalate

Example 11: Preparation of ET Dye Using L2 Linker

Preparation of fluorescein-rhodamine energy transfer dyes using the L2 linker with rhodamine dyes such as ROX rhodamine were performed by reaction of 4-aminomethyl-benzoic acid with 4-aminomethyl-5-carboxyfluorescein and subsequent conjugation to the rhodamine HNS ester (Scheme 14) (see, FIG. 2).

Synthesis of ROX-L2-NHS

A mixture of 5-ROX-NHS 54 (5 mg, 9 □mol) 4-aminomethylbenzoic acid 55 (3 mg, 19 □mol), and triethylamine (20 □l) was suspended in dimethylformamide (DMF, 200 □l) in a 1.5 ml Eppendorf tube (Scheme 14). The mixture was heated to 60 °C for 10 min. Reaction progress was monitored by TLC on silica gel with elution with a 400/30/10 mixture of dichloromethane, methanol and acetic acid. The insoluble 4-aminomethylbenzoic acid was separated by centrifugation and the DMF solution was decanted into 5% HCl (1 ml). The insoluble 4-aminomethylbenzoic acid -5-ROX 56 was separated by centrifugation, washed with 5% HCl (2×1 ml) and dried in a vacuum centrifuge.

Scheme 14

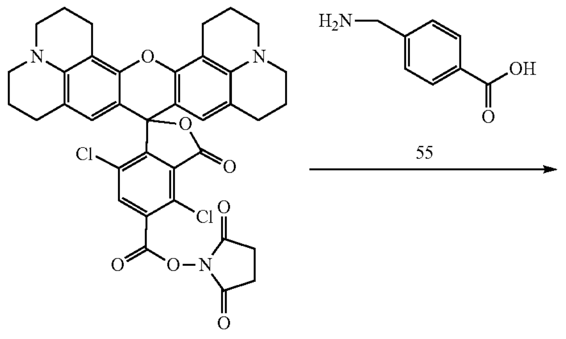

55

54

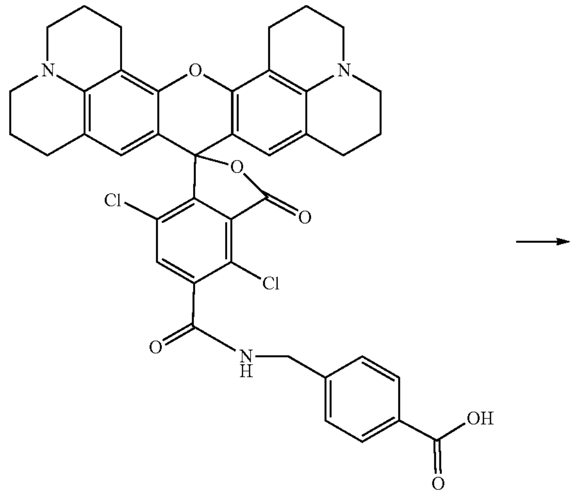

56

-continued

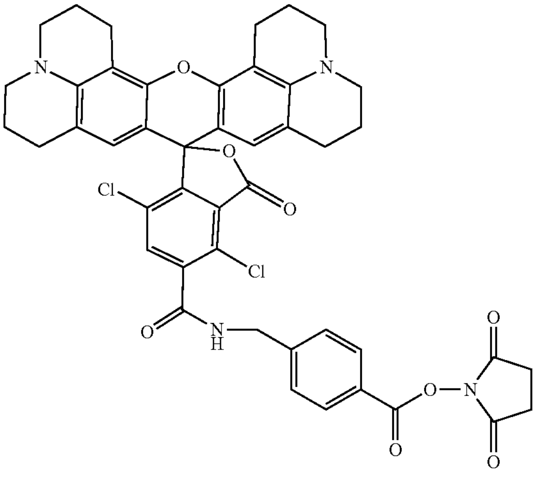

57

A solution of crude 4-aminomethylbenzoic acid -ROX 56 in DMF (125 ul), diisopropylethylamine (10 □l) and disuccinimidylcarbonate (10 mg) was combined in a 1.5 ml Eppendorf tube and heated to 60 °C Reaction progress was monitored by TLC on silica gel with elution with a 600/60/16 mixture of dichloromethane, methanol and acetic acid. After 5 min the reaction appeared to be complete. The solution was diluted into methylene chloride (3 ml) and washed with 250 mM carbonate/bicarbonate buffer, pH 9 (4×1 ml), the organic layer dried ($Na_2SO_4$) and concentrated to dryness in a vacuum centrifuge to give 57. The solid was dissolved in DMF (100 ul). The yield was determined by diluting an aliquot into pH 9 buffer and measuring the absorbance at 552 nm. Using an extinction coefficient of 50,000/cm/M, the concentration of 4-aminomethylbenzoic acid -5-ROX-NHS 57 was 4.8 mM for an 8% yield from 54.

Synthesis of FAM-ROX ET Dye

A solution of 4-aminomethylbenzoic acid -5ROX NHS 57 (1 □mol in 250 □l DMF) was combined with a solution of 4-aminomethyl-5-carboxyfluorescein 58 (19, 2.2 □mol in 100 □l DMSO) and triethylamine (20 □l) in a 1.5 ml Eppendorf tube (Scheme 15). The reaction was monitored by HPLC using a C8 reverse phase column with an elution gradient of 15-35% acetonitrile versus 0.1 M TEAA. HPLC analysis indicated that 57 was consumed, leaving the excess, unreacted 58. The reaction was diluted with 5% HCl (1 ml) and the FAM-ROX ET Dye acid product 59 separated by centrifugation, leaving the unreacted 58 in the aqueous phase. The solid was washed with 5% HCl (4×1 ml), dried in a vacuum centrifuge and taken up in DMF (300 □l). The yield was quantitative.

Scheme 15
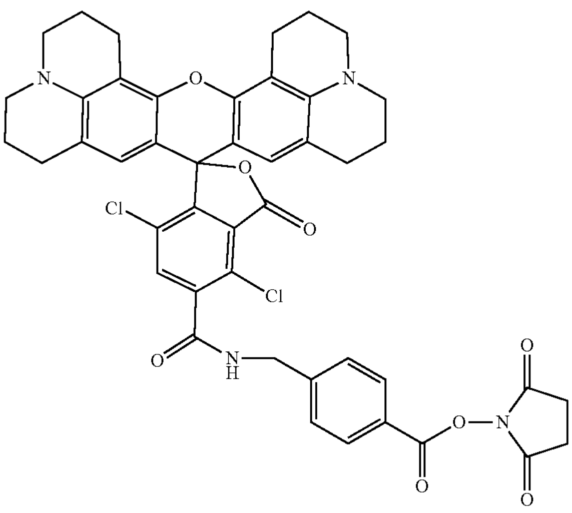
57
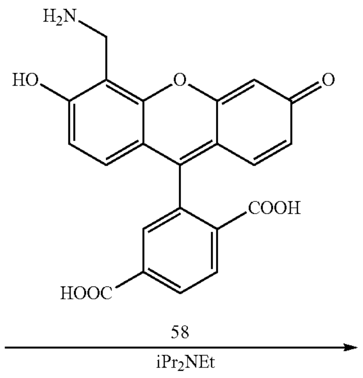
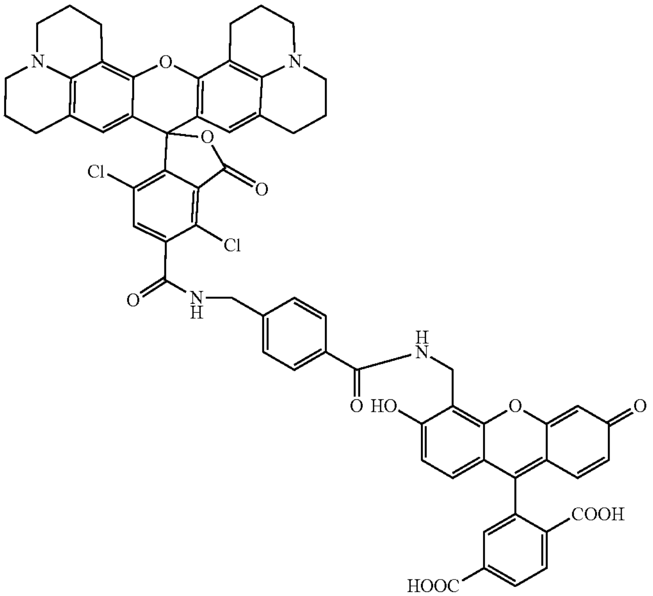
59

Synthesis of FAM-ROX ET-NHS

A solution of FAM-ROX ET Dye 59 (0.6 □mol in 100 □l DMF), 1-(3-dimethylaminopropyl)-3-ethylcarbodiimide hydrochloride (DEC, 2 mg) and N-hydroxysuccinimide (4 mg) were combined in a 1.5 ml Eppendorf tube (Scheme 16). The mixture was sonicated briefly and heated to 60 °C The reaction was monitored by TLC on silica gel with elution with a 600/60/16 mixture of dichloromethane, methanol and acetic acid. The reaction was complete in 30 min and diluted with 5% HCl. The precipitated product 60 was separated by centrifugation and dried in a vacuum centrifuge. The activated FAM-ROX ET Dye NHS 60 was dissolved in DMF (20 □l).

Scheme 16

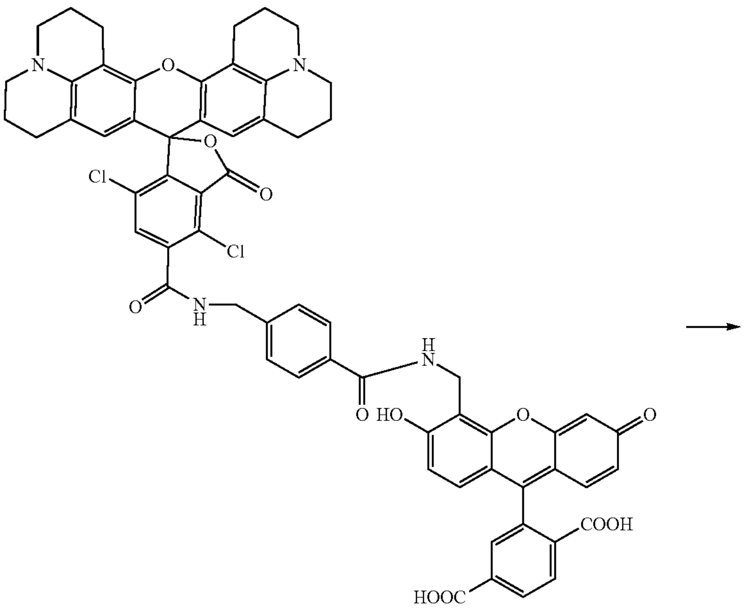

59

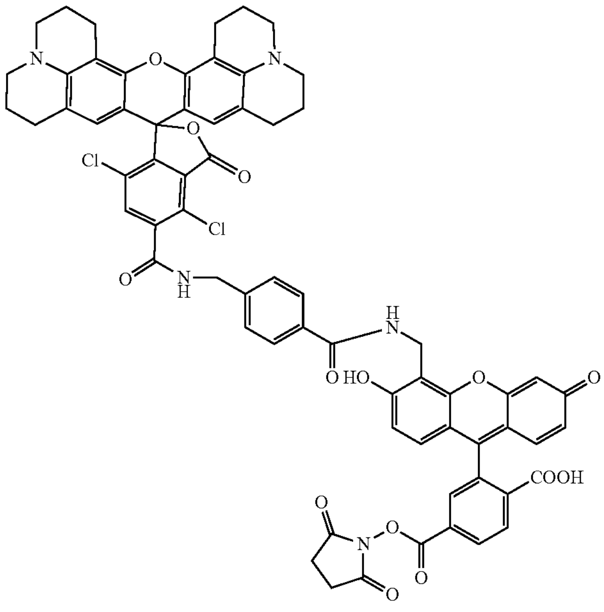

60

Preparation of ET Dye-Labeled Oligonucleotides

A representative preparation of L2 ET ROX-labeled oligonucleotide is described below (Scheme 17). A solution of 5-aminohexyl-functionalized oligonucleotide (10 □l, 1 mM) in carbonate/bicarbonate buffer (2 □l, 1 M) and ET ROX-NHS 60 (10 □l, 12 mM in dimethylsulfoxide) were combined. After 10 min at room temperature the solution was subjected to gel filtration on Sephadex G-25 to separate free dye. The fraction containing dye-labeled oligonucleotide and unlabeled oligonucleotide was collected and subjected to HPLC purification on a reverse phase column. The unlabeled oligonucleotide and each dye isomer of dye-labeled oligonucleotide were separated using an elution gradient of 10-30% acetonitrile versus 0.1 M TEAA. The solutions containing dye-labeled oligonucleotide were concentrated in a vacuum centrifuge and redissolved in TE buffer.

Scheme 17

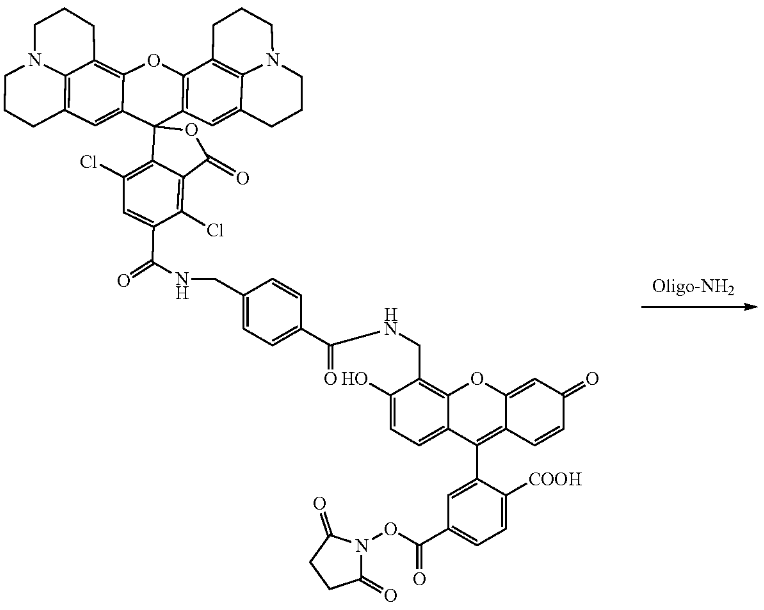

60

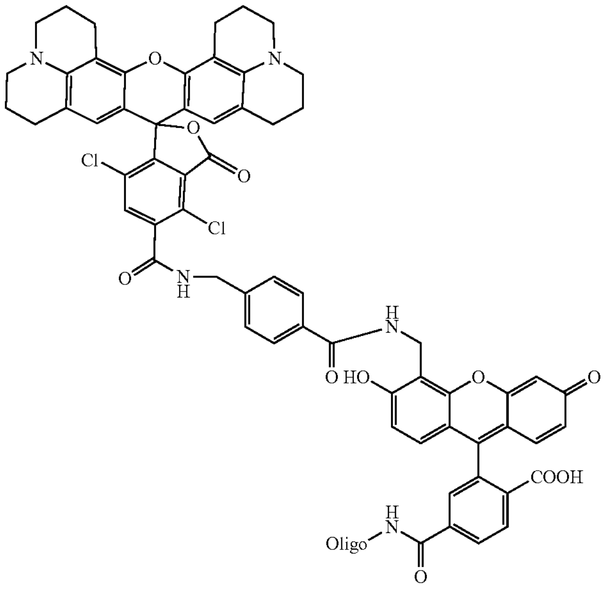

61

It is to be understood that, while the foregoing embodiments have been described in detail by way of illustration and example, numerous modifications, substitutions, and alterations are possible without departing from the spirit and scope of the invention as described in the following clauses and claims.

1. A fluorescent energy transfer dye conjugate comprising:
   i. a donor dye capable of absorbing light at a first wavelength and emitting excitation energy in response;
   ii. an acceptor dye capable of absorbing the excitation energy emitted by the donor dye and emitting light at a second wavelength in response; and
   iii. a linker covalently attaching the donor dye to the acceptor dye, wherein the linker comprises one or more of an alkyl portion, an amino-alkyl portion, an oxy-alkylene portion, an amino-alkylene-dialkoxy portion, an alkenylene portion, an alkynylene portion, a polyether portion, an arylene portion, an amide portion, or a phosphodiester portion.
2. The energy transfer dye conjugate of clause 1, wherein the second wavelength is longer than the first wavelength.
3. The energy transfer dye conjugate of clause 1 or 2, wherein the donor dye is selected from the group consisting of a xanthene dye, a cyanine dye, a BODIPY dye, a pyrene dye, a pyronine dye, and a coumarin dye.
4. The energy transfer dye conjugate of any one of the preceding clauses, wherein the donor dye is a fluorescein dye or a rhodamine dye.
5. The energy transfer dye conjugate of any one of the preceding clauses, wherein the acceptor dye is selected from the group consisting of a fluorescein dye, a cyanine dye, a rhodamine dye, a BODIPY dye, a pyrene dye, a pyronine dye, and a coumarin dye.
6. The energy transfer dye conjugate of any one of the preceding clauses, wherein the conjugate is linked to an analyte and having a basic structure selected from one of (LI)

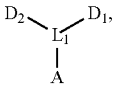

(LII)

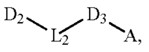 and (LIII)

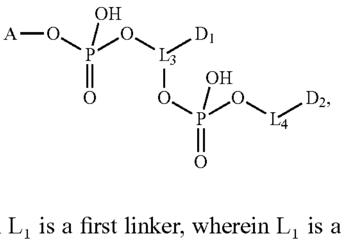

wherein $L_1$ is a first linker, wherein $L_1$ is attached to $D_1$, $D_2$ and A through a covalent bond or through a spacer comprising one or more intervening atoms;

wherein $L_2$ is a second linker, wherein $L_2$ is attached to each of $D_2$ and $D_3$ through a covalent bond or through a spacer comprising one or more intervening atoms;

wherein $L_3$ is a third linker, wherein $L_3$ is attached to each $PO_4H$ and $D_1$ through a covalent bond or through a spacer comprising one or more intervening atoms;

wherein $L_4$ is a fourth linker, wherein $L_4$ is attached to $PO_4H$ and $D_2$ through a covalent bond or through a spacer comprising one or more intervening atoms;

wherein A is the analyte;

wherein each of $D_1$, $D_2$, and $D_3$ is interchangeably a donor dye or an acceptor dye;

wherein the combination of $D_1$ and $D_2$ in $L_I$ and $L_{III}$ and $D_2$ and $D_3$ in $L_{II}$ forms an energy transfer dye pair.

7. The energy transfer dye conjugate of clause 6, wherein the $L_1$ linker comprises an arylene portion of the formula

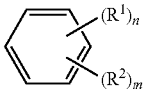

wherein each $R^1$ is independently —$C_1$-$C_{10}$ alkyl-N($R^3$)—*, —$C_2$-$C_{10}$ alkenyl-N($R^3$)—*, —$C_2$-$C_{10}$ alkynyl-N($R^3$)—*, —O$C_1$-$C_{10}$ alkyl-*, —$C_1$-$C_{10}$ alkyl-O—*, —N($R^3$)$C_1$-$C_6$ alkyl-*, —N($R^3$)$C_1$-$C_6$ alkyl-O—*, —O$C_1$-$C_6$ alkyl-N($R^3$)—*; or —N($R^3$)—*;

each $R^2$ is independently —C(O)N($R^4$), —$C_1$-$C_{10}$ alkyl-C(O)N($R^4$), —$C_2$-$C_{10}$ alkenyl-C(O)N($R^4$), —$C_2$-$C_{10}$ alkynyl-$R^4$, —C(O)N($R^4$), —N($R^3$)—C(O)N($R^4$), $C_1$-$C_6$ alkyl-O—C(O)N($R^4$), —O$C_1$-$C_6$ alkyl-C(O)N($R^4$), —N($R^4$), halogen, —$CO_2^-Z^+$, —$SO_3^-R^4$, or —$SO_3^-Z^+$;

each $R^3$ is independently H or $C_1$-$C_6$ alkyl;

each $R^4$ is independently H, $C_1$-$C_6$ alkyl, or a point of attachment to A, wherein the attachment to A is through a covalent bond or through a spacer comprising one or more intervening atoms;

each * represents a point of attachment to $D_1$ or $D_2$, wherein the attachment to $D_1$ or $D_2$ is through a covalent bond or through a spacer comprising one or more intervening atoms;

$Z^+$ is a cation(s) (e.g., $Na^+$, $K^+$, or $NH_4^+$);

n is 2, 3 or 4; and m is 0, 1, 2, 3, or 4, provided that n+m=3 to 6.

8. The energy transfer fluorescent dye conjugate of clause 6, wherein the $L_1$ linker comprises an arylene portion and one or more of a bis-alkylamino portion or a bis-carboxyamidyl portion, wherein the $L_1$ linker further comprises a point of attachment to A, wherein the attachment to A is through a covalent bond or through a spacer comprising one or more intervening atoms.
9. The energy transfer dye conjugate of clause 6, wherein the $L_2$ linker comprises an arylene portion of the formula

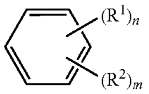

wherein each $R^1$ is independently —$C_1$-$C_{10}$ alkyl-N($R^3$)—*, —$C_2$-$C_{10}$ alkenyl-N($R^3$)—*, —$C_2$-$C_{10}$ alkynyl-N($R^3$)—*, —O$C_1$-$C_{10}$ alkyl-*, —$C_1$-$C_{10}$ alkyl-O—*, —N($R^3$)$C_1$-$C_6$ alkyl*-, —N($R^3$)$C_1$-$C_6$ alkyl-O—*, —O$C_1$-$C_6$ alkyl-N($R^3$)—*; or —N($R^3$)—*;

each $R^2$ is independently —C(O)N($R^3$)—*, —$C_1$-$C_{10}$ alkyl-C(O)N($R^3$)—*, —$C_2$-$C_{10}$ alkenyl-C(O)N $(R^3)$—*, —$C_2$-$C_{10}$ alkynyl-$(R^3)$—*, —C(O)N$(R^3)$—*, —N$(R^3)$—C(O)N$(R^3)$—*, $C_1$-$C_6$ alkyl-O—C(O)N$(R^3)$—*, —O$C_1$-$C_6$ alkyl-C(O)N$(R^3)$—*, —N$(R^3)$—*, halogen, —$CO_2^-Z^+$ or —$SO_3^-Z^+$;

each $R^3$ is independently H or $C_1$-$C_6$ alkyl;

each * represents a point of attachment to $D_2$ or $D_3$, wherein the attachment to $D_2$ or $D_3$ is through a covalent bond or through a spacer comprising one or more intervening atoms.

$Z^+$ is a cation(s) (e.g., $Na^+$, $K^+$, or $NH_4^+$);

n is 2, 3 or 4; and m is 0, 1, 2, 3, or 4, provided that n+m=2 to 6.

10. The energy transfer dye conjugate of any one of the preceding clauses, wherein the linker comprises a fragment of the formula

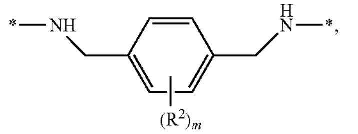

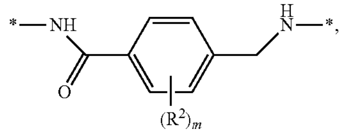

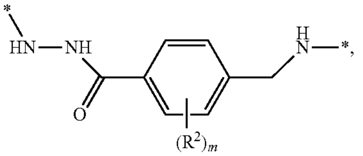

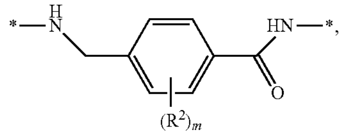

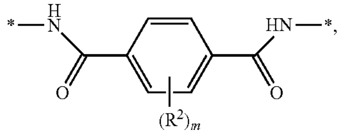

or

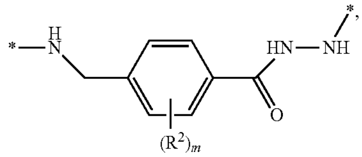

wherein each $R^2$, m and * is as defined above.

11. The energy transfer dye conjugate of clause 6, wherein the L3 linker comprises a fragment of the formula.

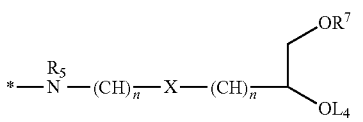

wherein $R^5$ is H or $C_1$-$C_6$ alkyl;

n is 2, 3 or 4;

X is O or $CH_2$;

$L_4$ is an attachment to $D_2$, wherein $L_4$ is a covalent bond or a spacer comprising one or more intervening atoms;

$R^7$ is a point of attachment to POSH-A, wherein the attachment to $PO_3H$-A is through a covalent bond or through a spacer comprising one or more intervening atoms; and wherein * represents a point of attachment to $D_1$, wherein the attachment to $D_1$ is through a covalent bond or through a spacer comprising one or more intervening atoms.

12. The energy transfer dye conjugate of clause 11, wherein the L4 linker comprises a phosphodiester portion of the formula

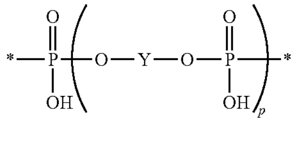

wherein

Y comprises one or more of an alkoxy portion, an alkyl portion, an arylene portion, or an oligonucleotide portion;

p is an integer from 0 to 10;

$D_2$ or A comprises an oxygen atom, wherein each * represents a point of attachment of the phosphodiester portion to the oxygen atom in $D_2$ or A, wherein the attachment of the phosphodiester to the oxygen atom in $D_2$ or A is through a covalent bond or through a spacer comprising one or more intervening atoms.

13. The energy transfer dye conjugate of clause 12, wherein Y is $C_1$-$C_{10}$alkyl or poly(alkylene glycol).

14. The energy transfer dye conjugate of any one of clauses 6-13, wherein a combination of the L3 and L4 linker comprises the formula

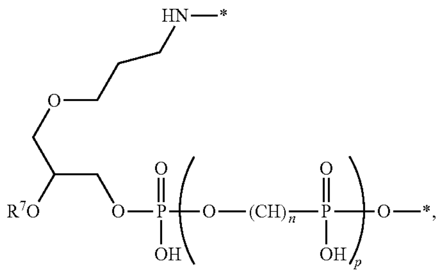

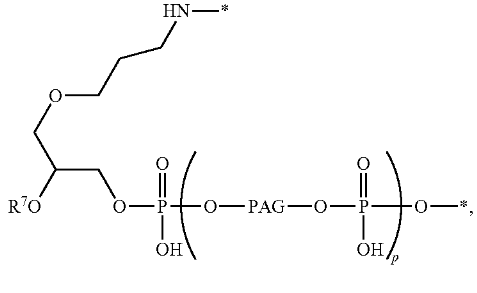

-continued

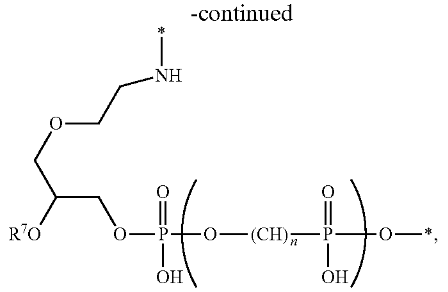

or

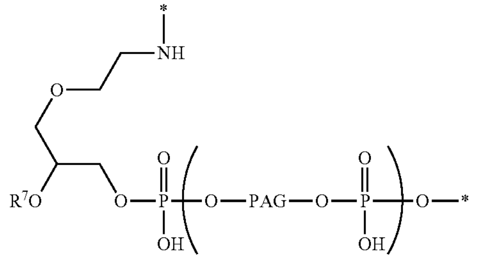

wherein $R^7$ comprises a phosphodiester group attached to A, wherein the phosphodiester group is attached to one or more of a phosphodiester portion, alkoxy portion, amino-alkyl portion, alkoxy portion, alkyl portion, polyether portion, or arylene portion, PAG is a poly(alkylene glycol), wherein the poly (alkylene glycol) is or comprises a $C_2$-$C_6$ linear or branched alkylene chain;

n is 2-6; and p is 1-4.

15. The energy transfer dye conjugate of clause 14, wherein the PAG is pentaethylene glycol.
16. The energy transfer dye conjugate of any one of clause 6-15, wherein the analyte is a biological molecule is selected from a nucleic acid molecule, a peptide, a polypeptide, a protein, and a carbohydrate.
17. The energy transfer dye conjugate of any one of the preceding clauses, wherein the energy transfer dye conjugate is covalently attached to an oligonucleotide (e.g., through a covalent bond or through a spacer comprising one or more intervening atoms).
18. An oligonucleotide probe comprising:
   i. an oligonucleotide; and
   ii. an energy transfer dye conjugate according to any one of clauses 1-17 covalently attached to the oligonucleotide (e.g., through a covalent bond or through a spacer comprising one or more intervening atoms).
19. The oligonucleotide probe of clause 17, further comprising a quencher dye covalently attached to the oligonucleotide (e.g., through a covalent bond or through a spacer comprising one or more intervening atoms).
20. The probe of clause 18 or 19, wherein the oligonucleotide comprises a modification.
21. The probe of clause 20, wherein the modification comprises a minor groove binder (MGB).
22. The probe of clause 21, wherein the modification comprises a locked nucleic acid (LNA).
23. The probe of clause 18, wherein the fluorescent energy transfer dye conjugate is covalently attached to the 3'-end, internally, or to the 5-end of the oligonucleotide.
24. The probe of clause 19, wherein fluorescent energy transfer dye conjugate is covalently attached to the 5'-end of the oligonucleotide.
25. The probe of clause 19, wherein the quencher dye is covalently attached to the 3'-end of the oligonucleotide.
26. The probe of clause 19, wherein the fluorescent energy transfer dye conjugate and the quencher dye are covalently attached to opposite ends of the oligonucleotide.
27. The probe of clause 19, wherein the fluorescent energy transfer dye conjugate is covalently attached to the 5'-end of the oligonucleotide and the quencher dye is covalently attached to the 3'-end of the oligonucleotide.
28. The probe of any of the preceding clauses, wherein the probe is a hydrolysis probe.
29. The probe of any of the preceding clauses, wherein the probe has a $T_m$ within the range of 60 to 75 C.
30. The probe of any of the preceding clauses, wherein the probe is between 5-40 nucleotides in length.
31. The probe of any of the preceding clauses, wherein the oligonucleotide comprises a portion that is complementary to a target nucleic acid molecule.
32. The probe of clause 31, wherein the oligonucleotide is at least 60% complementary to the target nucleic acid molecule.
33. The probe of clause 31, wherein the oligonucleotide is at least 90% complementary to the target nucleic acid molecule.
34. The probe of clause 18, wherein the oligonucleotide forms a stem loop structure.
35. The probe of clause 18, wherein the oligonucleotide comprises a target-specific portion and a tail portion.
36. The probe of clause 35, wherein the tail portion is a universal tail portion.
37. A system, comprising:
   a radiant source characterized by an average excitation wavelength;
   a sample disposed to receive radiation from the radiant source, the sample comprising:
      a first dye;
      a second dye; and
   a detector configured to measure emissions from the sample;
   a first emission spectral element characterized by a first average emission wavelength;
   a second emission spectral element characterized by a second average emission wavelength that is different than the first average emission wavelength;
   at least one processor comprising at least one memory including instructions to:
      illuminate the sample with the radiant source and, in response, (1) measure emissions from the sample using the detector and the first emission spectral element and (2) measure emissions from the sample using the detector and the second emission spectral element.
38. The system of clause 37, wherein the first dye is or comprises a first fluorophore and the second dye is or comprises a fluorescent energy transfer dye conjugate according to any of clauses 1-17.
39. The system of any of clauses 37-38, wherein the first fluorophore comprises a dye selected from the group consisting of a xanthene dye, a cyanine dye, a BODIPY dye, a pyrene dye, a pyronine dye, and a coumarin dye.
40. The system of any of clauses 37-39, wherein the second dye comprises a fluorophore selected from the group consisting of a fluorescein dye, a rhodamine dye, a pyronine dye, and a cyanine dye.

41. The system of any of clauses 37-40, wherein the first dye is covalently attached to a first probe and the second dye is covalently attached to a second probe, wherein the first and second probes are configured to bind to a first and a second target molecule, respectively.

42. The system of clause 41, wherein the first and second probes are oligonucleotide probes and the second probe is according to any of clauses 18-36.

43. The system of any of clauses 41-42, wherein the first and second target molecules are nucleic acid molecules.

44. The system of any of clauses 37-43, wherein the first dye comprises a first absorption spectrum comprising a first maximum absorption wavelength and the second dye comprises a second absorption spectrum comprising a second maximum absorption wavelength that is equal to or substantially equal to the first maximum absorption wavelength.

45. The system of clause 44, wherein one or more of the first maximum absorption wavelength or the second maximum absorption wavelength is an absolute maximum over an entirety of the respective absorption spectrum.

46. The system of any of clauses 37-45, wherein the first dye is an on-axis dye and the second dye is an off-axis dye.

47. The system of any of clauses 37 or 44-46, wherein:
the first dye comprises one or more of 5-FAM, 6-FAM, Oregon Green, or TET, R110; and
the second dye comprises one or more of FAM-TAMRA, FAM-ABY, or FAM-NED.

48. The system of any of clauses 37 or 44-47, wherein:
the average excitation wavelength of the first radiant source is 480±5 nanometers and/or the first radiant source is characterized by a wavelength band that is less than or equal to ±12 nanometers about the average excitation wavelength;
the first average emission wavelength of the first emission spectral element is 520±5 nanometers and/or the first emission spectral element is characterized by a wavelength band that is less than or equal to ±20 nanometers about the first average emission wavelength; and
the second average emission wavelength of the second emission spectral element is 587±5 nanometers and/or the second emission spectral element is characterized by a wavelength band that is less than or equal to ±12 nanometers about the second average emission wavelength.

49. The system of any of clauses 37 or 44-46, wherein:
the first dye comprises one or more of 5-FAM, 6-FAM, Oregon Green, TET, or R110; and
the second dye comprises one or more of FAM-PET, FAM-ROX, FAM-JUN, FAM-Texas Red, or TET-Alexa Fluor 594.

50. The system of clause 49, wherein:
the average excitation wavelength of the first radiant source is 480±5 nanometers and/or the first radiant source is characterized by a wavelength band that is less than or equal to ±12 nanometers about the average excitation wavelength;
the first average emission wavelength of the first emission spectral element is 520±5 nanometers and/or the first emission spectral element is characterized by a wavelength band that is less than or equal to ±18 nanometers about the first average emission wavelength; and
the second average emission wavelength of the second emission spectral element is 623±5 nanometers and/or the second emission spectral element is characterized by a wavelength band that is less than or equal to ±18 nanometers about the second average emission wavelength.

51. The system of any of clauses 37 or 44-46, wherein:
the first dye comprises one or more of NED, TAMRA, ABY, or DY-555; and
the second dye comprises one or more of ABY-Alexa Fluor 647, NED-Alexa Fluor 647, ABY-Cy5®, ABY-ATTO 647™, or ABY-DyLight 650™.

52. The system of clause 51, wherein:
the average excitation wavelength of the first radiant source is 550±5 nanometers and/or the first radiant source is characterized by a wavelength band that is less than or equal to ±14 nanometers about the average excitation wavelength;
the first average emission wavelength of the first emission spectral element is 587±5 nanometers and/or the first emission spectral element is characterized by a wavelength band that is less than or equal to ±12 nanometers about the first average emission wavelength; and
the second average emission wavelength of the second emission spectral element is 682±5 nanometers and/or the second emission spectral element is characterized by a wavelength band that is less than or equal to ±16 nanometers about the second average emission wavelength.

53. The system of any of clauses 37 or 44-46, wherein:
the first dye comprises one or more of NED, TAMRA, ABY, or DY-555; and
the second dye comprises one or more of NED-Alexa Fluor 676, NED DyLight 680™, NED-Cy5.5®, ABY-Alexa Fluor 676, ABY-DyLight 680™, or ABY-Cy5.5®.

54. The system of clause 53, wherein:
the average excitation wavelength of the first radiant source is 550±5 nanometers and/or the first radiant source is characterized by a wavelength band that is less than or equal to ±14 nanometers about the average excitation wavelength;
the first average emission wavelength of the first emission spectral element is 587±5 nanometers and/or the first emission spectral element is characterized by a wavelength band that is less than or equal to ±12 nanometers about the first average emission wavelength; and
the second average emission wavelength of the second emission spectral element is 711±5 nanometers and/or the second emission spectral element is characterized by a wavelength band that is less than or equal to ±16 nanometers about the second average emission wavelength.

55. A system, comprising:
a first radiant source characterized by a first average excitation wavelength;
a second radiant source characterized by a second average excitation wavelength that is different than the first average excitation wavelength;

a sample disposed to receive radiation from the radiant sources, the sample comprising:

a first dye;

a second dye; and a detector configured to measure emissions from the sample;

an emission spectral element characterized by an average emission wavelength;

at least one processor comprising at least one memory including instructions to:

illuminate the sample with the first radiant source and, in response, measure emissions from the sample using the detector and the emission spectral element;

illuminate the sample with the second radiant source and, in response, measure emissions from the sample using the detector and the emission spectral element.

56. The system of clause 55, wherein the first dye is or comprises a first fluorophore and the second dye is or comprises a fluorescent energy transfer dye conjugate according to any of clauses 1-17.

57. The system of any of clauses 55-56, wherein the first fluorophore is a dye selected from the group consisting of a xanthene dye, a cyanine dye, a BODIPY dye, a pyrene dye, a pyronine dye, and a coumarin dye.

58. The system of any of clauses 55-57, wherein the second dye comprises a fluorophore selected from the group consisting of a fluorescein dye, a rhodamine dye, a pyronine dye, and a cyanine dye.

59. The system of any of clauses 55-58, wherein the first dye is covalently attached to a first probe, and the second dye is covalently attached a second probe, wherein the first and second probes are configured to bind to a first and a second target molecule, respectively.

60. The system of clause 59, wherein the first and second probes are oligonucleotide probes and the second probe is according to any of clauses 18-36.

61. The system of any of clauses 59-60, wherein the first and second target molecules are nucleic acid molecules.

62. The system of any of clauses 55-61, wherein the first dye comprises a first emission spectrum comprising a first maximum emission wavelength and the second dye comprises a second emission spectrum comprising a second maximum emission wavelength that is equal to or substantially equal the first maximum emission wavelength.

63. The system of clause 62, wherein one or more of the first maximum emission wavelength or second maximum emission wavelength is an absolute maximum over an entirety of the respective absorption spectrum.

64. The system of any of clauses 55-63, wherein the second dye is an off-axis dye.

65. The system of any of clauses 55 or 62-64, wherein:

the first dye comprises one or more of NED, TAMRA, ABY, or DY-555; and the second dye comprises one or more of FAM-TAMRA, FAM-ABY, or FAM-NED.

66. The system of any of clauses 55 or 62-64, wherein:

the first average excitation wavelength of the first radiant source is 480±5 nanometers and/or the first radiant source is characterized by a wavelength band that is less than or equal to ±12 nanometers about the first average excitation wavelength;

the second average excitation wavelength of the second radiant source is 550±5 nanometers and/or the second radiant source is characterized by a wavelength band that is less than or equal to ±12 nanometers about the second average excitation wavelength;

the first average emission wavelength of the first emission spectral element is 587±5 nanometers and/or the second emission spectral element is characterized by a wavelength band that is less than or equal to ±12 nanometers about the average emission wavelength.

67. The system of any of clauses 55 or 62-64, wherein:

the first dye comprises one or more of FAM-PET, FAM-ROX, FAM-JUN, FAM-Texas Red, or TET-Alexa Fluor 594; and the second dye comprises one or more of PET, ROX, JUN, Texas Red, or Alexa Fluor 594.

68. The system of clause 67, wherein:

the first average excitation wavelength of the first radiant source is 480±5 nanometers and/or the first radiant source is characterized by a wavelength band that is less than or equal to ±12 nanometers about the first average excitation wavelength;

the second average excitation wavelength of the second radiant source is 580±5 nanometers and/or the second radiant source is characterized by a wavelength band that is less than or equal to ±12 nanometers about the second average excitation wavelength;

the average emission wavelength of the first emission spectral element is 623±5 nanometers and/or the second emission spectral element is characterized by a wavelength band that is less than or equal to ±18 nanometers about the average emission wavelength.

69. The system of any of clauses 55 or 62-64, wherein:

the first dye comprises one or more of ABY-Alexa Fluor 647, NED-Alexa Fluor 647, ABY-Cy5®, ABY-ATTO 647™, or ABY-DyLight 650™; and the second dye comprises one or more of Alexa Fluor 647, Cy5®, ATTO 647™, or DyLight 650™.

70. The system of clause 69, wherein:

the first average excitation wavelength of the first radiant source is 550±5 nanometers and/or the first radiant source is characterized by a wavelength band that is less than or equal to ±14 nanometers about the first average excitation wavelength;

the second average excitation wavelength of the second radiant source is 640±5 nanometers and/or the second radiant source is characterized by a wavelength band that is less than or equal to ±12 nanometers about the second average excitation wavelength;

the average emission wavelength of the first emission spectral element is 682±5 nanometers and/or the second emission spectral element is characterized by a wavelength band that is less than or equal to ±16 nanometers about the average emission wavelength.

71. The system of any of clauses 55 or 62-64, wherein:

the first dye comprises one or more of NED-Alexa Fluor 676, NED DyLight 680™ NED-Cy5.5®, ABY-Alexa Fluor 676, ABY-DyLight 680™, or ABY-Cy5.5®; and the second dye comprises one or more of Alexa Fluor 676, DyLight 680™, or Cy5.5®.

72. The system of clause 71, wherein:

the first average excitation wavelength of the first radiant source is 550±5 nanometers and/or the first radiant source is characterized by a wavelength band that is less than or equal to ±14 nanometers about the first average excitation wavelength;

the second average excitation wavelength of the second radiant source is 662±5 nanometers and/or the second radiant source is characterized by a wavelength band that is less than or equal to ±12 nanometers about the second average excitation wavelength; and the average emission wavelength of the first emission spectral element is 711±5 nanometers and/or the second emission spectral element is characterized by a wavelength band that is less than or equal to ±16 nanometers about the average emission wavelength.

73. A system, comprising:

a first radiant source characterized by a first average excitation wavelength;

a second radiant source characterized by a second average excitation wavelength that is different than the first average excitation wavelength;

a sample disposed to receive radiation from the radiant sources, the sample comprising:

a first dye;

a second dye; and a third dye;

a detector configured to measure emissions from the sample;

a first emission spectral element characterized by a first average emission wavelength;

a second emission spectral element characterized by a second average emission wavelength that is different than the first average emission wavelength;

at least one processor comprising at least one memory including instructions to:

illuminate the sample with the first radiant source and, in response, (1) measure emissions from the sample using the detector and the first emission spectral element and (2) measure emissions from the sample using the detector and the second emission spectral element;

illuminate the sample with the second radiant source and, in response, measure emissions from the sample using the detector and the second emission spectral element.

74. The system of clause 73, wherein the first dye and/or the third dye is or comprises a first fluorophore and the second dye is or comprises a fluorescent energy transfer dye conjugate according to any of clauses 1-17.

75. The system of any of clauses 73-74, wherein the first and/or the third fluorophore is a dye selected from the group consisting of a xanthene dye, a cyanine dye, a BODIPY dye, a pyrene dye, a pyronine dye, and a coumarin dye.

76. The system of clause 73-75, wherein the second dye comprises a fluorophore selected from the group consisting of a fluorescein dye, a rhodamine dye, a pyronine dye, and a cyanine dye 77. The system of any of clauses 73-75, wherein the first dye is covalently attached to a first probe, and the second dye is covalently attached to conjugate second probe, and the third dye is covalently attached to a third probe, wherein the first, second, and third probes are configured to bind to a first, a second, and a third target molecule, respectively.

78. The system of clause 77, wherein the first, the second, and the third probes are oligonucleotide probes and the second probe is according to any of clauses 18-36.

79. The system of clause 77-78, wherein the first, second, and third target molecules are nucleic acid molecules.

80. The system of any of clauses 73-79, wherein (1) the first dye comprises a first absorption spectrum comprising a first maximum absorption wavelength and the second dye comprises a second absorption spectrum comprising a second maximum absorption wavelength that is equal to or substantially equal to the first maximum absorption wavelength; and (2) the second dye comprises a second emission spectrum comprising a second maximum emission wavelength and the third dye comprises a third emission spectrum comprising a third maximum emission wavelength that is equal to or substantially equal to the second maximum emission wavelength.

81. The system of clause 80, wherein one or more of the first maximum absorption wavelength, the second maximum absorption wavelength, second maximum emission wavelength, or third maximum emission wavelength, is an absolute maximum over an entirety of the respective absorption spectrum.

82. The system of any of clauses 73-81, wherein the second dye is an off-axis dye.

83. The system of any of clauses 73 or 80-82, wherein:

the first dye comprises one or more of 5-FAM, 6-FAM, Oregon Green, or TET, R110;

the second dye comprises one or more of FAM-TAMRA, FAM-ABY, or FAM-NED; and the third dye comprises one or more of NED, TAMRA, ABY, or DY-555.

84. The system of any of clauses 73 or 80-83, wherein:

the first average excitation wavelength of the first radiant source is 480±5 nanometers and/or the first radiant source is characterized by a wavelength band that is less than or equal to ±12 nanometers about the first average excitation wavelength;

the second average excitation wavelength of the second radiant source is 550±5 nanometers and/or the second radiant source is characterized by a wavelength band that is less than or equal to ±12 nanometers about the second average excitation wavelength;

the first average emission wavelength of the first emission spectral element is 520±5 nanometers and/or the first emission spectral element is characterized by a wavelength band that is less than or equal to ±20 nanometers about the first average emission wavelength; and the second average emission wavelength of the second emission spectral element is 587±5 nanometers and/or the second emission spectral element is characterized by a wavelength band that is less than or equal to ±12 nanometers about the second average emission wavelength.

85. The system of any of clauses 73 or 80-82, wherein:

the first dye comprises one or more of 5-FAM, 6-FAM, Oregon Green, TET, or R110;

the second dye comprises one or more of FAM-PET, FAM-ROX, FAM-JUN, FAM-Texas Red, or TET-Alexa Fluor 594; and the third dye comprises one or more of PET, ROX, JUN, Texas Red, or Alexa Fluor 594.

86. The system of clause 85, wherein:

the first average excitation wavelength of the first radiant source is 480±5 nanometers and/or the first radiant source is characterized by a wavelength band that is less than or equal to ±12 nanometers about the first average excitation wavelength;

the second average excitation wavelength of the second radiant source is 580±5 nanometers and/or the second radiant source is characterized by a wavelength band that is less than or equal to ±12 nanometers about the second average excitation wavelength;

the first average emission wavelength of the first emission spectral element is s 520±5 nanometers and/or the first emission spectral element is characterized by a wavelength band that is less than or equal to ±18 nanometers about the first average emission wavelength; and the second average emission wavelength of the second emission spectral element is 623±5 nanometers and/or the second emission spectral element is characterized by a wavelength band that is less than or equal to ±18 nanometers about the second average emission wavelength.

87. The system of any of clauses 73 or 80-82, wherein:

the first dye comprises one or more of NED, TAMRA, ABY, or DY-555;

the second dye comprises one or more of ABY-Alexa Fluor 647, NED-Alexa Fluor 647, ABY-Cy5®, ABY-ATTO 647™, or ABY-DyLight 650™; and the third dye comprises one or more of Alexa Fluor 647, Cy5®, ATTO 647™, or DyLight 650™.

88. The system of clause 87, wherein:

the first average excitation wavelength of the first radiant source is 550±5 nanometers and/or the first radiant source is characterized by a wavelength band that is less than or equal to ±14 nanometers about the first average excitation wavelength;

the second average excitation wavelength of the second radiant source is 640±5 nanometers and/or the second radiant source is characterized by a wavelength band that is less than or equal to ±12 nanometers about the second average excitation wavelength;

the first average emission wavelength of the first emission spectral element is 587±5 nanometers and/or the first emission spectral element is characterized by a wavelength band that is less than or equal to ±12 nanometers about the first average emission wavelength; and the second average emission wavelength of the second emission spectral element is 682±5 nanometers and/or the second emission spectral element is characterized by a wavelength band that is less than or equal to ±16 nanometers about the second average emission wavelength.

89. The system of any of clauses 73 or 80-82, wherein:

the first dye comprises one or more of NED, TAMRA, ABY, or DY-555;

the second dye comprises one or more of NED-Alexa Fluor 676, NED DyLight 680™, NED-Cy5.5®, ABY-Alexa Fluor 676, ABY-DyLight 680™, or ABY-Cy5.5®; and the third dye comprises one or more of Alexa Fluor 676, DyLight 6807 or Cy5.5®.

90. The system of clause 89, wherein:

the first average excitation wavelength of the first radiant source is 550±5 nanometers and/or the first radiant source is characterized by a wavelength band that is less than or equal to ±14 nanometers about the first average excitation wavelength;

the second average excitation wavelength of the second radiant source is 662±5 nanometers and/or the second radiant source is characterized by a wavelength band that is less than or equal to ±12 nanometers about the second average excitation wavelength;

the first average emission wavelength of the first emission spectral element is 587±5 nanometers and/or the first emission spectral element is characterized by a wavelength band that is less than or equal to ±12 nanometers about the first average emission wavelength; and the second average emission wavelength of the second emission spectral element is 711±5 nanometers and/or the second emission spectral element is characterized by a wavelength band that is less than or equal to ±16 nanometers about the second average emission wavelength.

91. The system of any of clauses 73-90, wherein the at least one memory further comprises one or more instructions to perform an nucleic acid synthesis assay and wherein the instructions to illuminate and measure are executed during the nucleic acid synthesis assay and/or after the nucleic acid synthesis assay.

92. The system of clause 91, wherein the nucleic acid synthesis assay comprises a polymerase chain reaction (PCR) assay including cycling the solution through a plurality of the temperature cycles and measuring emissions of the dyes is performed after one or more of the temperature cycles.

93. The system of clause 91, wherein the nucleic acid synthesis assay comprises a polymerase chain reaction (PCR) assay including cycling the solution through a plurality of the temperature cycles and measuring emissions of the dyes is performed after a last temperature cycle.

94. The system of any of clauses 73-93, wherein the at least one memory includes instructions to:

produce a first amplicon from a first target molecule during amplification;

produce a second amplicon from a second target molecule during amplification; and/or produce a third amplicon from a third target molecule during amplification.

95. The system of clause 94, wherein the first amplicon, second amplicon, and/or third amplicon are produced simultaneously.

96. The system of any of clauses 73-82, wherein:

the system further comprises a third, fourth, fifth, and sixth radiant source, each of the third, fourth, fifth, and sixth radiant sources characterized by a respective third, fourth, fifth, and sixth average excitation wavelength, wherein each of the six average excitation wavelengths is different from the remaining average excitation wavelengths;

the sample further comprises fourth, fifth, sixth, seventh, and eighth dyes;

the system further comprises third, fourth, fifth, and sixth emission spectral elements each configured to pass emissions from the sample, each of the third, fourth, fifth, and sixth emission elements characterized by a respective third, fourth, fifth, and sixth average emission wavelength, wherein the each of the six average emission wavelengths of each of the wavelength sources is different from the average emission wavelengths of the remaining sources;

the at least one memory includes instructions to:

illuminate the sample with the third, fourth, fifth, and sixth radiant sources;

in response to illuminating the sample with each of the third, fourth, fifth, and sixth radiant sources, measure emissions from the sample using one or more of the emission spectral elements.

97. The system of clause 96, wherein the first, second, third, fourth, fifth, sixth, seventh, and eighth dyes are covalently attached to a respective first, second, third, fourth, fifth, sixth, seventh, and eighth probe, each probe configured to bind to a respective first, second, third, fourth, fifth, sixth, seventh, and eighth target molecule and the at least one memory further comprises instructions to determine an amount of the target molecules present in the sample based on the measured emissions.

98. The system of clause 97, wherein the first, second, third, fourth, fifth, sixth, seventh, and/or eighth probe further comprises a quencher moiety.

99. The system of clause 98, wherein the first, second, third, fourth, fifth, sixth, seventh, and eighth probes are oligonucleotide probes and the second probe is according to any of clauses 18-36.

100. The system of clause 99, wherein the first, second, third, fourth, fifth, sixth, seventh, and eighth target molecules are nucleic acid molecules.

101. The system of any of clauses 96-100, wherein the second dye and the fourth dye are off-axis dyes.

102. The system of any of clauses 96-101, wherein:
  - the second dye comprises a maximum absorption wavelength that is equal to or substantially equal to a maximum absorption wavelength of the first dye;
  - the fourth dye comprises a maximum absorption wavelength that is equal to or substantially equal to a maximum absorption wavelength of the first dye;
  - the second dye comprises a maximum emission wavelength that is equal to or substantially equal to a maximum emission wavelength of the third dye; and
  - the fourth dye comprises a maximum emission wavelength that is equal to or substantially equal to a maximum emission wavelength of the fifth dye 103. The system of any of clauses 73-82, wherein:
  - the system further comprises third, fourth, fifth, and sixth radiant sources, each of the third, fourth, fifth, and sixth radiant sources characterized by a respective third, fourth, fifth, and sixth average excitation wavelength, wherein the each of the six average excitation wavelengths is different from the remaining average excitation wavelengths;
  - the sample further comprises fourth, fifth, sixth, seventh, eighth, ninth, and tenth dyes;
  - the system further comprises third, fourth, fifth, and sixth emission spectral elements each configured to pass emissions from the sample, each of the third, fourth, fifth, and sixth emission elements characterized by a respective third, fourth, fifth, and sixth average emission wavelength, wherein the each of the six average emission wavelengths of each of the wavelength sources is different from the average emission wavelengths of the remaining sources;
  - the at least one memory includes instructions to:
    - illuminate the sample with the third, fourth, fifth, and sixth radiant sources;
    - in response to illuminating the sample with each of the third, fourth, fifth, and sixth radiant sources, measure emissions from the sample using one or more of the emission spectral elements.

104. The system of clause 103, wherein the first, second, third, fourth, fifth, sixth, seventh, eighth, ninth, and tenth dyes are covalently attached to a respective first, second, third, fourth, fifth, sixth, seventh, eighth, ninth, and tenth probe, respectively, each probe configured to bind to a respective first, second, third, fourth, fifth, sixth, seventh, eighth, ninth, and tenth target molecule and the at least one memory further comprises instructions to determine an amount of target molecules present in the sample based on the measured emissions.

105. The system of clause 104, wherein the first, second, third, fourth, fifth, sixth, seventh, eighth, ninth and/or tenth probe further comprises a quencher moiety.

106. The system of clause 105, wherein the first, second, third, fourth, fifth, sixth, seventh, eighth, ninth, and tenth probes are oligonucleotide probes and the second probe is according to any of clauses 18-36.

107. The system of clause 106, wherein the first, second, third, fourth, fifth, sixth, seventh, eighth, ninth, and tenth target molecules are nucleic acid molecules.

108. The system of any of clauses 103-107, wherein the second dye, the fourth dye, the ninth dye, and the tenth dye are off-axis dyes.

109. The system of any of clauses 103-108, wherein:
  - the second dye comprises a maximum absorption wavelength that is equal to or substantially equal to a maximum absorption wavelength of the first dye;
  - the fourth dye comprises a maximum absorption wavelength that is equal to or substantially equal to a maximum absorption wavelength of the first dye;
  - the ninth dye comprises a maximum absorption wavelength that is equal to or substantially equal to a maximum absorption wavelength of the third dye;
  - the tenth dye comprises a maximum absorption wavelength that is equal to or substantially equal to a maximum absorption wavelength of the third dye;
  - the second dye comprises a maximum emission wavelength that is equal to or substantially equal to a maximum emission wavelength of the third dye
  - the fourth dye comprises a maximum emission wavelength that is equal to or substantially equal to a maximum emission wavelength of the fifth dye
  - the ninth dye comprises a maximum emission wavelength that is equal to or substantially equal to a maximum emission wavelength of the seventh dye; and
  - the tenth dye comprises a maximum emission wavelength that is equal to or substantially equal to a maximum emission wavelength of the tenth dye 110. The system of any of clauses 96-109, wherein:
  - the first average excitation wavelength of the first radiant source is 480±5 nanometers and/or the first radiant source is characterized by a wavelength band that is less than or equal to ±12 nanometers about the first average excitation wavelength;
  - the second average excitation wavelength of the second radiant source is 520±5 nanometers and/or the second radiant source is characterized by a wavelength band that is less than or equal to ±12 nanometers about the second average excitation wavelength;
  - the third average excitation wavelength of the third radiant source is 550±5 nanometers and/or the third radiant source is characterized by a wavelength band that is less than or equal to ±12 nanometers about the third average excitation wavelength;
  - the fourth average excitation wavelength of the fourth radiant source is 580±5 nanometers and/or the fourth radiant source is characterized by a wavelength band that is less than or equal to ±12 nanometers about the fourth average excitation wavelength;
  - the fifth average excitation wavelength of the fifth radiant source is 640±5 nanometers and/or the fifth radiant source is characterized by a wavelength band that is less than or equal to ±12 nanometers about the fifth average excitation wavelength;

the sixth average excitation wavelength of the sixth radiant source is 662±5 nanometers and/or the sixth radiant source is characterized by a wavelength band that is less than or equal to ±12 nanometers about the sixth average excitation wavelength;

the first average emission wavelength of the first emission spectral element is 520±5 nanometers and/or the first emission spectral element is characterized by a wavelength band that is less than or equal to ±18 nanometers about the first average emission wavelength;

the second average emission wavelength of the second emission spectral element is 558±5 nanometers and/or the second emission spectral element is characterized by a wavelength band that is less than or equal to ±15 nanometers about the second average emission wavelength;

the third average emission wavelength of the third emission spectral element is 587±5 nanometers and/or the third emission spectral element is characterized by a wavelength band that is less than or equal to ±12 nanometers about the third average emission wavelength;

the fourth average emission wavelength of the fourth emission spectral element is 623±5 nanometers and/or the fourth emission spectral element is characterized by a wavelength band that is less than or equal to ±16 nanometers about the fourth average emission wavelength;

the fifth average emission wavelength of the fifth emission spectral element is 682±5 nanometers and/or the fifth emission spectral element is characterized by a wavelength band that is less than or equal to ±16 nanometers about the fifth average emission wavelength; and the sixth average emission wavelength of the sixth emission spectral element is 711±5 nanometers and/or the sixth emission spectral element is characterized by a wavelength band that is less than or equal to ±16 nanometers about the sixth average emission wavelength.

111. The system of any of clauses 96-110, wherein:

the first dye is at least one of 5-FAM, 6-FAM, Oregon Green, TET, or R110;

the second dye is at least one of FAM-TAM RA, FAM-ABY, or FAM-NED;

the third dye is at least one of NED, TAMRA, ABY, or DY-555;

the fourth dye is at least one of FAM-PET, FAM-ROX, FAM-JUN, FAM-Texas Red, or TET-Alexa Fluor 594;

the fifth dye is at least one of PET, ROX, JUN, Texas Red, or Alexa Fluor 594;

the sixth dye is at least one of VIC, HEX, JOE, Yakima Yellow, or R6G;

The seventh dye is at least one of Alexa Fluor 647, Cy5®, ATTO 647™, or DyLight 650™;

the eighth dye is at least one of Alexa Fluor 676, DyLight 680™, or Cy5.5®.

112. The system of any of clauses 103-111, wherein the ninth dye is at least one of ABY-Alexa Fluor 647, NED-Alexa Fluor 647, ABY-Cy5®, ABY-ATTO 647™, or ABY-DyLight 650™; and the tenth dye is at least one of NED-Alexa Fluor 676, NED DyLight 680™, NED-Cy5.5®, ABY-Alexa Fluor 676, ABY-DyLight 680™, or ABY-Cy5.5®.

113. The system of any of clauses 96-112, wherein the second and fourth dyes independently comprise a fluorophore selected from the group consisting of a fluorescein dye, a rhodamine dye, a pyronine dye, and a cyanine dye.

114. The system of any of clauses 103-112, wherein the second, fourth, ninth, and tenth dyes independently comprise a fluorophore selected from the group consisting of a fluorescein dye, a rhodamine dye, a pyronine dye, and a cyanine dye.

115. The system of any of clauses 37-114, wherein each of the radiant sources is characterized by radiation having a maximum wavelength and/or average wavelength in the visible light spectrum.

116. The system of any of clauses 37-114, wherein each of the sources is characterized by radiation having a maximum wavelength and/or average wavelength in the infrared wavelength band and/or ultraviolet wavelength band.

117. The system of any of clauses 37-114, wherein in at least one of the radiant sources comprises a light emitting diode (LED) or a laser.

118. The system of any of clauses 37-114, wherein the first average excitation wavelength of the first radiant source and the second average excitation wavelength of the second radiant source differ by at least 50 nanometers or by at least 60 nanometers.

119. The system of any of clauses 37-114, wherein:

the first radiant source comprises a radiant generator and a first filter are configured to filter radiation from the radiant generator; and the second radiant source comprises the radiant generator and a second filter are configured to filter radiation from the radiant generator.

120. The system of clause 119, further comprising a filter wheel comprising the filters.

121. The system of any of clauses 37-114, wherein the radiant sources each comprise a radiant generator and chromatically dispersive optical element configured to transmit or reflect radiation from the radiant generator, each radiant source including a different portion of a spectrum from the chromatically dispersive optical element.

122. The system of any of clauses 37-121, wherein the radiant generator comprises a light source.

123. The system of any of clauses 37-121, wherein the radiant generator comprises a white light source characterized by over at least a portion of the visible band of radiation.

124. The system of any of clauses 37-121, wherein the radiant generator comprises a light emitting diode or a halogen lamp.

125. The system of any of clauses 37-114, wherein the detector comprises an array sensor comprising an array of sensors or pixels.

126. The system of clause 125, wherein the array sensor comprises a charge coupled device (CCD) or a complementary metal-oxide-semiconductor (CMOS).

127. The system of any of clauses 37-114, wherein the emission spectral elements comprise a dispersive optical element configure to disperse emissions from the sample along a first optical path and second optical path, wherein the detector comprises a first detector configured to receive emissions along the first optical path and a second detector configured to receive emissions along the second optical path.

128. The system of clause 127, wherein the first detector comprises a first location on a CCD detector or CMOS detector and the second comprises a second location on a CCD detector or CMOS detector that is spatially separated from the first location.

129. The system of clause 128, wherein the first location comprises a pixel or a group of pixels, and the second location comprises a different pixel or group of pixels.

130. The system of any of clauses 37-54 or 73-129, wherein:

the first emission spectral element comprises a first spectral filter; and the second emission spectral element comprises a second spectral filter.

131. The system of any of clauses 37-54 or 73-130, wherein the first average emission wavelength and the second average emission wavelength differ by at least 25 nanometers.

132. The system of any of clauses 37-54 or 73-131, further comprising a filter wheel comprising the emission spectral elements, the filter wheel being configured to sequentially place the emission spectral element along an optical path between the sample and the detector in order to measure emissions from the sample.

133. The system of any of clauses 37-54 or 73-132, wherein:

the first emission spectral element comprises a first spectral filter configured to pass radiation within a first emission wavelength band;

the second emission spectral element comprises a second spectral filter configured to pass radiation within a second emission wavelength band that does not overlap the first emission wavelength band.

134. The system of any of clauses 73-95 or 115-133, further comprising:

providing a third radiant source characterized by a third average excitation wavelength that is different than the first average excitation wavelength of the first radiant source or the second average excitation wavelength of the second radiant source;

illuminating the sample with radiation from a third radiant source and, in response, measuring an emission from the sample using one or more of the first emission spectral element or the second emission spectral element;

wherein determining the amount of one or more of target molecules is based on the measured emission(s) from the sample in response to illuminating the sample with radiation from the third radiant source.

135. The system of clause 134, wherein determining the amount of the one or more of target molecules comprises adjusting one or more of the measured emissions from the sample in response to illuminating the sample with radiation from the first radiant source and/or the second radiant source.

136. The system of any of clauses 73-135, wherein:

the first dye is characterized by a first emission spectral signature, the second dye is characterized by a second emission spectral signature, and third dye is characterized by a third emission spectral signature;

the first spectral signature comprises an amount of emitted energy within each of emission wavelength bands when the first dye is illuminated by each of the radiant sources individually;

the second spectral signature comprises an amount of emitted energy within each of emission wavelength bands when the second dye is illuminated by each of the radiant sources individually;

the third spectral signature comprises an amount of emitted energy within each of emission wavelength bands when the third dye is illuminated by each of the radiant sources individually; and spectral signature each dye is different from the spectral signature of the remaining dyes.

137. The system of any of clauses 73-136, wherein measuring of emission from each of the three dyes occurs sequentially in time.

138. The system of any of clauses 73-137, wherein measuring of emission from the three dyes occurs simultaneously.

139. The system of any of clauses 73-138, wherein the first dye is FAM, the second dye is ROX, and the third dye is FAM-ROX.

140. The system of any of clauses 73-139, wherein the second maximum emission wavelength that is greater than the second maximum absorption wavelength.

141. The system of any of clauses 73-140, wherein the second maximum emission wavelength that is less than the second maximum absorption wavelength.

142. The system of any of clauses 73-141, wherein the second dye is an energy-transfer dye conjugate comprising:

a donor dye characterized by a maximum absorption wavelength that is equal to or substantially equal to the maximum absorption wavelength of the first dye, the donor dye configured to absorb radiation from the first radiant source and, in response, to generate energy; and an acceptor dye characterized by a maximum emission wavelength that is equal to or substantially equal to the maximum emission wavelength of the third dye, wherein the dyes are configured to transfer at least some of the energy generated by the donor to the acceptor dye.

143. The system of clause 142, wherein the first dye comprises a first fluorophore, and wherein the donor dye and the first fluorophore are the same.

144. The system of clause 142, wherein the third dye comprises a third fluorophore, and wherein the donor dye and the third fluorophore are different.

145. The system of clause 142, wherein the first dye is characterized by a first spectral signature, the third dye is characterized by a third spectral signature, the donor dye is characterized by a donor dye spectral signature, and (1) the donor dye spectral signature is equal to the third emission spectral signature and/or (2) a maximum emission wavelength of the donor dye is equal to maximum emission wavelength the third dye.

146. The system of clause 142, wherein the donor dye has an emission wavelength band and the acceptor dye an absorption wavelength band that does not overlap the donor dye emission wavelength band.

147. The system of clause 142, wherein the donor dye has a different chemical structure than either the first dye or the third dye.

148. The system of clause 142, wherein the first dye is characterized by a first spectral signature, the third dye is characterized by a third spectral signature, the donor dye is characterized by a donor dye spectral signature, and (1) the donor dye spectral signature is different than the third spectral signature and/or (2) the donor dye maximum emission wavelength is different to the maximum emission wavelength of the third dye.

149. The system of any of clauses 37-148, wherein the sample is a biological sample.

150. The system of clause 149 wherein the biological sample comprises one or more target molecules.

151. The system of clause 150, wherein the one or more target molecules comprise one or more nucleic acid molecules.

152. The system of any of clauses 149-151, wherein the at least one memory includes instructions to determine an amount of any of the target molecules present in the sample based on the measured emissions.

153. A method, comprising:

providing a sample comprising a first dye and a second dye;

illuminating the sample with a radiant source and, in response, measuring an emission from the sample using a detector and a first emission spectral element characterized by a first average emission wavelength and measuring an emission from the sample using a detector and a second emission spectral element characterized by a second average emission wavelength that is different than the first average emission wavelength.

154. The method of clause 153, wherein first dye is or comprises first fluorophore and second dye is or comprises a fluorescent energy transfer dye conjugate according to any of clauses 1-17.

155. The method of any of clauses 153-154, wherein the first fluorophore is selected from the group consisting of a xanthene dye, a cyanine dye, a BODIPY dye, a pyrene dye, a pyronine dye, and a coumarin dye.

156. The method of any of clauses 153-155, wherein the second dye comprises a fluorophore selected from the group consisting of a fluorescein dye, a rhodamine dye, a pyronine dye, and a cyanine dye.

157. The method of any of clauses 153-156, wherein the first dye is covalently attached to a first probe, and the second dye is covalently attached to a second probe, wherein the first and second probes are configured to bind to a first and a second target molecule, respectively.

158. The method of clause 157, wherein the first and second probes are oligonucleotide probes and the second probe is according to any of clauses 18-36.

159. The method of any of clauses 153-158, wherein the first and second target molecules are nucleic acid molecules.

160. The method of any of clauses 153-159, wherein the first dye comprises a maximum absorption wavelength that is equal to or substantially equal to a maximum absorption wavelength of the second dye.

161. The method of clause 160, wherein one or more of the first maximum absorption wavelength or second maximum absorption wavelength is an absolute maximum over an entirety of the respective spectrum.

162. The method of any of clauses 153-161, wherein the first dye is an on-axis dye and the second dye is an off-axis dye.

163. The method of any of clauses 153-162, wherein the first dye is configured to bind to a first target molecule and the second dye is configured to bind to a second target molecule, the method further comprising determining an amount of any target molecules present in the sample based on the measured emissions.

164. A method, comprising:

providing a sample comprising a first dye and a second dye;

performing an amplification assay on the sample;

illuminating the sample with a first radiant source characterized by a first average excitation wavelength and, in response, measuring an emission from the sample using a detector and a first emission spectral element characterized by a first average emission wavelength; and illuminating the sample with a second radiant source characterized by a second average excitation wavelength that is different than the first average excitation wavelength and, in response, measuring an emission from the sample using the detector and the second emission spectral element.

165. The method of clause 164, wherein first dye is or comprises first fluorophore and second dye is or comprises a fluorescent energy transfer dye conjugate according to any of clauses 1-17.

166. The method of any of clauses 164-165, wherein the first fluorophore is selected from the group consisting of a xanthene dye, a cyanine dye, a BODIPY dye, a pyrene dye, a pyronine dye, and a coumarin dye.

167. The method of any of clauses 164-166, wherein the second dye comprises a fluorophore selected from the group consisting of a fluorescein dye, a rhodamine dye, a pyronine dye, and a cyanine dye.

168. The method of any of clauses 164-167, wherein the first dye is covalently attached to a first probe, and the second dye is a covalently attached to conjugate second probe, wherein the first and second probes are configured to bind to a first and a second target molecule, respectively.

169. The method of clause 168, wherein the first and second probes are oligonucleotide probes and the second probe is according to any of clauses 18-36.

170. The method of any of clauses 168-169, wherein the first and second target molecules are nucleic acid molecules.

171. The method of any of clauses 164-170, wherein the first dye comprises a maximum emission wavelength that is equal to or substantially equal to a maximum emission wavelength of the second dye.

172. The method of clause 171, wherein one or more of the first maximum emission wavelength or second maximum emission wavelength is an absolute maximum over an entirety of the respective spectrum.

173. The method of any of clauses 164-172, wherein the second dye is an off-axis dye.

174. The method of any of clauses 164-173, wherein the first dye configured to bind to a first target molecule and the second dye configured to bind to a second target molecule, the method further comprising determining an amount of any target molecules present in the sample based on the measured emissions.

175. A method, comprising:

providing a sample comprising a first dye, a second dye, and a third dye configure to bind to a third target molecule;

illuminating the sample with a first radiant source characterized by a first average excitation wavelength and, in response, (1) measuring an emission from the sample using a detector and a first emission spectral element characterized by a first average emission wavelength and (2) measuring an emission from the sample using the detector and a second emission spectral element characterized by a second average emission wavelength that is different than the first average emission wavelength;

illuminating the sample with a second radiant source characterized by a second average excitation wavelength that is different than the first average excitation wavelength and, in response, measuring an emission from the sample using the detector and the second emission spectral element.

176. The method of clause 175, wherein first dye is or comprises first fluorophore and second dye is or comprises a fluorescent energy transfer dye conjugate according to any of clauses 1-17.

177. The method of any of clauses 175-186, wherein the first fluorophore is selected from the group consisting of a xanthene dye, a cyanine dye, a BODIPY dye, a pyrene dye, a pyronine dye, and a coumarin dye.

178. The method of any of clauses 175-177, wherein the first dye is covalently attached to a first probe, and the second dye is covalently attached to conjugate second probe, and the third dye is covalently attached to a third probe, wherein the first, second, and third probes are configured to bind to a first, a second, and a third target molecule, respectively.

179. The system of clause 178, wherein the first, the second, and the third probes are oligonucleotide probes and the second probe is according to any of clauses 18-36.

180. The system of clause 178-179, wherein the first, second, and third target molecules are nucleic acid molecules.

181. The method of any of clauses 175-181, wherein (1) the first dye comprises a first absorption spectrum comprising a first maximum absorption wavelength and the second dye comprises a second absorption spectrum comprising a second maximum absorption wavelength that is equal to or substantially equal to the first maximum absorption wavelength; and (2) the second dye comprises a second emission spectrum comprising a second maximum emission wavelength and the third dye comprises a third emission spectrum comprising a third maximum emission wavelength that is equal to or substantially equal to the second maximum emission wavelength.

182. The method of clause 181, wherein one or more of the first maximum absorption wavelength, the second maximum absorption wavelength, second maximum emission wavelength, or third maximum emission wavelength, is an absolute maximum over an entirety of the respective spectrum.

183. The method of any of clauses 175-182, wherein the second dye is an off-axis dye.

184. The method of any of clauses 175-183, wherein the first dye configured to bind to a first target molecule and the second dye configured to bind to a second target molecule, the method further comprising determining an amount of the target molecules present in the sample based on the measured emissions.

185. The method of any of clauses 175-184, wherein:

the first dye comprises one or more of 5-FAM, 6-FAM, Oregon Green, or TET, R110;

the second dye comprises one or more of FAM-TAM RA, FAM-ABY, or FAM-NED; and the third dye comprises one or more of NED, TAM RA, ABY, or DY-555.

186. The method of any of clauses 175-185, wherein:

the first average excitation wavelength of the first radiant source is 480±5 nanometers and/or the first radiant source is characterized by a wavelength band that is less than or equal to ±12 nanometers about the first average excitation wavelength;

the second average excitation wavelength of the second radiant source is 550±5 nanometers and/or the second radiant source is characterized by a wavelength band that is less than or equal to ±12 nanometers about the second average excitation wavelength;

the first average emission wavelength of the first emission spectral element is 520±5 nanometers and/or the first emission spectral element is characterized by a wavelength band that is less than or equal to ±20 nanometers about the first average emission wavelength;

the second average emission wavelength of the second emission spectral element is 587±5 nanometers and/or the second emission spectral element is characterized by a wavelength band that is less than or equal to ±12 nanometers about the second average emission wavelength.

187. The method of any of clauses 175-184, wherein:

the first dye comprises one or more of 5-FAM, 6-FAM, Oregon Green, TET, R110;

the second dye comprises one or more of FAM-PET, FAM-ROX, FAM-JUN, FAM-Texas Red, or TET-Alexa Fluor 594; and the third dye comprises one or more of PET, ROX, JUN, Texas Red, or Alexa Fluor 594.

188. The method of clause 187, wherein:

the first average excitation wavelength of the first radiant source is 480±5 nanometers and/or the first radiant source is characterized by a wavelength band that is less than or equal to ±12 nanometers about the first average excitation wavelength;

the second average excitation wavelength of the second radiant source is 580±5 nanometers and/or the second radiant source is characterized by a wavelength band that is less than or equal to ±12 nanometers about the second average excitation wavelength;

the first average emission wavelength of the first emission spectral element is 520±5 nanometers and/or the first emission spectral element is characterized by a wavelength band that is less than or equal to ±18 nanometers about the first average emission wavelength;

the second average emission wavelength of the second emission spectral element is 623±5 nanometers and/or the second emission spectral element is characterized by a wavelength band that is less than or equal to ±18 nanometers about the second average emission wavelength.

189. The method of any of clauses 175-184, wherein:

the first dye comprises one or more of NED, TAM RA, ABY, DY-555;

the second dye comprises one or more of ABY-Alexa Fluor 647, NED-Alexa Fluor 647, ABY-Cy5®, ABY-ATTO 647™, or ABY-DyLight 650™; and the third dye comprises one or more of Alexa Fluor 647, Cy5®, ATTO 647™, or DyLight 650™.

190. The method of clause 189, wherein:

the first average excitation wavelength of the first radiant source is 550±5 nanometers and/or the first radiant source is characterized by a wavelength band that is less than or equal to ±14 nanometers about the first average excitation wavelength;

the second average excitation wavelength of the second radiant source is 640±5 nanometers and/or the second radiant source is characterized by a wavelength band that is less than or equal to ±12 nanometers about the second average excitation wavelength;

the first average emission wavelength of the first emission spectral element is 587±5 nanometers and/or the first emission spectral element is characterized by a wavelength band that is less than or equal to ±12 nanometers about the first average emission wavelength;

the second average emission wavelength of the second emission spectral element is 682±5 nanometers and/or the second emission spectral element is characterized by a wavelength band that is less than or equal to ±16 nanometers about the second average emission wavelength.

191. The method of any of clauses 175-184, wherein:

the first dye comprises one or more of NED, TAMRA, ABY, DY-555;

the second dye comprises one or more of NED-Alexa Fluor 676, NED DyLight 680™ NED-Cy5.5®, ABY-Alexa Fluor 676, ABY-DyLight 680™, ABY-Cy5.5®; and the third dye comprises one or more of Alexa Fluor 676, DyLight 680™, or Cy5.5®.

192. The method of clause 191, wherein:

the first average excitation wavelength of the first radiant source is 550±5 nanometers and/or the first radiant source is characterized by a wavelength band that is less than or equal to ±14 nanometers about the first average excitation wavelength;

the second average excitation wavelength of the second radiant source is 662±5 nanometers and/or the second radiant source is characterized by a wavelength band that is less than or equal to ±12 nanometers about the second average excitation wavelength;

the first average emission wavelength of the first emission spectral element is 587±5 nanometers and/or the first emission spectral element is characterized by a wavelength band that is less than or equal to ±12 nanometers about the first average emission wavelength;

the second average emission wavelength of the second emission spectral element is 711±5 nanometers and/or the second emission spectral element is characterized by a wavelength band that is less than or equal to ±16 nanometers about the second average emission wavelength.

193. The method of any of clauses 175-192, further comprising performing a nucleic acid synthesis assay and illuminating and measuring during the nucleic acid synthesis assay and/or after the nucleic acid synthesis assay.

194. The method of clause 193, wherein the nucleic acid synthesis assay comprises a PCR assay including cycling the solution through a plurality of the temperature cycles and measuring emissions of the dyes is performed after one or more of the temperature cycles.

195. The method of clause 193, wherein the nucleic acid synthesis assay comprises a PCR assay including cycling the solution through a plurality of the temperature cycles and measuring emissions of the dyes is performed after a last temperature cycle.

196. The method of clause 178, further comprising:

producing a first amplicon from the first target molecule;

producing a second amplicon from the second target molecule; and/or producing a third amplicon from the third target molecule.

197. The method of any of clauses 175-184, further comprising:

providing third, fourth, fifth, and sixth radiant sources, each of the third, fourth, fifth, and sixth radiant sources characterized by a respective third, fourth, fifth, and sixth average excitation wavelength, wherein the each of the six average excitation wavelengths is different from the remaining average excitation wavelengths providing in the sample fourth, fifth, sixth, seventh, and eighth dyes;

providing third, fourth, fifth, and sixth emission spectral elements each configured to pass emissions from the sample, each of the third, fourth, fifth, and sixth emission elements characterized by a respective third, fourth, fifth, and sixth average emission wavelength, wherein the each of the six average emission wavelengths of each of the wavelength sources is different from the average emission wavelengths of the remaining sources;

illuminating the sample with third, fourth, fifth, and sixth radiant sources; and in response to illuminating the sample with each of the third, fourth, fifth, and sixth radiant sources, measure emissions from the sample using one or more of the emission spectral elements.

198. The method of clause 197, wherein the fourth, fifth, sixth, seventh, and eighth dyes are configured to bind to respective fourth, fifth, sixth, seventh, and eighth target molecules, the method further comprising determining an amount of the target molecules present in the sample based on the measured emissions.

199. The method of any of clauses 197-198, wherein the second dye and the fourth dye are off-axis dyes.

200. The method of any of clauses 197-199, wherein:

the second dye comprises a maximum absorption wavelength that is equal to or substantially equal to a maximum absorption wavelength of the first dye;

the fourth dye comprises a maximum absorption wavelength that is equal to or substantially equal to a maximum absorption wavelength of the first dye;

the second dye comprises a maximum emission wavelength that is equal to or substantially equal to a maximum emission wavelength of the third dye; and the fourth dye comprises a maximum emission wavelength that is equal to or substantially equal to a maximum emission wavelength of the fifth dye.

201. The method of any of clauses 175-184, further comprising:

providing third, fourth, fifth, and sixth radiant sources, each of the third, fourth, fifth, and sixth radiant sources characterized by a respective third, fourth, fifth, and sixth average excitation wavelength, wherein the each of the six average excitation wavelengths is different from the remaining average excitation wavelengths;

providing in the sample fourth, fifth, sixth, seventh, eighth, ninth, and tenth dyes;

providing third, fourth, fifth, and sixth emission spectral elements each configured to pass emissions from the sample, each of the third, fourth, fifth, and sixth emission elements characterized by a respective third, fourth, fifth, and sixth average emission wavelength, wherein the each of the six average emission wavelengths of each of the wavelength sources is different from the average emission wavelengths of the remaining sources;

illuminating the sample with third, fourth, fifth, and sixth radiant sources;

in response to illuminating the sample with each of the first, second, third, fourth, fifth, and sixth radiant sources, measuring emissions from the sample using the emission spectral elements;

determining an amount of the target molecules present in the sample based on the measured emissions.

202. The method of clause 201, wherein the fourth, fifth, sixth, seventh, eighth, ninth, and tenth dyes are configured to bind to respective fourth, fifth, sixth, seventh, eighth, ninth, and tenth target molecules, the method further comprising determining an amount of the target molecules present in the sample based on the measured emissions.

203. The method of any of clauses 201-202, wherein the second dye, the fourth dye, the ninth dye, and the tenth dye are off-axis dyes.

204. The method of any of clauses 201-203, wherein:

the second dye comprises a maximum absorption wavelength that is equal to or substantially equal to a maximum absorption wavelength of the first dye;

the fourth dye comprises a maximum absorption wavelength that is equal to or substantially equal to a maximum absorption wavelength of the first dye;

the ninth dye comprises a maximum absorption wavelength that is equal to or substantially equal to a maximum absorption wavelength of the third dye;

the tenth dye comprises a maximum absorption wavelength that is equal to or substantially equal to a maximum absorption wavelength of the third dye;

the second dye comprises a maximum emission wavelength that is equal to or substantially equal to a maximum emission wavelength of the third dye;

the fourth dye comprises a maximum emission wavelength that is equal to or substantially equal to a maximum emission wavelength of the fifth dye;

the ninth dye comprises a maximum emission wavelength that is equal to or substantially equal to a maximum emission wavelength of the seventh dye; and the second dye comprises a maximum emission wavelength that is equal to or substantially equal to a maximum emission wavelength of the tenth dye 205. The method of any of clauses 197-204, wherein:

the first average excitation wavelength of the first radiant source is 480±5 nanometers and/or the first radiant source is characterized by a wavelength band that is less than or equal to ±12 nanometers about the first average excitation wavelength;

the second average excitation wavelength of the second radiant source is 520±5 nanometers and/or the second radiant source is characterized by a wavelength band that is less than or equal to ±12 nanometers about the second average excitation wavelength;

the third average excitation wavelength of the third radiant source is 550±5 nanometers and/or the third radiant source is characterized by a wavelength band that is less than or equal to ±12 nanometers about the third average excitation wavelength;

the fourth average excitation wavelength of the fourth radiant source is 580±5 nanometers and/or the fourth radiant source is characterized by a wavelength band that is less than or equal to ±12 nanometers about the fourth average excitation wavelength;

the fifth average excitation wavelength of the fifth radiant source is 640±5 nanometers and/or the fifth radiant source is characterized by a wavelength band that is less than or equal to ±12 nanometers about the fifth average excitation wavelength;

the sixth average excitation wavelength of the sixth radiant source is 662±5 nanometers and/or the sixth radiant source is characterized by a wavelength band that is less than or equal to ±12 nanometers about the sixth average excitation wavelength;

the first average emission wavelength of the first emission spectral element is 520±5 nanometers and/or the first emission spectral element is characterized by a wavelength band that is less than or equal to ±18 nanometers about the first average emission wavelength;

the second average emission wavelength of the second emission spectral element is 558±5 nanometers and/or the second emission spectral element is characterized by a wavelength band that is less than or equal to ±15 nanometers about the second average emission wavelength;

the third average emission wavelength of the third emission spectral element is 587±5 nanometers and/or the third emission spectral element is characterized by a wavelength band that is less than or equal to ±12 nanometers about the third average emission wavelength;

the fourth average emission wavelength of the fourth emission spectral element is 623±5 nanometers and/or the fourth emission spectral element is characterized by a wavelength band that is less than or equal to ±16 nanometers about the fourth average emission wavelength;

the fifth average emission wavelength of the fifth emission spectral element is 682±5 nanometers and/or the fifth emission spectral element is characterized by a wavelength band that is less than or equal to ±16 nanometers about the fifth average emission wavelength; and the sixth average emission wavelength of the sixth emission spectral element is 711±5 nanometers and/or the sixth emission spectral element is characterized by a wavelength band that is less than or equal to ±16 nanometers about the sixth average emission wavelength.

206. The method of any of clauses 197-205, wherein:

the first dye is at least one of 5-FAM, 6-FAM, Oregon Green, TET, or R110;

the second dye is at least one of FAM-TAMRA, FAM-ABY, or FAM-NED;

the third dye is at least one of NED, TAMRA, ABY, or DY-555;

the fourth dye is at least one of FAM-PET, FAM-ROX, FAM-JUN, FAM-Texas Red, or TET-Alexa Fluor 594;

the fifth dye is at least one of PET, ROX, JUN, Texas Red, or Alexa Fluor 594;

the sixth dye is at least one of VIC, HEX, JOE, Yakima Yellow, or R6G;

The seventh dye is at least one of Alexa Fluor 647, Cy5®, ATTO 647™, or DyLight 650™.

the eighth dye is at least one of Alexa Fluor 676, DyLight 680™, or Cy5.5®.

207. The method of any of clauses 201-206, wherein the ninth dye is at least one of ABY-Alexa Fluor 647, NED-Alexa Fluor 647, ABY-Cy5®, ABY-ATTO 647™, or ABY-DyLight 650™; and the tenth dye is at least one of NED-Alexa Fluor 676, NED DyLight 680™, NED-Cy5.5®, ABY-Alexa Fluor 676, ABY-DyLight 680™, or ABY-Cy5.5®.

208. The method of any of clauses 197-207, wherein the second and fourth dyes independently comprise a fluorophore selected from the group consisting of a fluorescein dye, a rhodamine dye, a pyronine dye, and a cyanine dye.

209. The method of any of clauses 201-208, wherein the second, fourth, ninth, and tenth dyes independently comprise a fluorophore selected from the group consisting of a fluorescein dye, a rhodamine dye, a pyronine dye, and a cyanine dye.

210. The method of any of clauses 153-196, wherein each of the radiant sources is characterized by radiation having a maximum wavelength and/or average wavelength in the visible light spectrum.

211. The method of any of clauses 153-196, wherein each of the sources is characterized by radiation having a maximum wavelength and/or average wavelength in the infrared wavelength band and/or ultraviolet wavelength band.

212. The method of any of clauses 153-196, wherein at least one of the radiant sources comprises a light emitting diode (LED) or a laser.

213. The method of any of clauses 153-196, wherein:
the first a source of radiation and a first filter are configured to filter radiation from the source of radiation; and
the second radiant source comprises the source of radiation and a second filter are configured to filter radiation from the source of radiation.

214. The method of any of clauses 153-196, wherein the first average excitation wavelength of the first radiant source and the second average excitation wavelength of the second radiant source differ by at least 50 nanometers or by at least 60 nanometers.

215. The method of any of clauses 153-196, further comprising a filter wheel comprising the radiant sources.

216. The method of any of clauses 153-196, wherein measuring comprises using a detector to measure emissions from the sample.

217. The method of clause 216, wherein the detector comprises an array sensor comprising an array of sensors or pixels.

218. The method of clause 217, wherein the array sensor comprises a charge coupled device (CCD) or a complementary metal-oxide-semiconductor (CMOS).

219. The method of clause 216, wherein the emission spectral elements comprise a dispersive optical element configure to disperse emissions from the sample along a first optical path and second optical path, the method further comprising using the dispersive optical element to:
direct emissions from the sample along a first optical path to the first detector; and
direct emissions from the sample along a second optical path to the second detector.

220. The method of clause 219, wherein the first detector comprises a first location on a CCD detector or CMOS detector and the second comprises a second location on a CCD detector or CMOS detector that is spatially separated from the first location.

221. The method of clause 220, wherein the first location comprises a pixel or a group of pixels, and the second location comprises a different pixel or group of pixels.

222. The method of any of clauses 175-221, wherein:
the first emission spectral element comprises a first spectral filter;
the second emission spectral element comprises a second spectral filter; and measuring comprises sequentially placing the first spectral filter and the second spectral filter along an optical path between the sample and the detector.

223. The method of any of clauses 148-163 or 175-222, wherein the first average emission wavelength and the second average emission wavelength differ by at least 25 nanometers.

224. The method of any of clauses 175-223, further comprising a filter wheel comprising the emission spectral elements, wherein illuminating the sample includes using the filter wheel to sequentially place the emission spectral elements along an optical path between the sample and a detector for measuring emissions from the sample.

225. The method of any of clauses 175-224, wherein:
the first emission spectral element comprises a first spectral filter configured to pass radiation within a first emission wavelength band;
the second emission spectral element comprises a second spectral filter configured to pass radiation within a second emission wavelength band that does not overlap the first emission wavelength band.

226. The method of clause 178, wherein the first, the second, or the third probe further comprises a quencher moiety.

227. The method of any of clauses 175-226, further comprising:
providing a third radiant source characterized by a third average excitation wavelength that is different than the first average excitation wavelength of the first radiant source or the second average excitation wavelength of the second radiant source; and
illuminating the sample with radiation from a third radiant source and, in response, measuring an emission from the sample using one or more of the first emission spectral element or the second emission spectral element;
wherein determining the amount of one or more of target molecules is based on the measured emission(s) from the sample in response to illuminating the sample with radiation from the third radiant source.

228. The method of clause 227, wherein determining the amount of the one or more of target molecules comprises adjusting one or more of the measured emissions from the sample in response to illuminating the sample with radiation from the first radiant source and/or the second radiant source.

229. The method of any of clauses 175-228, wherein:
the first dye is characterized by a first emission spectral signature, the second dye is characterized by a second emission spectral signature, and third dye is characterized by a third emission spectral signature;
the first spectral signature comprises an amount of emitted energy within each of emission wavelength bands when the first dye is illuminated by each of the radiant sources individually;
the second spectral signature comprises an amount of emitted energy within each of emission wavelength bands when the second dye is illuminated by each of the radiant sources individually;

the third spectral signature comprises an amount of emitted energy within each of emission wavelength bands when the third dye is illuminated by each of the radiant sources individually; and spectral signature each dye is different from the spectral signature of the remaining dyes.

230. The method of any of clauses 175-229, wherein measuring of emission from each of the three dyes occurs sequentially in time.

231. The method of any of clauses 175-230, wherein measuring of emission from the three dyes occurs simultaneously.

232. The method of any of clauses 175-231, wherein the first dye is FAM, the second dye is ROX, and the third dye is FAM-ROX.

233. The method of any of clauses 175-232, wherein the second maximum absorption wavelength that is greater than the first maximum absorption wavelength.

234. The method of any of clauses 175-233, wherein the second maximum absorption wavelength that is less than the first maximum absorption wavelength.

235. The method of any of clauses 175-234, wherein the second dye is an energy-transfer dye conjugate comprising:

a donor dye characterized by a maximum absorption wavelength that is equal to or substantially equal to the maximum absorption wavelength of the first dye, the donor dye configured to absorb radiation from the first radiant source and, in response, to generate energy; and an acceptor dye characterized by a maximum emission wavelength that is equal to or substantially equal to the maximum emission wavelength of the third dye, wherein the dyes are configured to transfer at least some of the energy generated by the donor to the acceptor dye.

236. The method of clause 235, wherein the first dye comprises a first fluorophore, and wherein the donor dye and the first fluorophore are the same.

237. The method of clause 235, wherein the third dye comprises a third fluorophore, and wherein the donor dye and the third fluorophore are different.

238. The method of clause 235, wherein the first dye is characterized by a first spectral signature, the third dye is characterized by a third spectral signature, the donor dye is characterized by a donor dye spectral signature, and (1) the donor dye spectral signature is equal to the third emission spectral signature and/or (2) a maximum emission wavelength of the donor dye is equal to maximum emission wavelength the third dye.

239. The method of clause 235, wherein the donor dye has an emission wavelength band and the acceptor dye an absorption wavelength band that does not overlap the donor dye emission wavelength band.

240. The method of clause 235, wherein the donor dye has a different chemical structure than either the first dye or the third dye.

241. The method of clause 235, wherein the first dye is characterized by a first spectral signature, the third dye is characterized by a third spectral signature, the donor dye is characterized by a donor dye spectral signature, and (1) the donor dye spectral signature is different than the third spectral signature and/or (2) the donor dye maximum emission wavelength is different to the maximum emission wavelength of the third dye.

242. The method of clause 235, wherein the first dye is characterized by a first spectral signature, the third dye is characterized by a third spectral signature, the donor dye is characterized by a donor dye spectral signature, and (1) the donor dye spectral signature is different than the third spectral signature and/or (2) the donor dye maximum emission wavelength is different to the maximum emission wavelength of the third dye.

243. A method performing a quantitative polymerase chain reaction (qPCR) assay, comprising:

providing a biological sample comprising an off-axis dye and an on-axis dye;

performing a qPCR assay on the sample;

during a first cycle of the of the qPCR assay, performing a first series of illuminations of the sample with two or more excitation channels;

in response to each illumination of the first series of illuminations, measuring a corresponding first series of emission signals from two or more emission channels;

during a second cycle of the of the qPCR assay, performing a second series of illuminations of the sample with the two or more excitation channels;

in response to each illumination of the second series of illuminations, measuring a corresponding second series of emission signals from the two or more emission channels;

calculating an amount of the off-axis dye based on at least one measurement from the first series of measurements; and calculating an amount of the on-axis dye based on at least one measurement from the second series of measurements.

244. The method of clause 243, calculating an amount of the off-axis dye present during the second series of measurements based on at least one measurement from the first series of measurements.

245. The method of clause 243, wherein calculating an amount of at least one of the dyes is based at least in part on an ex-em space signature of the at least one dye.

246. A method performing a quantitative polymerase chain reaction (qPCR) assay, comprising:

providing a biological sample comprising an off-axis dye and an on-axis dye;

performing a qPCR assay on the sample;

during a first cycle of the of the qPCR assay, performing a first series of illuminations of the sample with two or more excitation channels;

in response to each illumination of the first series of illuminations, measuring a corresponding first series of emission signals from two or more emission channels;

during a second cycle of the of the qPCR assay, performing a second series of illuminations of the sample with the two or more excitation channels;

in response to each illumination of the second series of illuminations, measuring a corresponding second series of emission signals from the two or more emission channels;

calculating an amount of the on-axis dye based on at least one measurement from the first series of measurements; and calculating an amount of the off-axis dye based on at least one measurement from the second series of measurements.

247. The method of clause 246, calculating an amount of the on-axis dye present during the second series of measurements based on at least one measurement from the first series of measurements.

248. The method of clause 246, wherein calculating an amount of at least one of the dyes is based at least in part on an ex-em space signature of the at least one dye.
249. The method of any of clauses 153-248, wherein the sample is a biological sample.
250. The method of clause 249, wherein the biological sample comprises one or more target molecules.
251. The method of clause 250, wherein the one or more target molecules comprise one or more nucleic acid molecules.
252. The method of any of clauses 249-251, wherein the at least one memory includes instructions to determine an amount of any of the target molecules present in the sample based on the measured emissions.
253. A composition comprising a set of fluorescently-labeled oligonucleotide probes, wherein the set comprises:
 i. a first probe covalently attached to a first fluorophore, wherein the first fluorophore is characterized by a first absorption wavelength and a first emission wavelength; and
 ii. a second probe covalently attached to an energy transfer dye conjugate of any of clauses 1-17.
254. The composition of clause 253, wherein the donor dye of the conjugate is characterized by a second absorption wavelength and emits excitation energy in response.
255. The composition of clause 253, wherein the acceptor dye of the conjugate is capable of absorbing the excitation energy emitted by the donor dye and in response emits radiation characterized by a second emission wavelength.
256. The composition of clause 255, wherein the first absorption wavelength and the second absorption wavelength differ by 50 nanometers or greater.
257. The composition of clause 255, wherein the first emission wavelength and the second emission wavelength are within 10 nanometers of each other.
258. The composition of clause 255, further comprising:
 iii. a third probe covalently attached to a second fluorophore, wherein the second fluorophore is characterized by a third absorption wavelength and a third emission wavelength.
259. The composition of clause 258, wherein the first, second, and/or third probe is an oligonucleotide probe.
260. The composition of clause 258, wherein the first, second, and/or third probe further comprise a quencher moiety.
261. The composition of clause 258, wherein the third absorption wavelength differs from the second absorption wavelength by 50 nm or greater.
262. The composition of clause 258, wherein the third emission wavelength is within 20 nm of the second emission wavelength.
263. The composition of any of clauses 258-262, wherein the first fluorophore and the second fluorophore is independently selected from the group consisting of a fluorescein dye, a cyanine dye, a rhodamine dye, a BODIPY dye, a pyrene dye, a pyronine dye, and a coumarin dye.
264. The composition of any of clauses 258-263, wherein the first fluorophore and the donor dye are the same.
265. The composition of any of clauses 258-263, wherein the second fluorophore and the acceptor dye are the same.

266. The composition of any of clauses 258-265, wherein the first fluorophore and the donor dye is a fluorescein dye or a rhodamine dye; and
 the second fluorophore and the acceptor dye is a rhodamine dye, a pyronine dye, or a cyanine dye.
267. The composition of any of clauses 258-265, wherein the first fluorophore and the donor dye is a fluorescein dye; and
 the second fluorophore and the acceptor dye is a cyanine dye or a pyronine dye.
268. The composition of any of clauses 258-265, wherein the first fluorophore and the donor dye is a fluorescein dye; and
 the second fluorophore and the acceptor dye is a rhodamine dye.
269. The composition of any of clauses 258-265, wherein the first fluorophore and the donor dye is a rhodamine dye; and
 the second fluorophore and the acceptor dye is a cyanine or a pyronine dye.
270. A composition comprising a set of fluorescently-labeled oligonucleotide probes, wherein the set comprises:
 i. a first oligonucleotide probe covalently attached to a first fluorophore, wherein the first fluorophore is characterized by a first absorption wavelength and a first emission wavelength; and
 ii. a second oligonucleotide probe covalently attached to the energy transfer dye conjugate of any of clauses 1-17, wherein
 a) the donor dye is characterized by a second absorption wavelength and emits excitation energy in response, and
 b) the acceptor dye is capable of absorbing the excitation energy emitted by the donor dye and in response emits radiation characterized by second emission wavelength;
 wherein the first absorption wavelength and the second absorption wavelength are within 20 nanometers of each other, and
 wherein the first emission wavelength and the second emission wavelength differ by greater than 50 nanometers.
271. A method of detecting or quantifying a target nucleic acid molecule in a sample by polymerase chain reaction (PCR), the method comprising:
 (i) contacting the sample comprising one or more target nucleic acid molecules with a) at least one oligonucleotide probe of any of clauses 18-36, said oligonucleotide probe having a sequence that is at least partially complementary to the target nucleic acid molecule, where the at least one probe undergoes a detectable change in fluorescence upon amplification of the one or more target nucleic acid molecules; and with b) at least one oligonucleotide primer pair;
 (ii) incubating the mixture of step (i) with a DNA polymerase under conditions sufficient to amplify one or more target nucleic acid molecules; and
 (iii) detecting the presence or absence or quantifying the amount of the amplified target nucleic acid molecules by measuring fluorescence of the probe.
272. A kit for polymerase chain reaction (PCR), the kit comprising:
 i. one or more buffering agents, a purification medium, an organic solvent, a nucleic acid synthesis enzyme; and
 ii. an oligonucleotide probe of clause 18 or clause 19; and
 iii. instructions for performing a PCR assay.

273. A composition comprising:
a) a first labeled oligonucleotide comprising an energy transfer dye conjugate according to any of clauses 1-17; and
b) a polymerase.
274. The composition of clause 273, wherein the polymerase is a DNA polymerase.
275. The composition of clause 273, wherein the polymerase is thermostable.
276. The composition of clause 273, wherein the composition further comprises a reverse transcriptase (RT).
277. The composition of clause 273, further comprising at least one deoxyribonucleoside triphosphate (dNTP).
278. The composition of any of clauses 273-277, further comprising one or more of the following:
a) a passive reference control;
b) glycerol;
c) one or more PCR inhibitor blocking agents;
d) a uracil DNA glycosylase;
e) a detergent;
f) one or more salts; and
g) a buffering agent.
279. The composition of clause 278, wherein the one or more salts is a magnesium chloride and/or a potassium chloride.
280. The composition of any of clauses 273-279, wherein the composition further comprises one or more hot start components.
281. The composition of clause 280, wherein the one or more hot start components is selected from the group consisting of a chemical modification to the polymerase, oligonucleotide that is inhibitory to the polymerase, and an antibody specific to the polymerase.
282. The composition of clauses 273-281, further comprising one or more of the following:
a) a nucleic acid sample;
b) at least one primer oligonucleotide specific for amplification of a target nucleic; or
c) an amplified nucleic acid product (i.e., an amplicon).
283. The composition of clause 282, wherein the nucleic acid sample is RNA.
284. The composition of clause 282, wherein the nucleic acid sample is DNA.
285. The composition of clause 282, wherein the nucleic acid sample is a cDNA.
286. The composition of any of clauses 258-271, wherein the composition further comprises a second labeled oligonucleotide comprising an energy transfer dye conjugate according to any of clauses 1-17, wherein energy transfer dye conjugate of the first and the second labeled oligonucleotides are different.
287. The composition of any of clauses 258-271, wherein the first and/or second labeled oligonucleotide comprises at least one modified nucleotide.
288. The composition of clause 287, wherein the at least one modified nucleotide comprises a locked nucleic acid (LNA).
289. The composition of clause 287, wherein the at least one modified nucleotide comprises a minor groove binder (MGB).

A composition comprising
a) a fluorescent energy transfer dye conjugate of any of clauses 273-289;
b) a nucleic acid molecule.

A composition comprising
a) a fluorescent energy transfer dye conjugate of any of clauses 273-290; A composition comprising
a) a fluorescent energy transfer dye conjugate of any one of the preceding clauses; and
b) a fluorophore having an excitation wavelength that is within 20 nm of the excitation wavelength of the donor dye in the energy transfer dye conjugate or within 20 nm of the emission wavelength of the acceptor dye in the energy transfer dye conjugate.

The composition of clause 59, wherein the fluorophore is or comprises a dye selected from the group consisting of a xanthene dye, a cyanine dye, a BODIPY dye, a pyrene dye, a pyronine dye, and a coumarin dye.

The probe of any of clauses 18-36, wherein the fluorescent energy transfer dye conjugate is covalently attached to the 5'-end of the oligonucleotide and the quencher dye is covalently attached to the 3'-end of the oligonucleotide.

The probe of any of clauses 18-36, wherein the oligonucleotide is at least 60% complementary to the target nucleic acid molecule. The probe of any of clauses 18-36, wherein the oligonucleotide is at least 90% complementary to the target nucleic acid molecule.

The probe of clause 35 or 36, wherein the tail portion is a universal tail portion.

290. A composition comprising:
a) a fluorescent energy transfer dye conjugate of any of clauses 1-17;
b) an analyte.
291. The composition of clause 290, wherein the analyte is selected from the group consisting of a nucleic acid molecule, a protein or peptide, and a carbohydrate.
292. The composition of clause 290, wherein the nucleic acid molecule is an oligonucleotide.
293. The composition of clause 290, wherein the protein is an antibody.
294. A composition comprising:
a) a fluorescent energy transfer dye conjugate of any of 1-17; and
b) an enzyme.
295. The composition of clause 294, wherein the enzyme is a polymerase and/or a reverse transcriptase.
296. A method of detecting or quantifying a target nucleic acid molecule in a sample:
(i) contacting the sample comprising one or more target nucleic acid molecules with a) at least one oligonucleotide probe of any of clauses 18-36, said probe having a sequence that is at least partially complementary to the target nucleic acid molecule; and
(ii) detecting the presence or absence or quantifying the amount of the target nucleic acid molecules by measuring fluorescence of the probe.
297. The system or method of any of clauses 37-252, comprises the fluorescent energy transfer dye conjugate of any of clauses 1-17.
298. A kit for detecting a biological molecule in a sample, the kit comprising:
i. an oligonucleotide probe of any of clauses 18-36; and
iii. instructions for performing an assay for detecting the biological molecule.
299. A composition, method, kit, or system of any of clauses 1-36, 38-54, 56-72, 74-152, 154-163, 165-174, 176-298, wherein the fluorescent energy transfer dye conjugate is water-soluble.
300. The system of clauses 37-152, further comprising a calibration plate configured to reduce a cross-talk between two or more of the dyes.

301. The system of clause 300, wherein the calibration plate comprises four calibration on-axis dyes and two calibration off-axis dyes.

302. The system of clause 300, wherein the calibration plate comprises two calibration on-axis dyes and four calibration off-axis dyes.

303. The system of clauses 301 or 302, wherein the calibration off-axis dyes comprise one or more:

one of the dyes FAM-TAMRA, FAM-ABY, or FAM-NED;

one of the dyes FAM-PET, FAM-ROX, FAM-JUN, FAM-Texas Red, or TET-Alexa Fluor 594;

one of the dyes ABY-Alexa Fluor 647, NED-Alexa Fluor 647, ABY-Cy5®, ABY-ATTO 647™, or ABY-DyLight 650™; and/or one of the dyes NED-Alexa Fluor 676, NED DyLight 680™, NED-Cy5.5®, ABY-Alexa Fluor 676, ABY-DyLight 680™, or ABY-Cy5.5®.

304. The system of clauses 301-303, wherein the calibration on-axis dyes comprise one or more the dyes FAM or VIC:

305. A method, comprising:

providing a system for performing the method of clauses 153-252 or 271;

calibrating a system using a calibration plate configured to reduce a cross-talk between two or more of the dyes.

306. The method of clause 305, wherein the calibration plate comprises four calibration on-axis dyes and two calibration off-axis dyes.

307. The method of clause 305, wherein the calibration plate comprises two calibration on-axis dyes and four calibration off-axis dyes.

308. The method of clauses 306 or 307, wherein the calibration off-axis dyes comprise one or more:

one of the dyes FAM-TAMRA, FAM-ABY, or FAM-NED;

one of the dyes FAM-PET, FAM-ROX, FAM-JUN, FAM-Texas Red, or TET-Alexa Fluor 594;

one of the dyes ABY-Alexa Fluor 647, NED-Alexa Fluor 647, ABY-Cy5®, ABY-ATTO 647™, or ABY-DyLight 650™; and/or one of the dyes NED-Alexa Fluor 676, NED DyLight 680™, NED-Cy5.5®, ABY-Alexa Fluor 676, ABY-DyLight 680™, or ABY-Cy5.5®.

309. The method of clauses 305-308, wherein the calibration on-axis dyes comprise one or more the dyes FAM or VIC.

310. A system comprising a calibration plate configured to reduce a cross-talk between two or more dyes, wherein the calibration plate comprises:

four calibration on-axis dyes and two calibration off-axis dyes; or two calibration on-axis dyes and four calibration off-axis dyes.

311. The system of clauses 310, wherein the calibration off-axis dyes comprise one or more:

one of the dyes FAM-TAMRA, FAM-ABY, or FAM-NED;

one of the dyes FAM-PET, FAM-ROX, FAM-JUN, FAM-Texas Red, or TET-Alexa Fluor 594;

one of the dyes ABY-Alexa Fluor 647, NED-Alexa Fluor 647, ABY-Cy5®, ABY-ATTO 647™, or ABY-DyLight 650™; and/or one of the dyes NED-Alexa Fluor 676, NED DyLight 680™, NED-Cy5.5®, ABY-Alexa Fluor 676, ABY-DyLight 680™, or ABY-Cy5.5®.

312. The system of clauses 310-311, wherein the calibration on-axis dyes comprise one or more the dyes FAM or VIC:

313. A method, comprising:

providing a system for performing the method of clauses 153-252 or 271;

calibrating a system using a calibration plate configured to reduce a cross-talk between two or more of the dyes.

314. The system of clauses 313, wherein the calibration off-axis dyes comprise one or more:

one of the dyes FAM-TAMRA, FAM-ABY, or FAM-NED;

one of the dyes FAM-PET, FAM-ROX, FAM-JUN, FAM-Texas Red, or TET-Alexa Fluor 594;

one of the dyes ABY-Alexa Fluor 647, NED-Alexa Fluor 647, ABY-Cy5®, ABY-ATTO 647™, or ABY-DyLight 650™; and/or one of the dyes NED-Alexa Fluor 676, NED DyLight 680™, NED-Cy5.5®, ABY-Alexa Fluor 676, ABY-DyLight 680™, or ABY-Cy5.5®.

315. The system of clauses 301-303, wherein the calibration on-axis dyes comprise one or more the dyes FAM or VIC.

316. A method performing an amplification assay, comprising:

providing a biological sample comprising a plurality of target molecules, one or more off-axis dyes configured to bind to a respective one or more of the plurality of target molecules, and one or more on-axis dyes configured to bind to a respective one or more of the plurality of target molecules;

performing at least one amplification cycle on the sample;

during or after the at least one amplification cycle, illuminating the sample with two or more excitation channels;

in response to each of the illuminations, measuring emission signals from two or more emission channels;

calculating an amount of the on-axis dye and the off-axis dye based on the emission signals.

317. A method of clause 316, further comprising calculating an amount of one or more of the target molecules based on the emission signals.

318. A method of any of clauses 316-317, wherein the amplification assay comprises a quantitative polymerase chain reaction (qPCR) assay.

319. A method of any of clauses 316-317, wherein the biological sample is segregated into a plurality of reaction regions and the amplification assay comprises a digital polymerase chain reaction (dPCR) assay on at least some of the reaction regions.

320. A method of any of clauses 316-317 or 319, wherein the number of reaction regions is greater than or equal to 3,000 reaction regions.

321. A method of any of clauses 316-317 or 319, wherein the number of reaction regions is greater than or equal to 20,000 reaction regions.

322. A method of any of clauses 316-317 or 319, wherein the number of reaction regions is greater than or equal to 100,000 reaction regions.

323. A method of any of clauses 316-317 or 319, wherein the number of reaction regions is greater than or equal to 1,000,000 reaction regions.

324. A method of any of clauses 316-317 or 319-323, wherein at least some of the reaction regions contain none of the target molecules.

325. A method of any of clauses 316-317 or 319-324, wherein at least some of the reaction regions contain only one of the target molecules.

326. A method of any of clauses 316-317 or 319-325, wherein the biological sample comprises at least three target molecules.

327. A method of any of clauses 316-317 or 319-326, at least some of the reaction regions contain more than one of the target molecules and less than all the at least three target molecules.

328. The method of any of clauses 316-327, wherein first dye is or comprises first fluorophore and second dye is or comprises a fluorescent energy transfer dye conjugate according to any of clauses 1-17.

329. The method of any of clauses 316-328, wherein the first fluorophore is selected from the group consisting of a xanthene dye, a cyanine dye, a BODIPY dye, a pyrene dye, a pyronine dye, and a coumarin dye.

330. The method of any of clauses 316-329, wherein the second dye comprises a fluorophore selected from the group consisting of a fluorescein dye, a rhodamine dye, a pyronine dye, and a cyanine dye.

331. The method of any of clauses 316-330, wherein the first dye is covalently attached to a first probe, and the second dye is covalently attached to a second probe, wherein the first and second probes are configured to bind to a first and a second target molecule, respectively.

332. The method of clause 331, wherein the first and second probes are oligonucleotide probes and the second probe is according to any of clauses 18-36.

333. The method of any of clauses 316-332, wherein the first and second target molecules are nucleic acid molecules.

334. The method of any of clauses 316-333, wherein the first dye comprises a maximum absorption wavelength that is equal to or substantially equal to a maximum absorption wavelength of the second dye.

335. he method of clause 334, wherein one or more of the first maximum absorption wavelength or second maximum absorption wavelength is an absolute maximum over an entirety of the respective spectrum.

336. The method of any of clauses 316-335, wherein the first dye is an on-axis dye and the second dye is an off-axis dye.

337. The method of any of clauses 316-336, wherein the first dye is configured to bind to a first target molecule and the second dye is configured to bind to a second target molecule, the method further comprising determining an amount of any target molecules present in the sample based on the measured emissions.

338. A method, comprising:
- providing a system for performing the method of clauses 316-337;
- calibrating a system using a calibration plate configured to reduce a cross-talk between two or more of the dyes.

339. The method of clause 338, wherein the calibration plate comprises four calibration on-axis dyes and two calibration off-axis dyes.

340. The method of clause 338, wherein the calibration plate comprises two calibration on-axis dyes and four calibration off-axis dyes.

341. The method of clauses 339 or 340, wherein the calibration off-axis dyes comprise one or more:
- one of the dyes FAM-TAMRA, FAM-ABY, or FAM-NED;
- one of the dyes FAM-PET, FAM-ROX, FAM-JUN, FAM-Texas Red, or TET-Alexa Fluor 594;
- one of the dyes ABY-Alexa Fluor 647, NED-Alexa Fluor 647, ABY-Cy5®, ABY-ATTO 647™, or ABY-DyLight 650™; and/or
- one of the dyes NED-Alexa Fluor 676, NED DyLight 680™, NED-Cy5.5®, ABY-Alexa Fluor 676, ABY-DyLight 680™, or ABY-Cy5.5®.

342. The method of clauses 338-341, wherein the calibration on-axis dyes comprise one or more the dyes FAM or VIC.

We claim:

1. A system, comprising:
- a first radiant source characterized by a first average excitation wavelength;
- a second radiant source characterized by a second average excitation wavelength that is different than the first average excitation wavelength;
- a sample disposed to receive radiation from the radiant sources, the sample comprising:
  - a first dye;
  - a second dye; and
  - a third dye;
- a detector configured to measure emissions from the sample;
- a first emission spectral element characterized by a first average emission wavelength;
- a second emission spectral element characterized by a second average emission wavelength that is different than the first average emission wavelength;
- at least one processor comprising at least one non-transitory memory encoded with instructions that are executed by the processor to:
- illuminate the sample with the first radiant source and, in response, (1) measure emissions from the sample using the detector and the first emission spectral element and (2) measure emissions from the sample using the detector and the second emission spectral element;
- illuminate the sample with the second radiant source and, in response, measure emissions from the sample using the detector and the second emission spectral element;
- wherein (1) the first dye comprises a first absorption spectrum comprising a first maximum absorption wavelength and the second dye comprises a second absorption spectrum comprising a second maximum absorption wavelength that is equal to or substantially equal to the first maximum absorption wavelength; and (2) the second dye comprises a second emission spectrum comprising a second maximum emission wavelength and the third dye comprises a third emission spectrum comprising a third maximum emission wavelength that is equal to or substantially equal to the second maximum emission wavelength-;
- wherein at least one of the first dye, the second dye, and the third dye is an off-axis dye, an off-axis dye being a dye having a maximum absorption or excitation wavelength that is an absolute maximum over an entire spectrum of the dye and having a maximum absorption or excitation wavelength that is a local maximum and is separated from the absolute maximum by at least 60 nanometers; and wherein each radiant source is characterized by electromagnetic radiation within the visible light range, near infrared range, infrared range, or ultraviolet range.

2. The system of claim 1, wherein the first dye comprises a first emission spectrum comprising a first maximum emission wavelength and the second dye comprises a second emission spectrum comprising a second maximum emission wavelength that is equal to or substantially equal the first maximum emission wavelength.

3. The system of claim 1, wherein:

the average excitation wavelength of the first radiant source is 480±5 nanometers and/or the first radiant source is characterized by a wavelength band that is less than or equal to ±12 nanometers about the average excitation wavelength; the first average emission wavelength of the first emission spectral element is 520±5 nanometers and/or the first emission spectral element is characterized by a wavelength band that is less than or equal to ±20 nanometers about the first average emission wavelength; and the second average emission wavelength of the second emission spectral element is 587±5 nanometers and/or the second emission spectral element is characterized by a wavelength band that is less than or equal to ±12 nanometers about the second average emission wavelength;

the average excitation wavelength of the first radiant source is 480±5 nanometers and/or the first radiant source is characterized by a wavelength band that is less than or equal to ±12 nanometers about the average excitation wavelength; the first average emission wavelength of the first emission spectral element is 520±5 nanometers and/or the first emission spectral element is characterized by a wavelength band that is less than or equal to ±18 nanometers about the first average emission wavelength; and the second average emission wavelength of the second emission spectral element is 623±5 nanometers and/or the second emission spectral element is characterized by a wavelength band that is less than or equal to ±18 nanometers about the second average emission wavelength;

the first average excitation wavelength of the first radiant source is 550±5 nanometers and/or the first radiant source is characterized by a wavelength band that is less than or equal to ±14 nanometers about the first average excitation wavelength; the second average excitation wavelength of the second radiant source is 640±5 nanometers and/or the second radiant source is characterized by a wavelength band that is less than or equal to ±12 nanometers about the second average excitation wavelength; the average emission wavelength of the first emission spectral element is 682±5 nanometers and/or the second emission spectral element is characterized by a wavelength band that is less than or equal to ±16 nanometers about the average emission wavelength;

or the first average excitation wavelength of the first radiant source is 550±5 nanometers and/or the first radiant source is characterized by a wavelength band that is less than or equal to ±14 nanometers about the first average excitation wavelength; the second average excitation wavelength of the second radiant source is 662±5 nanometers and/or the second radiant source is characterized by a wavelength band that is less than or equal to ±12 nanometers about the second average excitation wavelength; and the average emission wavelength of the first emission spectral element is 711±5 nanometers and/or the second emission spectral element is characterized by a wavelength band that is less than or equal to ±16 nanometers about the average emission wavelength.

4. The system of claim 1, wherein:

the system further comprises a fourth, fifth, and sixth radiant source, each of the fourth, fifth, and sixth radiant sources characterized by a respective fourth, fifth, and sixth average excitation wavelength, wherein each of the six average excitation wavelengths is different from the remaining average excitation wavelengths;

the sample further comprises fourth, fifth, sixth, seventh, and eighth dyes;

the system further comprises third, fourth, fifth, and sixth emission spectral elements each configured to pass emissions from the sample, each of the third, fourth, fifth, and sixth emission elements characterized by a respective third, fourth, fifth, and sixth average emission wavelength, wherein the each of the six average emission wavelengths of each of the wavelength sources is different from the average emission wavelengths of the remaining sources;

the at least one non-transitory memory encoded with instructions that are executed by the processor to:

illuminate the sample with the third, fourth, fifth, and sixth radiant sources;

in response to illuminating the sample with each of the third, fourth, fifth, and sixth radiant sources, measure emissions from the sample using one or more of the emission spectral elements;

wherein each radiant source is characterized by electromagnetic radiation within the visible light range, near infrared range, infrared range, or ultraviolet range.

5. The system of claim 4, wherein the second dye and the fourth dye are off-axis dyes, an off-axis dye being a dye having a maximum absorption or excitation wavelength that is an absolute maximum over an entire spectrum of the dye and having a maximum absorption or excitation wavelength that is a local maximum and is separated from the absolute maximum by at least 60 nanometers.

6. The system of claim 4, wherein:

the second dye comprises a maximum absorption wavelength that is equal to or substantially equal to a maximum absorption wavelength of the first dye;

the fourth dye comprises a maximum absorption wavelength that is equal to or substantially equal to a maximum absorption wavelength of the first dye;

the second dye comprises a maximum emission wavelength that is equal to or substantially equal to a maximum emission wavelength of the third dye; and the fourth dye comprises a maximum emission wavelength that is equal to or substantially equal to a maximum emission wavelength of the fifth dye.

7. The system of claim 1, wherein the first and second emission spectral elements comprise a dispersive optical element configure to disperse emissions from the sample along a first optical path and second optical path, wherein the detector comprises a first detector configured to receive emissions along the first optical path and a second detector configured to receive emissions along the second optical path; optionally wherein the first detector comprises a first location on a CCD detector or CMOS detector and the second comprises a second location on a CCD detector or CMOS detector that is spatially separated from the first location.

8. The system of claim 1, wherein the second dye is an energy-transfer dye conjugate comprising:

a donor dye characterized by a maximum absorption wavelength that is equal to or substantially equal to the maximum absorption wavelength of the first dye, the donor dye configured to absorb radiation from the first radiant source and, in response, to generate energy; and an acceptor dye characterized by a maximum emission wavelength that is equal to or substantially equal to the maximum emission wavelength of the third dye, wherein the dyes are configured to transfer at least some of the energy generated by the donor to the acceptor dye.

9. The system of claim 8, wherein the first dye is characterized by a first spectral signature, the third dye is characterized by a third spectral signature, the donor dye is characterized by a donor dye spectral signature, and (1) the donor dye spectral signature is equal to the third emission spectral signature and/or (2) a maximum emission wavelength of the donor dye is equal to maximum emission wavelength the third dye.

10. The system of claim 8, wherein the donor dye has an emission wavelength band and the acceptor dye an absorption wavelength band that does not overlap the donor dye emission wavelength band.

11. A method, comprising:

providing a sample comprising a first dye, a second dye, and a third dye configured to bind to a first, second and third target molecule;

illuminating the sample with a first radiant source characterized by a first average excitation wavelength and, in response, (1) measuring an emission from the sample using a detector and a first emission spectral element characterized by a first average emission wavelength and (2) measuring an emission from the sample using the detector and a second emission spectral element characterized by a second average emission wavelength that is different than the first average emission wavelength;

illuminating the sample with a second radiant source characterized by a second average excitation wavelength that is different than the first average excitation wavelength and, in response, measuring an emission from the sample using the detector and the second emission spectral element;

wherein at least one of the first dye, the second dye, and the third dye is an off-axis dye, an off-axis dye being a dye having a maximum absorption or excitation wavelength that is an absolute maximum over an entire spectrum of the dye and having a maximum absorption or excitation wavelength that is a local maximum and is separated from the absolute maximum by at least 60 nanometers; and wherein each radiant source is characterized by electromagnetic radiation within the visible light range, near infrared range, infrared range, or ultraviolet range.

12. The method of claim 11, wherein (1) the first dye comprises a first absorption spectrum comprising a first maximum absorption wavelength and the second dye comprises a second absorption spectrum comprising a second maximum absorption wavelength that is equal to or substantially equal to the first maximum absorption wavelength; and (2) the second dye comprises a second emission spectrum comprising a second maximum emission wavelength and the third dye comprises a third emission spectrum comprising a third maximum emission wavelength that is equal to or substantially equal to the second maximum emission wavelength.

* * * * *